United States Patent
Li et al.

(10) Patent No.: US 11,245,078 B2
(45) Date of Patent: *Feb. 8, 2022

(54) THERMALLY ACTIVATED DELAYED FLUORESCENT MATERIAL BASED ON 9,10-DIHYDRO-9,9-DIMETHYLACRIDINE ANALOGUES FOR PROLONGING DEVICE LONGEVITY

(71) Applicant: Arizona Board of Regents, Scottsdale, AZ (US)

(72) Inventors: Jian Li, Tempe, AZ (US); Diajun Feng, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 45 days.

This patent is subject to a terminal disclaimer.

(21) Appl. No.: 16/279,145

(22) Filed: Feb. 19, 2019

(65) Prior Publication Data

US 2020/0075868 A1 Mar. 5, 2020

Related U.S. Application Data

(63) Continuation of application No. 15/246,754, filed on Aug. 25, 2016, now Pat. No. 10,211,411.

(60) Provisional application No. 62/209,647, filed on Aug. 25, 2015.

(51) Int. Cl.
| | |
|---|---|
| C07D 471/22 | (2006.01) |
| C07D 519/00 | (2006.01) |
| C09K 11/06 | (2006.01) |
| H01L 51/00 | (2006.01) |
| C07D 471/06 | (2006.01) |
| C07F 9/6561 | (2006.01) |
| C07F 9/572 | (2006.01) |
| H01L 51/50 | (2006.01) |

(52) U.S. Cl.
CPC ........ *H01L 51/0072* (2013.01); *C07D 471/06* (2013.01); *C07D 519/00* (2013.01); *C07F 9/5728* (2013.01); *C07F 9/6561* (2013.01); *C09K 11/06* (2013.01); *H01L 51/0067* (2013.01); *C09K 2211/1007* (2013.01); *C09K 2211/1022* (2013.01); *C09K 2211/1029* (2013.01); *C09K 2211/1044* (2013.01); *C09K 2211/1048* (2013.01); *C09K 2211/1059* (2013.01); *C09K 2211/1096* (2013.01); *H01L 51/007* (2013.01); *H01L 51/5016* (2013.01); *Y02E 10/549* (2013.01)

(58) Field of Classification Search
CPC .... C07D 471/22; C07D 519/00; C09K 11/06; H01L 51/0072
See application file for complete search history.

(56) References Cited

U.S. PATENT DOCUMENTS

| | | |
|---|---|---|
| 8,106,199 B2 | 1/2012 | Jabbour |
| 8,389,725 B2 | 3/2013 | Li |
| 8,669,364 B2 | 3/2014 | Li |
| 8,816,080 B2 | 8/2014 | Li |
| 8,846,940 B2 | 9/2014 | Li |
| 8,927,713 B2 | 1/2015 | Li |
| 8,946,417 B2 | 2/2015 | Jian |
| 9,076,974 B2 | 7/2015 | Li |
| 9,082,989 B2 | 7/2015 | Li |
| 9,203,039 B2 | 12/2015 | Li |
| 9,221,857 B2 | 12/2015 | Li |
| 9,224,963 B2 | 12/2015 | Li |
| 9,238,668 B2 | 1/2016 | Li |
| 9,312,502 B2 | 4/2016 | Li |
| 9,318,725 B2 | 4/2016 | Li |
| 9,324,957 B2 | 4/2016 | Li |
| 9,382,273 B2 | 7/2016 | Li |
| 9,385,329 B2 | 7/2016 | Li |
| 9,425,415 B2 | 8/2016 | Li |
| 9,502,671 B2 | 11/2016 | Li |
| 9,550,801 B2 | 1/2017 | Li |
| 9,598,449 B2 | 3/2017 | Li |
| 9,617,291 B2 | 4/2017 | Li |
| 9,673,409 B2 | 6/2017 | Li |
| 9,698,359 B2 | 7/2017 | Li |
| 9,711,739 B2 | 7/2017 | Li |
| 9,711,741 B2 | 7/2017 | Li |
| 9,711,742 B2 | 7/2017 | Li |
| 9,755,163 B2 | 9/2017 | Li |
| 9,818,959 B2 | 11/2017 | Li |
| 9,865,825 B2 | 1/2018 | Li |
| 9,879,039 B2 | 1/2018 | Li |
| 9,882,150 B2 | 1/2018 | Li |
| 9,899,614 B2 | 2/2018 | Li |

(Continued)

FOREIGN PATENT DOCUMENTS

| | | | |
|---|---|---|---|
| KR | 20110066763 | | 6/2011 |
| KR | 20130043460 A | * | 4/2013 |

(Continued)

OTHER PUBLICATIONS

STN Abstract of KR 2013043460 A (Year: 2013).*
U.S. Appl. No. 16/668,010, filed Oct. 30, 2019, has not yet published. Inventor: Li et al.
U.S. Appl. No. 16/739,480, filed Jan. 10, 2020, has not yet published. Inventors: Li et al.
U.S. Appl. No. 16/751,561, filed Jan. 24, 2020, has not yet published. Inventor: Li.

(Continued)

*Primary Examiner* — Bruck Kifle
(74) *Attorney, Agent, or Firm* — Riverside Law LLP

(57) ABSTRACT

Thermally activated delayed fluorescent compounds and uses thereof are described. The thermally activated delayed fluorescent compounds are an analogues of 9,10-dihydro-9,9-dimethylacridine compounds.

20 Claims, No Drawings

(56) References Cited

U.S. PATENT DOCUMENTS

| | | |
|---|---|---|
| 9,920,242 B2 | 3/2018 | Li |
| 9,923,155 B2 | 3/2018 | Li |
| 9,941,479 B2 | 4/2018 | Li |
| 9,947,881 B2 | 4/2018 | Li |
| 9,985,224 B2 | 5/2018 | Li |
| 10,020,455 B2 | 7/2018 | Li |
| 10,033,003 B2 | 7/2018 | Li |
| 10,056,564 B2 | 8/2018 | Li |
| 10,056,567 B2 | 8/2018 | Li |
| 10,158,091 B2 | 12/2018 | Li |
| 10,177,323 B2 | 1/2019 | Li |
| 10,211,411 B2 | 2/2019 | Li |
| 10,211,414 B2 | 2/2019 | Li |
| 10,263,197 B2 | 4/2019 | Li |
| 10,294,417 B2 | 5/2019 | Li |
| 10,392,387 B2 | 8/2019 | Li |
| 10,411,202 B2 | 9/2019 | Li |
| 10,414,785 B2 | 9/2019 | Li |
| 10,516,117 B2 | 12/2019 | Li |
| 10,566,553 B2 | 2/2020 | Li |
| 10,566,554 B2 | 2/2020 | Li |
| 2008/0269491 A1 | 10/2008 | Jabbour |
| 2009/0136779 A1 | 5/2009 | Cheng |
| 2011/0028723 A1 | 2/2011 | Li |
| 2011/0066763 A1 | 3/2011 | Minot |
| 2011/0301351 A1 | 12/2011 | Li |
| 2012/0095232 A1 | 4/2012 | Li |
| 2012/0108806 A1 | 5/2012 | Li |
| 2012/0202997 A1 | 8/2012 | Parham |
| 2012/0215001 A1 | 8/2012 | Li |
| 2012/0264938 A1 | 10/2012 | Li |
| 2012/0302753 A1 | 11/2012 | Li |
| 2013/0137870 A1 | 5/2013 | Li |
| 2013/0203996 A1 | 8/2013 | Li |
| 2013/0237706 A1 | 9/2013 | Li |
| 2014/0066628 A1 | 3/2014 | Li |
| 2014/0073798 A1 | 3/2014 | Li |
| 2014/0114072 A1 | 4/2014 | Li |
| 2014/0147996 A1 | 5/2014 | Vogt |
| 2014/0148594 A1 | 5/2014 | Li |
| 2014/0249310 A1 | 9/2014 | Li |
| 2014/0330019 A1 | 11/2014 | Li |
| 2014/0364605 A1 | 12/2014 | Li |
| 2015/0008419 A1 | 1/2015 | Li |
| 2015/0018558 A1 | 1/2015 | Li |
| 2015/0105556 A1 | 4/2015 | Li |
| 2015/0162552 A1 | 6/2015 | Li |
| 2015/0194616 A1 | 7/2015 | Li |
| 2015/0207086 A1 | 7/2015 | Li |
| 2015/0228914 A1 | 8/2015 | Li |
| 2015/0274762 A1 | 10/2015 | Li |
| 2015/0287938 A1 | 10/2015 | Li |
| 2015/0311456 A1 | 10/2015 | Li |
| 2015/0318500 A1 | 11/2015 | Li |
| 2015/0349279 A1 | 12/2015 | Li |
| 2016/0028028 A1 | 1/2016 | Li |
| 2016/0028029 A1 | 1/2016 | Li |
| 2016/0043331 A1 | 2/2016 | Li |
| 2016/0133861 A1 | 5/2016 | Li |
| 2016/0133862 A1 | 5/2016 | Li |
| 2016/0194344 A1 | 7/2016 | Li |
| 2016/0197291 A1 | 7/2016 | Li |
| 2016/0285015 A1 | 9/2016 | Li |
| 2016/0359120 A1 | 12/2016 | Li |
| 2016/0359125 A1 | 12/2016 | Li |
| 2017/0005278 A1 | 1/2017 | Li |
| 2017/0012224 A1 | 1/2017 | Li |
| 2017/0040555 A1 | 2/2017 | Li |
| 2017/0047533 A1 | 2/2017 | Li |
| 2017/0066792 A1 | 3/2017 | Li |
| 2017/0069855 A1 | 3/2017 | Li |
| 2017/0077420 A1 | 3/2017 | Li |
| 2017/0125708 A1 | 5/2017 | Li |
| 2017/0267923 A1 | 9/2017 | Li |
| 2017/0271611 A1 | 9/2017 | Li |
| 2017/0301871 A1 | 10/2017 | Li |
| 2017/0305881 A1 | 10/2017 | Li |
| 2017/0331056 A1 | 11/2017 | Li |
| 2017/0342098 A1 | 11/2017 | Li |
| 2017/0373260 A1 | 12/2017 | Li |
| 2018/0006246 A1 | 1/2018 | Li |
| 2018/0053904 A1 | 2/2018 | Li |
| 2018/0130960 A1 | 5/2018 | Li |
| 2018/0138428 A1 | 5/2018 | Li |
| 2018/0148464 A1 | 5/2018 | Li |
| 2018/0159051 A1 | 6/2018 | Li |
| 2018/0166655 A1 | 6/2018 | Li |
| 2018/0175329 A1 | 6/2018 | Li |
| 2018/0194790 A1 | 7/2018 | Li |
| 2018/0219161 A1 | 8/2018 | Li |
| 2018/0226592 A1 | 8/2018 | Li |
| 2018/0226593 A1 | 8/2018 | Li |
| 2018/0277777 A1 | 9/2018 | Li |
| 2018/0301641 A1 | 10/2018 | Li |
| 2018/0312750 A1 | 11/2018 | Li |
| 2018/0331307 A1 | 11/2018 | Li |
| 2018/0334459 A1 | 11/2018 | Li |
| 2018/0337345 A1 | 11/2018 | Li |
| 2018/0337349 A1 | 11/2018 | Li |
| 2018/0337350 A1 | 11/2018 | Li |
| 2019/0013485 A1 | 1/2019 | Li |
| 2019/0067602 A1 | 2/2019 | Li |
| 2019/0109288 A1 | 4/2019 | Li |
| 2019/0194536 A1 | 6/2019 | Li |
| 2019/0259963 A1 | 8/2019 | Li |
| 2019/0276485 A1 | 9/2019 | Li |
| 2019/0312217 A1 | 10/2019 | Li |
| 2019/0367546 A1 | 12/2019 | Li |
| 2019/0389893 A1 | 12/2019 | Li |
| 2020/0006678 A1 | 1/2020 | Li |
| 2020/0071330 A1 | 3/2020 | Li |
| 2020/0075868 A1 | 3/2020 | Li |
| 2020/0119288 A1 | 4/2020 | Li |
| 2020/0152891 A1 | 5/2020 | Li |
| 2020/0239505 A1 | 7/2020 | Li |
| 2020/0243776 A1 | 7/2020 | Li |

FOREIGN PATENT DOCUMENTS

| | | |
|---|---|---|
| KR | 20140027030 | 3/2014 |
| WO | 2009086209 | 7/2009 |
| WO | 2009111299 | 9/2009 |
| WO | 2010050778 | 5/2010 |
| WO | 2010105141 | 9/2010 |
| WO | 2010118026 | 10/2010 |
| WO | 2011137429 | 11/2011 |
| WO | 2011137431 | 11/2011 |
| WO | 2012074909 | 6/2012 |
| WO | 2012112853 | 8/2012 |
| WO | 2012142387 | 10/2012 |
| WO | 2012162488 | 11/2012 |
| WO | 2013130483 | 9/2013 |
| WO | 2014031977 | 2/2014 |
| WO | 2014047616 | 3/2014 |
| WO | 2014109814 | 7/2014 |
| WO | 2015027060 | 2/2015 |
| WO | 2015099507 | 7/2015 |
| WO | 2015131158 | 9/2015 |
| WO | 2016025921 | 2/2016 |
| WO | 2016029137 | 2/2016 |
| WO | 2016029186 | 2/2016 |
| WO | 2016197019 | 12/2016 |
| WO | 2018071697 | 4/2018 |
| WO | 2018140765 | 8/2018 |
| WO | 2019079505 | 4/2019 |
| WO | 2019079508 | 4/2019 |
| WO | 2019079509 | 4/2019 |
| WO | 2019236541 | 12/2019 |
| WO | 2020018476 | 1/2020 |

(56) References Cited

OTHER PUBLICATIONS

U.S. Appl. No. 16/751,586, filed Jan. 24, 2020, has not yet published. Inventor: Li et al.
Uoyama et al., "Highly efficient organic light-emitting diodes from delayed fluorescence" Nature, 492:234-238, (2012).
Yan, et al. Organic & Biomolecular Chemistry, 11(45), 2013, 7966-7977.

* cited by examiner

THERMALLY ACTIVATED DELAYED FLUORESCENT MATERIAL BASED ON 9,10-DIHYDRO-9,9-DIMETHYLACRIDINE ANALOGUES FOR PROLONGING DEVICE LONGEVITY

CROSS REFERENCE TO RELATED APPLICATIONS

This application is a continuation of U.S. patent application Ser. No. 15/246,754, filed Aug. 25, 2016, now allowed, which claims benefit to U.S. Provisional Application No. 62/209,647, filed Aug. 25, 2015, all of which are incorporated by reference herein in their entireties.

BACKGROUND OF THE INVENTION

A. Field of the Invention

The present disclosure relates to an organic electroluminescence device, and electronic equipment.

B. Description of Related Art

In the past decade, much progress has been achieved in research of OLEDs, therefore successively leading to applications to full-color display such as television and mobile telephones. The organic electroluminescent device is the light-emitting diodes device in which holes from the anode, also electrons from the cathode are injected into the emissive layer, then wherein holes and electrons are recombined, and excitons are formed. According to the electron spin of the statistical law, singlet excitons and triplet excitons are produced at a ratio of 25%:75%. Thus, in this case, the internal quantum efficiency of fluorescent light emitted by a singlet exciton is limited to 25% because of the nonradiative decay of the spin-forbidden triplet exciton.

On the other hand, the phosphorescence-based OLEDs have been developed to address this issue, where the internal quantum efficiency can be increased to 100% because noble-metal-based organometallic phosphors possess emissive triplet states through performing the intersystem crossing efficiently from the singlet excitons. However, the noble metals are expensive and the abundances of them are very limited, moreover the blue PHOLEDs need to be further investigated to obtain decent device longevity. Against this background, new concepts have been considered for the fluorescence OLEDs with high efficiency utilizing the delayed fluorescence, such as, triplet-triplet annihilation, which is a phenomenon of generating singlet excitons by the fusion of two triplet excitons.

The internal quantum is just theoretically limited to 40%. Efficient OLEDs based on charge-transfer (CT) Cu(I) complexes have also attracted much interest in the last decade. However, high-performance blue OLEDs based on Cu(I) complexes have not been reported, due to the poor device reliability arising from oxidation of metal center. Therefore, in order to achieve further internal quantum efficiency, the organic EL element utilizing a mechanism involving other delayed fluorescence has been investigated, such as, TADF (thermally activated delayed fluorescence, or thermal activation delay fluorescence). The TADF mechanism utilizes the phenomenon that the reverse intersystem crossing from the triplet exciton to the singlet excitons can be realized when using the material with a small energy difference between the singlet level and triplet level ($\Delta$ST). The OLEDs involving this TADF mechanism are described by Taiki et al. (*Nature,* 2012, V. 492 volume, p. 234-238) where carbazolyl dicyanobenzene (CDCB) acts as the TADF luminescent material. However, these conventional OLEDs using TADF luminescent materials suffer from short operation time.

SUMMARY OF THE INVENTION

The present invention provides a solution to the problems associated with the above-mentioned TADF luminescent material. The solution is premised on novel organic compounds, which can function as a TADF light emitting material that improve the luminous efficiency of the corresponding devices. The new TADF materials may exhibit low degradation during the course of device operation, thereby providing stable organic electroluminescent device.

With the apparent conventional wisdom, a chemical structural change will affect the electronic structure of the compounds, thereby affecting the optical properties of the compounds (e.g., emission and absorption spectra). Thus, a particular emission or absorption energy can be achieved by tuning or tailoring the chemical structure. For example, compounds bearing altered electron donating substituents or electron withdrawing substituents generally exhibit different optical properties, including different emission and absorption spectra. In some aspects, an emission spectrum can be modified to be narrower or broader, and exhibit a blue shift or a red shift, or a combination thereof, by altering, adding, or removing one or more of the substitution groups.

On the other hand, degradation of the materials during the course of device operation can be significantly suppressed by optimization of molecule structure, and thereby longevity of device can meet the need of market of them. For example, bearing donor moiety interlocked with backbone structure, TADF emitter can facilitate formation of the stable hole, therefore relieving degradation of the emitter, and thus improve the reliability of the device.

As described herein, a TADF composition may include one or more compounds of the formulas:

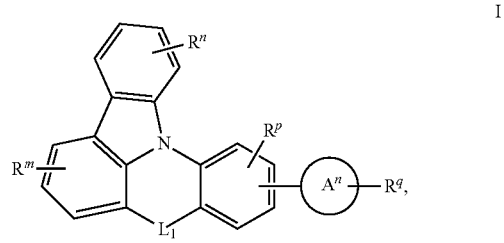

I

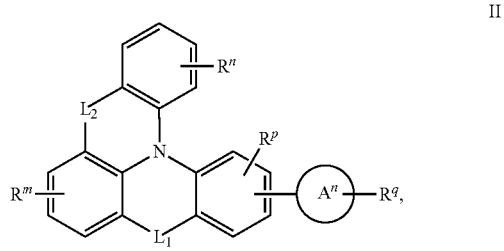

II

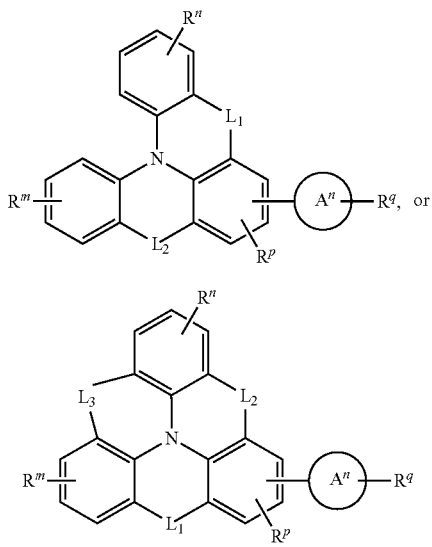

where for each of the one or more compounds: $A^n$ where n=1, 2, or 3 can: 1) independently represent one or more acceptor moieties of the compound, 2) be a substituted or unsubstituted electron-deficient moeity, 3) contribute to the LUMO level of the compound, or any combination of thereof. In some embodiments $A^n$ can include where $A^n$ is nitrogen-containing heteroaryl group, a $R^qMO$ group, where M is C, S, P, or As, or a $R^qSO_2$ group, or any combination thereof. $L_1$, $L_2$, and $L_3$ can be linkage groups, that can include an (O) linker, a sulfur (S) linker, a nitrogen (N) linker, a carbon (C) linker, a phosphorous (P) linker, a silicon (Si) linker, or a boron (B), preferably a carbon linker or a silicon linker. In some cases, at least, one of $L_1$ and $L_2$ are present, or both of them are present and whereas $L_3$ may not be present. $R^m$, $R^n$, $R^p$, and $R^q$ each independently represents mono-, di-, tri, or tetra-substitution, and each independently represents one or more of deuterium, a halogen atom, a hydroxyl group, a thiol group, a nitro group, a cyano group, a substituted or unsubstituted alkyl group, a substituted or unsubstituted haloalkyl group, a substituted or unsubstituted aralkyl group, a substituted or unsubstituted alkenyl group, a substituted or unsubstituted alkynyl group, a substituted or unsubstituted aryl group, a substituted or unsubstituted amino group, a substituted or unsubstituted mono- or dialkylamino group, a substituted or unsubstituted mono- or diarylamino group, a substituted or unsubstituted alkoxy group, a substituted or unsubstituted aryloxy group, a substituted or unsubstituted heteroaryl group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a mercapto group, a sulfo group, a carboxyl group, a hydrazino group, a substituted silyl group, a polymeric group, or a combination thereof.

In a second general aspect, a light emitting device includes the composition of the first general aspect. In some cases, the light emitting device includes an organic light emitting diode. In certain cases, the light emitting device is an organic light emitting diode.

In a third general aspect, a device includes the composition of the first general aspect or the light emitting device of the second general aspect. The device may include, for example, a full color display, a photovoltaic device, or a luminescent or phosphorescent display device. In some cases, the device includes an organic light emitting diode. In certain cases, the device is an organic light emitting diode.

Additional aspects will be set forth in the description, which follows. Advantages will be realized and attained by means of the elements and combinations particularly pointed out in the claims. It is to be understood that both the foregoing general description and the following detailed description are exemplary and explanatory only and are not restrictive.

The following includes definitions of various terms and phrases used throughout this specification.

As used in the specification and the appended claims, the singular forms "a", "an", and "the" include plural referents unless the context clearly dictates otherwise. Thus, for example, reference to "a component" includes mixtures of two or more components.

In some aspects, ranges expressed herein as from "about" one particular value to "about" another particular value include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

Disclosed are the components to be used to prepare the compositions described herein as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions. Thus, if there are a variety of additional steps that can be performed it is understood that each of these additional steps can be performed with any specific embodiment or combination of embodiments of the methods.

As referred to herein, a linking atom can connect two groups such as, for example, a N and C group. The linking atom can optionally, if valency permits, have other chemical moieties attached. For example, in one aspect, an oxygen would not have any other chemical groups attached as the valency is satisfied once it is bonded to two atom (e.g., N or C). In contrast, when carbon is the linking atom, two additional chemical moieties can be attached to the carbon. Suitable chemical moieties include, but are not limited to, hydrogen, hydroxyl, alkyl, alkoxy, =O, halogen, nitro, amine, amide, thiol, aryl, heteroaryl, cycloalkyl, and heterocycle.

The term "cyclic structure" or the like terms used herein refer to any cyclic chemical structure, which includes, but is not limited to, aryl, heteroaryl, cycloalkyl, cycloalkenyl, heterocycle, carbene, and N-heterocyclic carbene.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more, and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. In addition, the terms "substitution" or "substituted with" include the implicit proviso, that such substitution is in accordance with permitted valence of the substituted atom and the substituent, and that the substitution results in a stable compound (e.g., a compound that does not spontaneously undergo transformation such as by rearrangement, cyclization, elimination, etc.). It is also contemplated that, in certain aspects, unless expressly indicated to the contrary, individual substituents can be further optionally substituted (i.e., further substituted or unsubstituted).

In defining various terms, "$Z_a$," "$Z_b$," "$Z_c$,", and "$Z_d$," are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The terms "amine" or "amino" as used herein are represented by the formula $NZ_aZ_bZ_c$, where $Z_aZ_bZ_c$ are independently hydrogen, optionally substituted alkyl, cycloalkyl, alkenyl, cycloalkenyl, alkynyl, cycloalkynyl, aryl, or heteroaryl group as described herein.

The terms "alkoxy" and "alkoxyl" as used herein to refer to an alkyl or cycloalkyl group bonded through an ether linkage; that is, an "alkoxy" group can be defined as $—OZ_a$ where $Z_a$ is alkyl or cycloalkyl as defined above. "Alkoxy" also includes polymers of alkoxy groups as just described; that is, an alkoxy can be a polyether such as $—OZ_a—OZ_b$ or $—OZ_a—(OZ_b)_n-OZ_c$, where "n" is an integer of from 1 to 200 $Z_a$, $Z_b$, and $Z_c$ are each independently alkyl groups, cycloalkyl groups, or a combination thereof.

The term "alkenyl" as used herein is a hydrocarbon group of from 2 to 24 carbon atoms with a structural formula containing at least one carbon-carbon double bond. Asymmetric structures such as $(AZ_aZ_b)C=C(Z_cZ_d)$ are intended to include both the E and Z isomers. This can be presumed in structural formulas herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bond. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The term "alkylamino" as used herein is represented by the formula —NH(-alkyl) where alkyl is as described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is as described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$Z_a$ or —C(O)O$Z'$, where $Z_a$ can be alkyl, cycloalkyl, alkenyl, cycloalkenyl, alkynyl, cycloalkynyl, aryl, or heteroaryl as described herein. The term "polyester" as used herein is represented by the formula —($Z_a$O(O)C—$Z_b$—C(O)O)$_n$— or —($Z_a$(O)C—$Z_b$—OC(O))$_n$—, where $Z_a$ and $Z_b$ can be, independently, an alkyl, cycloalkyl, alkenyl, cycloalkenyl, alkynyl, cycloalkynyl, aryl, or heteroaryl group described herein and "n" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $Z_a$O$Z_b$, where $Z_a$ and $Z_b$ can be, independently, an alkyl, cycloalkyl, alkenyl, cycloalkenyl, alkynyl, cycloalkynyl, aryl, or heteroaryl group described herein. The term "polyether" as used herein is represented by the formula —($Z_a$O—$Z_b$O)n-, where $Z_a$ and $Z_b$ can be, independently, an alkyl, cycloalkyl, alkenyl, cycloalkenyl, alkynyl, cycloalkynyl, aryl, or heteroaryl group described herein and "n" is an integer of from 1 to 500. Examples of polyether groups include polyethylene oxide, polypropylene oxide, and polybutylene oxide.

The term "polymeric" includes polyalkylene, polyether, polyester, and other groups with repeating units, such as, but not limited to, —(CH$_2$O)$_n$—CH$_3$, —(CH$_2$CH$_2$O)$_n$—CH$_3$, —[CH$_2$CH(CH$_3$)]$_n$—CH$_3$, —[CH$_2$CH(COOCH$_3$)]$_n$—CH$_3$, —[CH$_2$CH(COO CH$_2$CH$_3$)]n-CH$_3$, and —[CH$_2$CH (COOtBu)]$_n$—CH$_3$, where n is an integer (e.g., n>1 or n>2).

The term "halide" as used herein refers to the halogens fluorine, chlorine, bromine, and iodine.

The term "heterocycle," as used herein refers to single and multi-cyclic non-aromatic ring systems and "heteroaryl as used herein refers to single and multi-cyclic aromatic ring systems: in which at least one of the ring members is other than carbon. The term includes azetidine, dioxane, furan, imidazole, isothiazole, isoxazole, morpholine, oxazole, oxazole, including, 1,2,3-oxadiazole, 1,2,5-oxadiazole and 1,3, 4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $Z_aC(O)R_b$, where $Z_a$ and $Z_a$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiZ_aZ_bZ_c$, where $Z_a$, $Z_b$, and $Z_c$ can be, independently, hydrogen atom or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)Z_a$, —$S(O)_2Z_a$, —$OS(O)_2Z_a$, or —$OS(O)_2Z_a$, where $Z_a$ can be hydrogen atom or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2Z_a$, where $Z_a$ can be hydrogen atom or an alkyl, cycloalkyl, alkenyl, cycloalkenyl, alkynyl, cycloalkynyl, aryl, or heteroaryl group as described herein. The term "sulfone" as used herein is represented by the formula $Z_a(O)_2Z_a$, where $Z_a$ and $Z_b$ can be, independently, an alkyl, cycloalkyl, alkenylcycloalkenyl, alkynyl, cycloalkynyl, aryl, or heteroaryl group as described herein. The term "sulfoxide" as used herein is represented by the formula $Z_aS(O)Z_b$, where $Z_a$ and $Z_b$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R", "$R_1$," "$R_2$," "$R_3$," . . . "$R_n$," where n is an integer or "R′" or "R″" where n is an integer or character can independently possess one or more of the groups listed above. For example, if "$R_1$," is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

A structure of a compound may be represented by a formula:

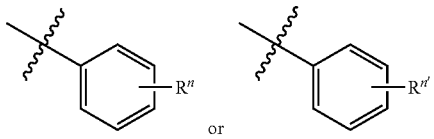

where n is a digit or character, and can be understood an equivalent to a formula:

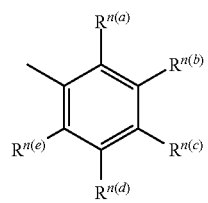

That is, R″ is understood to represent five independent substituents, R″(a), R″(b), R″(c), R″(d), R″(e). By "independent substituents," it is meant that each R″ substituent can be independently defined. For example, if in one instance R″(a) is halogen, then R″(b) is not necessarily halogen in that instance.

A structure of a compound may be represented by a formula:

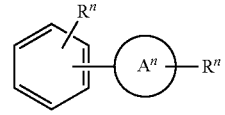

which can be understood an equivalent to a formula:

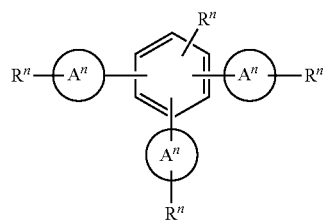

where n is typically an integer and R″ is as defined above. That is, $A″$ where n is an integer of 1, 2, or 3 is understood to represent one to three independent acceptors, $A^1$, $A^2$, $A^3$. By "independent substituents," it is meant that each A substituent can be independently defined.

where Z is any structure herein and the squiggly line represents a point of connection between two compounds.

Compounds described herein may contain "optionally substituted" moieties. In general, the term "substituted,"

whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The present disclosure can be understood more readily by reference to the following detailed description and the Examples included therein. Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing, example methods and materials are now described.

DETAILED DESCRIPTION OF THE INVENTION

The thermally activated delayed fluorescent compounds of the present invention provide solutions to short operation time in optical devices. The solution is premised on analogues of 9,10-dihydro-9,9-dimethylacridine compounds. The compounds can improve both the luminescent efficiency and operational stability of a TADF device. Furthermore, the compounds of the present invention may exhibit low degradation during the course of device operation, and therefore facilitate and enhance the longevity of the corresponding TADF device. These and other features of thermally activated delayed fluorescent materials will be described in further detail.

A. Thermally Activated Delayed Fluorescent Compounds

As described herein, a composition may include one or more compounds of the formulas:

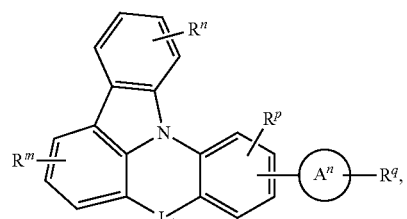

I

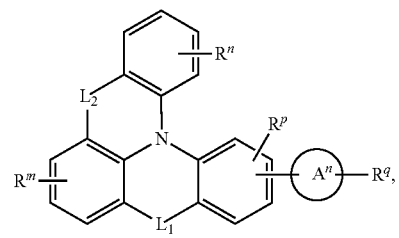

II

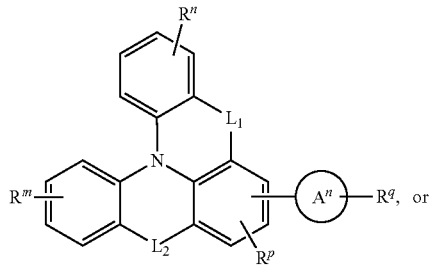

III

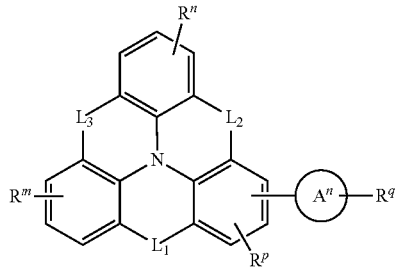

IV $A''$ can independently represent one or more acceptor moieties of the compound, where n is 1 to 3, and contribute to the LUMO level of the compound. In some embodiments, $A''$ is an electron-deficient aromatic group. Non-limiting examples of A include:

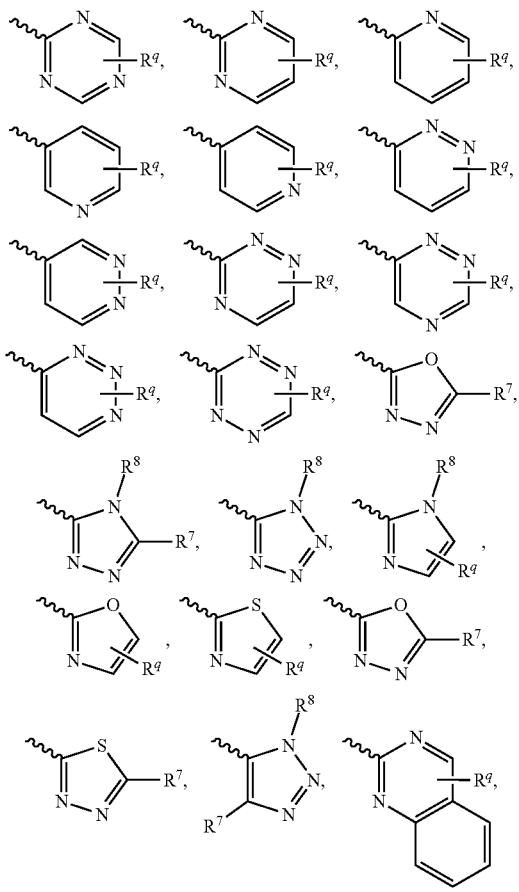

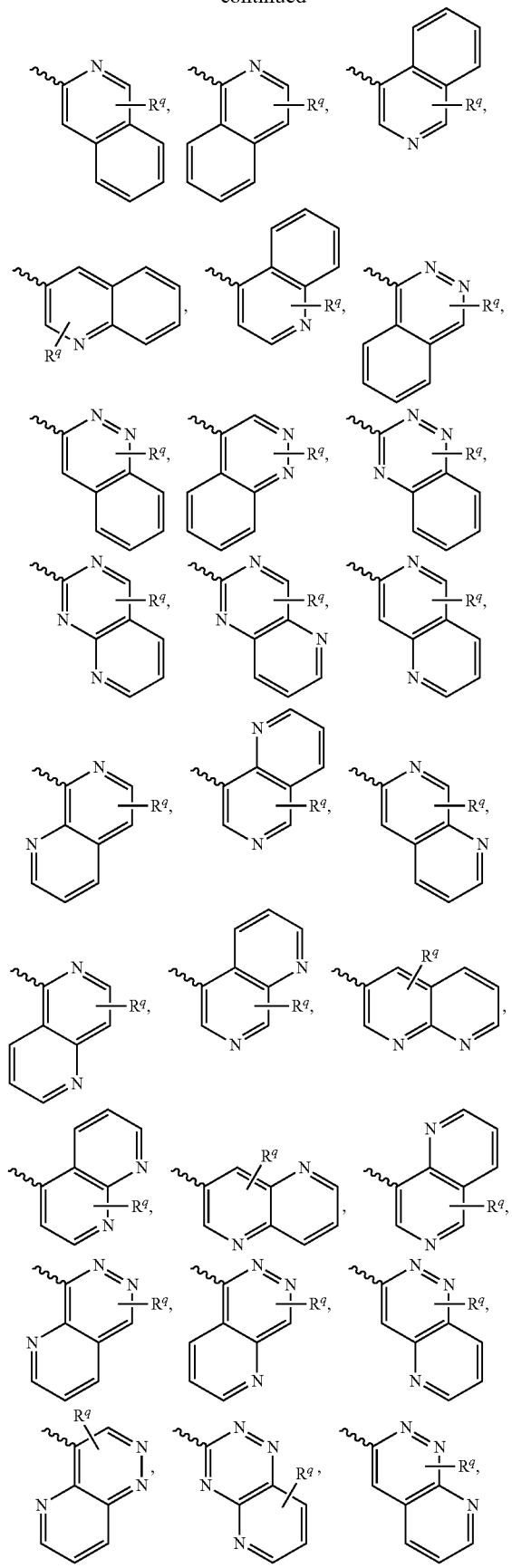
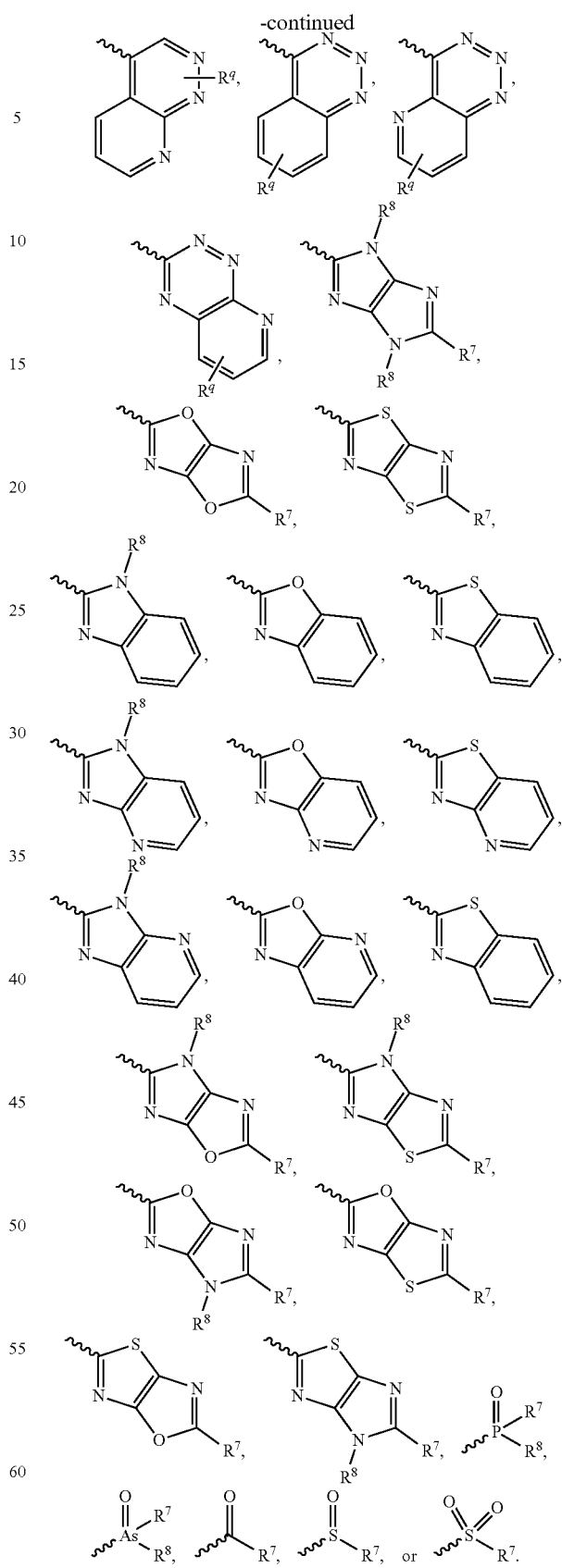
$R^q$, $R^7$, and $R^8$ can each independently be a hydrogen atom, a deuterium atom, a halogen atom, a hydroxyl group, a thiol group, a nitro group, a cyano group, a substituted or unsubstituted alkyl group, a substituted or unsubstituted haloalkyl group, a substituted or unsubstituted aralkyl group, a substituted or unsubstituted alkenyl group, a substituted or unsubstituted alkynyl group, a substituted or unsubstituted aryl group, an amino group, a mono- or dialkylamino group, a mono- or diarylamino group, a substituted or unsubstituted alkoxy group, a substituted or unsubstituted aryloxy group, a substituted or unsubstituted heteroaryl group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a mercapto group, a sulfo group, a carboxyl group, a hydrazino group, a substituted silyl group, a polymeric group, or a combination thereof. In some embodiments, A is a nitrogen-containing aromatic ring or substituted nitrogen-containing aromatic ring. In a preferred embodiment, A is:

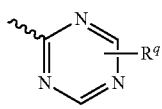

where $R^q$ is defined above.

$L_1$, $L_2$, and $L_3$ can be linkage groups, and can include an oxygen (O) containing group, a sulfur (S) containing group, a nitrogen (N) containing group, a carbon (C) containing group, a phosphorous (P) containing group, a silicon (Si) containing group, or a boron (B) containing group. In some embodiments, $L_1$, $L_2$ and $L_3$ can each independently be:

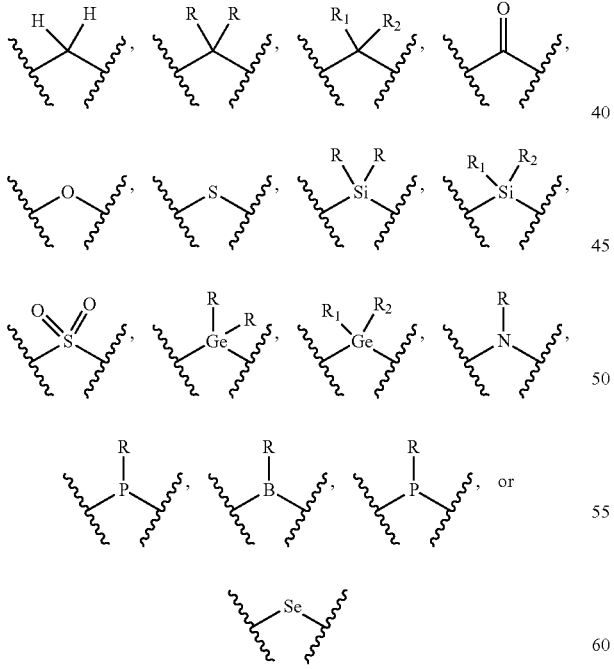

where R, $R_1$ and $R_2$ each independently represents a hydrogen atom, deuterium, a halogen atom, a hydroxyl group, a thiol group, a nitro group, a cyano group, a substituted or unsubstituted alkyl group, a substituted or unsubstituted haloalkyl group, a substituted or unsubstituted aralkyl group, a substituted or unsubstituted alkenyl group, a substituted or unsubstituted alkynyl group, a substituted or unsubstituted aryl group, an amino group, a mono- or dialkylamino group, a mono- or diarylamino group, a substituted or unsubstituted alkoxy group, a substituted or unsubstituted aryloxy group, a substituted or unsubstituted heteroaryl group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a mercapto group, a sulfo group, a carboxyl group, a hydrazino group, a substituted silyl group, a polymeric group, a substituted or unsubstituted heterocyclic group, a carbene group, or a N-heterocyclic carbene, or a combination thereof.

$R^m$, $R^n$, and $R^p$ each independently represents mono-, di-, tri, or tetra-substitution, and each independently represents one or more of a hydrogen atom, a deuterium atom, a halogen atom, a hydroxyl group, a thiol group, a nitro group, a cyano group, a substituted or unsubstituted alkyl group, a substituted or unsubstituted haloalkyl group, a substituted or unsubstituted aralkyl group, a substituted or unsubstituted alkenyl group, a substituted or unsubstituted alkynyl group, a substituted or unsubstituted aryl group, a substituted or unsubstituted amino group, a substituted or unsubstituted mono- or dialkylamino group, a substituted or unsubstituted mono- or diarylamino group, a substituted or unsubstituted alkoxy group, a substituted or unsubstituted aryloxy group, a substituted or unsubstituted heteroaryl group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a mercapto group, a sulfo group, a carboxyl group, a hydrazino group, a substituted silyl group, a polymeric group, or a combination thereof.

Non-limiting examples of the above structures I-IV include:

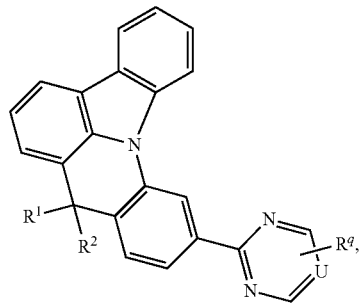

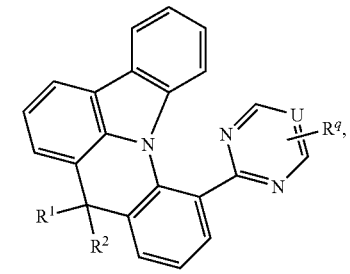

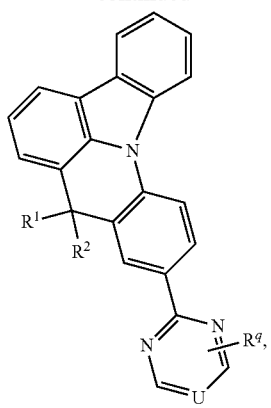
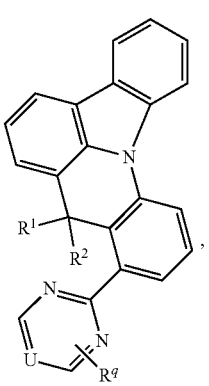
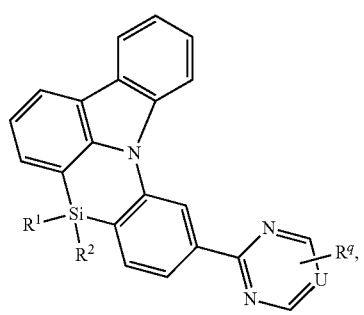
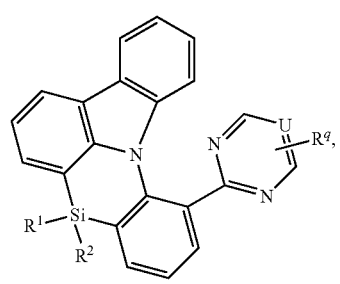
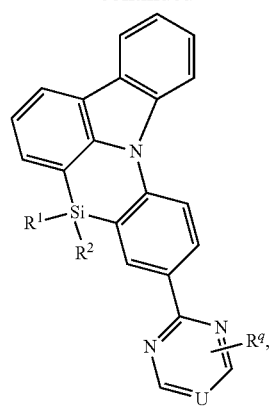
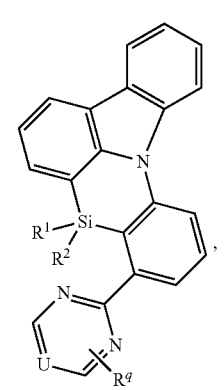
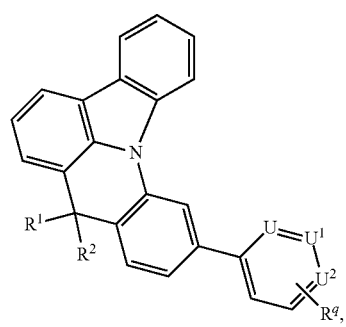
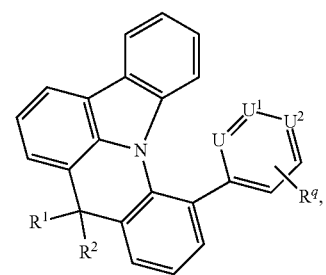

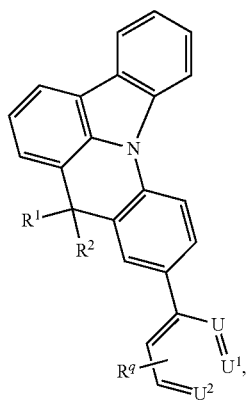
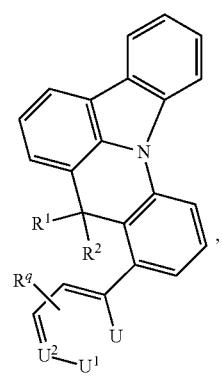
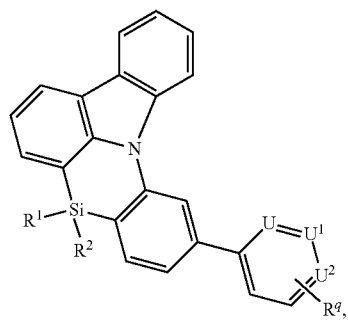
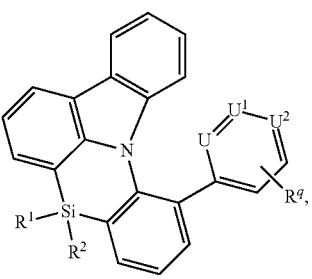
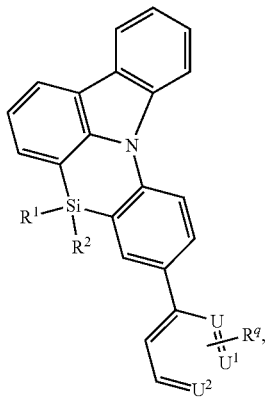
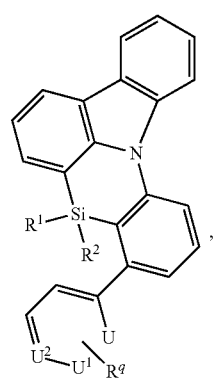
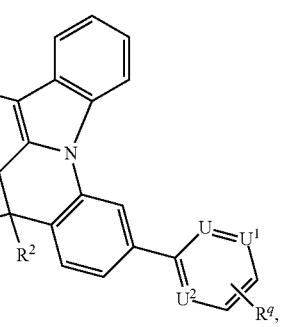
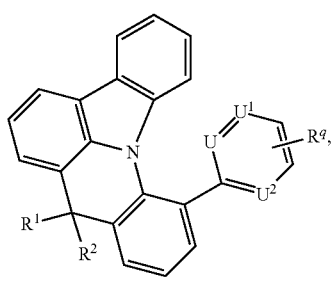

-continued
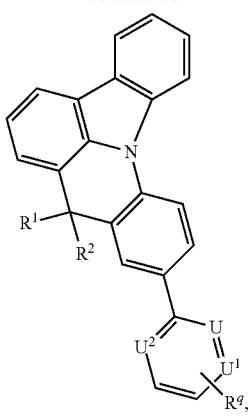
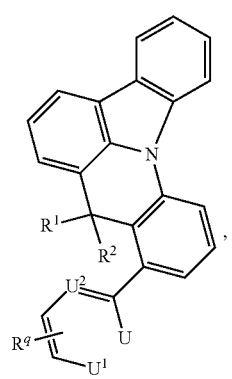
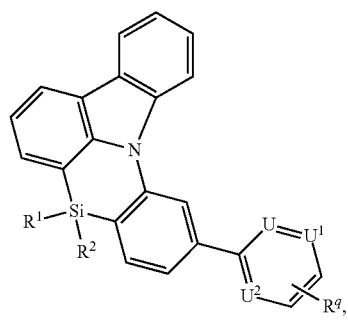
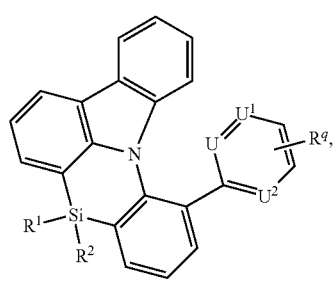
-continued
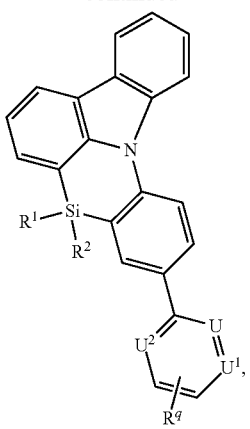
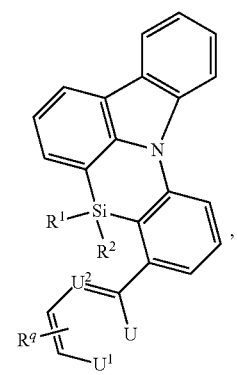
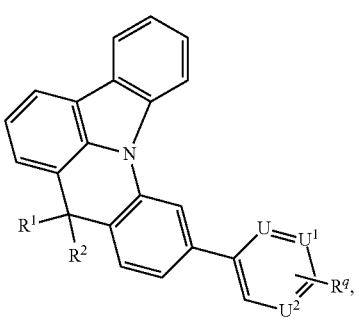
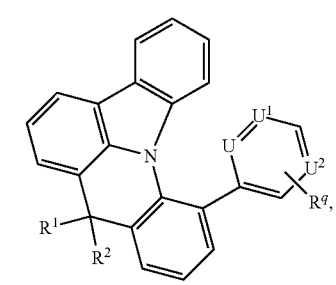

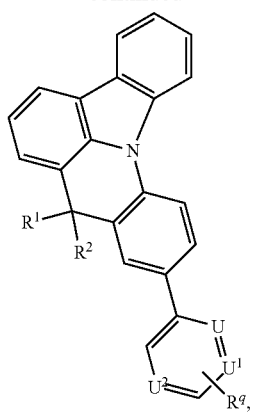
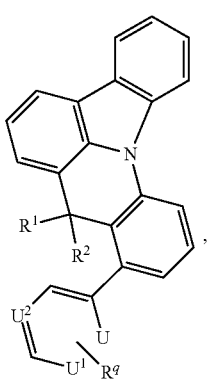
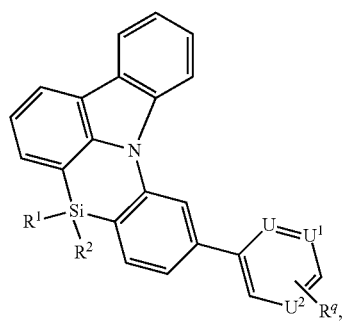
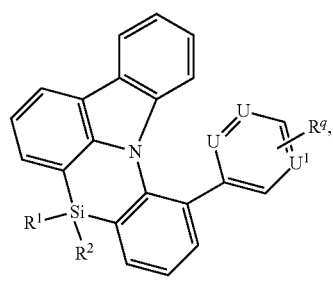
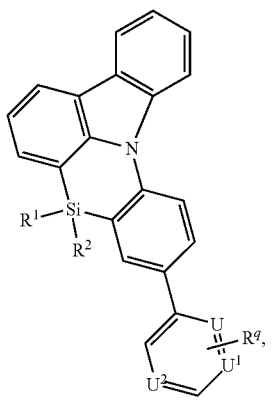
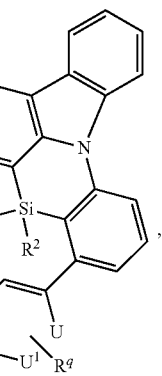
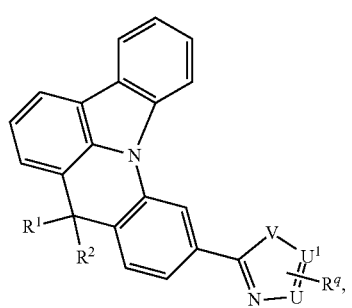
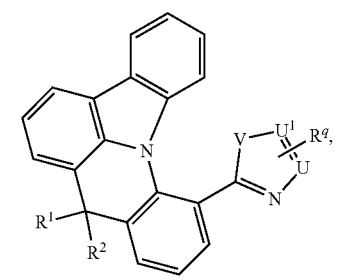

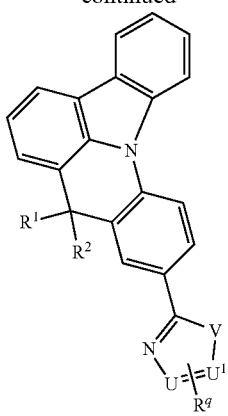
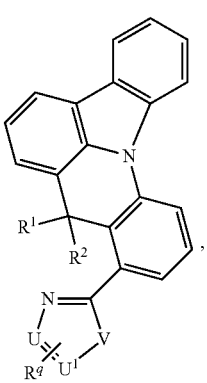
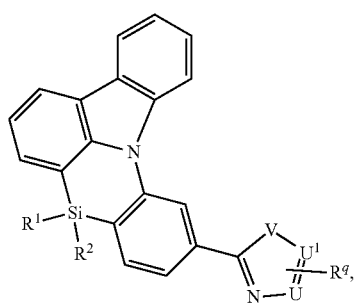
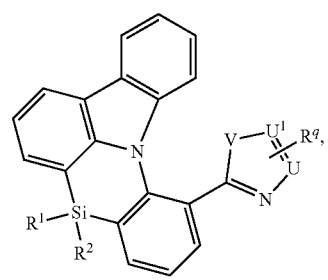
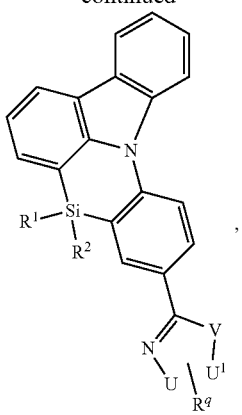
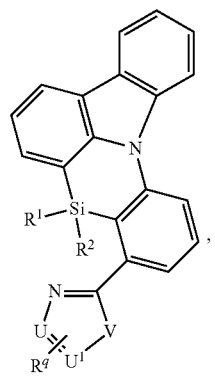
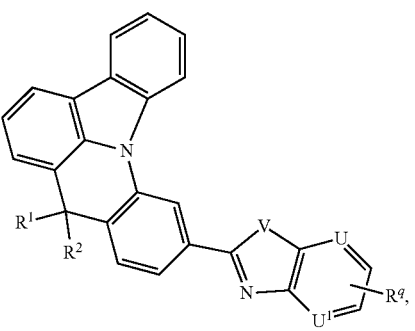
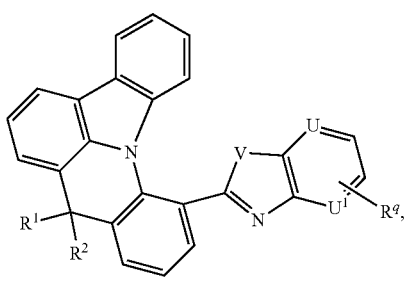

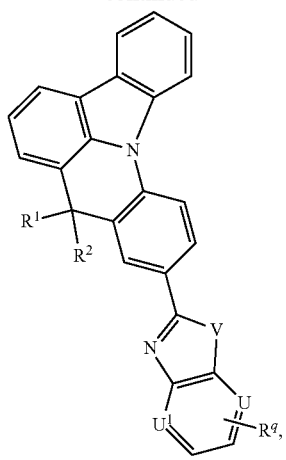
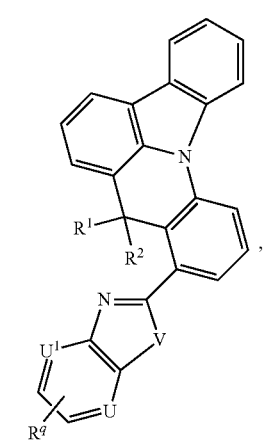
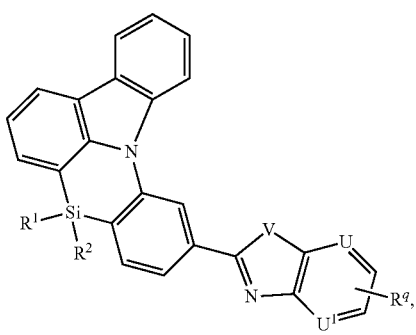
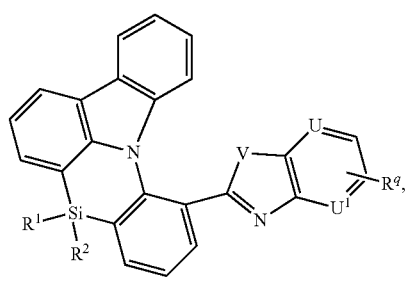
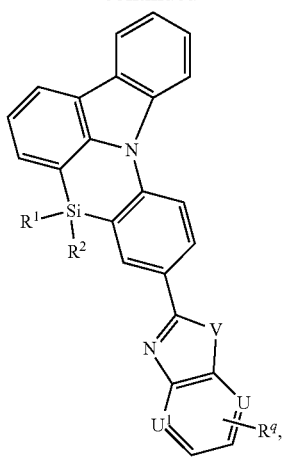
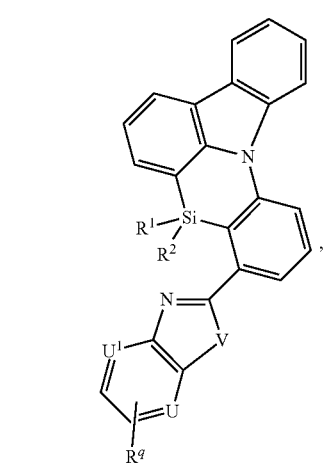
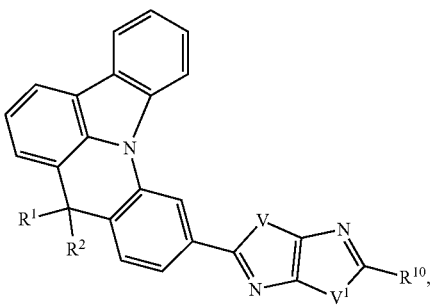
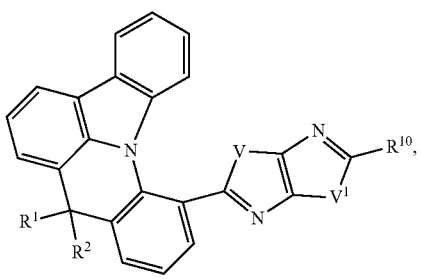

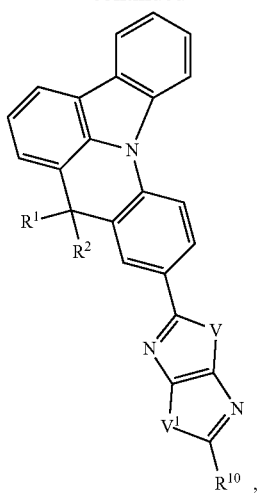
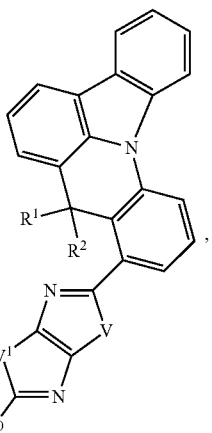
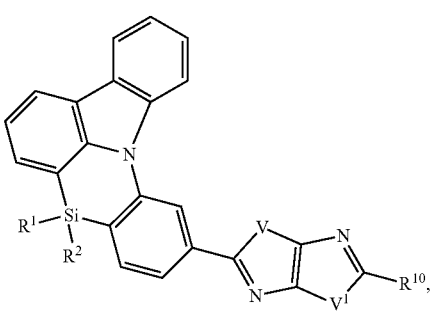
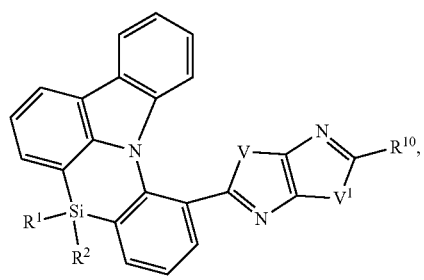
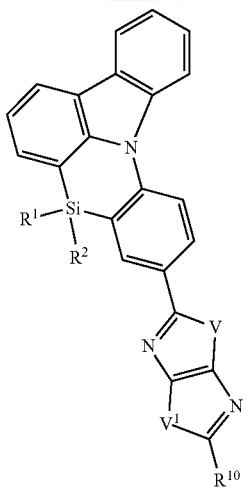
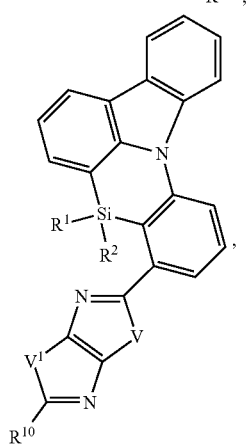
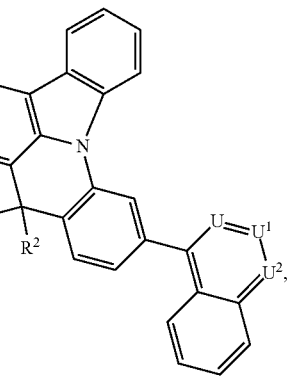
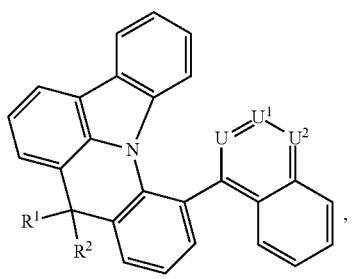

-continued
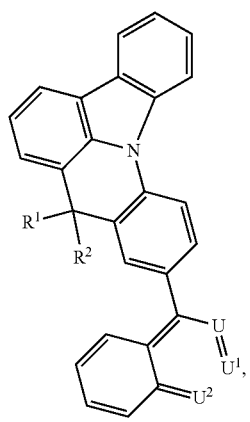
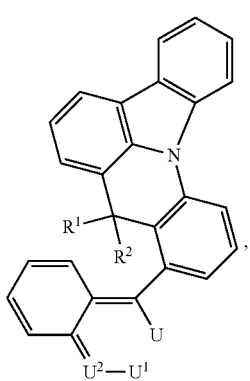
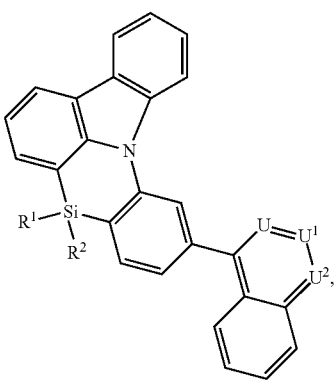
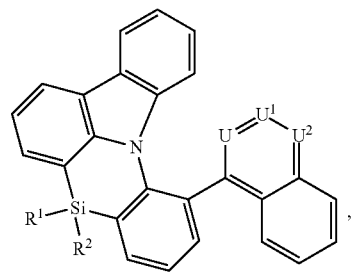
-continued
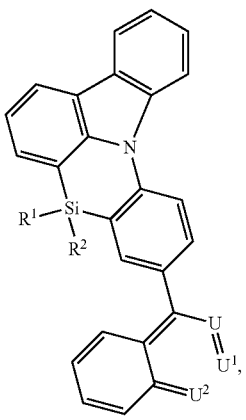
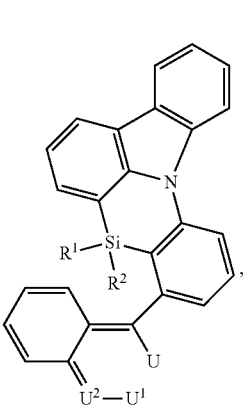
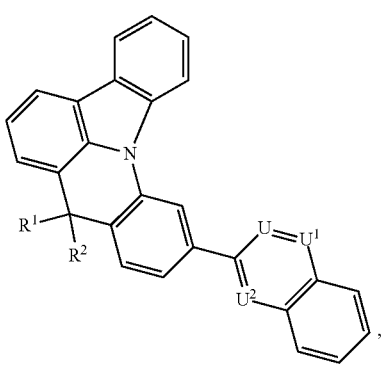
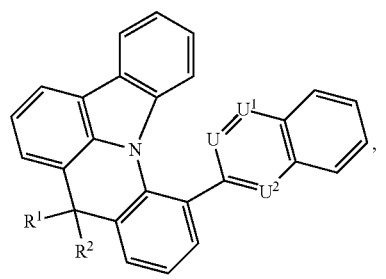

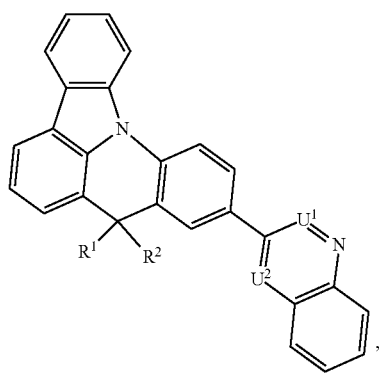
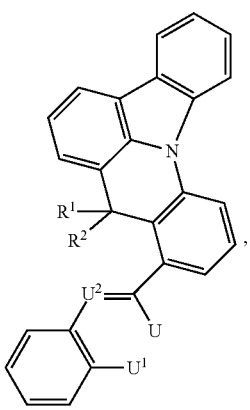
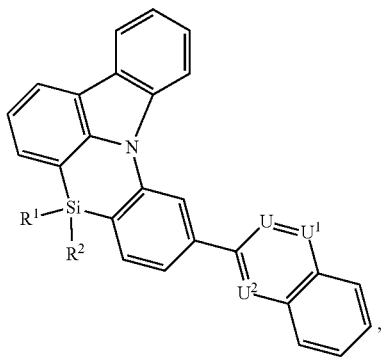
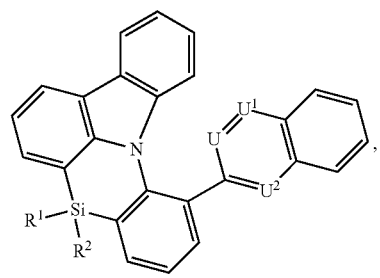
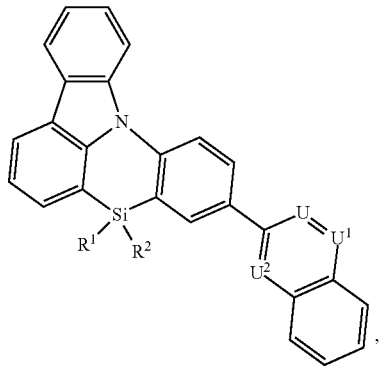
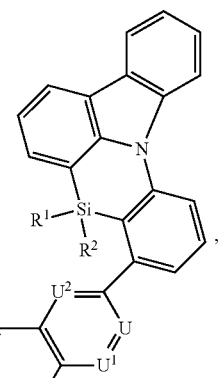
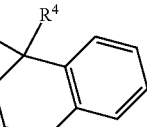
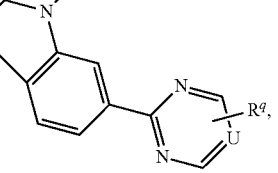
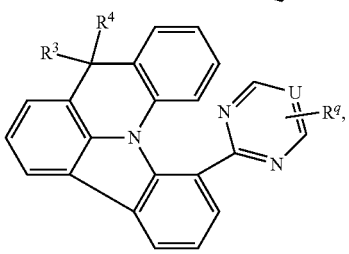
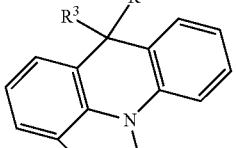
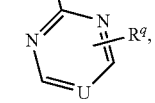

35
-continued
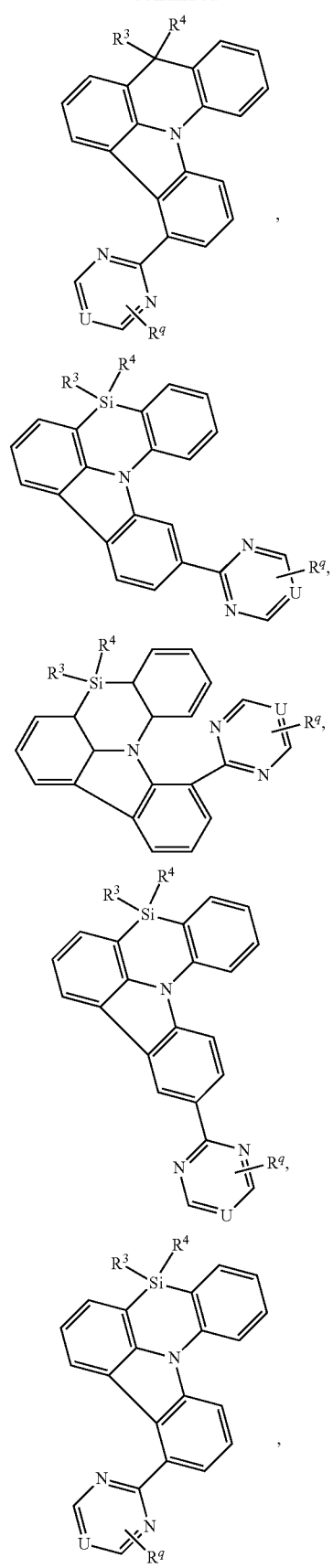
36
-continued
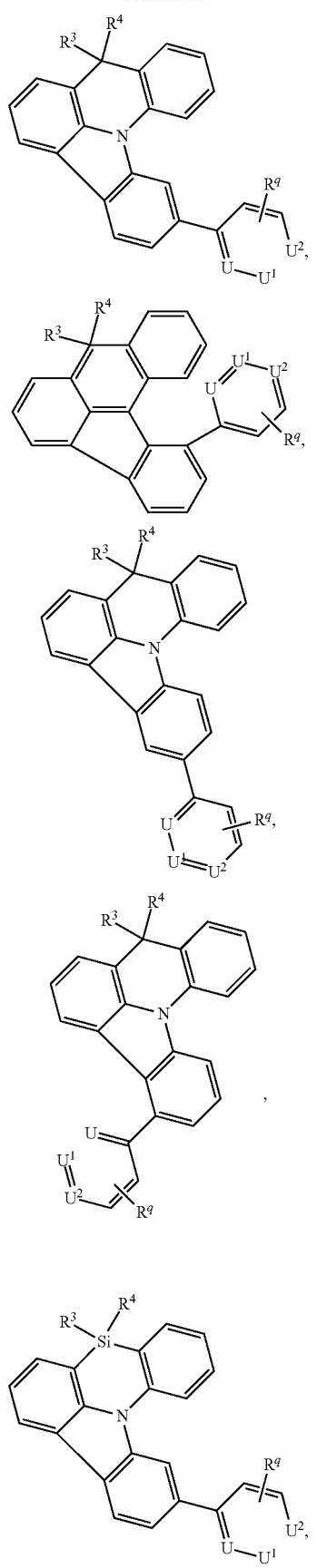

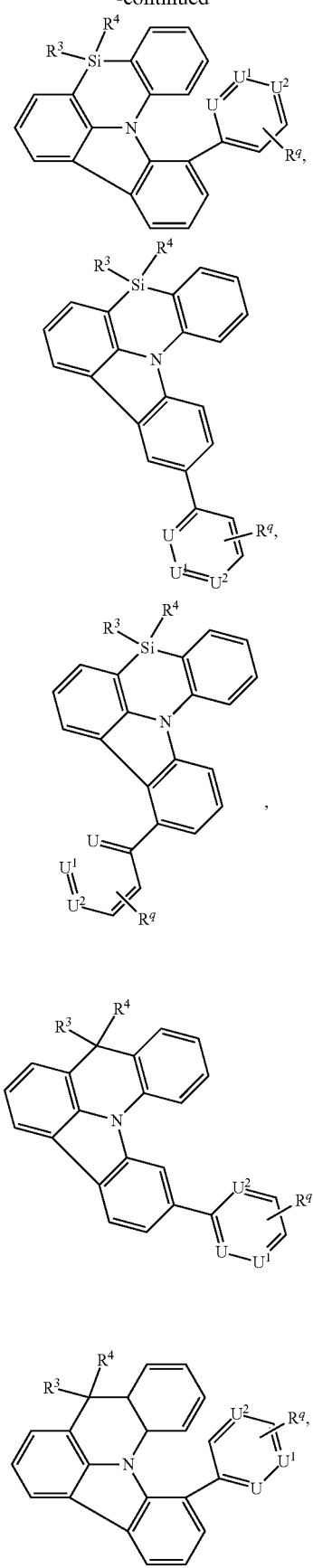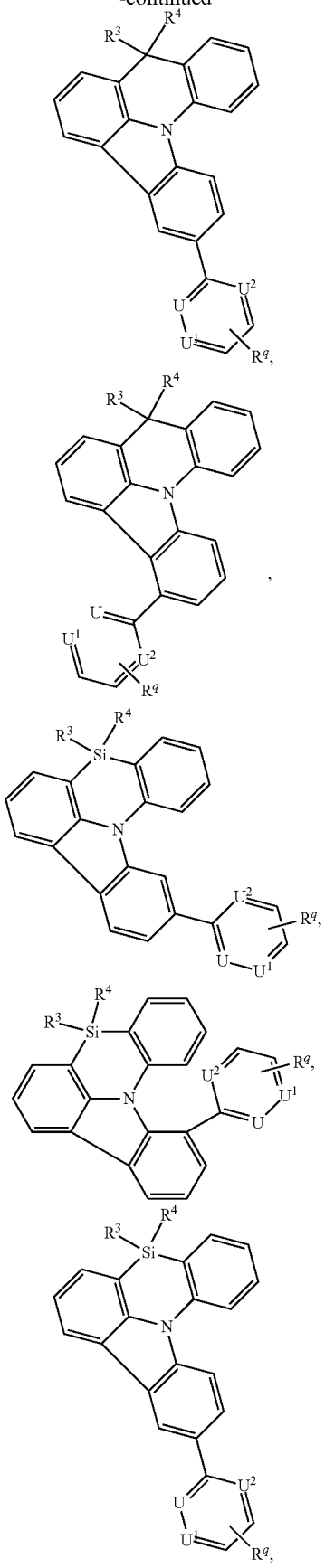

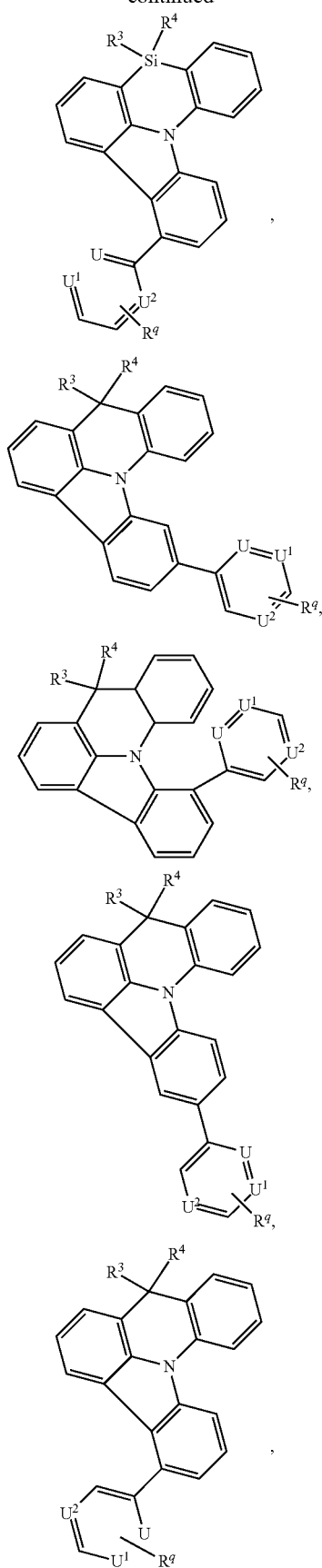
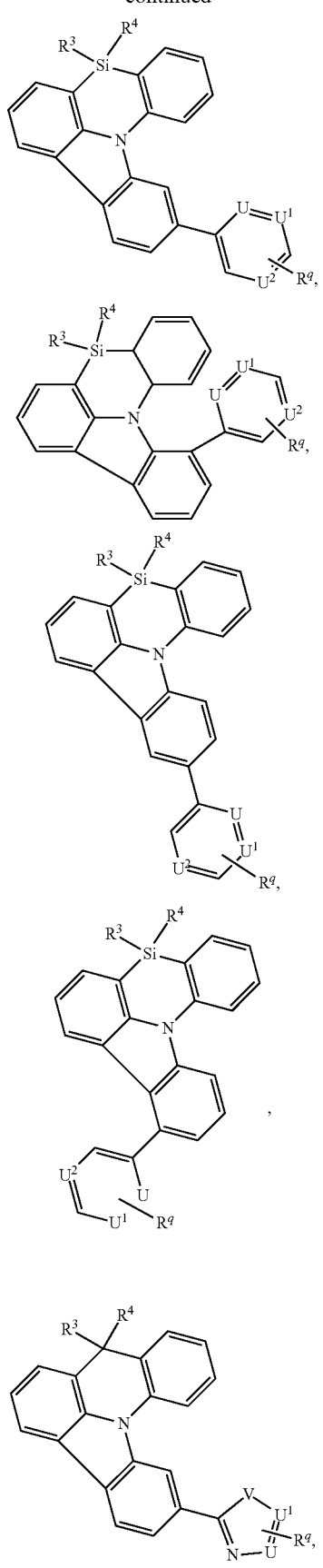

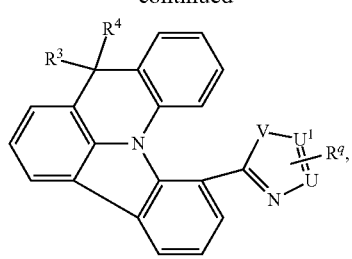
,
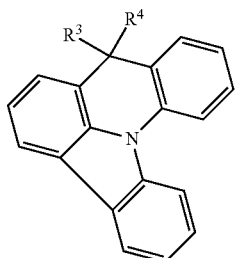
,
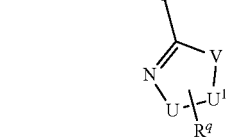
,
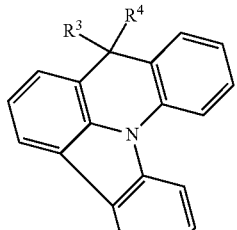
,
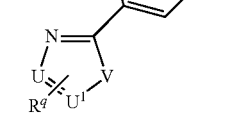
,
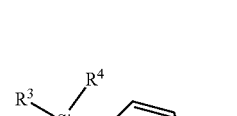
,
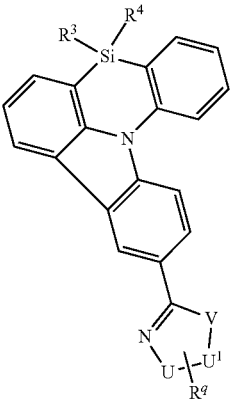
,
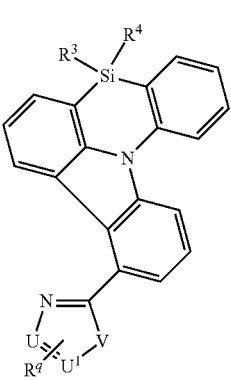
,
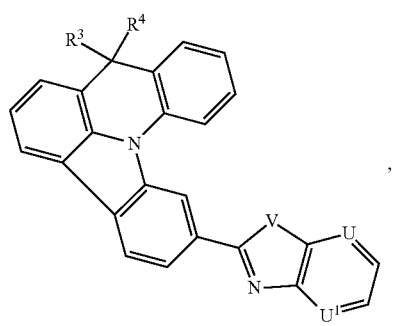
,
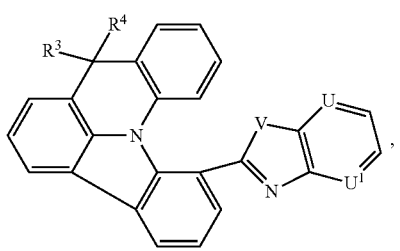
, 43
-continued
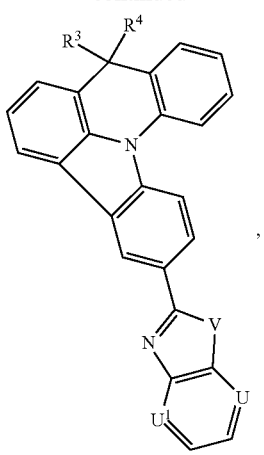
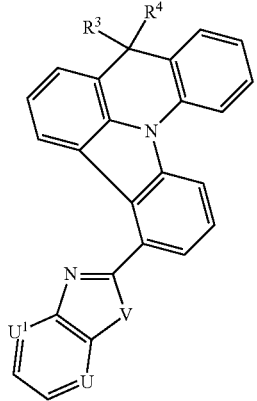
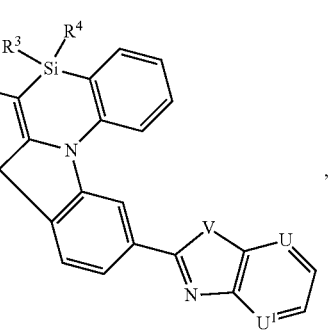
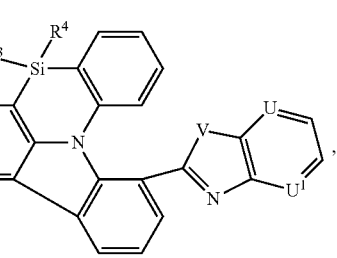
44
-continued
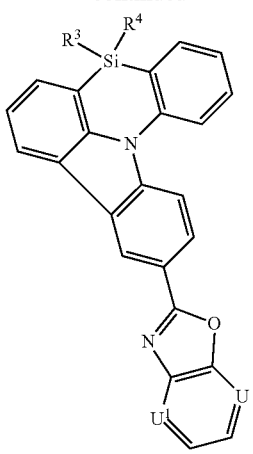
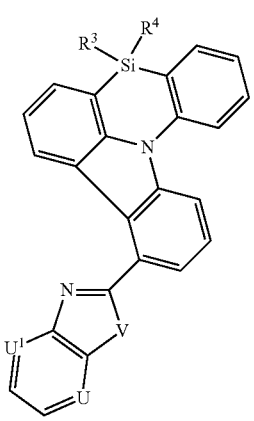
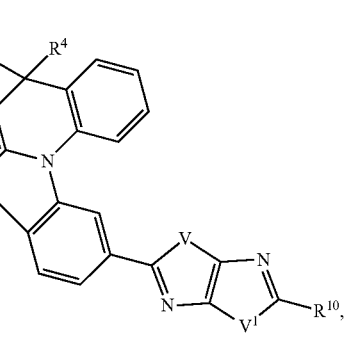
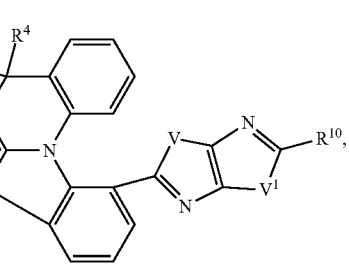

-continued
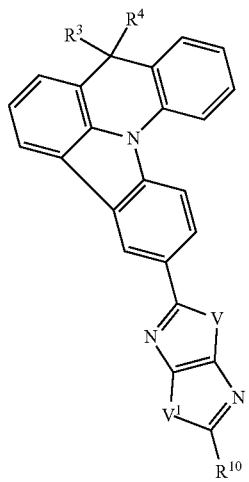
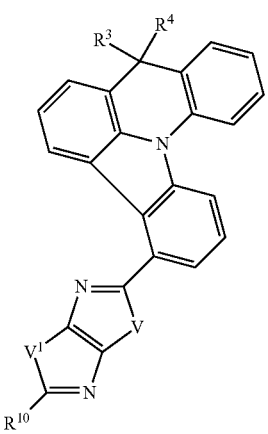
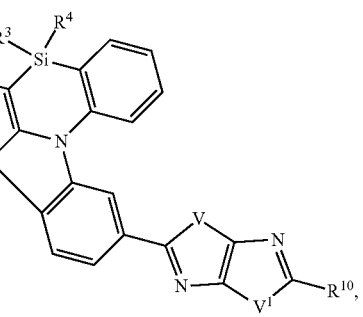
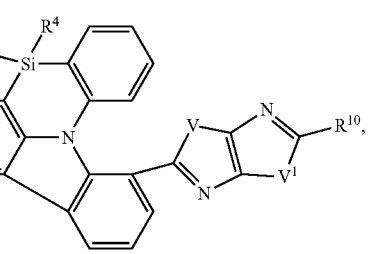
-continued
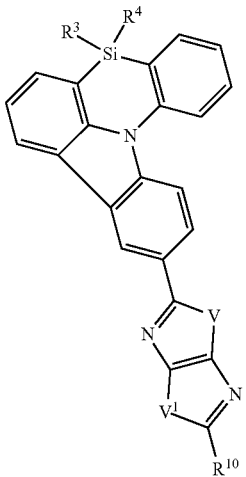
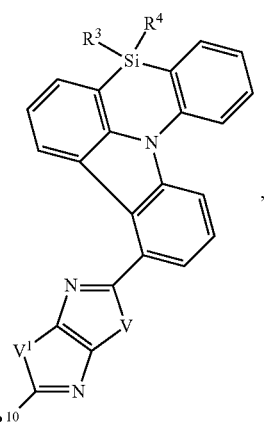
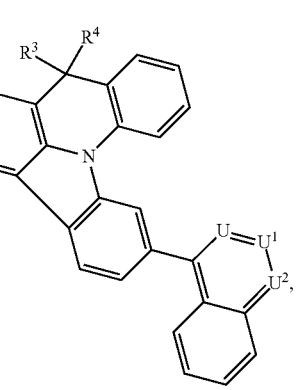
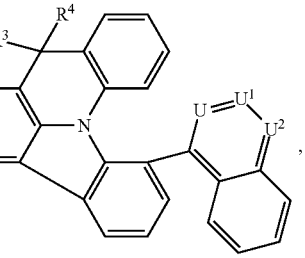

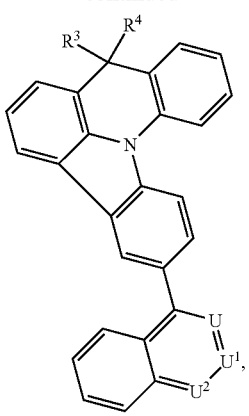
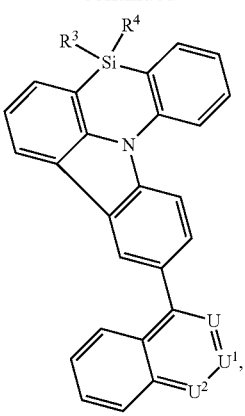
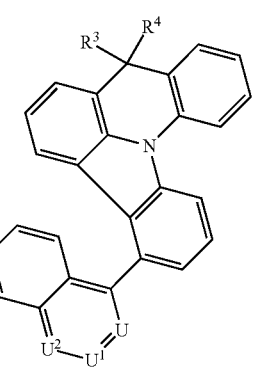
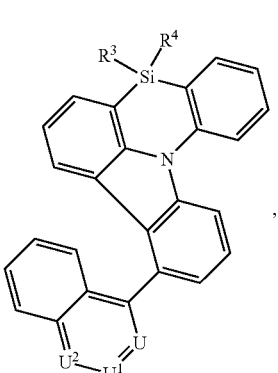
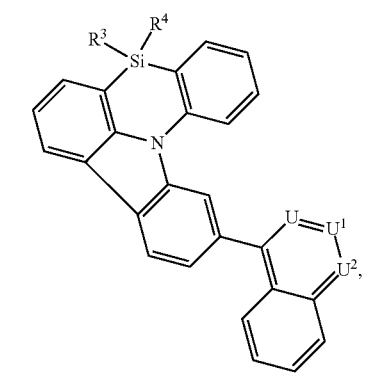
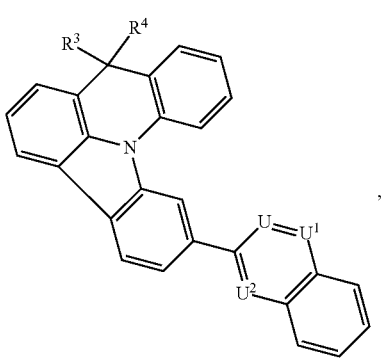
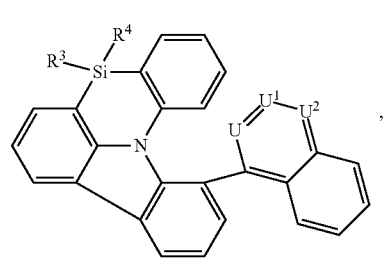
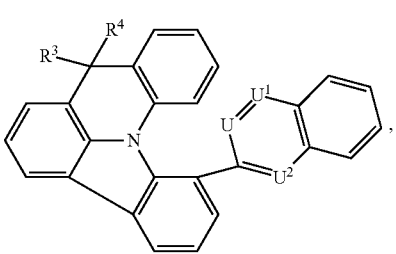

-continued
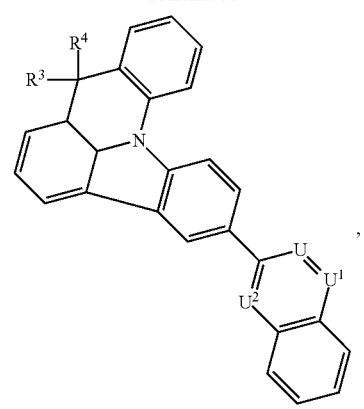
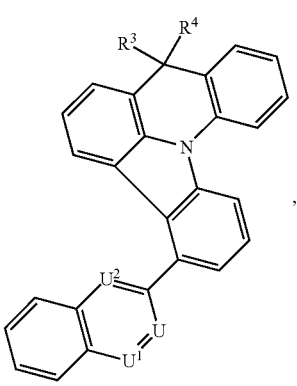
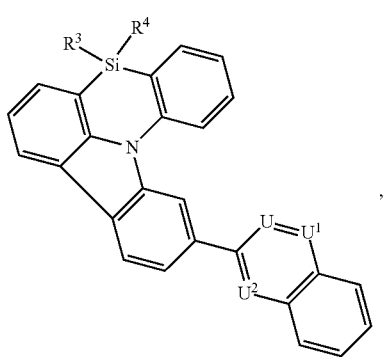
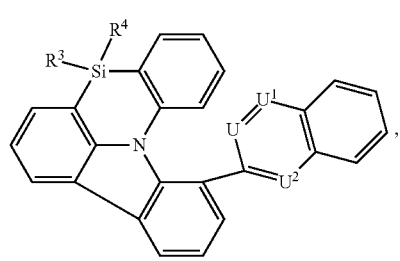
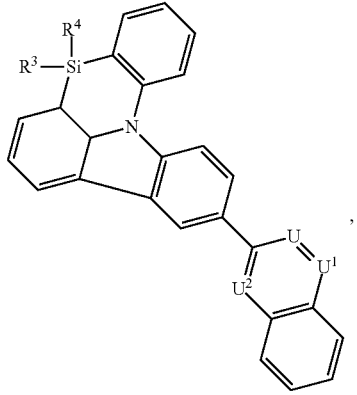
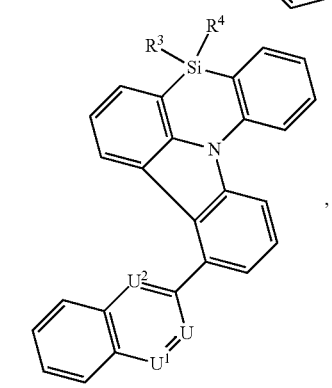
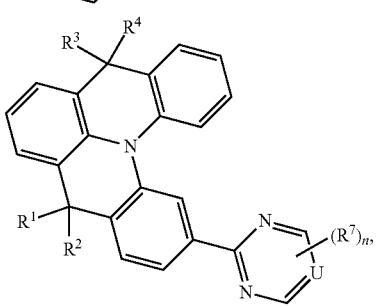
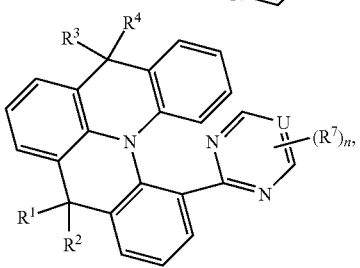
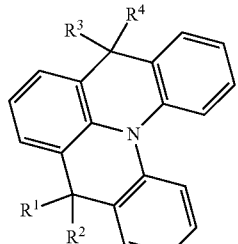
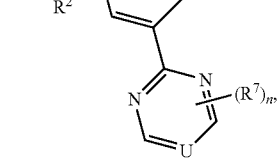

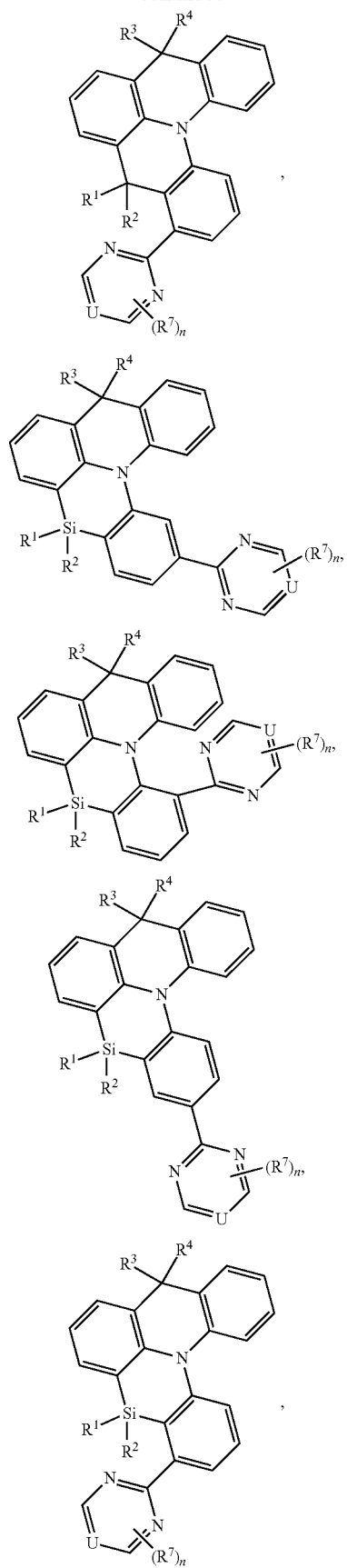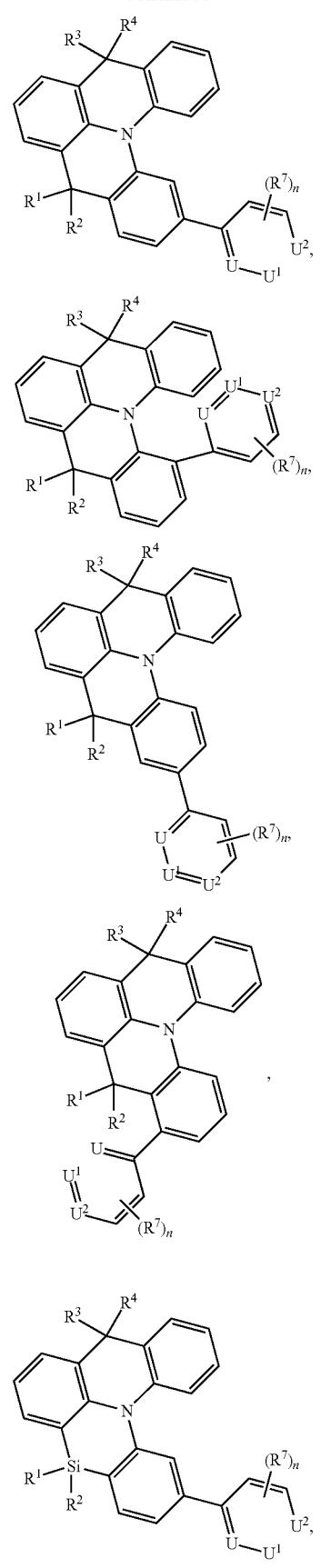

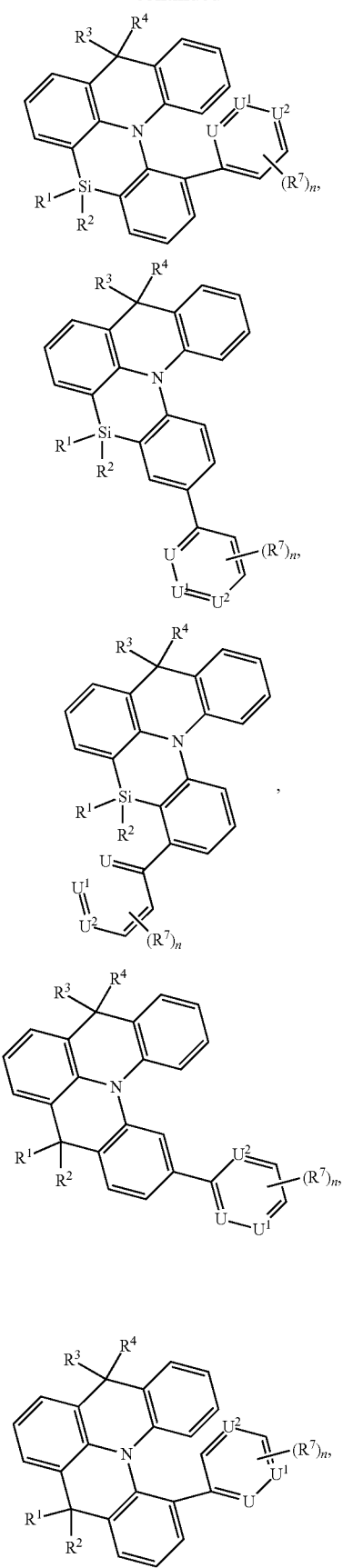
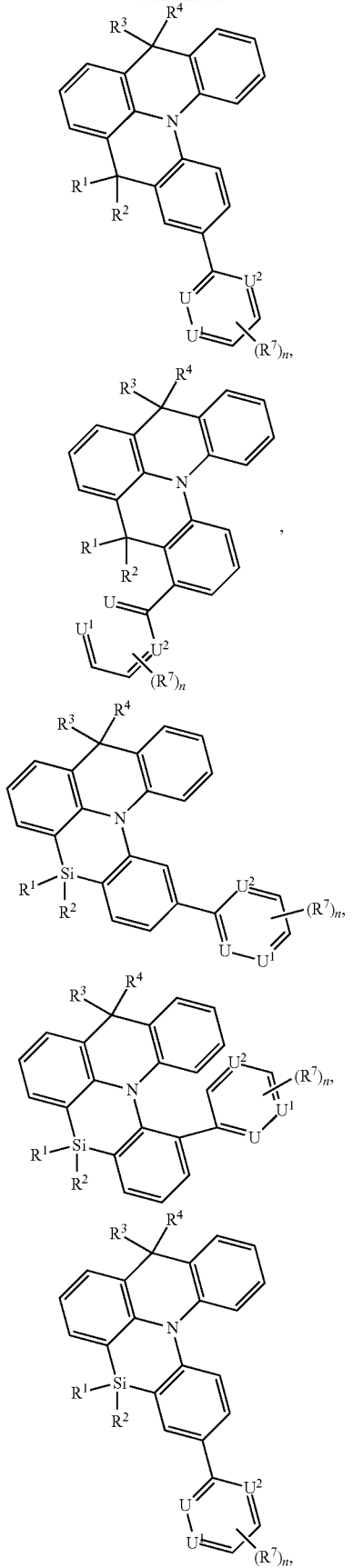

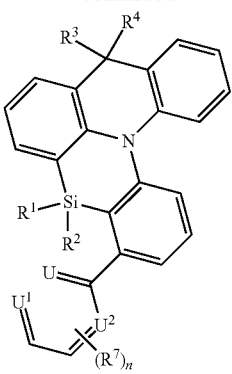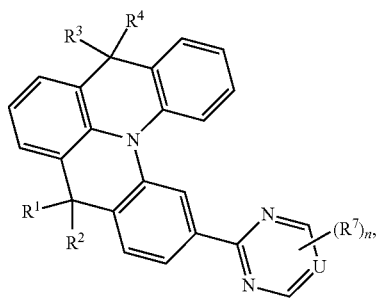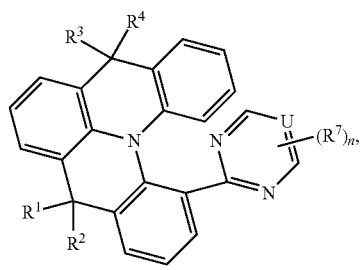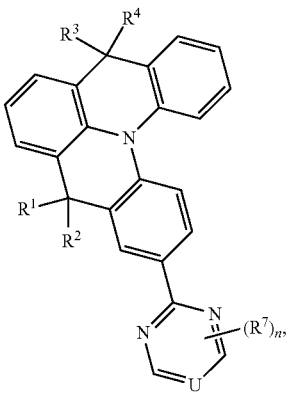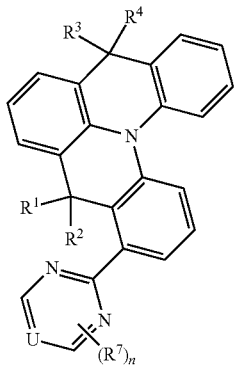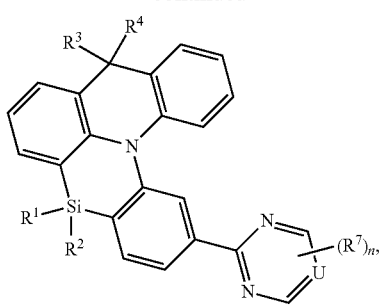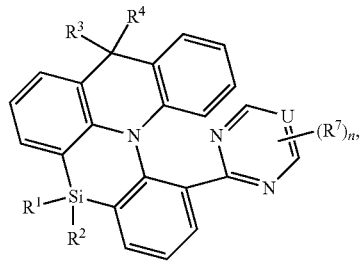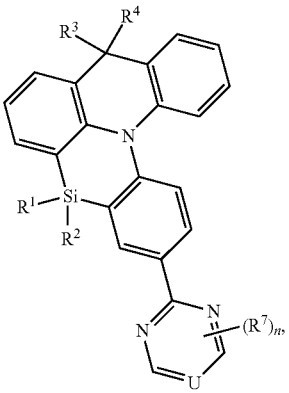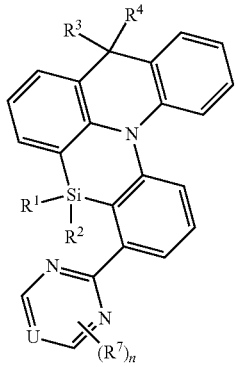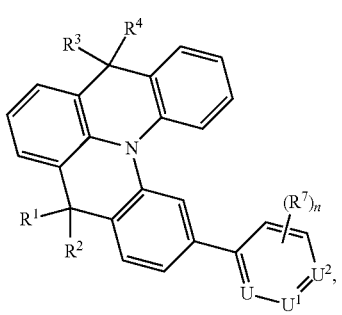

-continued
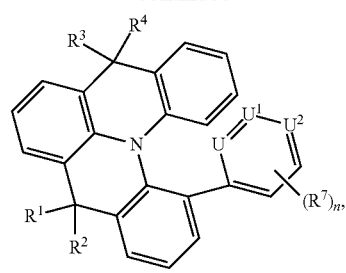
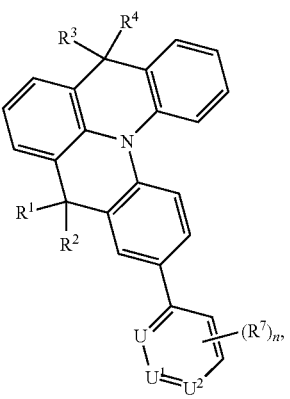
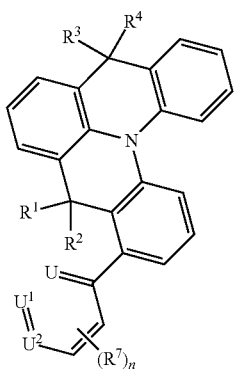
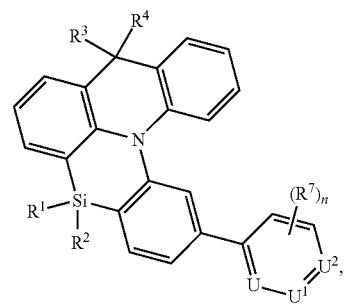
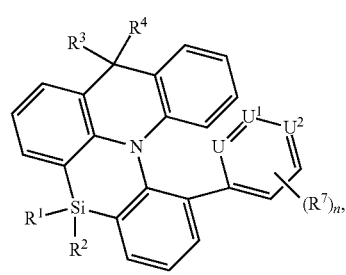
-continued
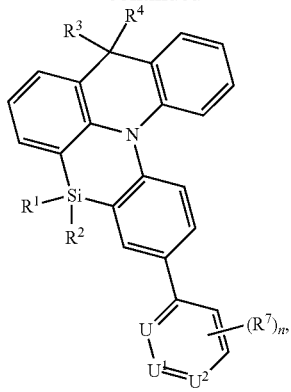
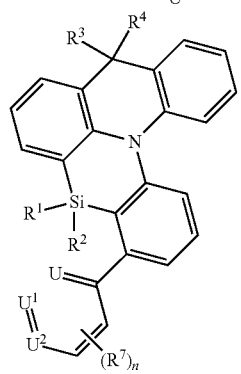
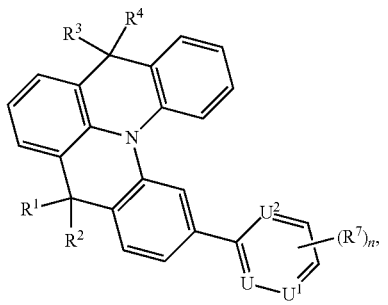
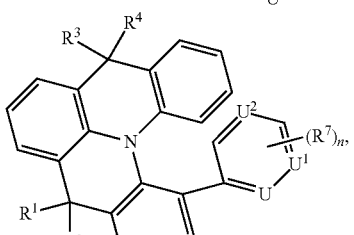
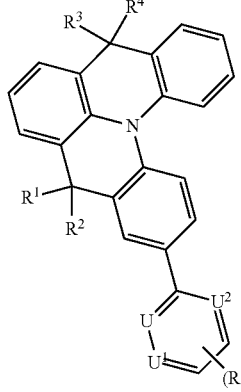

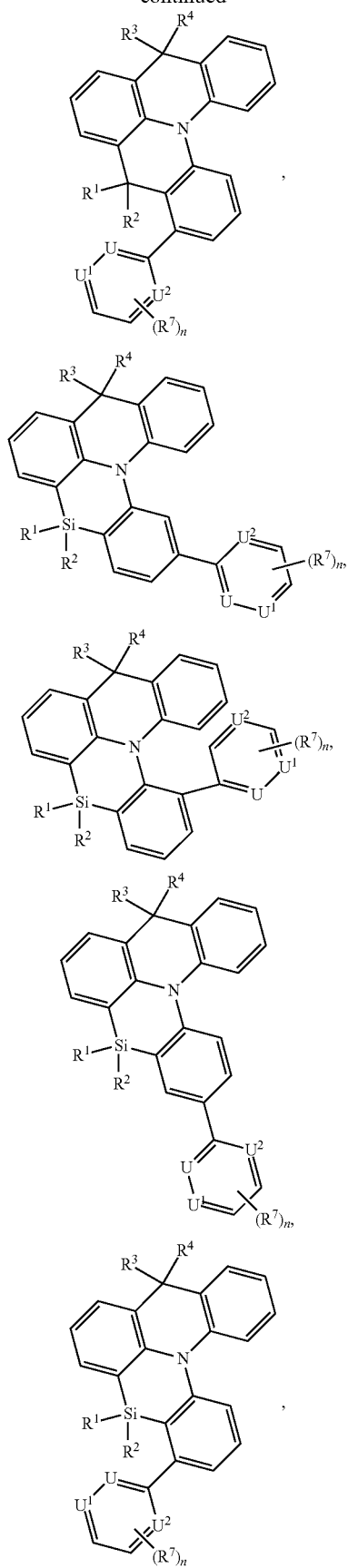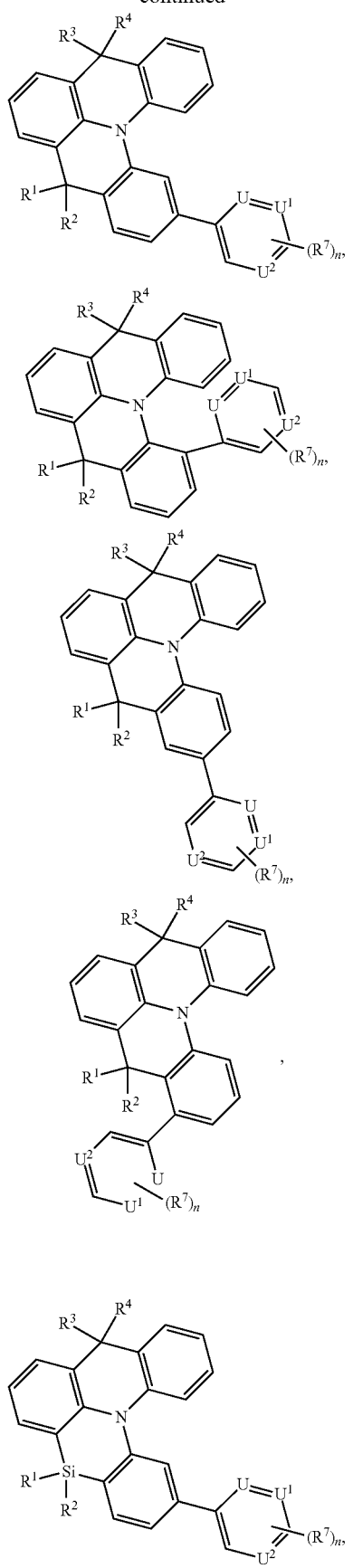

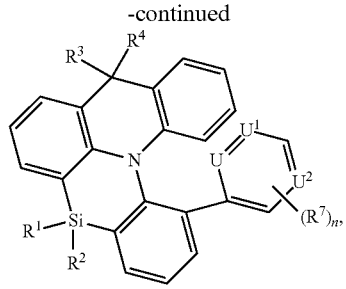
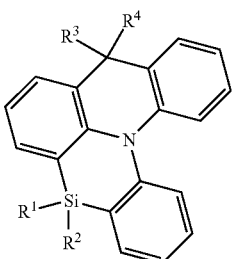
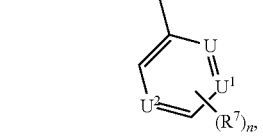
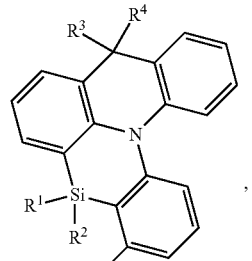
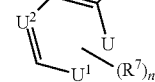
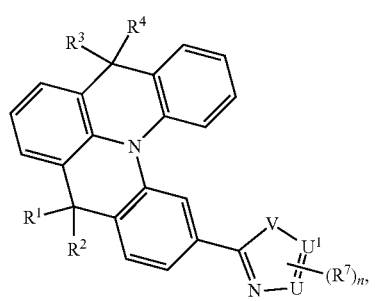
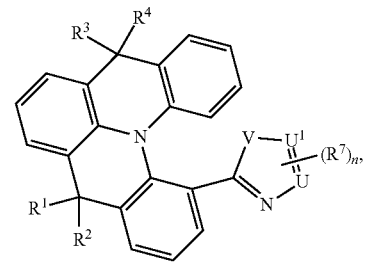
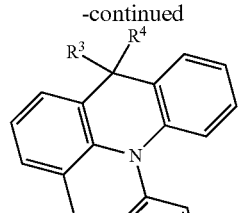
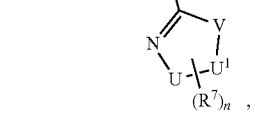
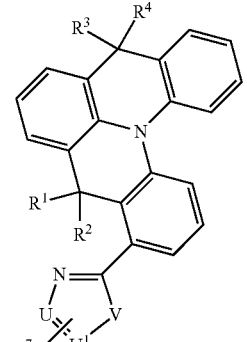
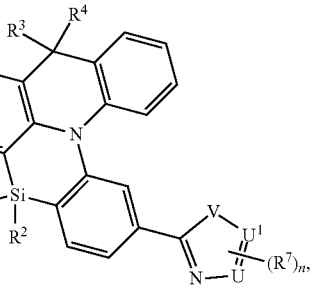
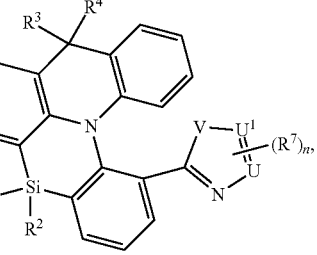
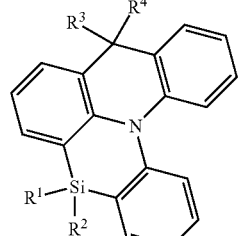
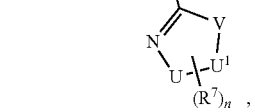

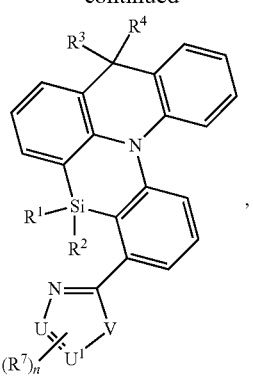,
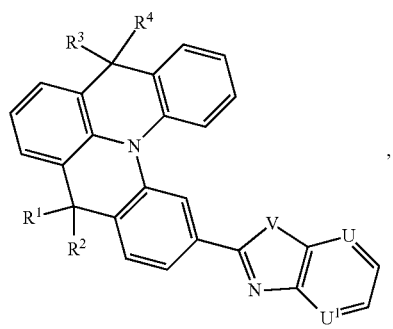,
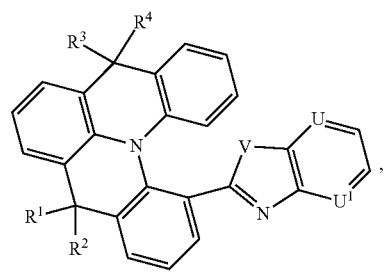,
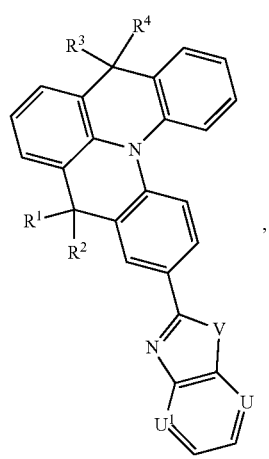,
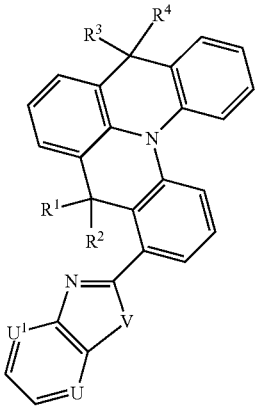,
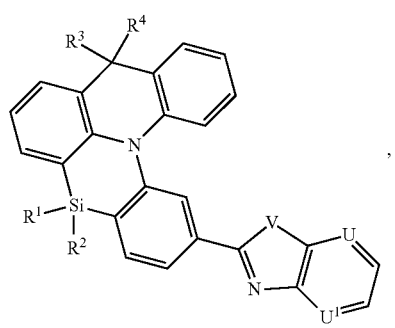,
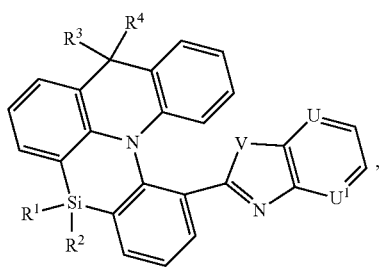,
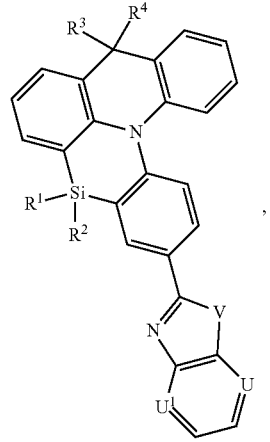,

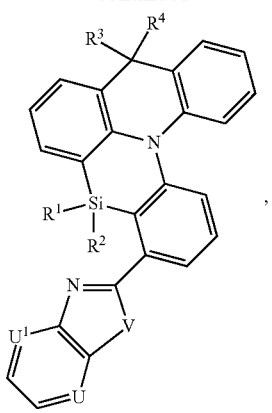
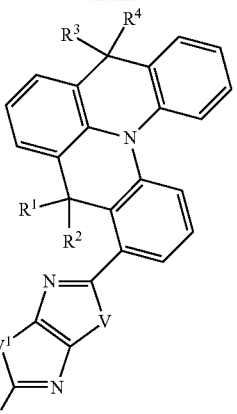
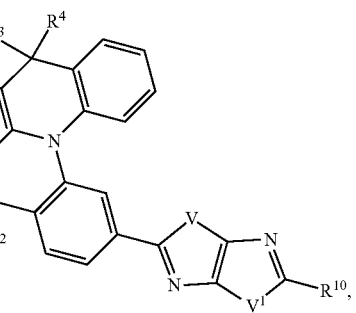
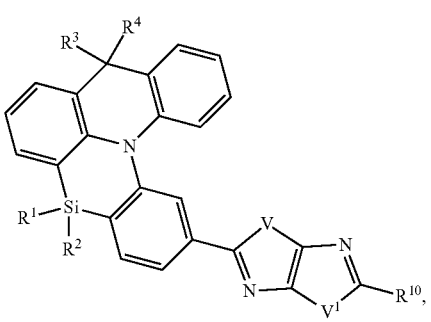
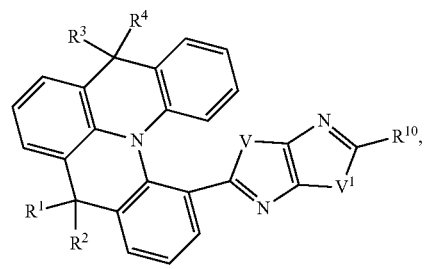
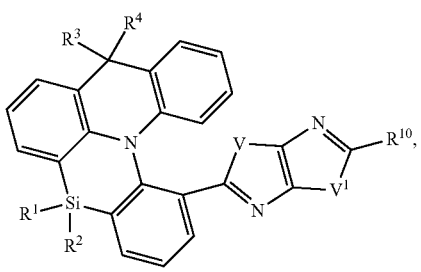
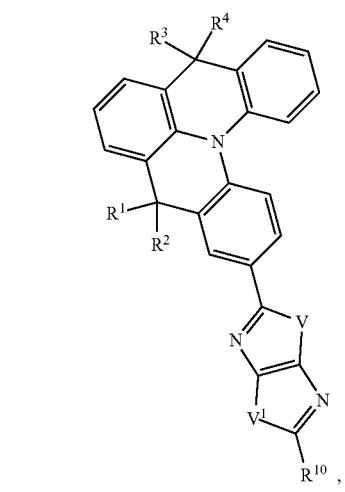
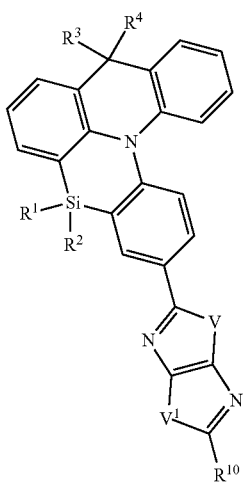

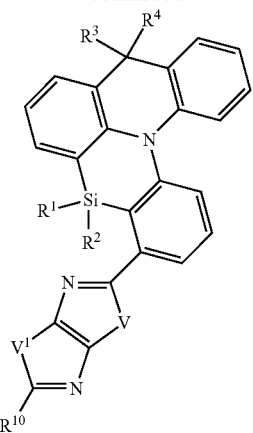
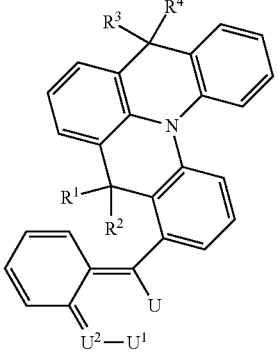
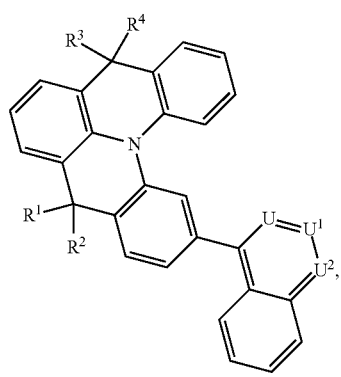
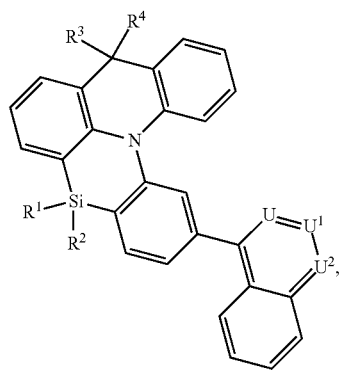
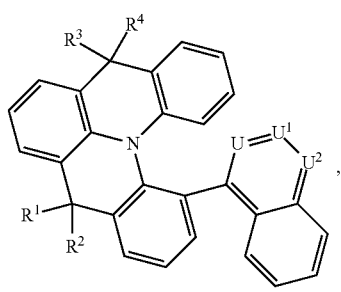
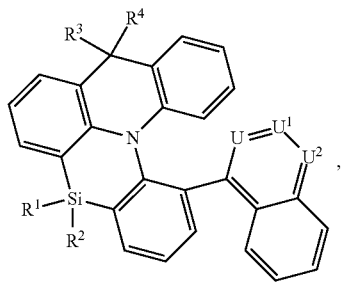
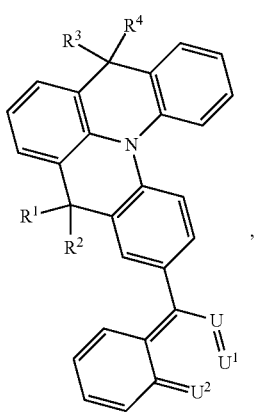
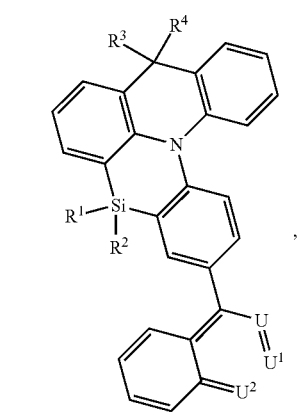

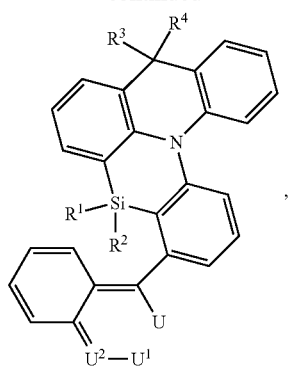
,
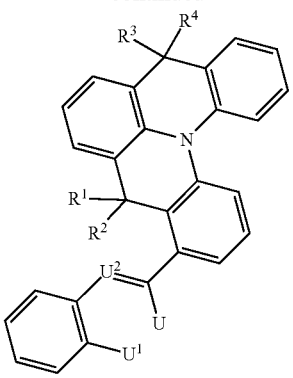
,
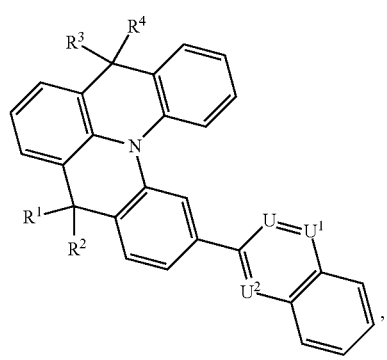
,
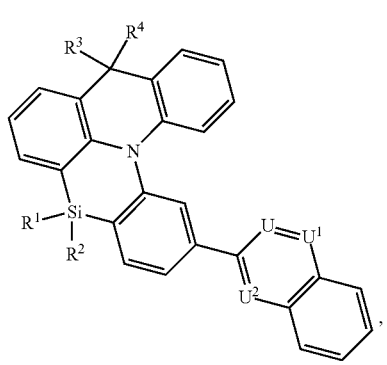
,
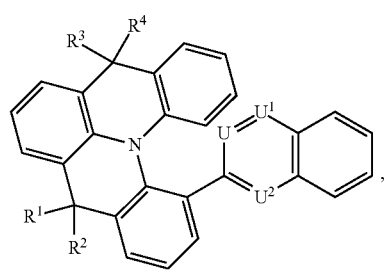
,
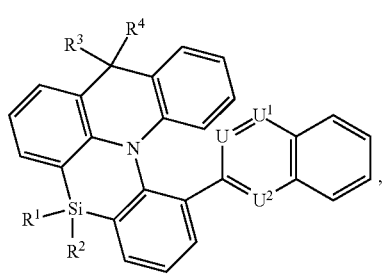
,
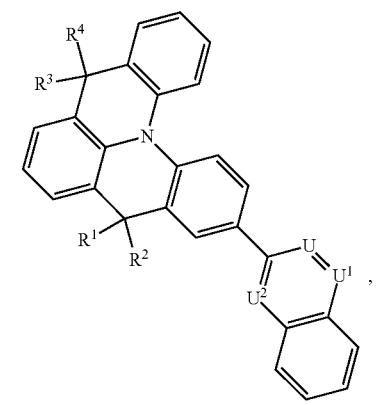
,
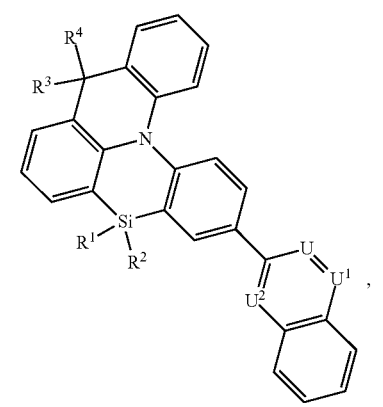
, -continued
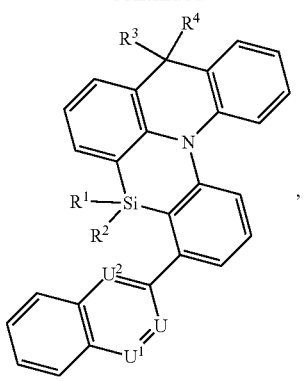
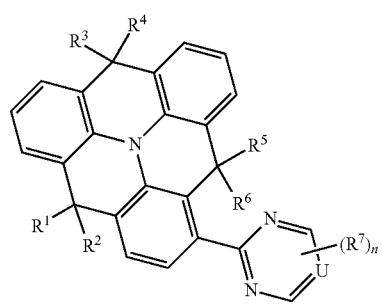
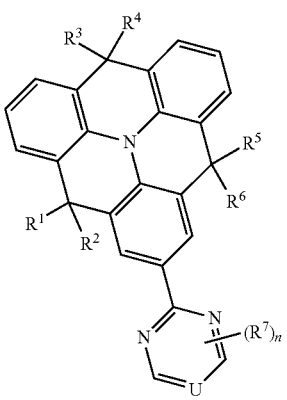
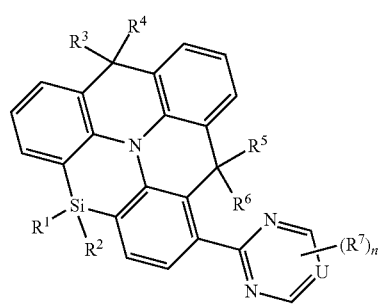
-continued
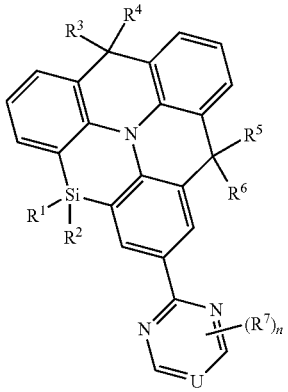
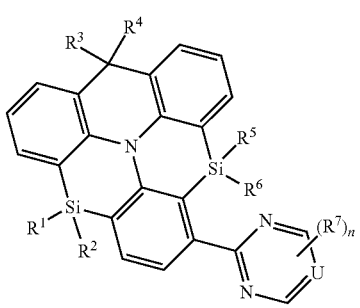
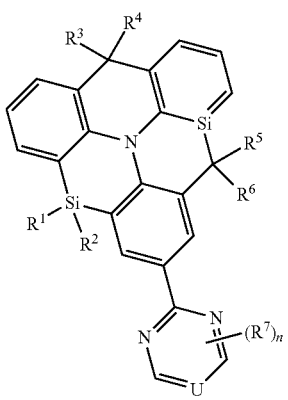
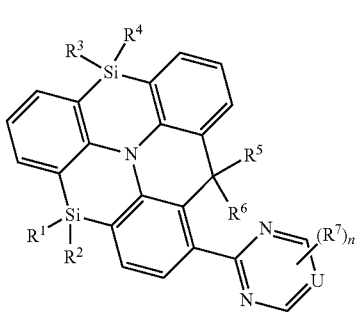

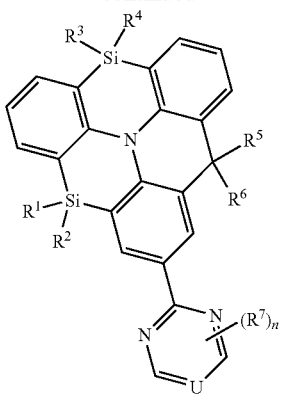
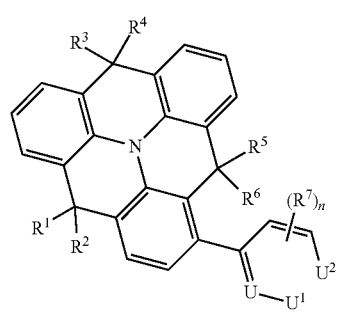
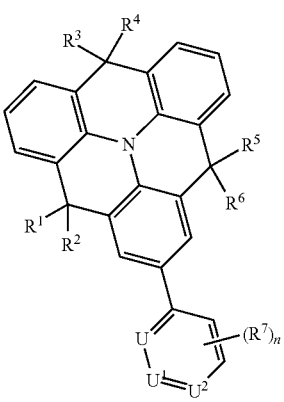
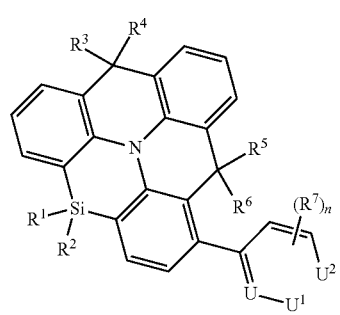
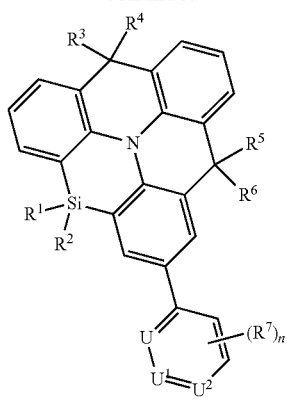
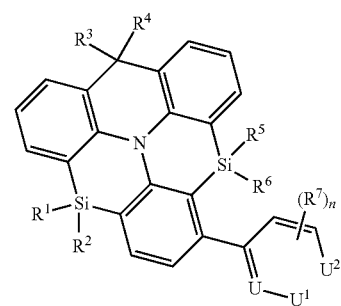
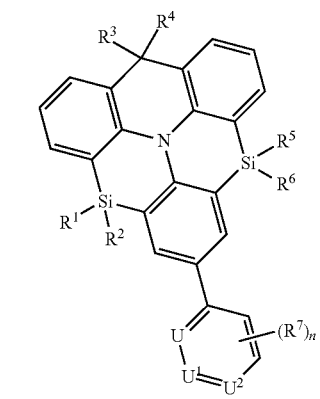
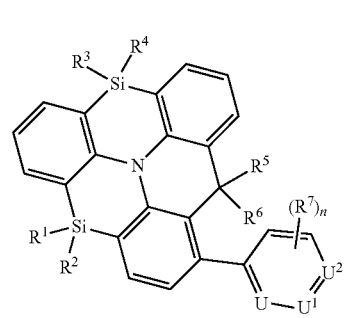

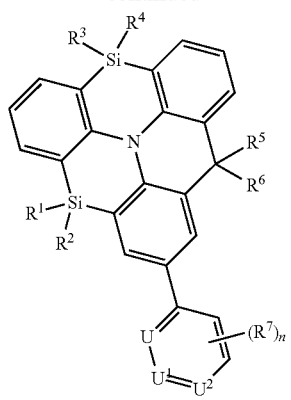
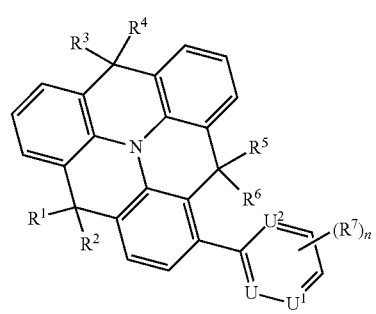
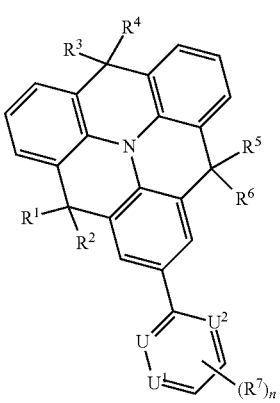
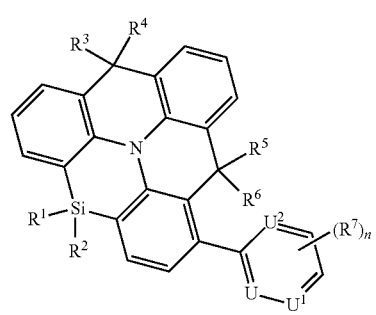
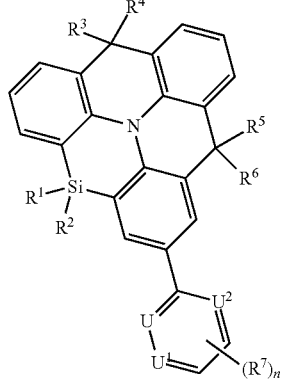
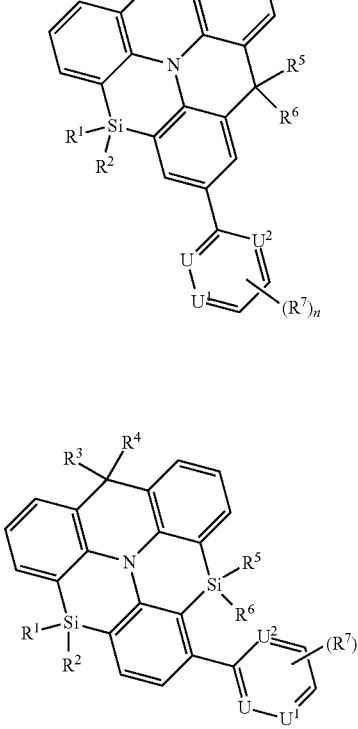
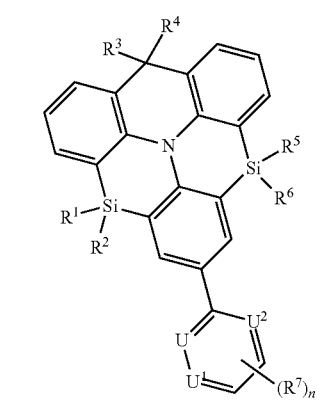
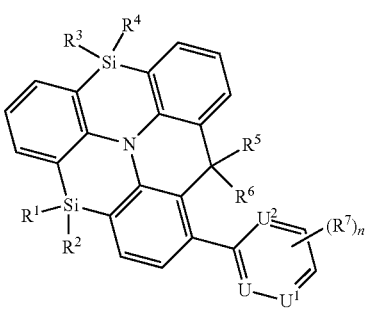

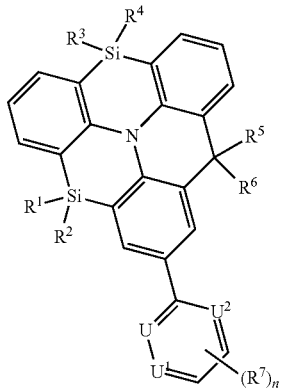
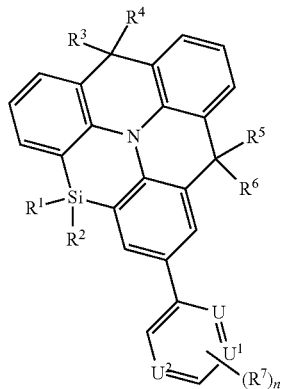
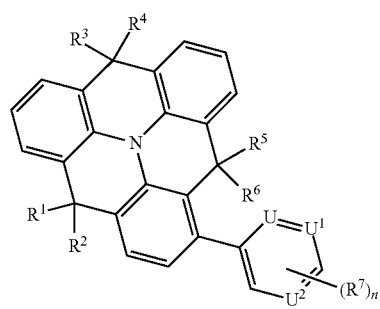
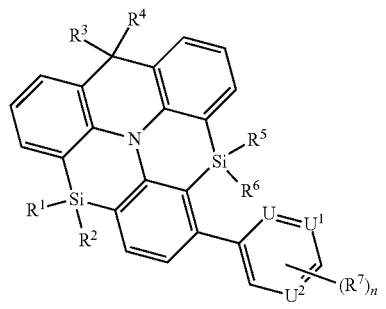
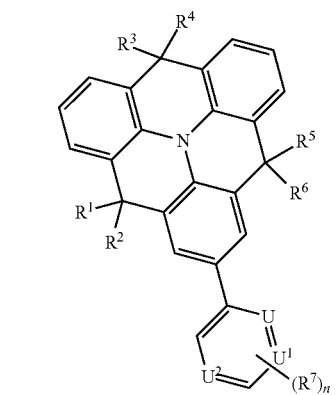
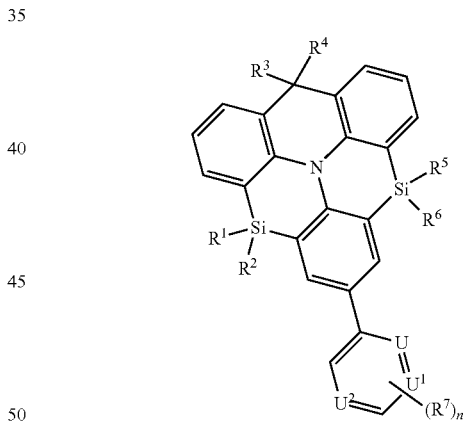
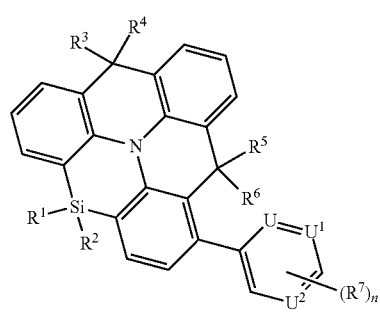
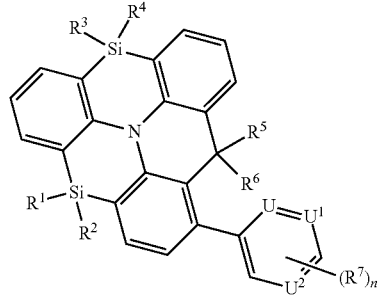

-continued
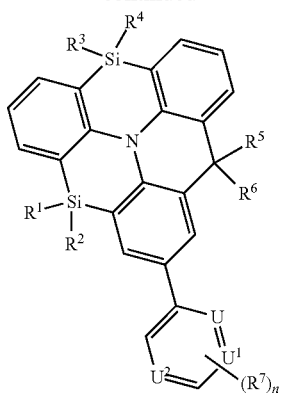
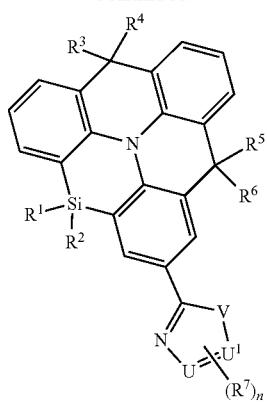
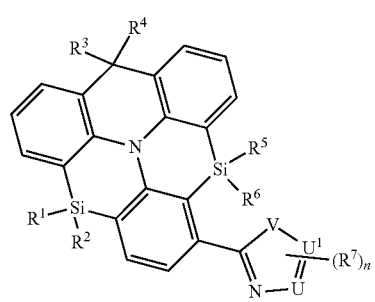
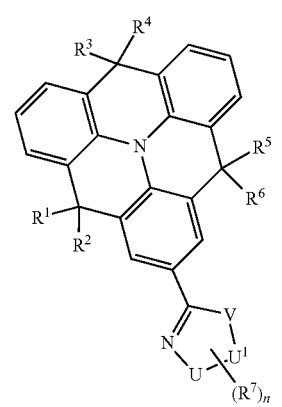
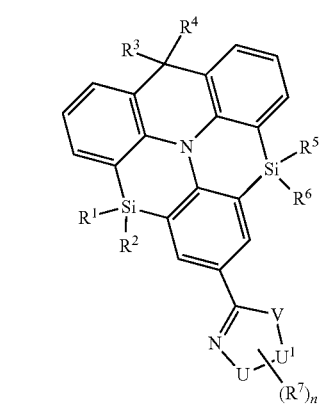
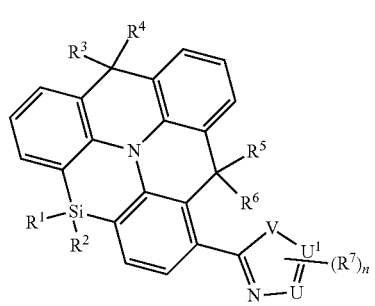

81
-continued
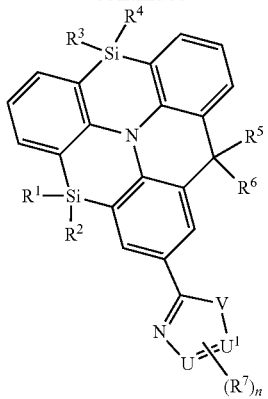
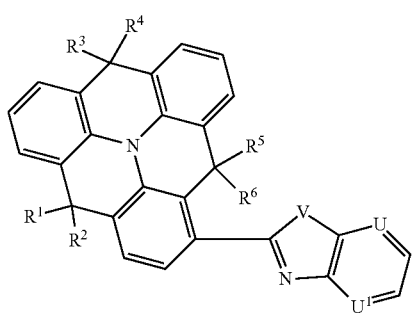
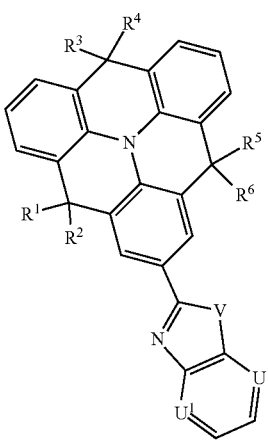
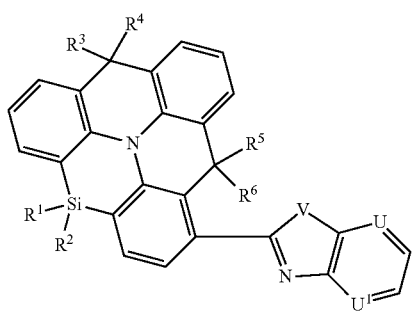
82
-continued
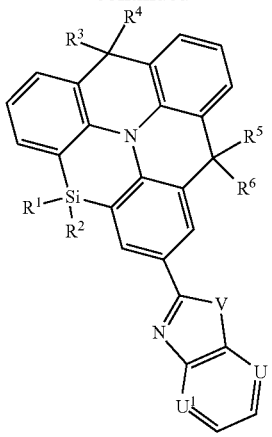
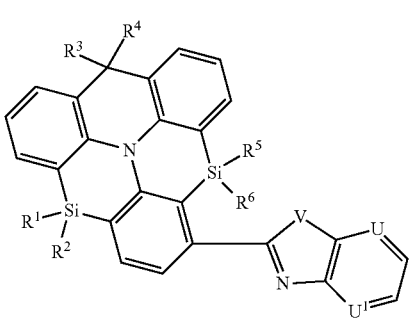
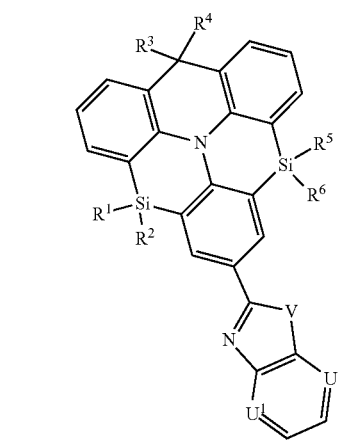
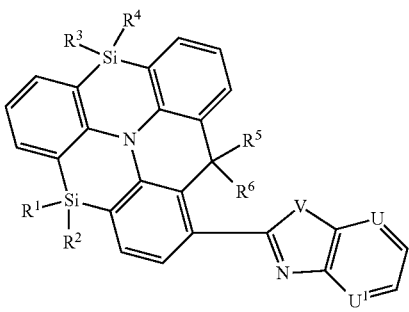

83
-continued
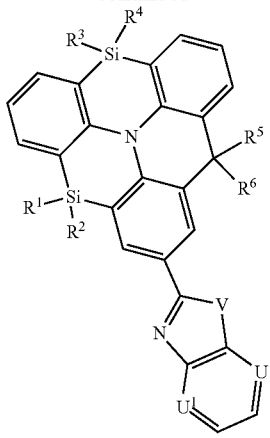
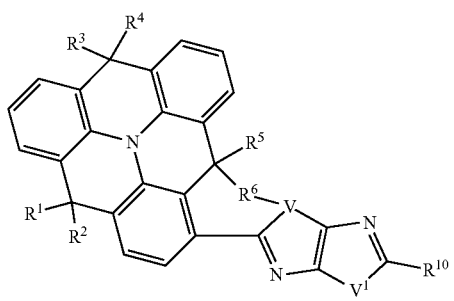
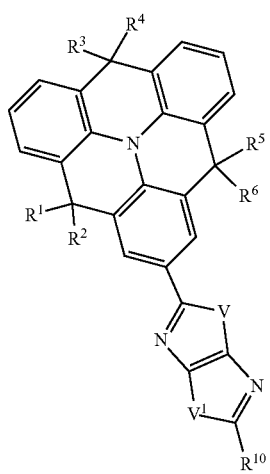
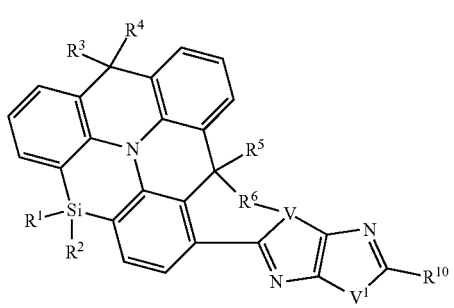
84
-continued
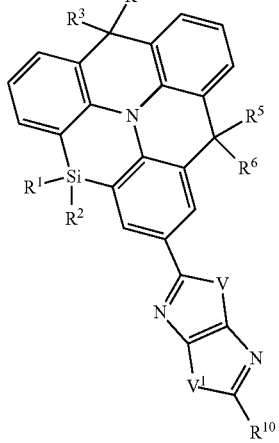
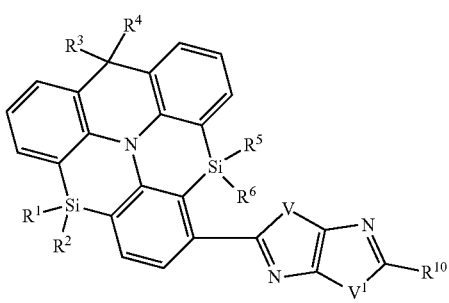
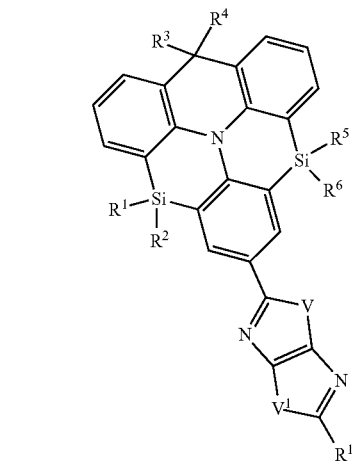
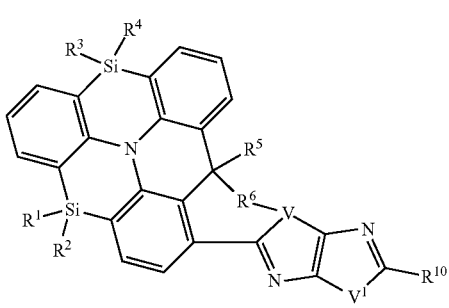

-continued
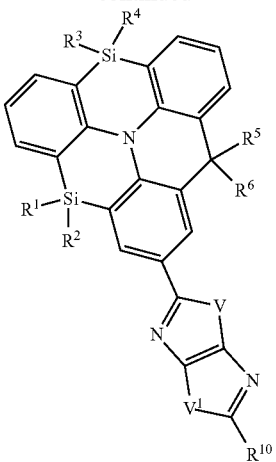
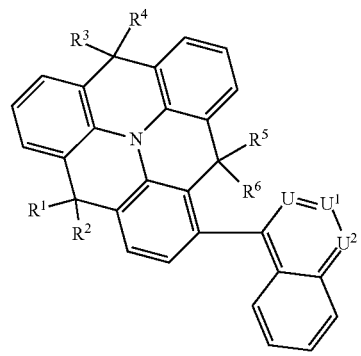
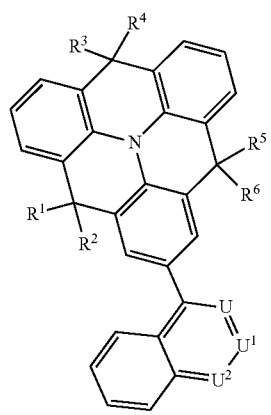
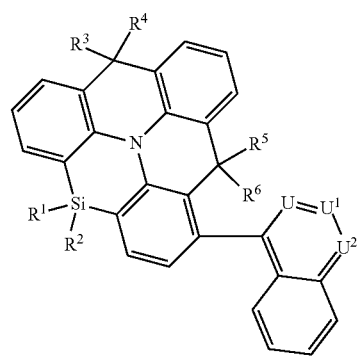
-continued
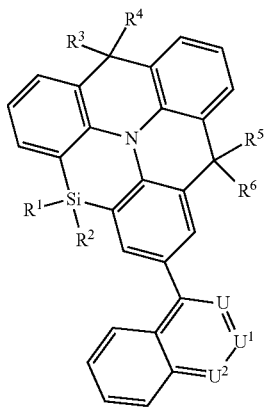
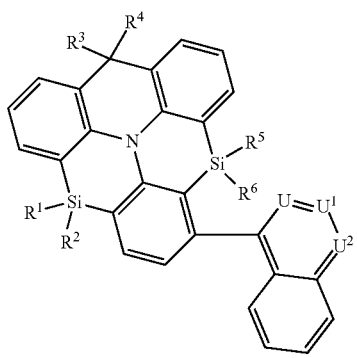
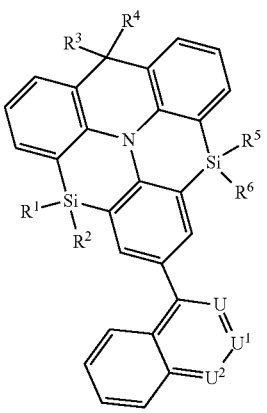
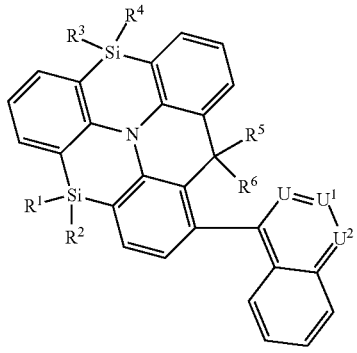

87
-continued
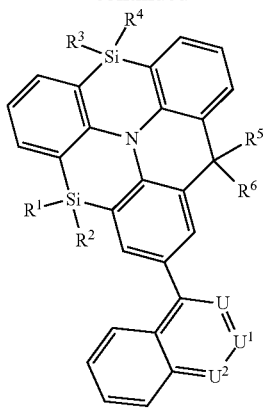
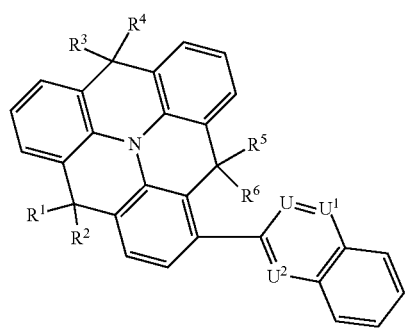
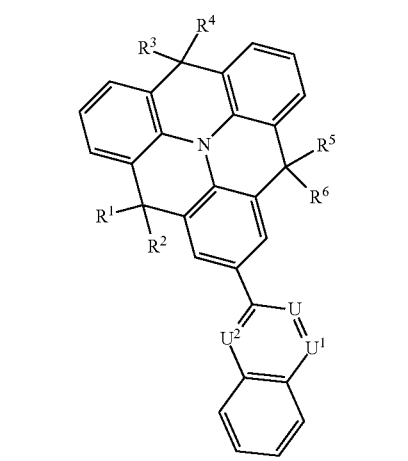
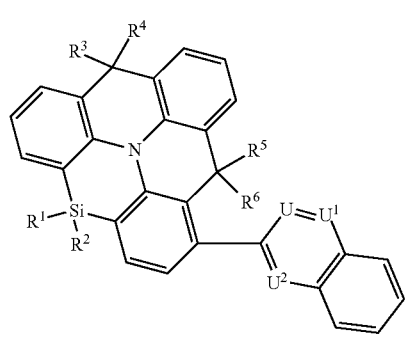
88
-continued
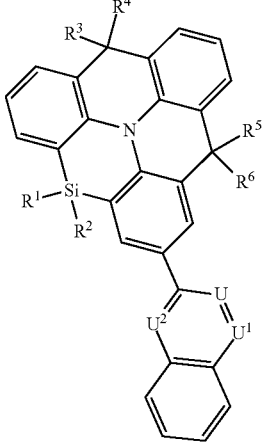
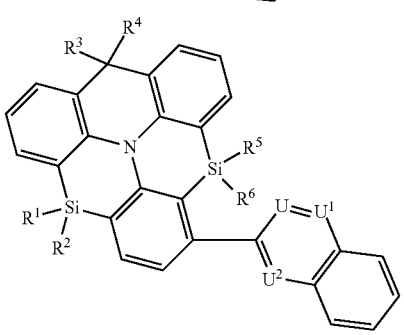
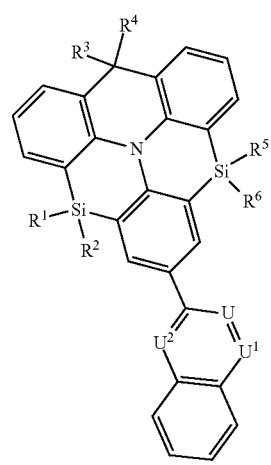
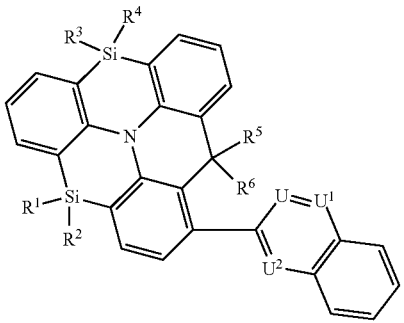

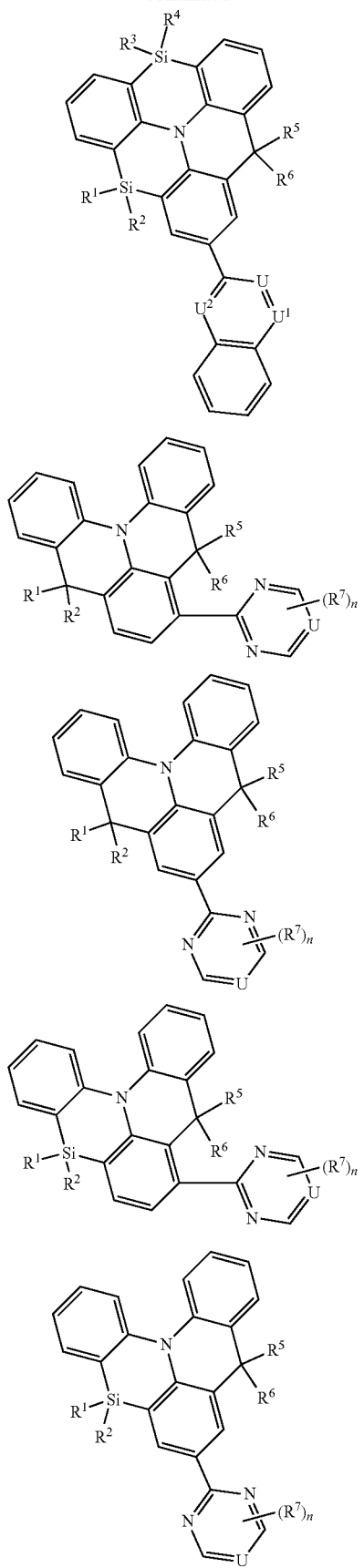
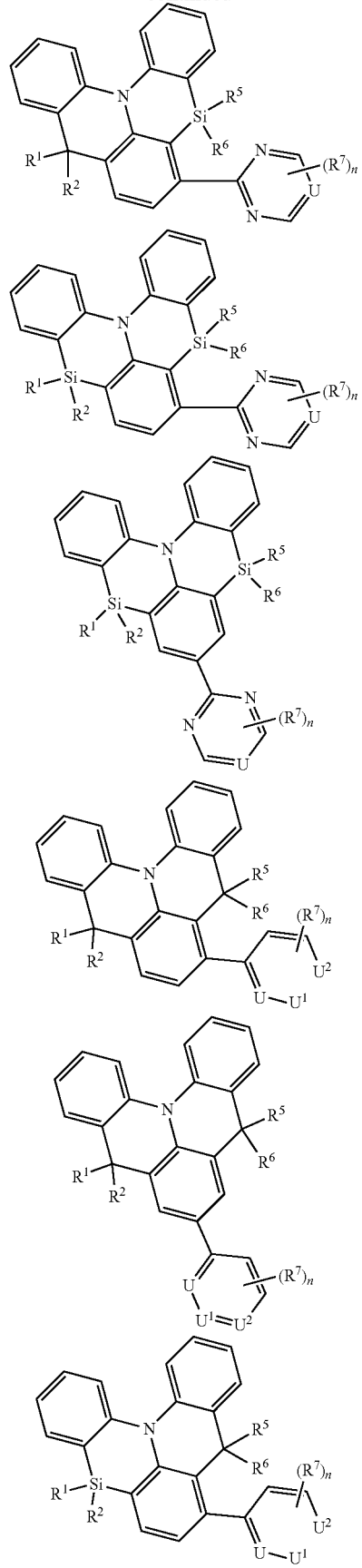

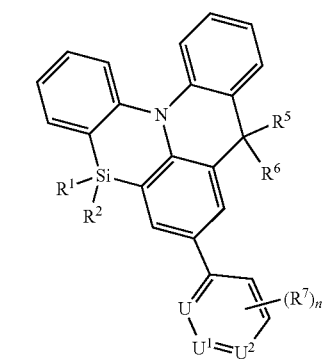
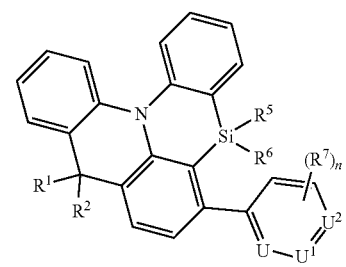
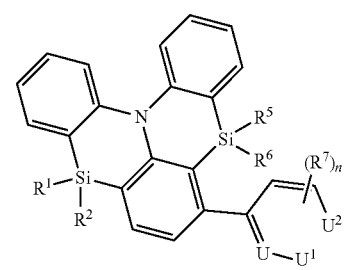
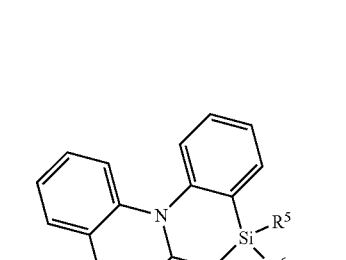
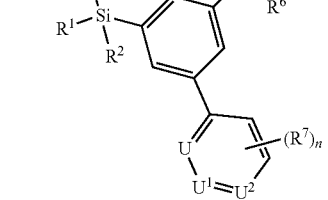
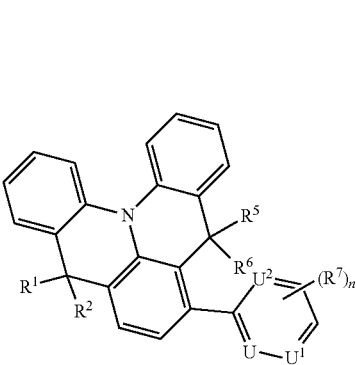
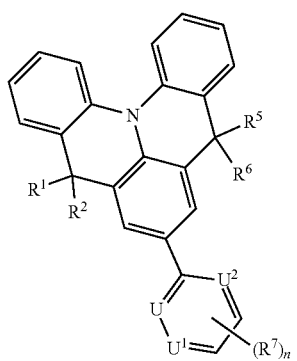
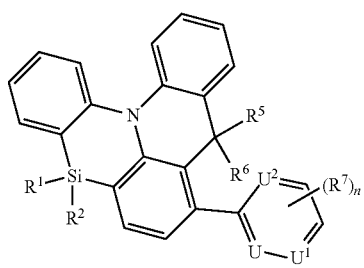
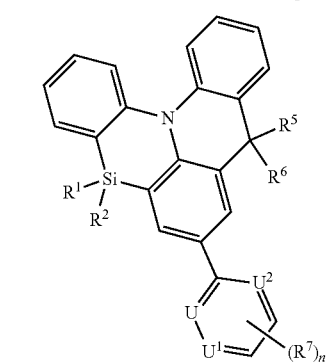
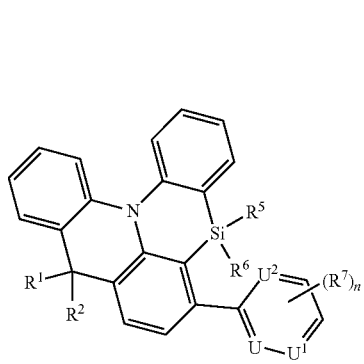
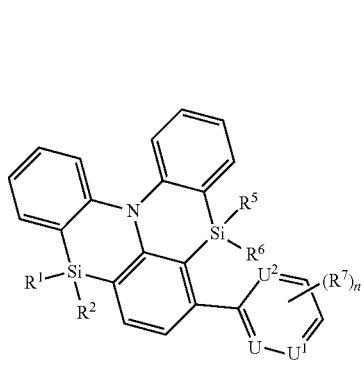

-continued
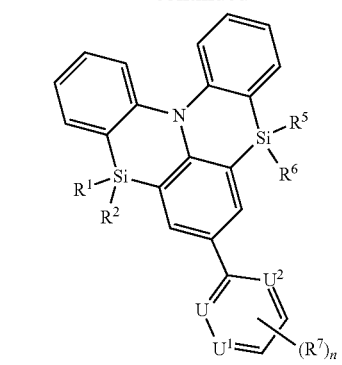
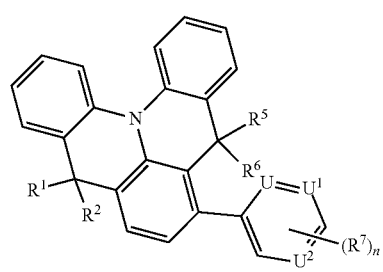
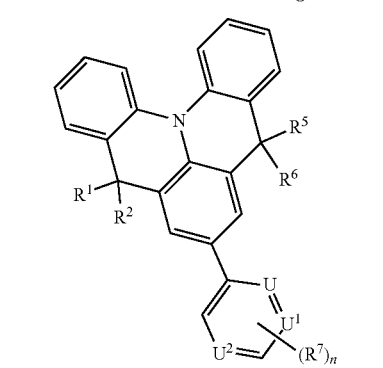
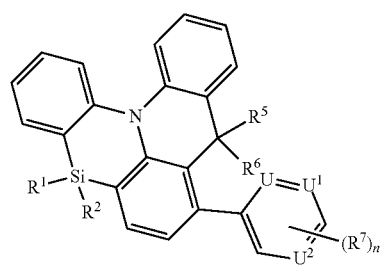
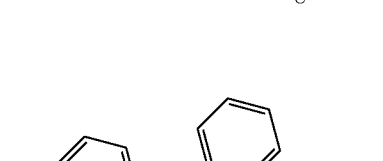
-continued
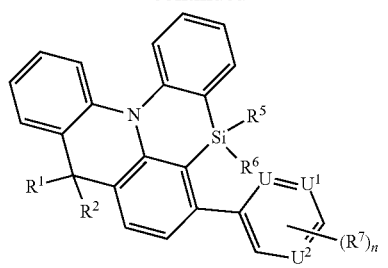
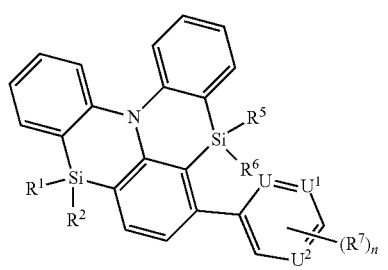
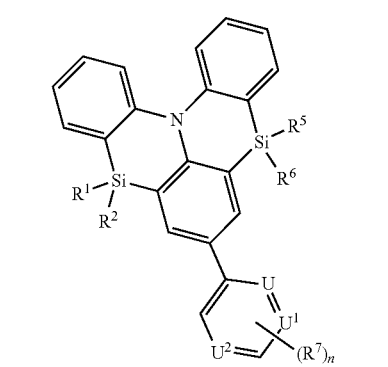
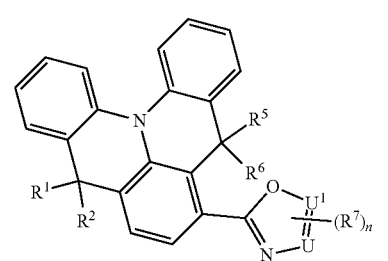
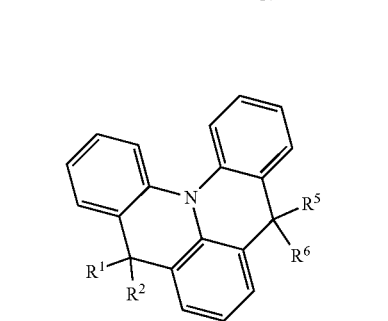

-continued
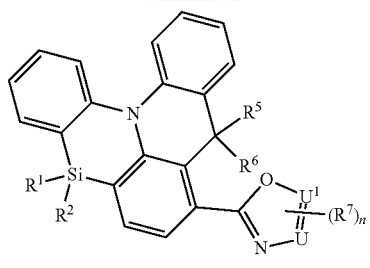
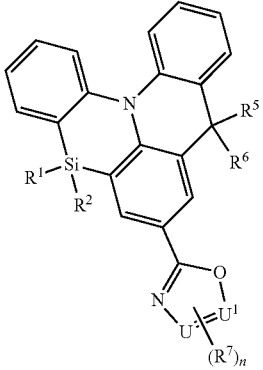
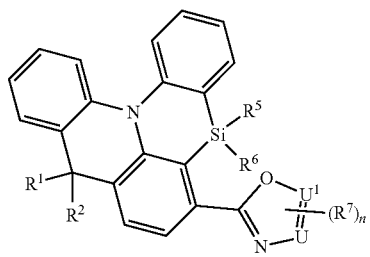
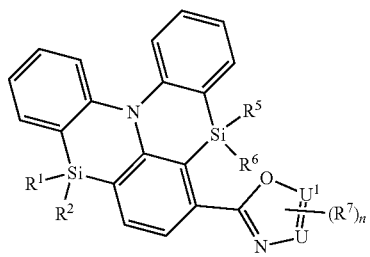
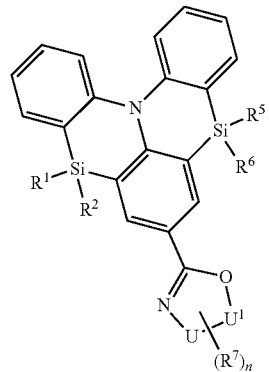
-continued
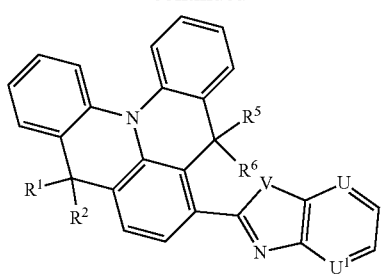
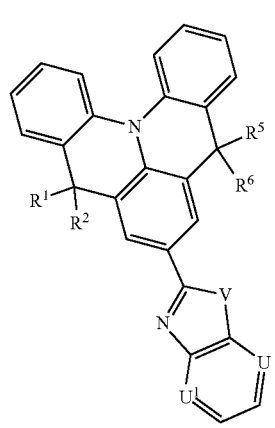
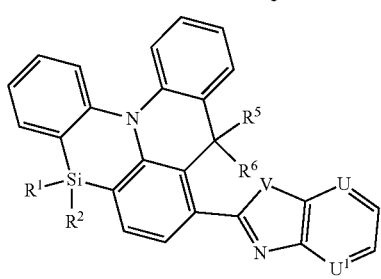
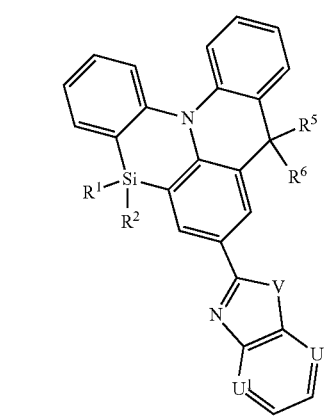
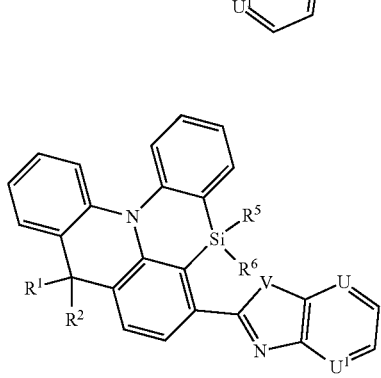

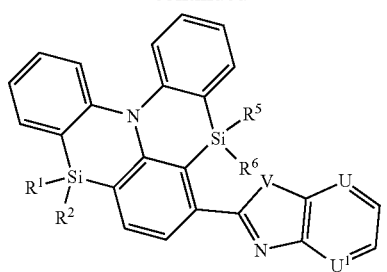
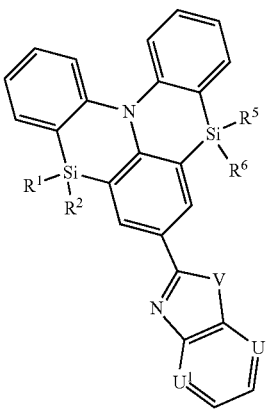
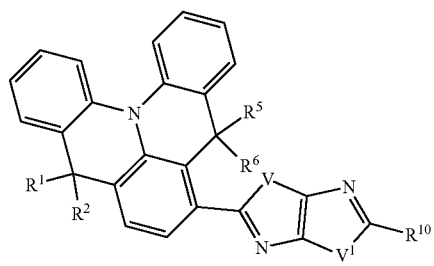
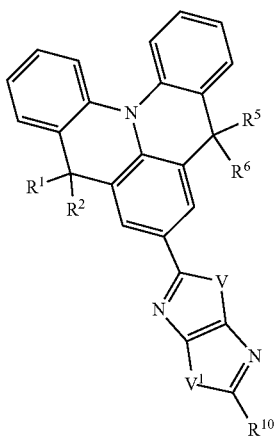
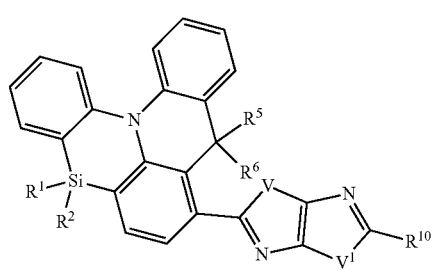
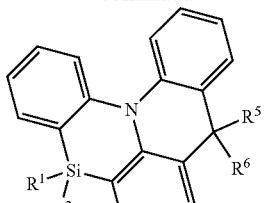
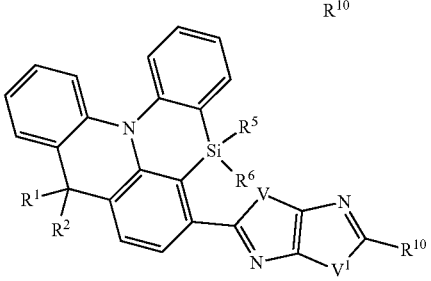
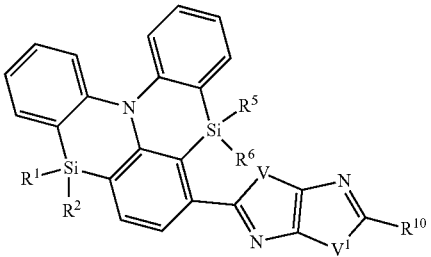
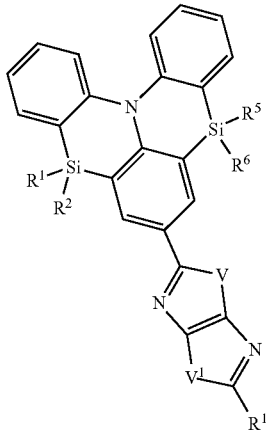
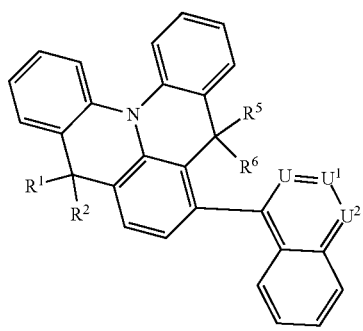

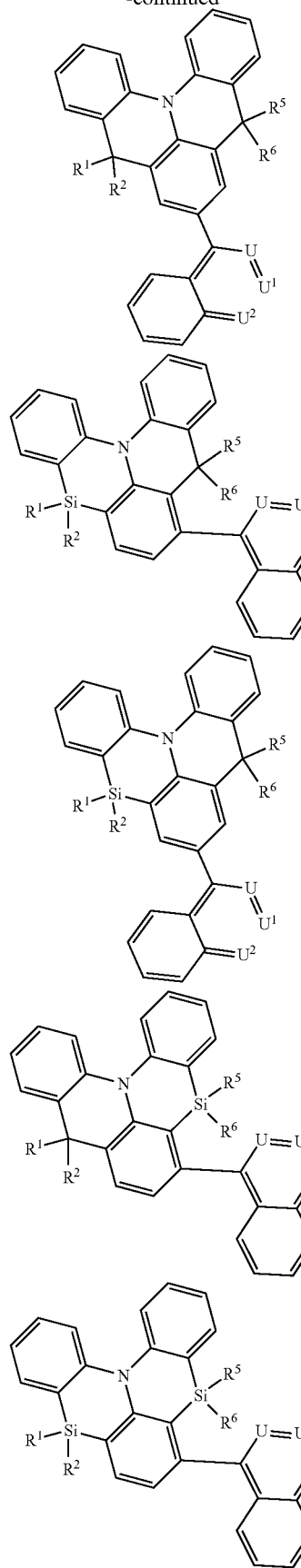
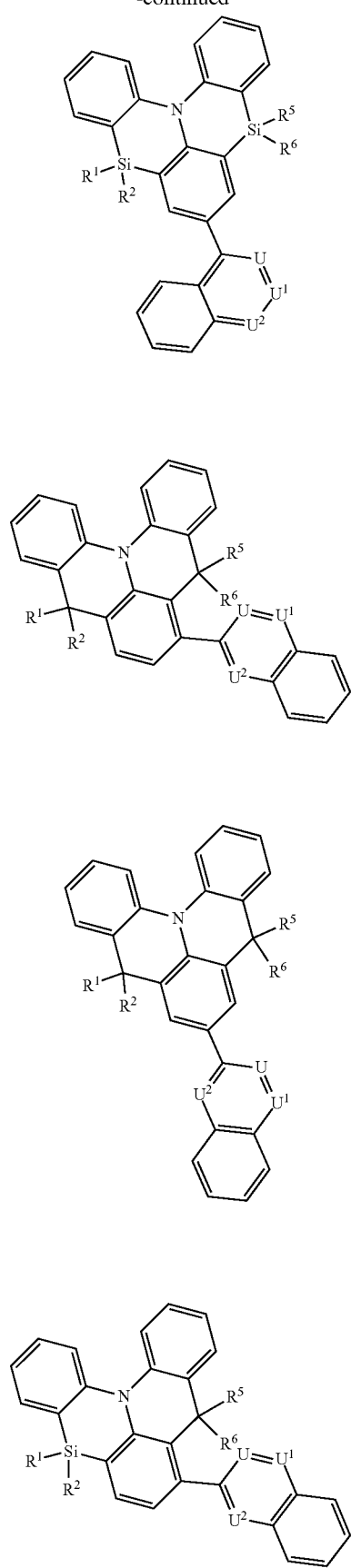

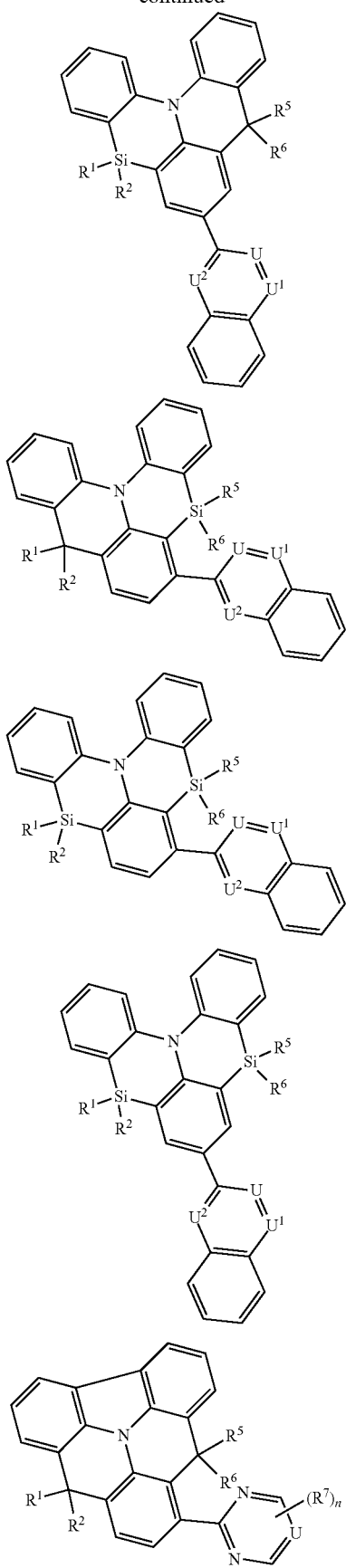
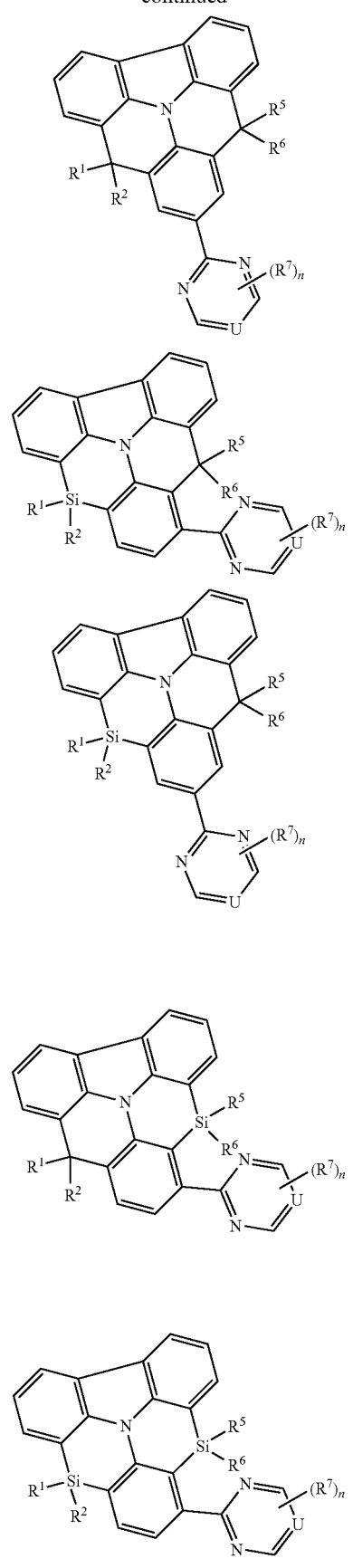

-continued
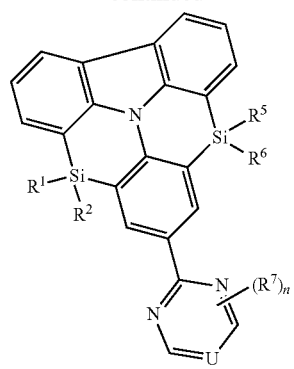
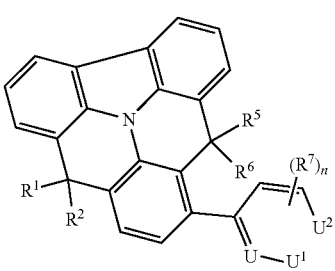
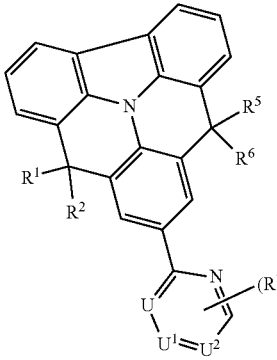
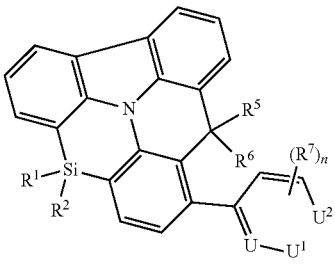
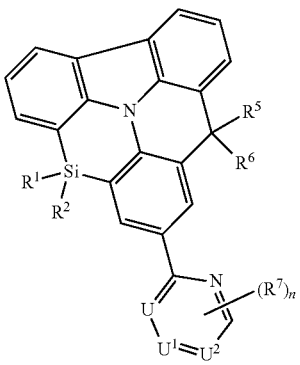
-continued
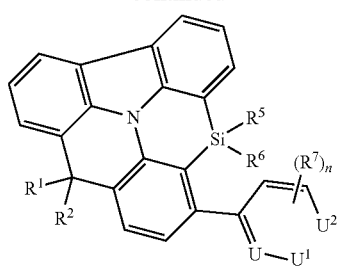
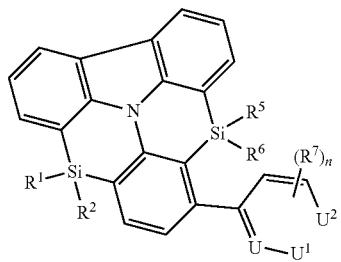
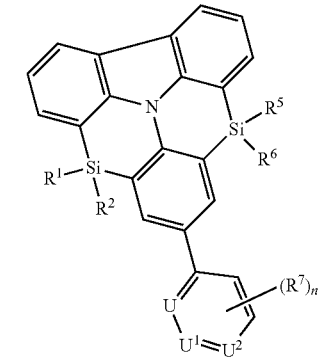
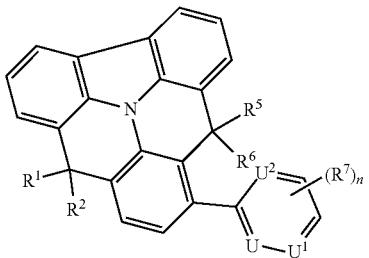
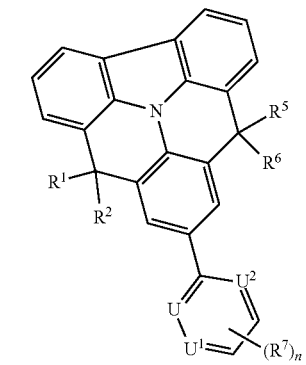

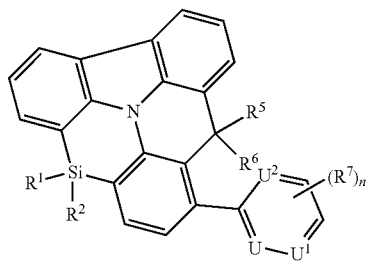

107
-continued
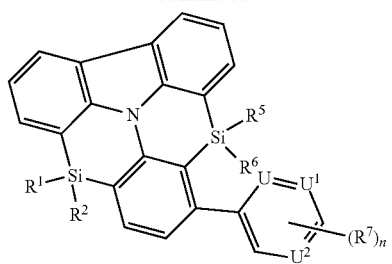
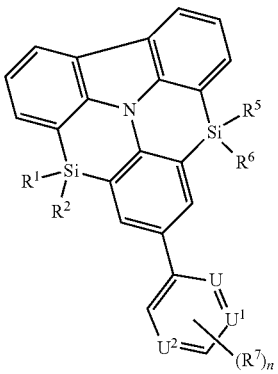
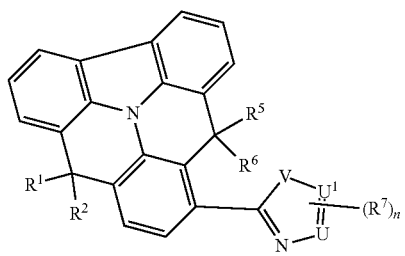
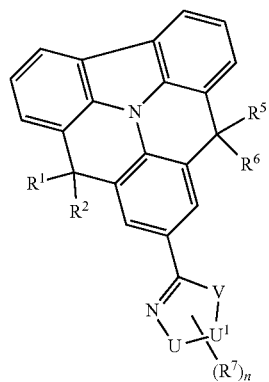
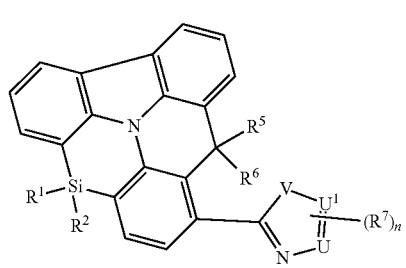
108
-continued
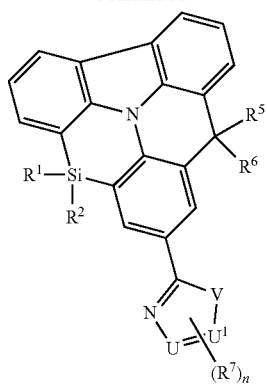
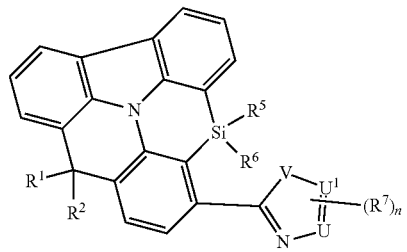
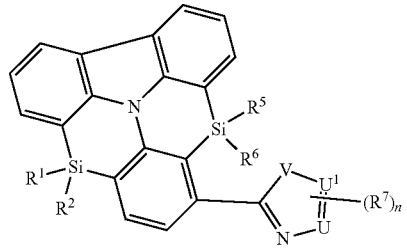
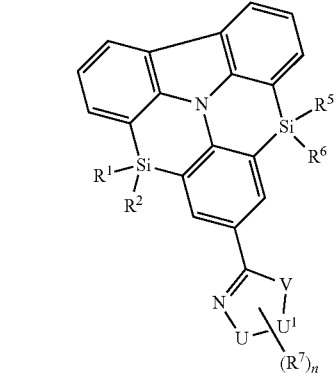
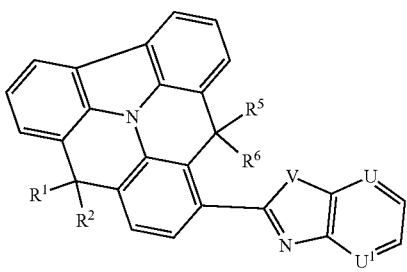

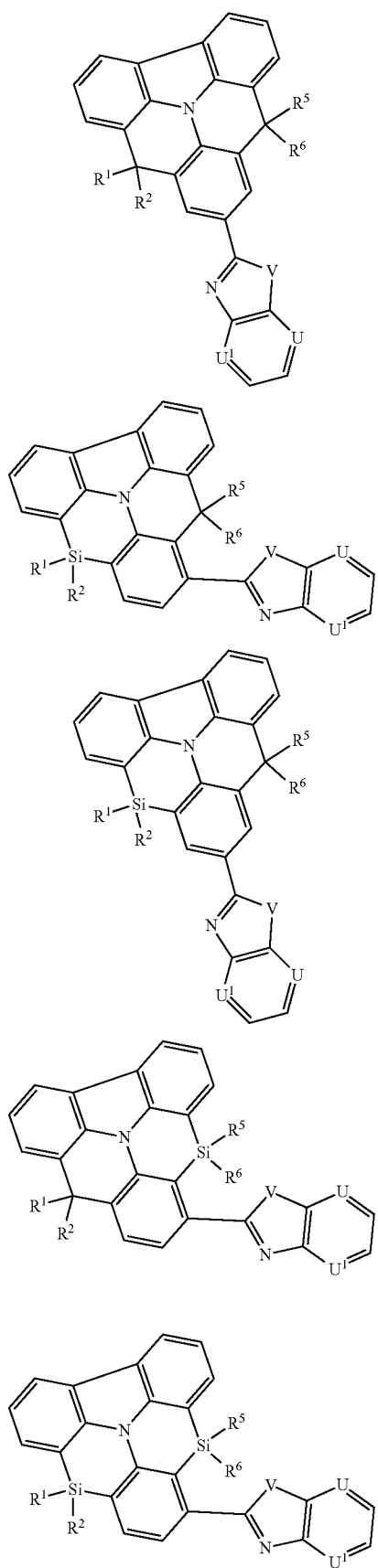
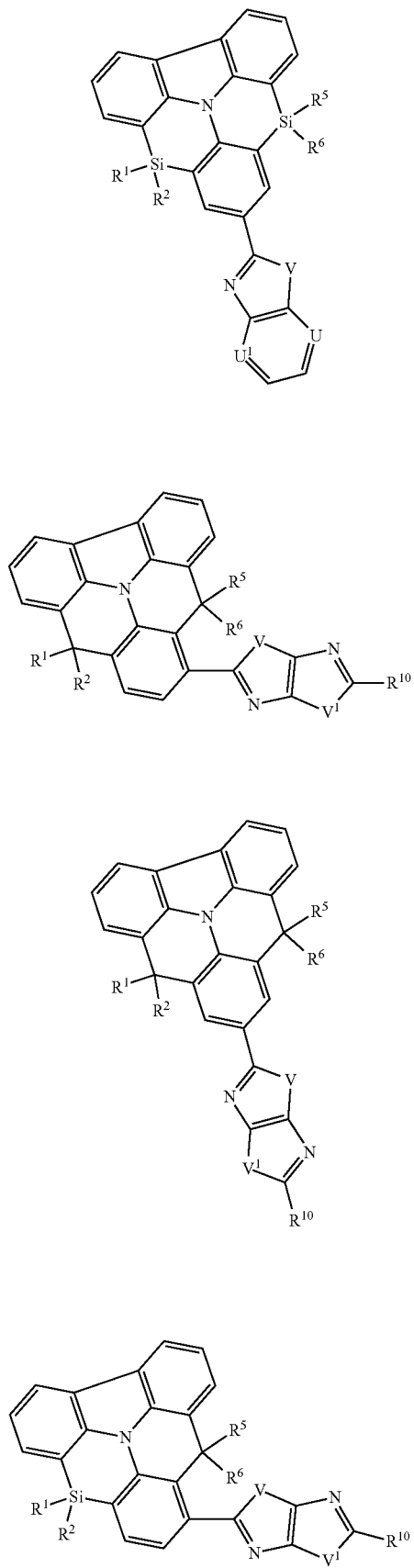

111
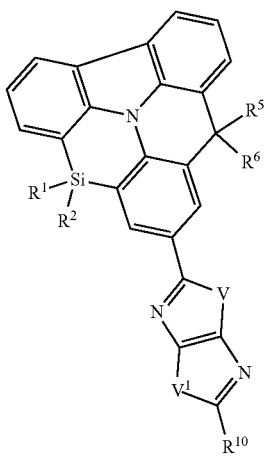
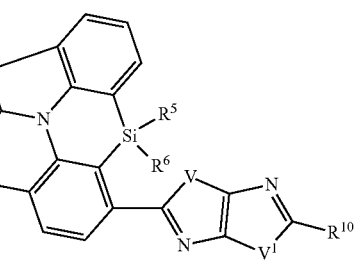
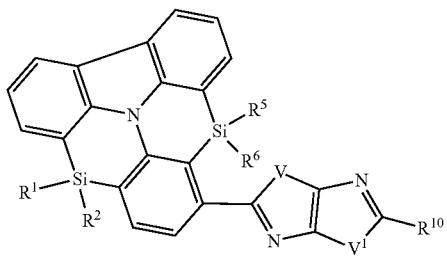
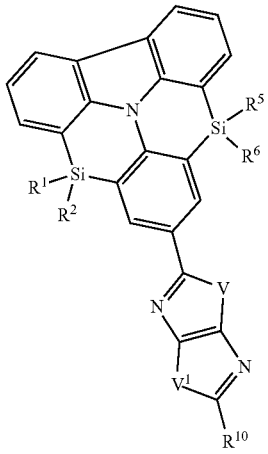
112
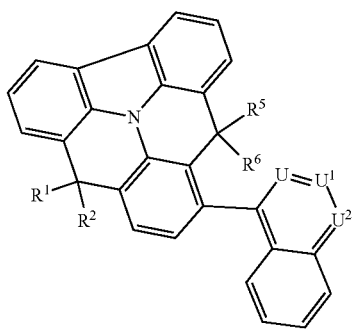
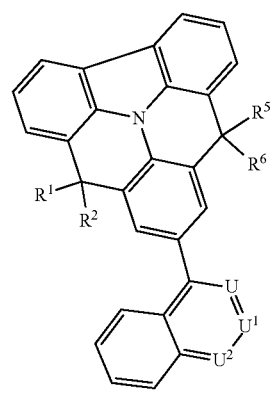
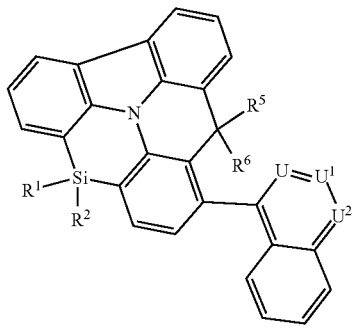
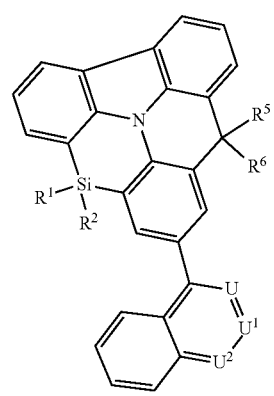

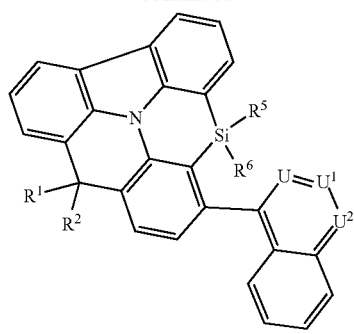
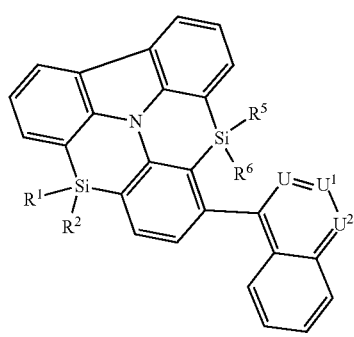
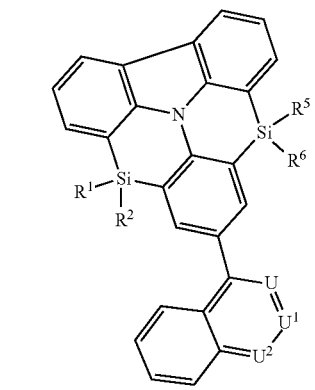
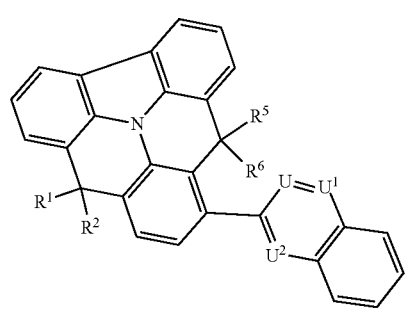
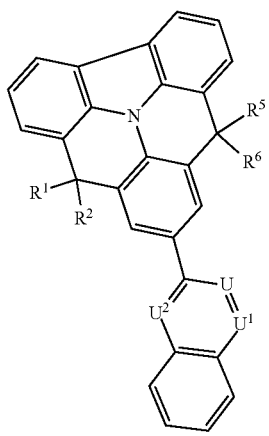
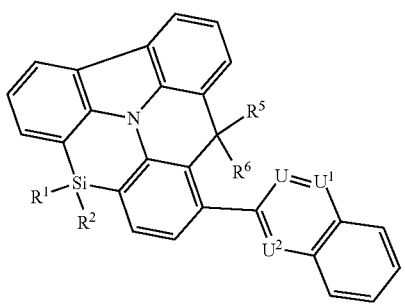
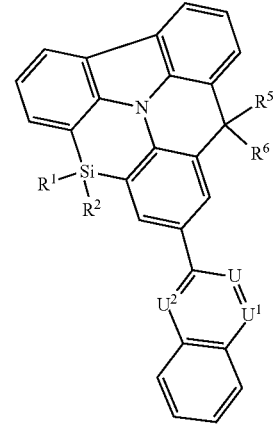
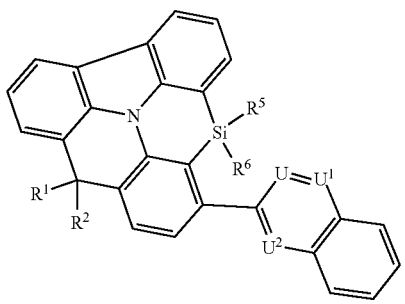

115
-continued
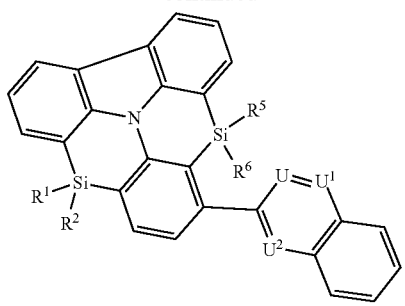
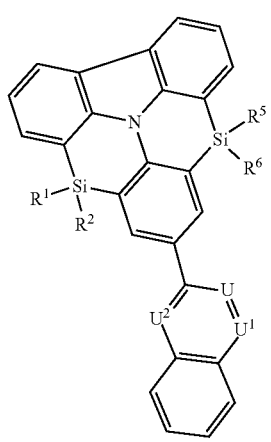
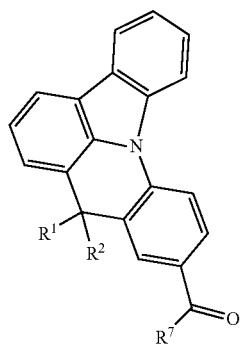
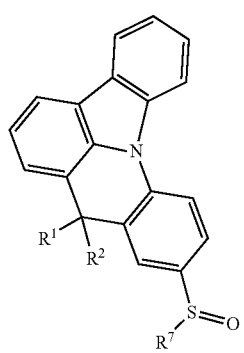
116
-continued
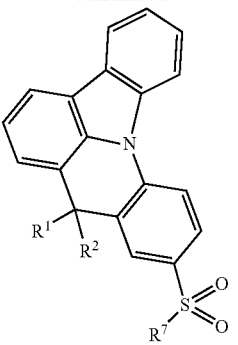
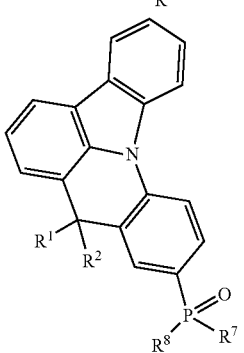
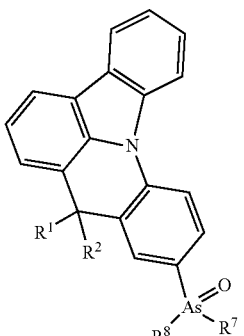
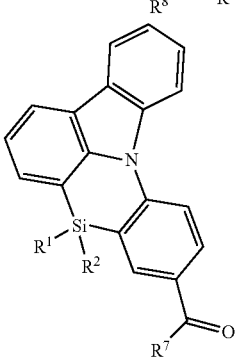
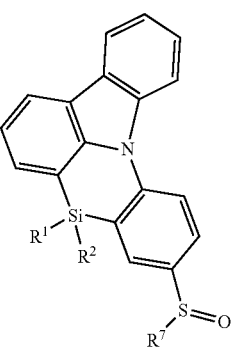

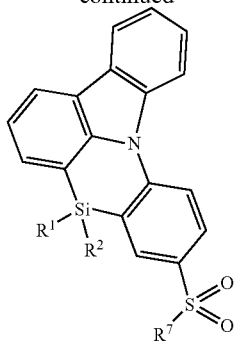
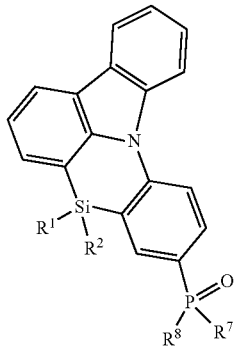
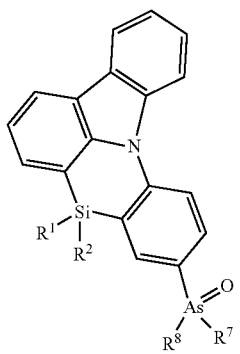
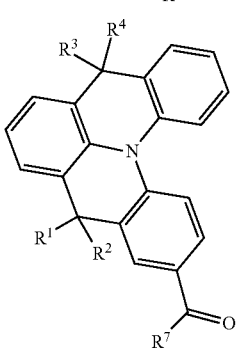
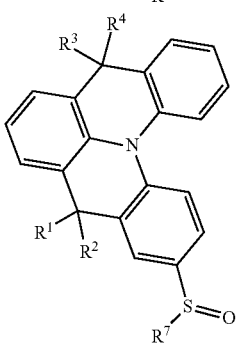
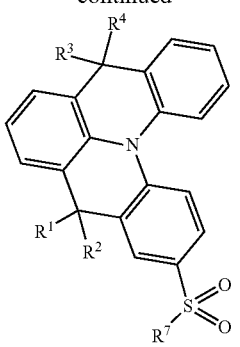
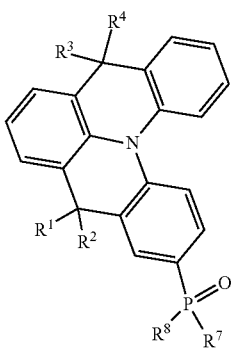
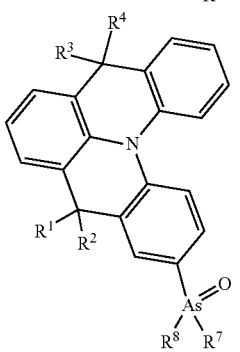
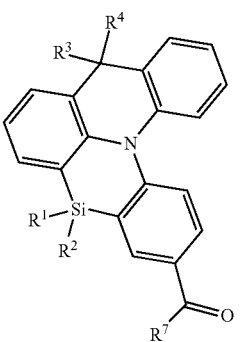
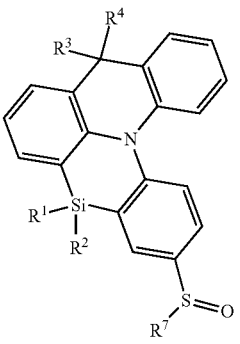

-continued
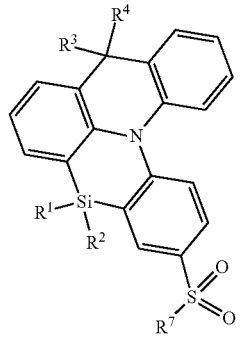
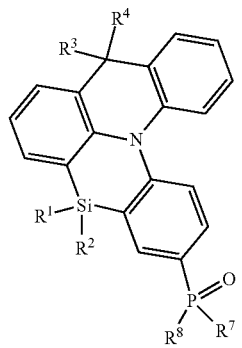
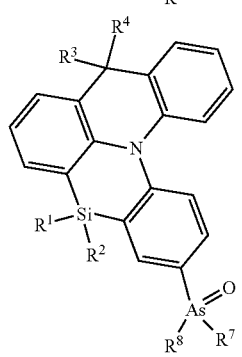
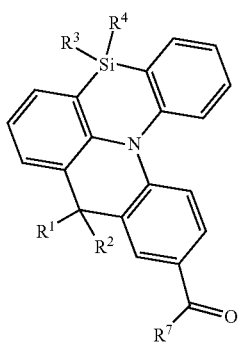
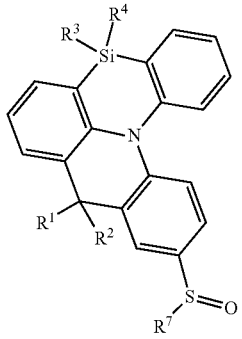
-continued
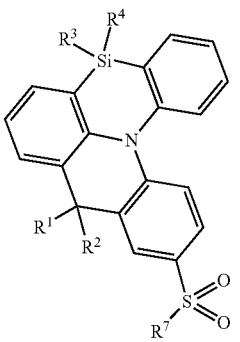
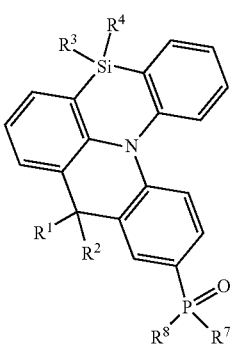
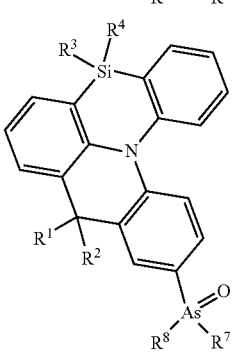
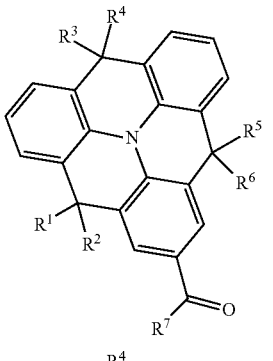
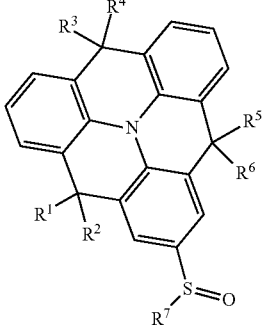

121
-continued
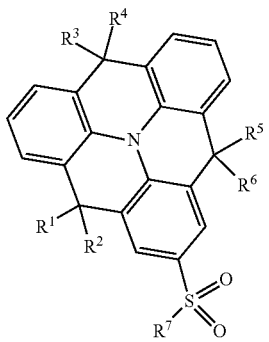
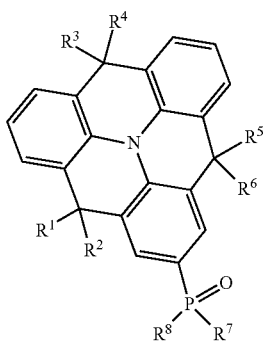
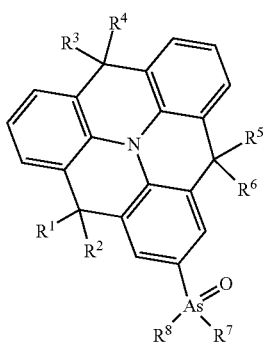
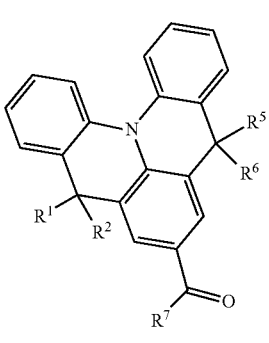
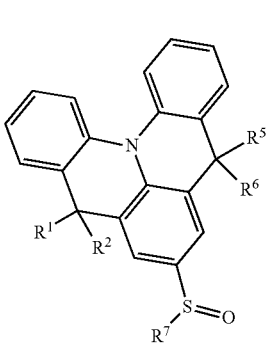
122
-continued
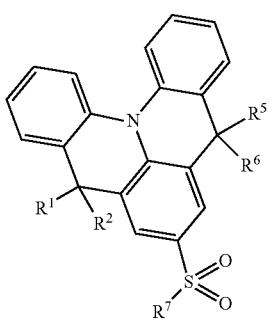
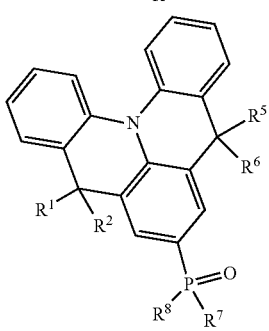
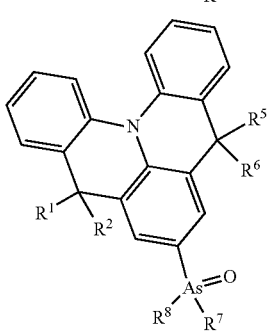
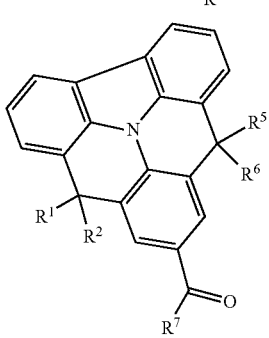
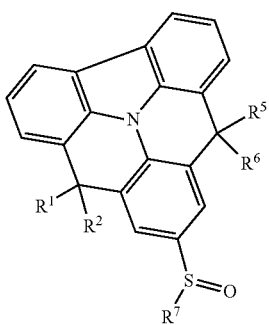

-continued
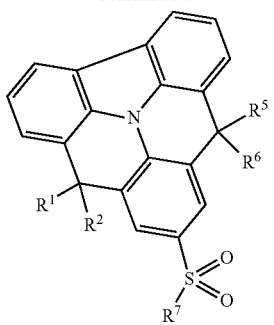
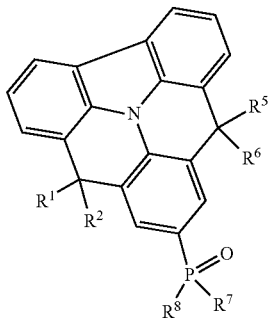
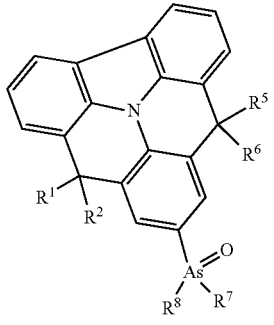
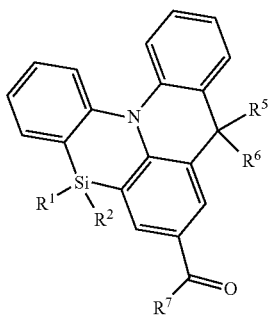
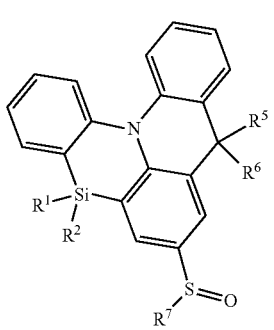
-continued
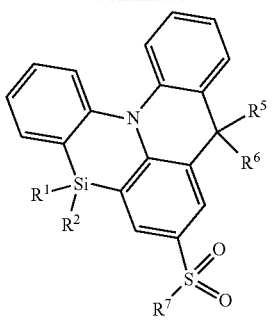
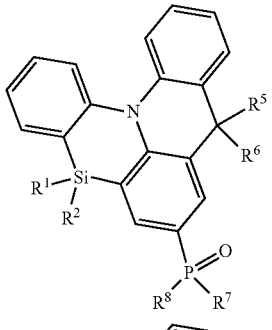
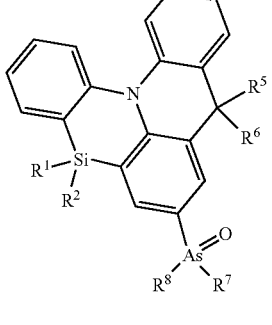
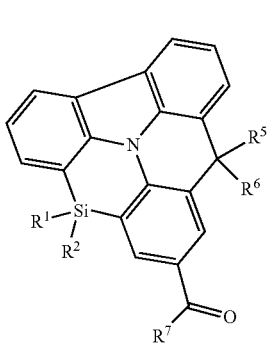
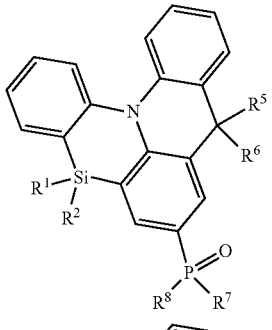

-continued

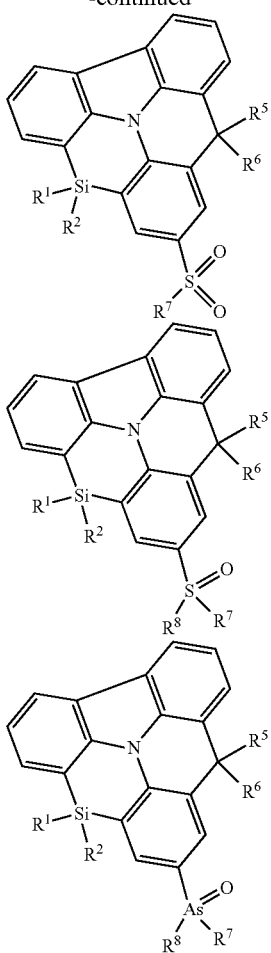

where $R^q$, $R^1$, $R^2$, $R^3$, $R^4$, $R^5$, $R^6$, $R^7$, and $(R^7)_n$ are each independently a hydrogen atom, a deuterium atom, a halogen atom, a hydroxyl group, a thiol group, a nitro group, a cyano group, a substituted or unsubstituted alkyl group, a substituted or unsubstituted haloalkyl group, a substituted or unsubstituted aralkyl group, a substituted or unsubstituted alkenyl group, a substituted or unsubstituted alkynyl group, a substituted or unsubstituted aryl group, an amino group, a mono- or dialkylamino group, a mono- or diarylamino group, a substituted or unsubstituted alkoxy group, a substituted or unsubstituted aryloxy group, a substituted or unsubstituted heteroaryl group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a mercapto group, a sulfo group, a carboxyl group, a hydrazino group, a substituted silyl group, a polymeric group, or a combination thereof. U, $U^1$, and $U^2$ each independently represents N or C of an aromatic ring, with the proviso that when U, $U^1$ and $U^2$ present in the same structure, at least one of them is N. V, and $V^1$ each independently represents NR, O, S, where R can be a alkyl, cycloalkyl, aryl, heteroaryl. In some instances, $R^1$, $R^2$, $R^3$, $R^4$, $R^5$, $R^6$, $R^7$, and $(R^7)_n$ are each independently a hydrogen atom, an alkyl group (e.g., methyl, ethyl or propyl group), or an aromatic (e.g., phenyl) group. In some embodiments, $(R^7)_n$ includes two aromatic groups and hydrogen atoms.

In certain embodiments, structures I, II, or III can include two acceptor moieties, and can be represented by the following general structures.

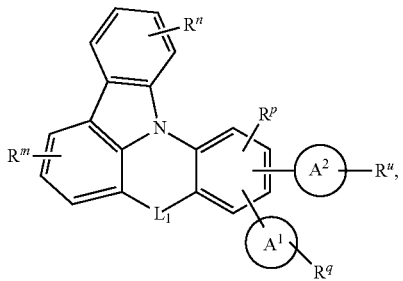

V

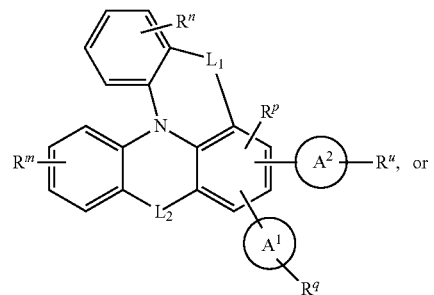

VI

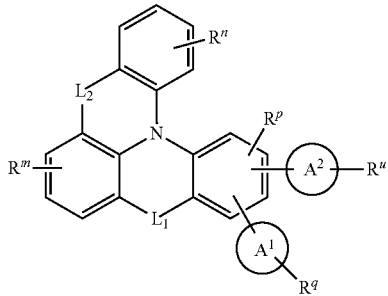

VII where $L_1$, $L_2$, $R^m$, $R^n$, $R^p$, $R^q$, $A^1$, and $A^2$ have been previously defined, and $R^u$ can represent mono-, di-, tri, or tetra-substitution, and each independently represents one or more of a hydrogen atom, a deuterium atom, a halogen atom, a hydroxyl group, a thiol group, a nitro group, a cyano group, a substituted or unsubstituted alkyl group, a substituted or unsubstituted haloalkyl group, a substituted or unsubstituted aralkyl group, a substituted or unsubstituted alkenyl group, a substituted or unsubstituted alkynyl group, a substituted or unsubstituted aryl group, a substituted or unsubstituted amino group, a substituted or unsubstituted mono- or dialkylamino group, a substituted or unsubstituted mono- or diarylamino group, a substituted or unsubstituted alkoxy group, a substituted or unsubstituted aryloxy group, a substituted or unsubstituted heteroaryl group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a mercapto group, a sulfo group, a carboxyl group, a hydrazino group, a substituted silyl group, a polymeric group, or a combination thereof. Non-limiting examples of the above structures include:
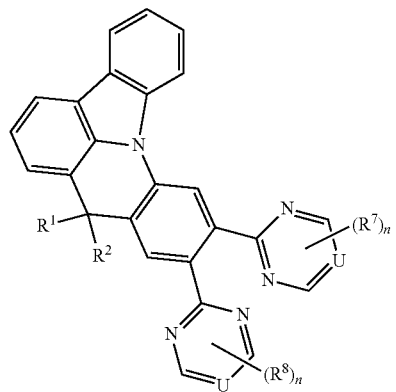
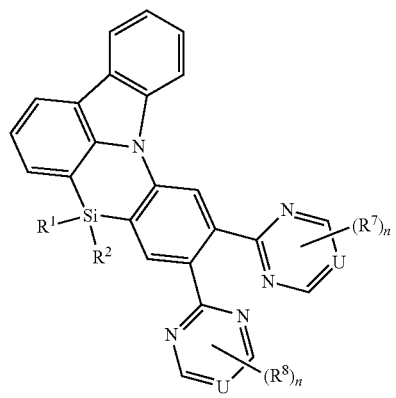
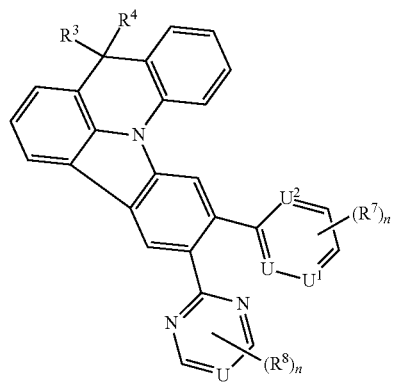
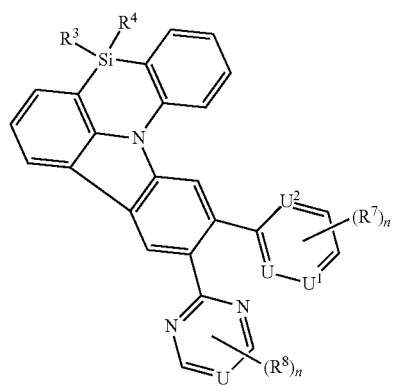
-continued
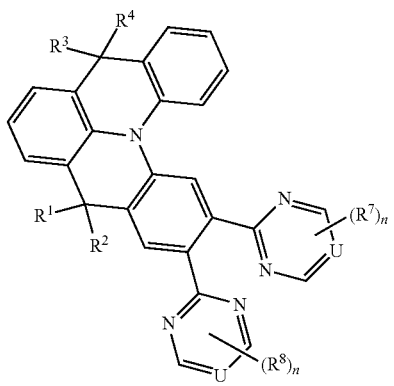
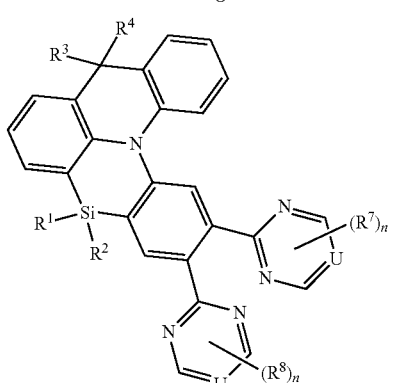
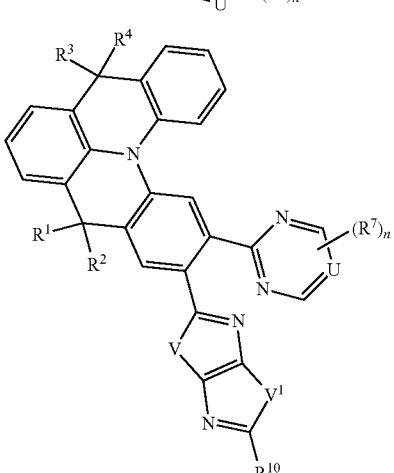
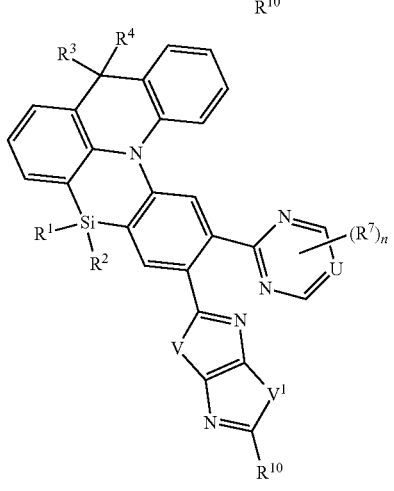

-continued
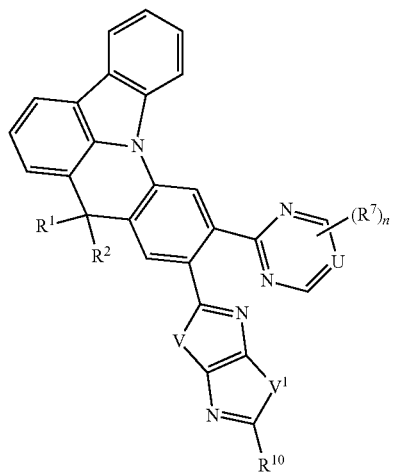
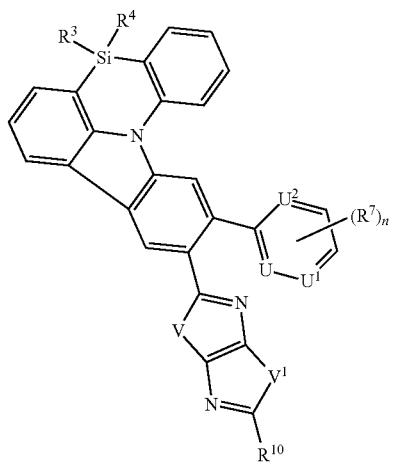
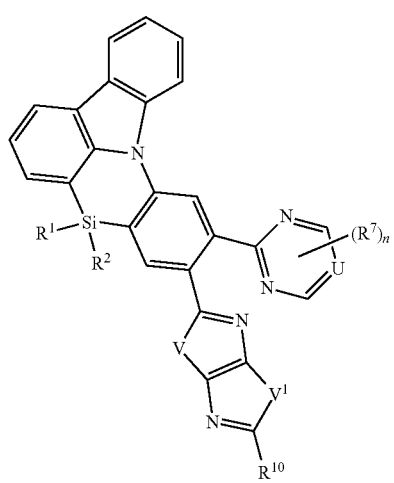
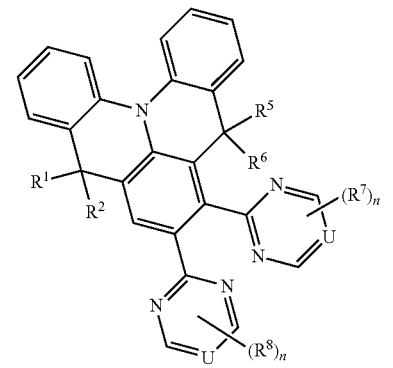
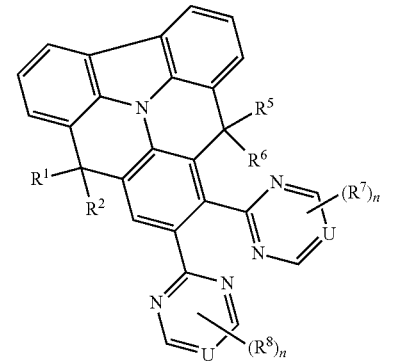
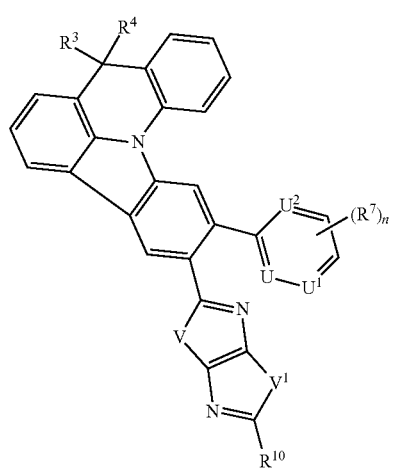
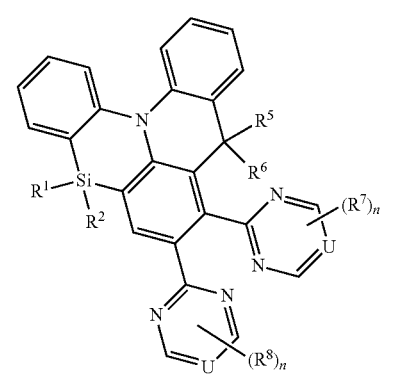

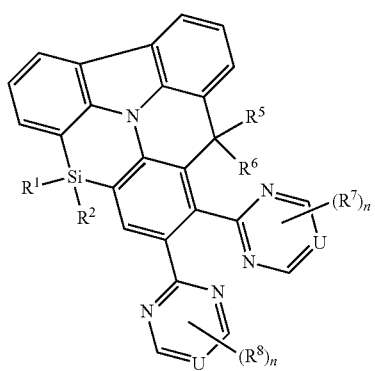
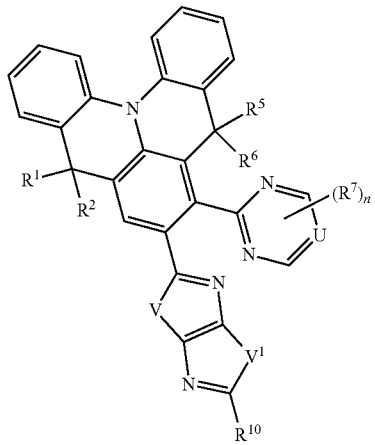
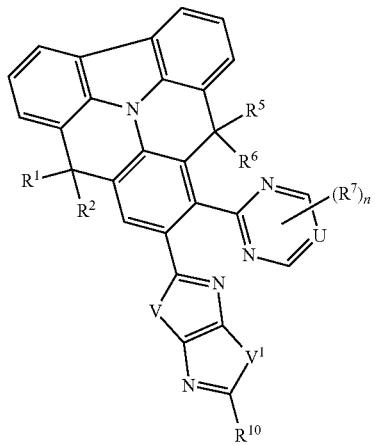
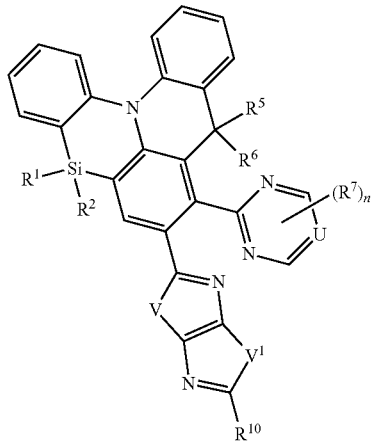
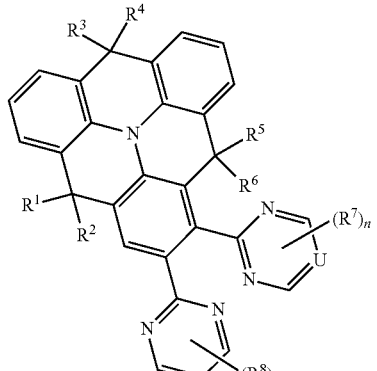
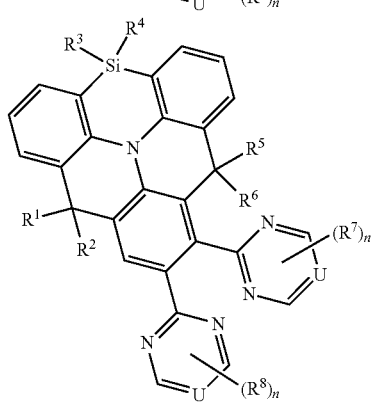
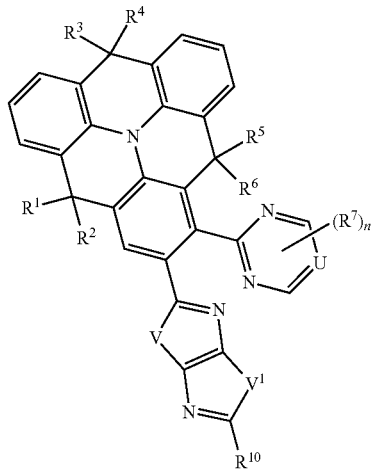
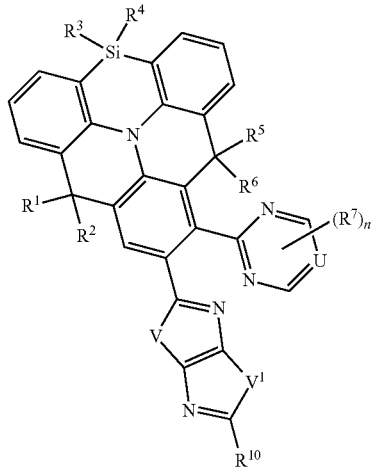

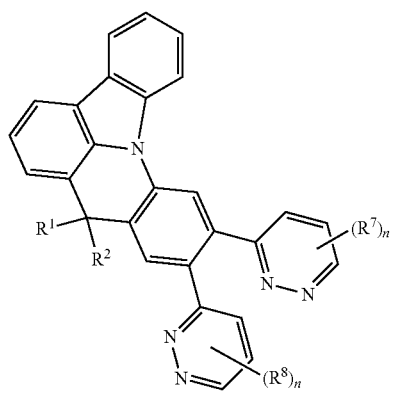
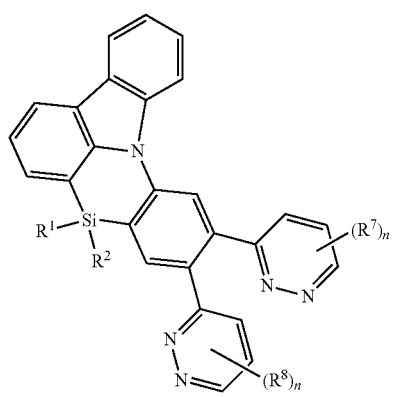
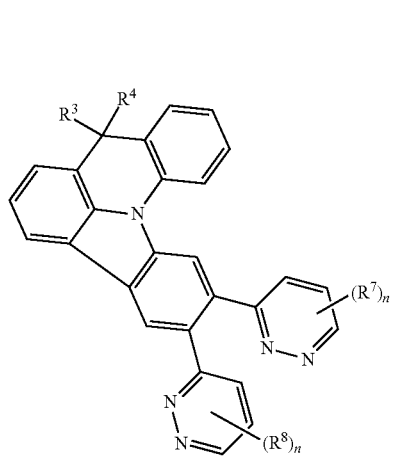
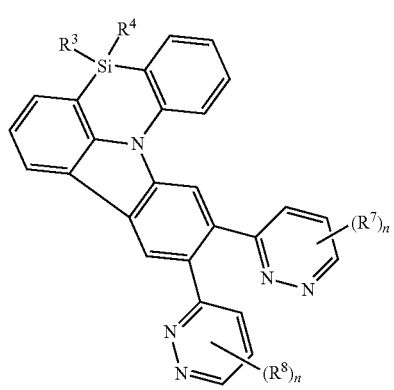
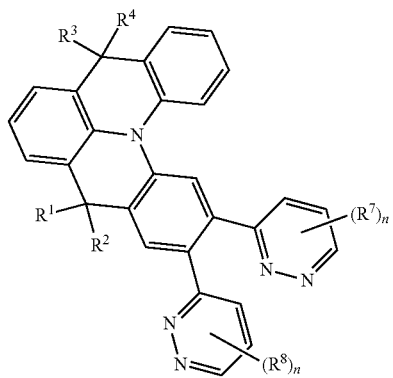
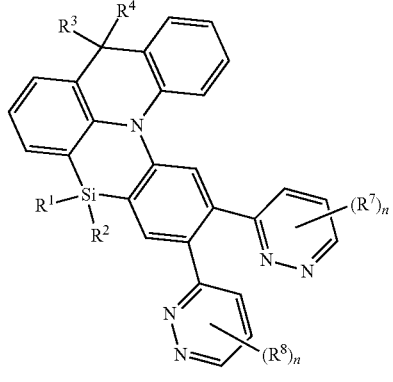
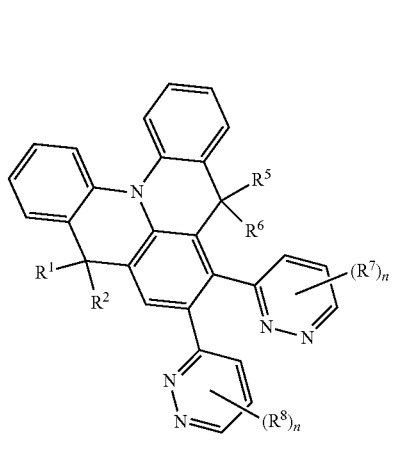
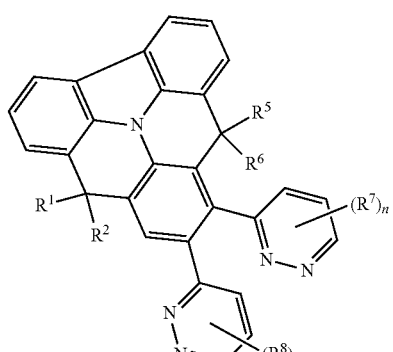

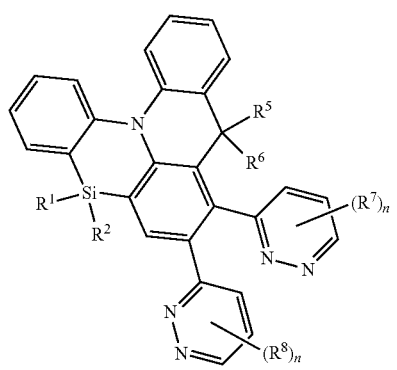
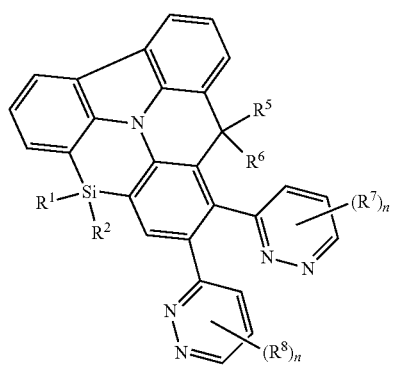
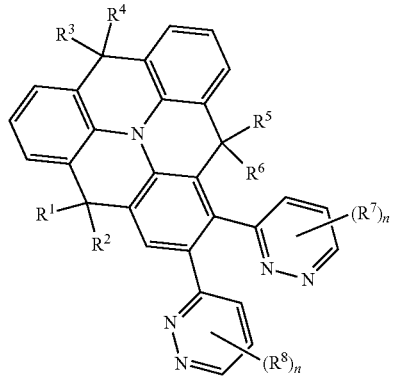
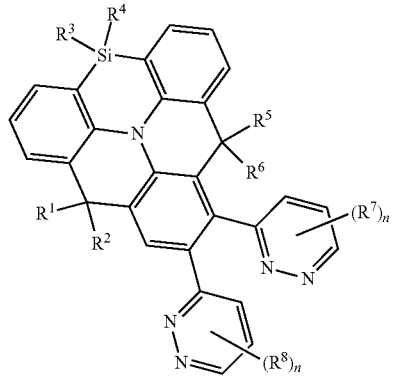
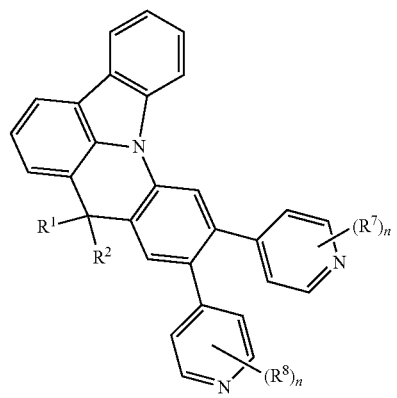
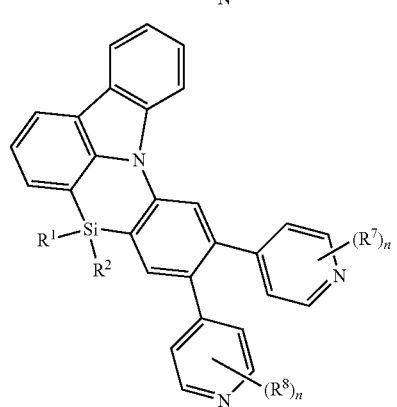
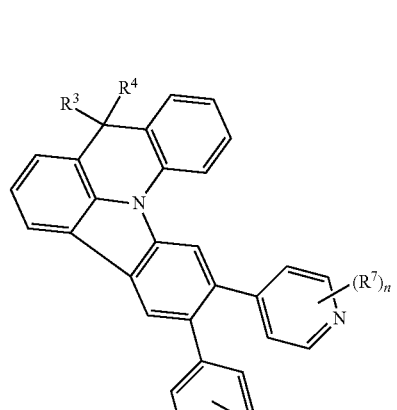
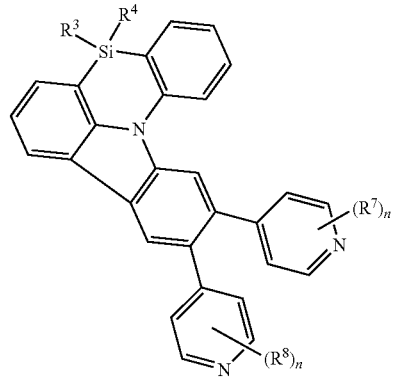

-continued
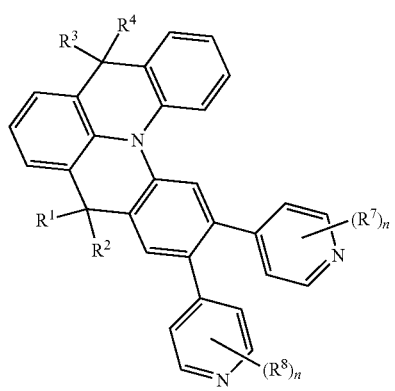
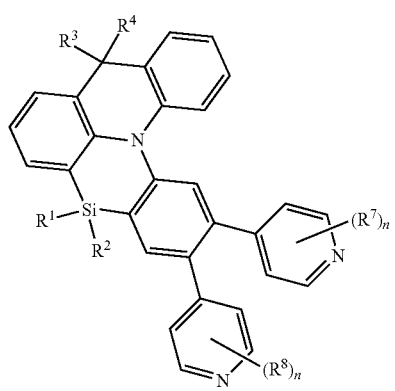
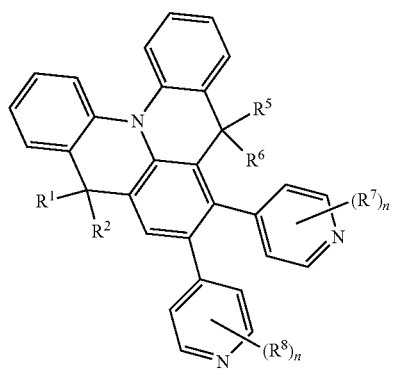
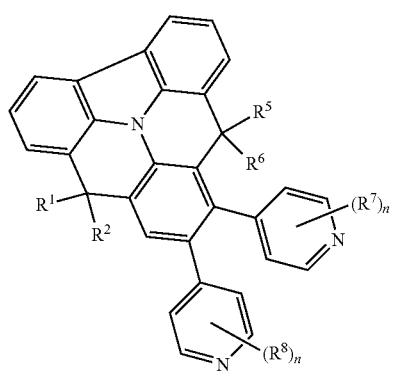
-continued
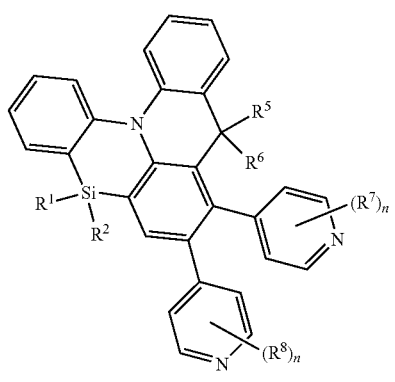
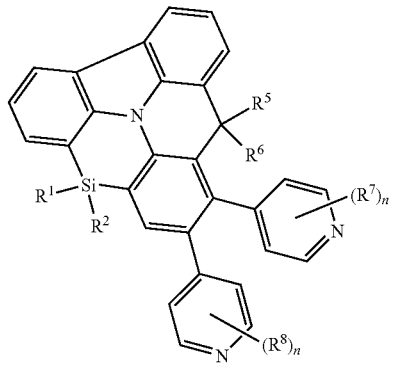
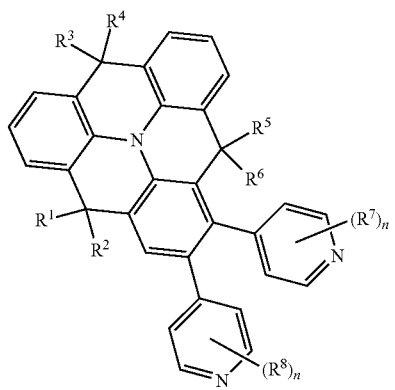
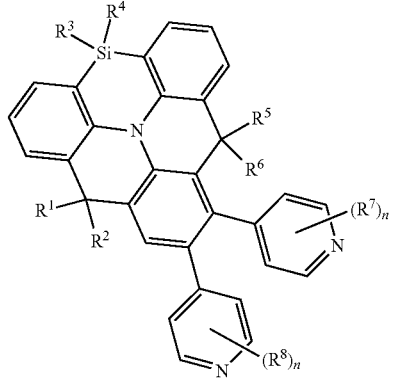

-continued
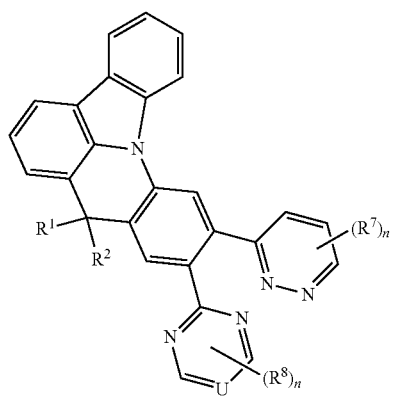
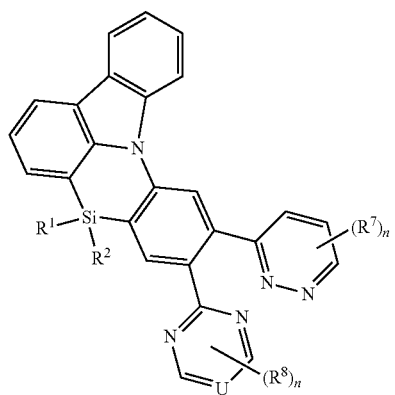
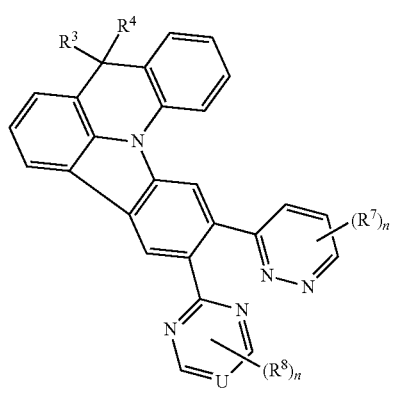
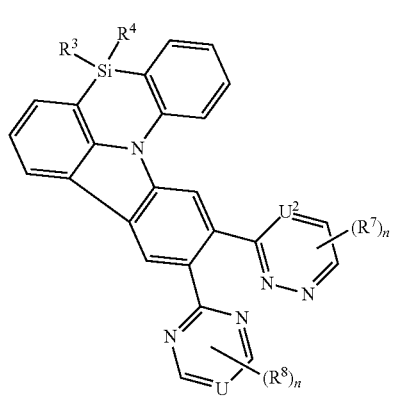
-continued
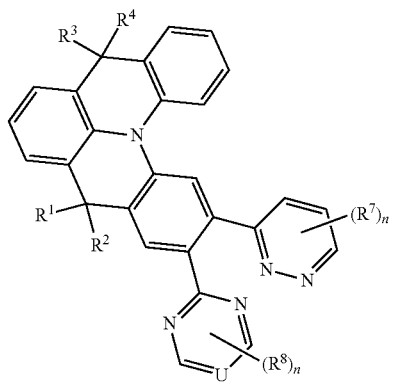
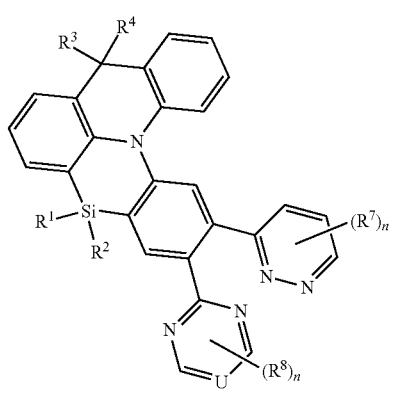
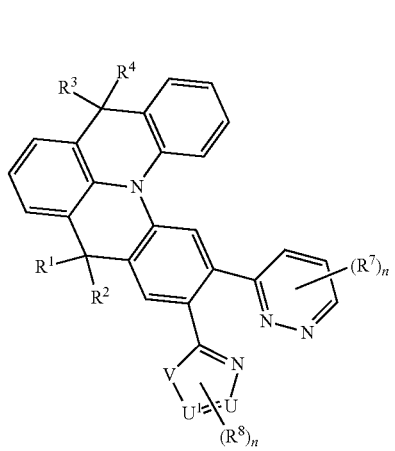
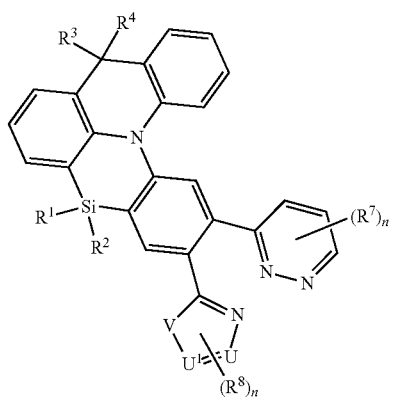

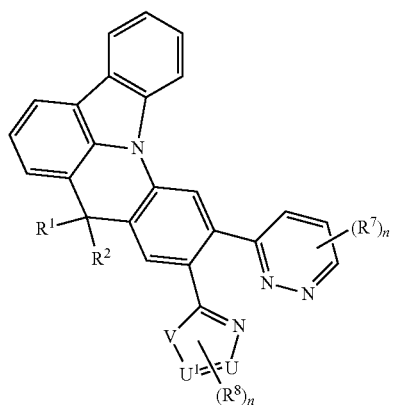
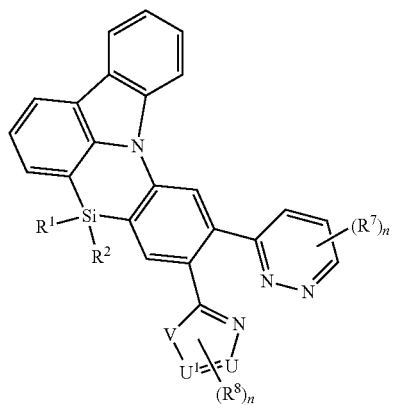
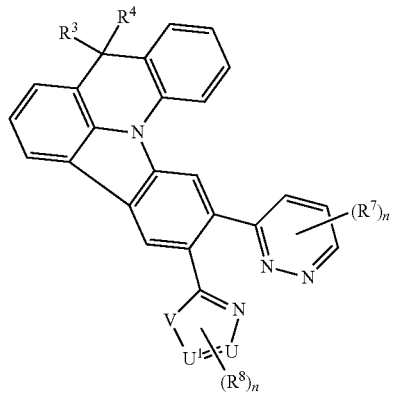
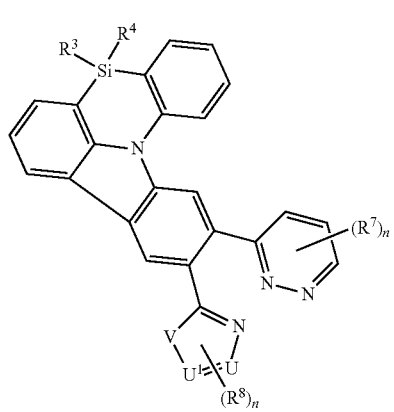
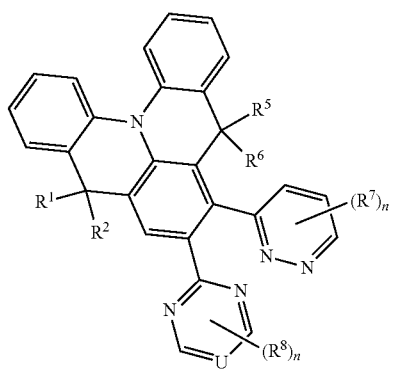
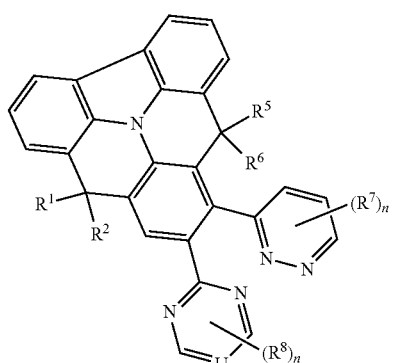
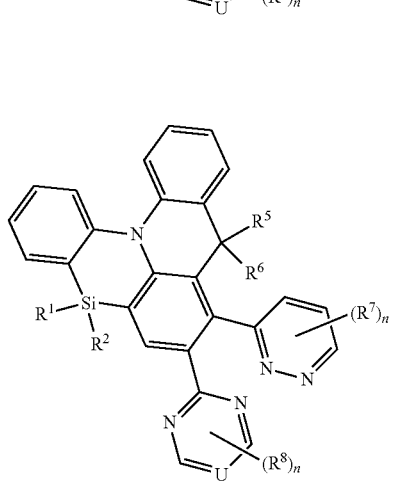
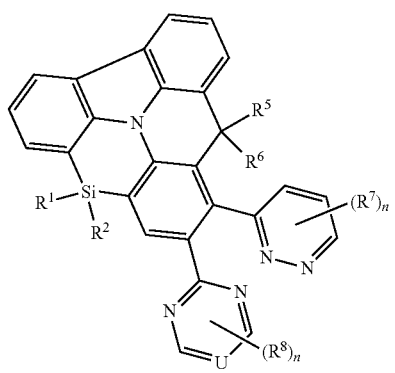

-continued

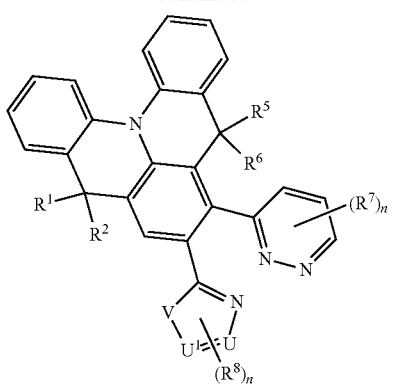

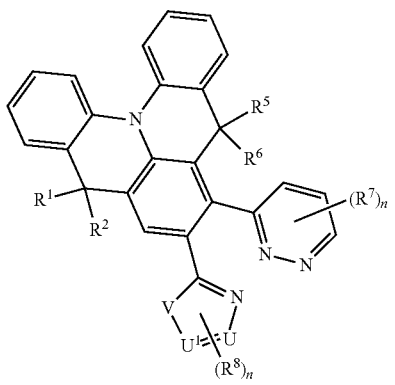

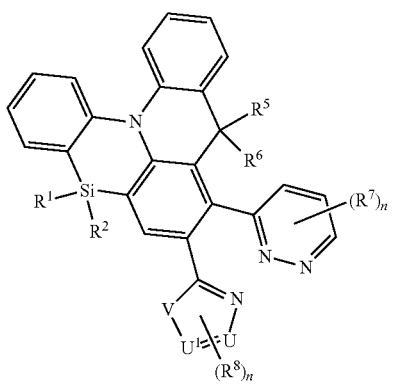

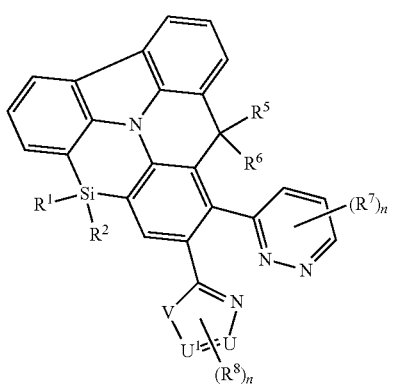

-continued

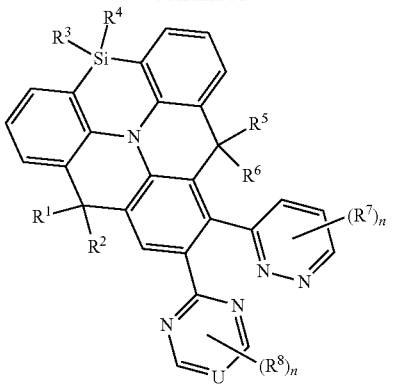

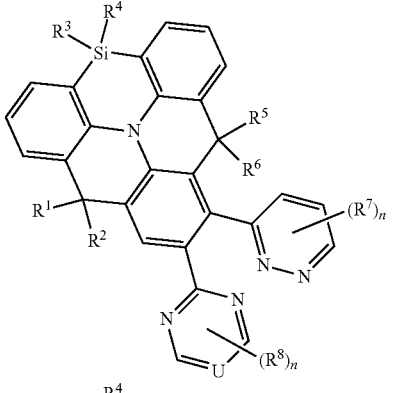

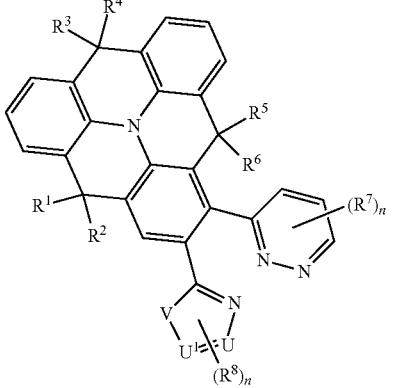

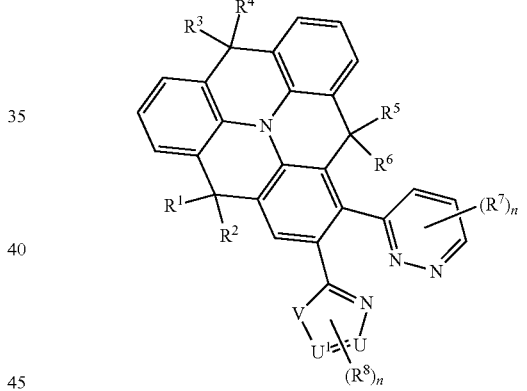

where $R^1$, $R^2$, $R^3$, $R^4$, $R^5$, $R^6$, $R^7$, $(R^7)_n$ and $(R^8)_n$ are as defined above. In some instances, $R^1$, $R^2$, $R^3$, $R^4$, $R^5$, $R^6$, $R^7$, $(R^7)_n$ and $(R^8)_n$ are each independently a hydrogen atom, a deuterium atom, a halogen atom, a hydroxyl group, a thiol group, a nitro group, a cyano group, a substituted or unsubstituted alkyl group, a substituted or unsubstituted haloalkyl group, a substituted or unsubstituted aralkyl group, a substituted or unsubstituted alkenyl group, a substituted or unsubstituted alkynyl group, a substituted or unsubstituted aryl group, an amino group, a mono- or dialkylamino group, a mono- or diarylamino group, a substituted or unsubstituted alkoxy group, a substituted or unsubstituted aryloxy group, a substituted or unsubstituted heteroaryl group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a mercapto group, a sulfo group, a carboxyl group, a hydrazino group, a substituted silyl group, a polymeric group, or a combination thereof. U, $U^1$, and $U^2$ each independently represents N or C of an aromatic ring, with the proviso that when U, $U^1$ and $U^2$ present in the same structure, at least one of them is N. V, and $V^1$ each independently represents NR, O, S, wherein R represents alkyl, cycloalkyl, aryl, heteroaryl. In some instances, $R^1$, $R^2$, $R^3$, $R^4$, $R^5$, $R^6$, $R^7$, $(R^7)_n$, and $(R^8)_n$ are each independently a hydrogen atom, an alkyl group (e.g., methyl, ethyl or propyl group), or an aromatic (e.g., phenyl) group. In some embodiments, $(R^7)_n$ and $(R^8)_n$ include two aromatic groups with the balance of the substituents being hydrogen atoms.

In certain embodiments, structures I, II, or III can include three acceptor moieties and can be represented by the following general structures.

where $L_1$, $L_2$, $R^m$, $R^n$, $R^p$, $R^q$, $R^U$ $A^1$, $A^2$, and $A^3$ have been previously defined, and $R^v$ can represent mono-, di-, tri, or tetra-substitution, and each independently represents one or more of a hydrogen atom, a deuterium atom, a halogen atom, a hydroxyl group, a thiol group, a nitro group, a cyano group, a substituted or unsubstituted alkyl group, a substituted or unsubstituted haloalkyl group, a substituted or unsubstituted aralkyl group, a substituted or unsubstituted alkenyl group, a substituted or unsubstituted alkynyl group, a substituted or unsubstituted aryl group, a substituted or unsubstituted amino group, a substituted or unsubstituted mono- or dialkylamino group, a substituted or unsubstituted mono- or diarylamino group, a substituted or unsubstituted alkoxy group, a substituted or unsubstituted aryloxy group, a substituted or unsubstituted heteroaryl group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a mercapto group, a sulfo group, a carboxyl group, a hydrazino group, a substituted silyl group, a polymeric group, or a combination thereof. Non-limiting examples of the above structures VIII, IX, and X include:

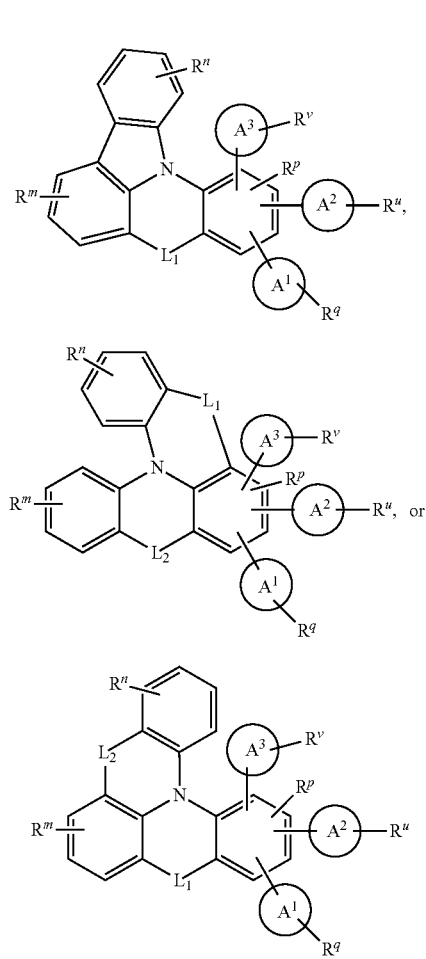

VIII

IX

X

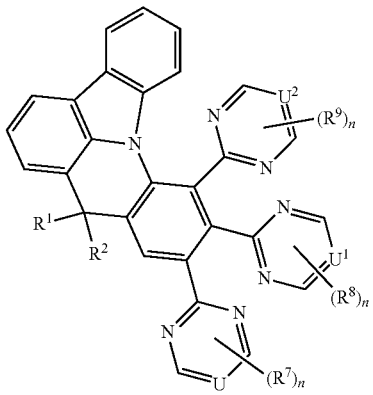

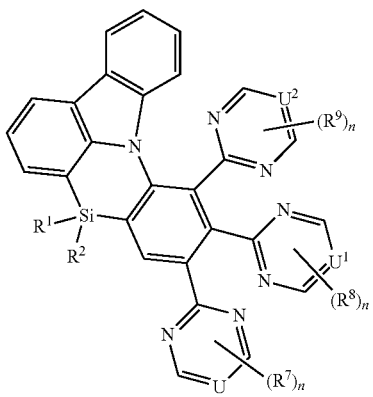

147
-continued
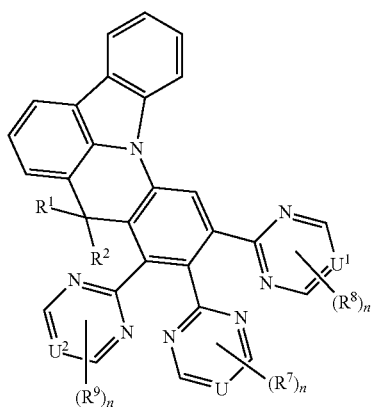
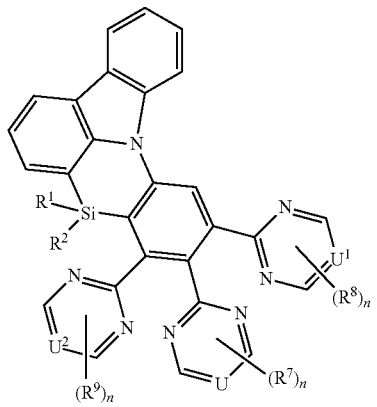
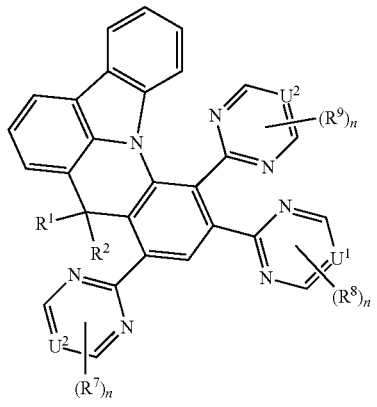
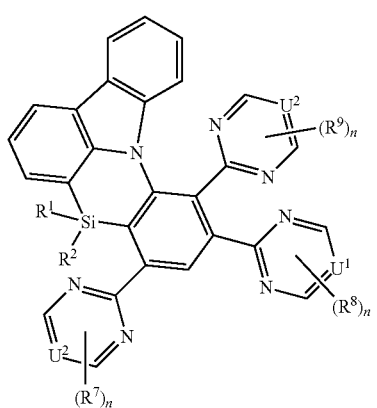
148
-continued
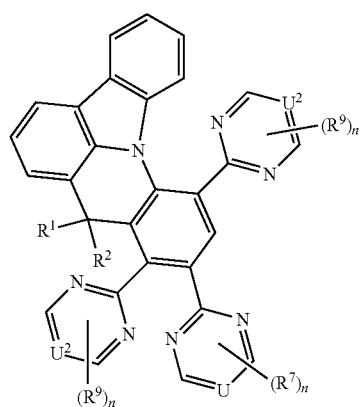
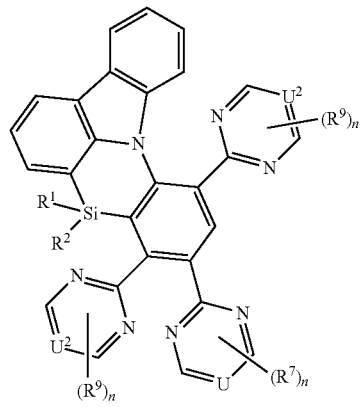
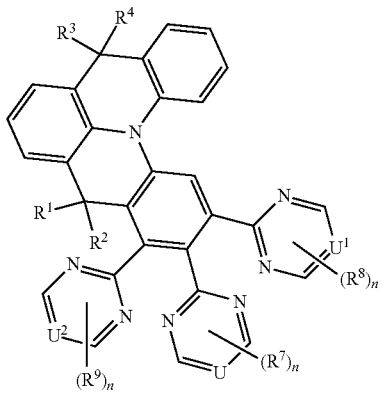
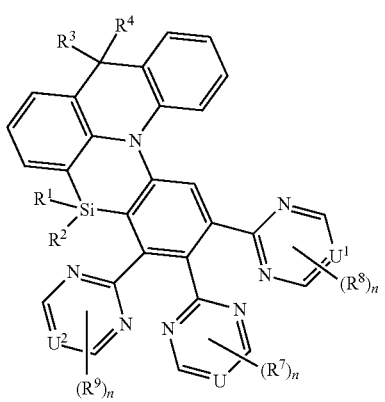

149
-continued
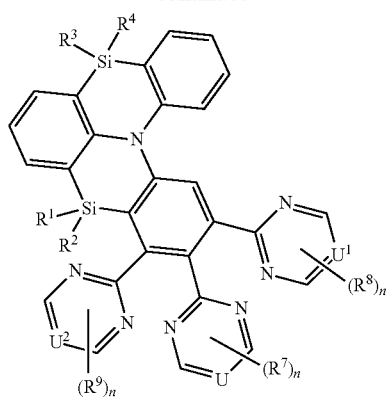
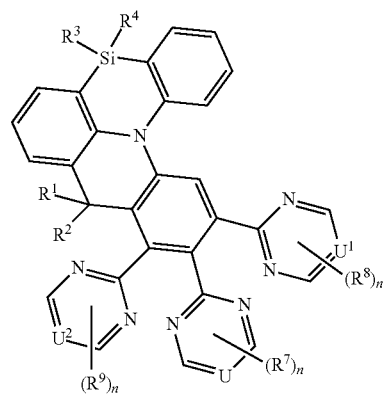
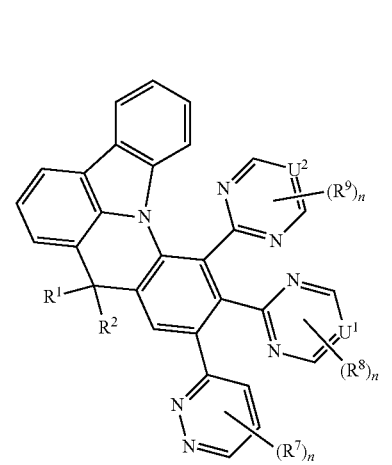
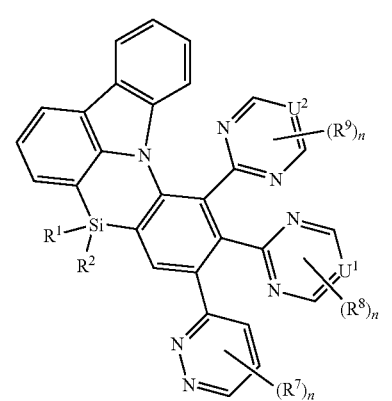
150
-continued
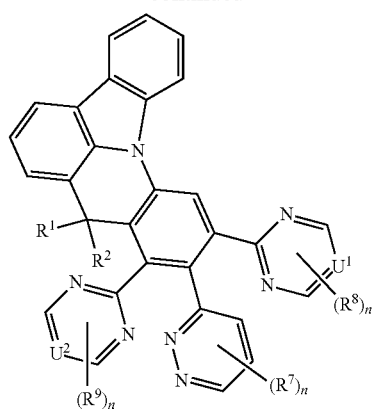
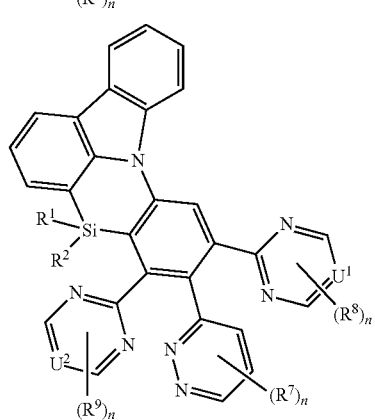
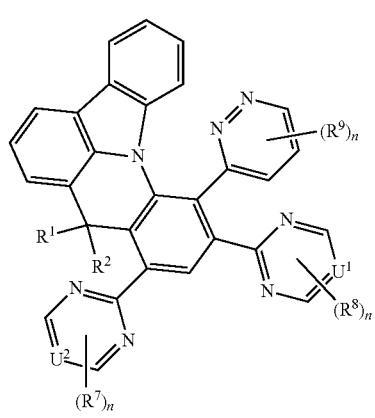
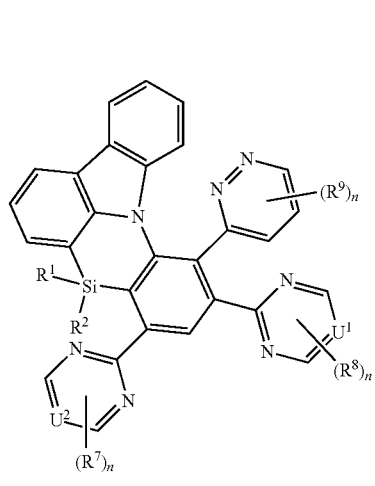

151
-continued
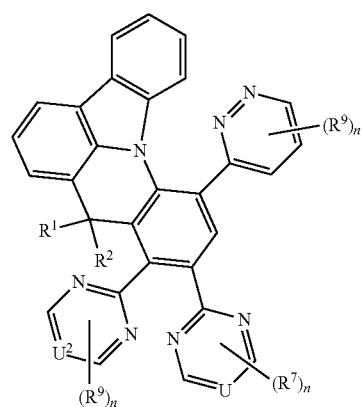
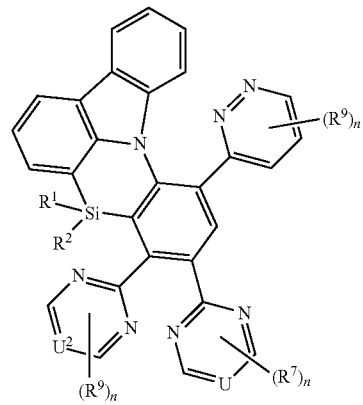
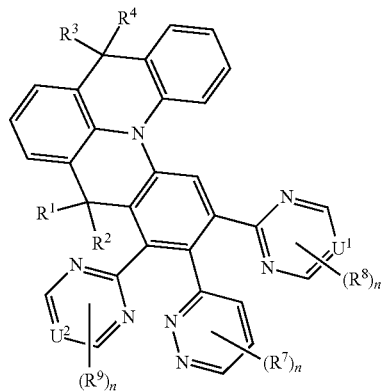
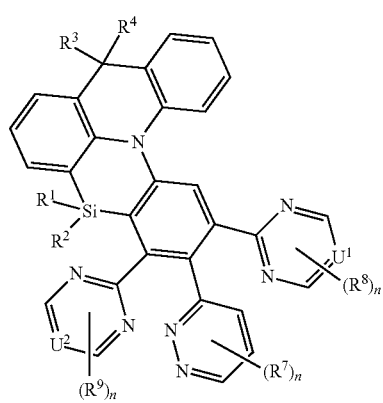
152
-continued
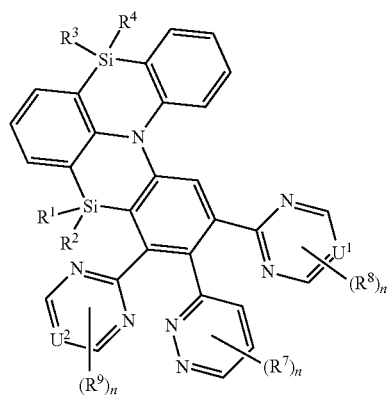
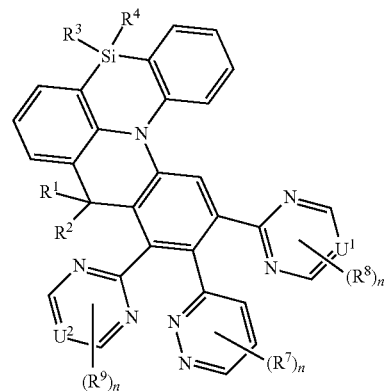
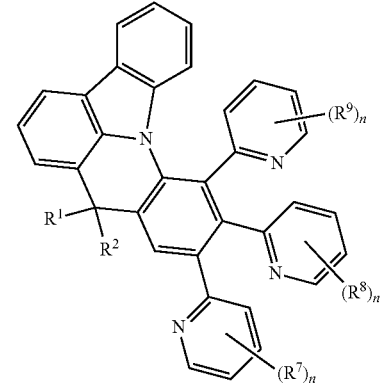
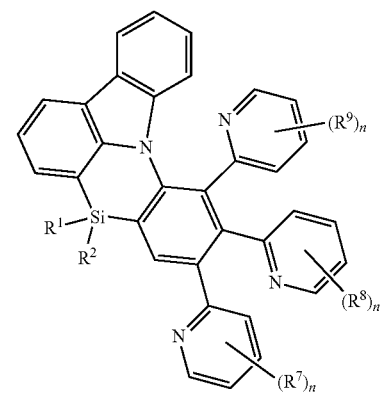

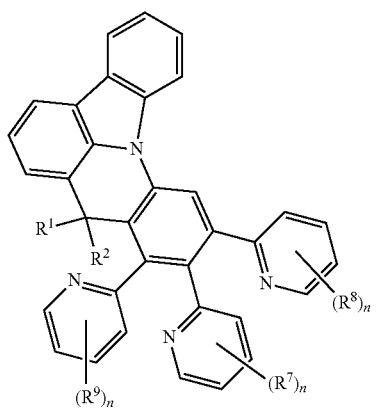
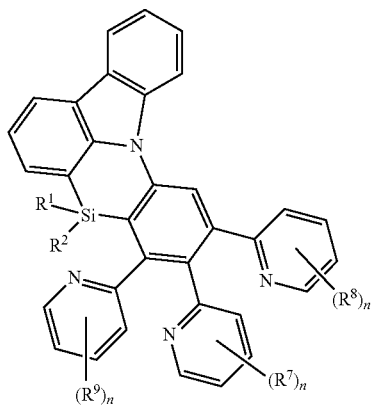
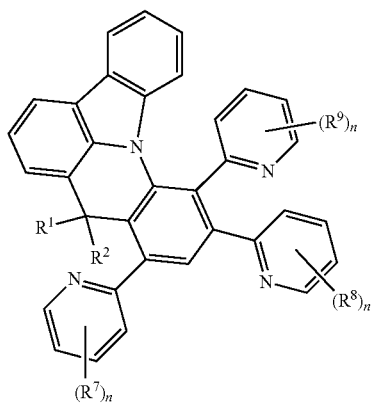
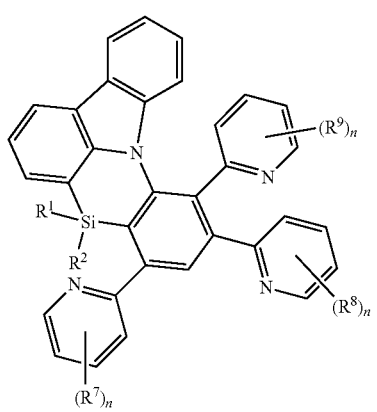
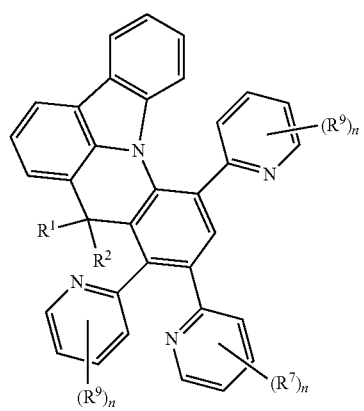
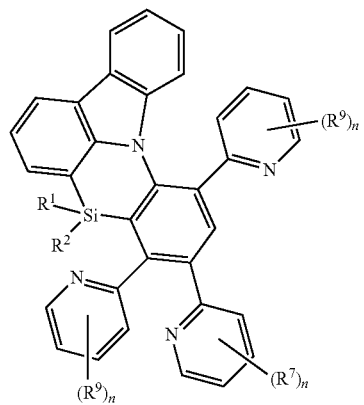
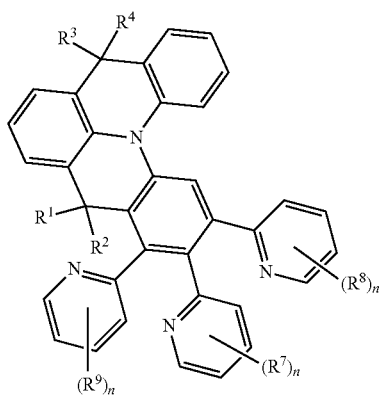
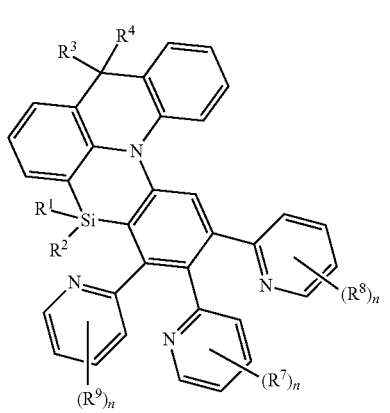

-continued
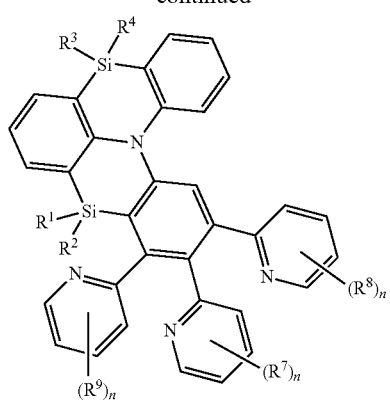
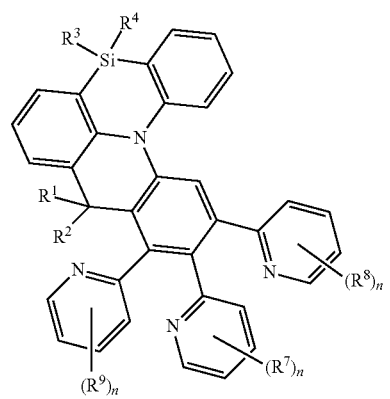
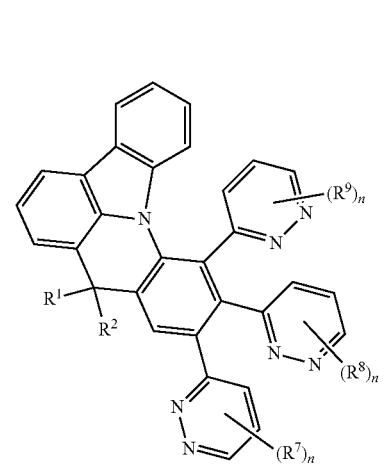
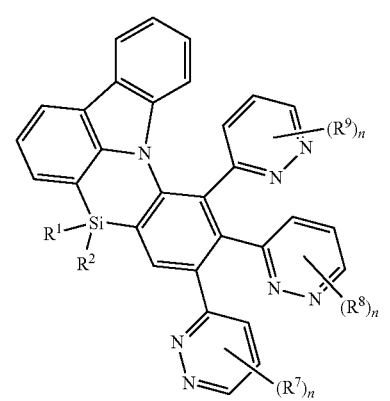
-continued
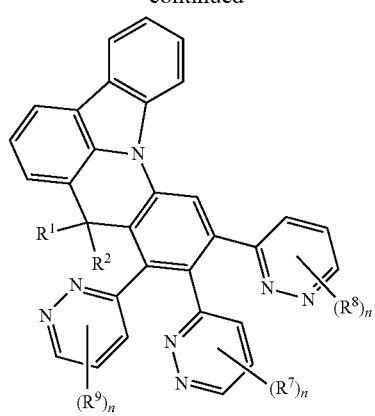
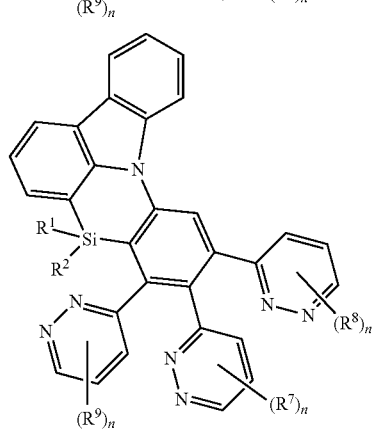
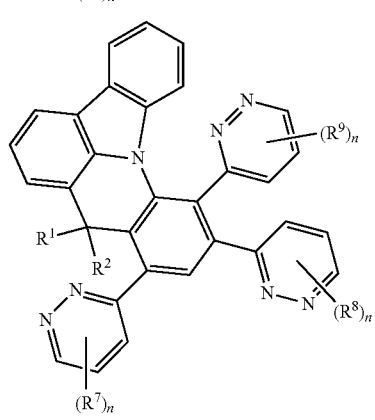
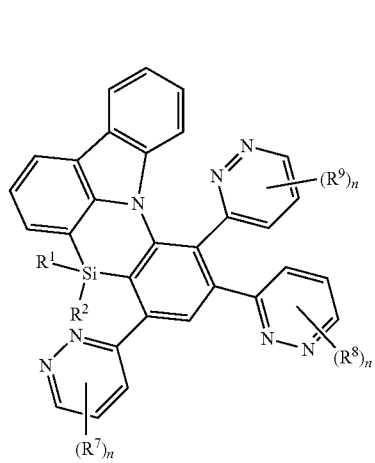

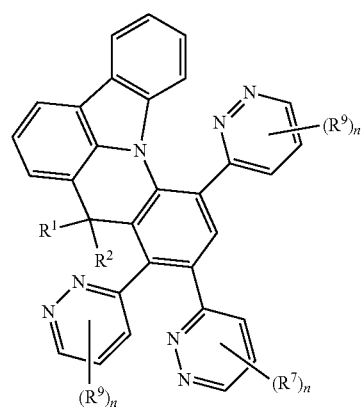
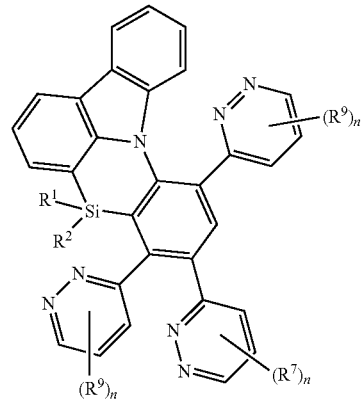
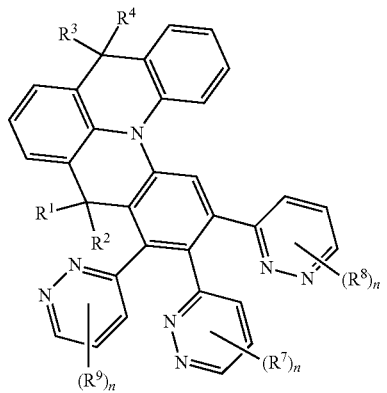
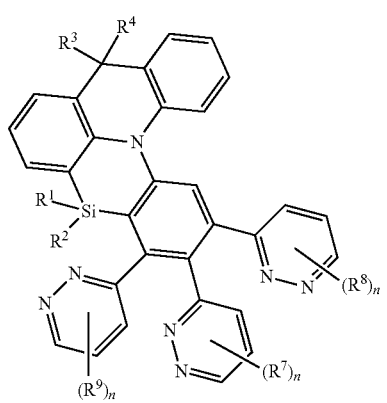
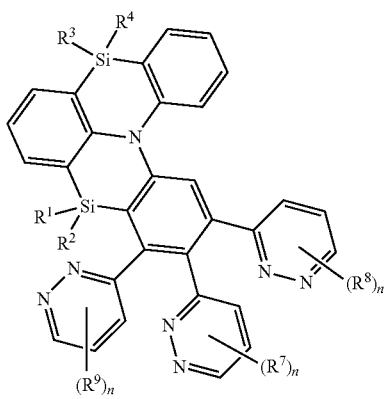
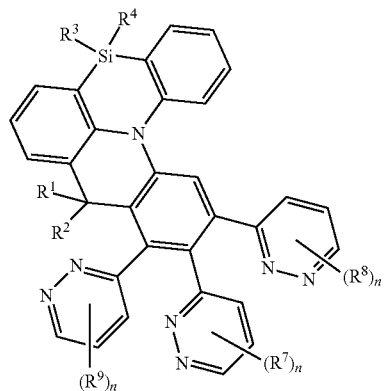
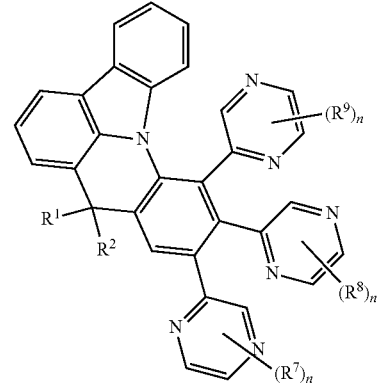
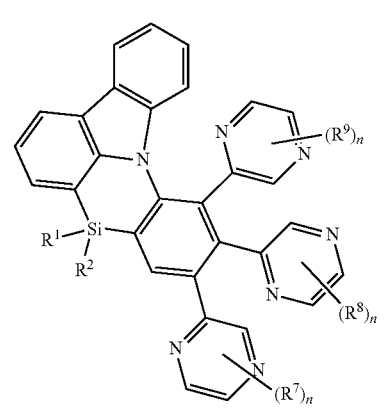

-continued
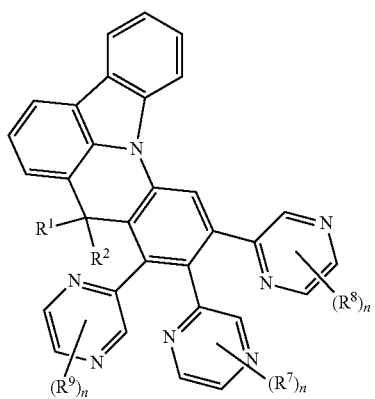
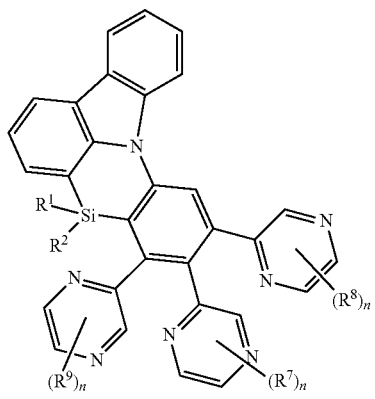
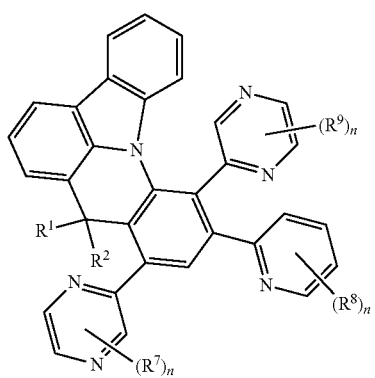
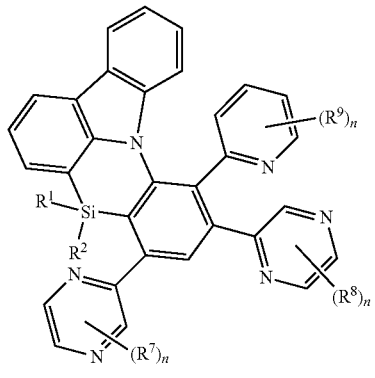
-continued
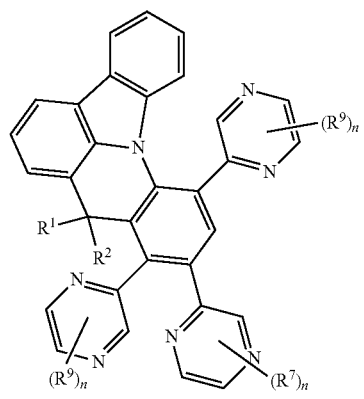
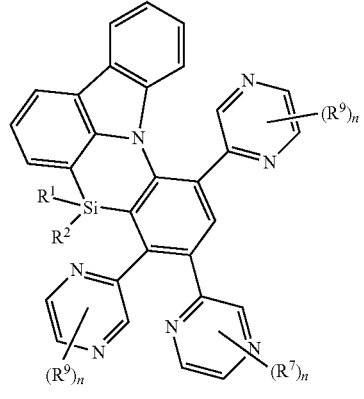
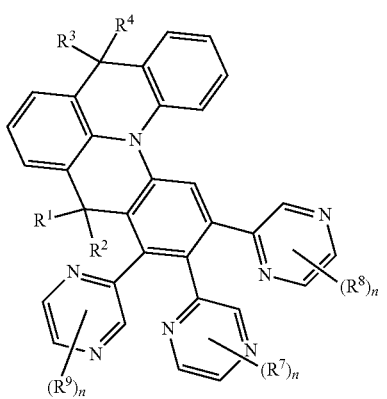
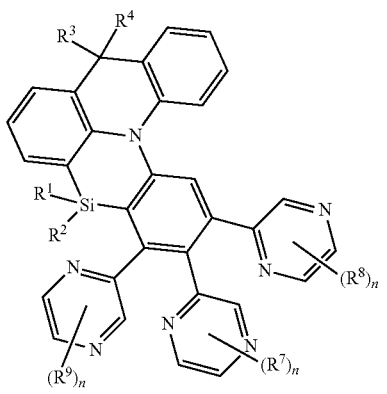

161
-continued
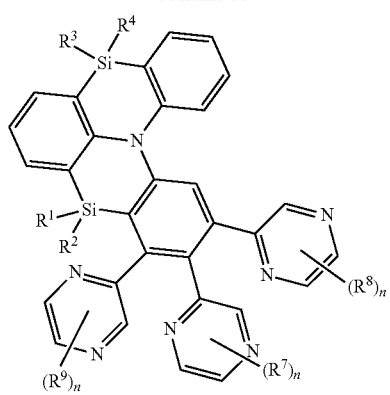
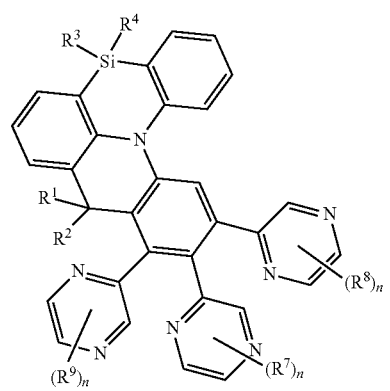
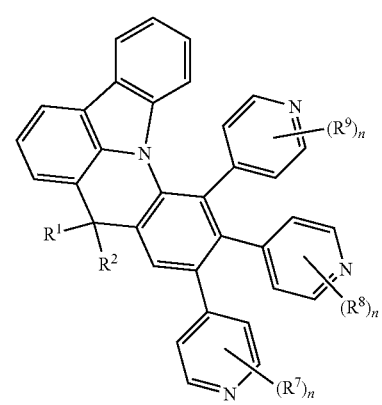
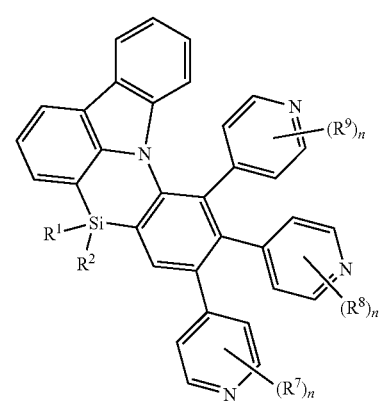
162
-continued
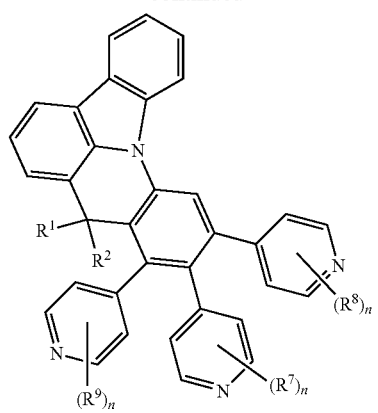
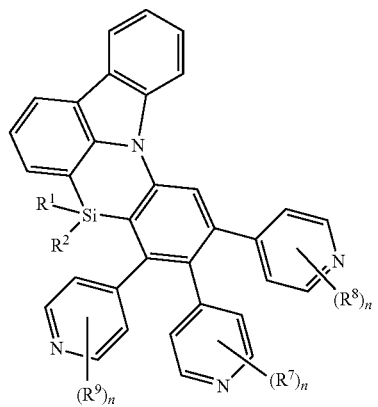
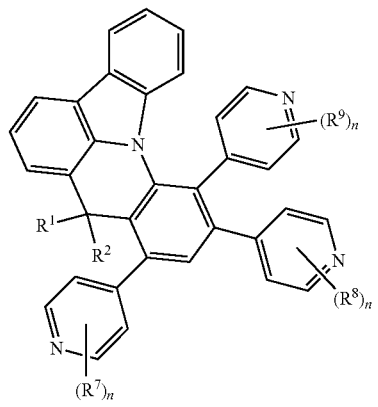
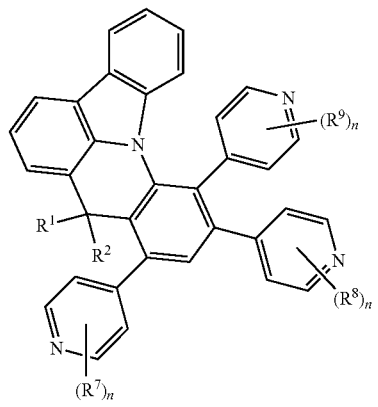

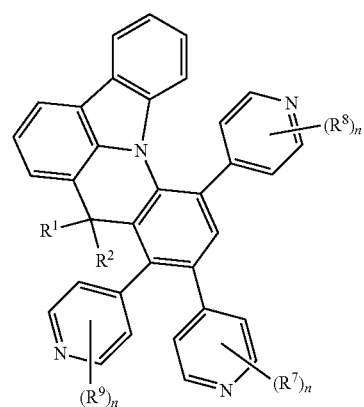
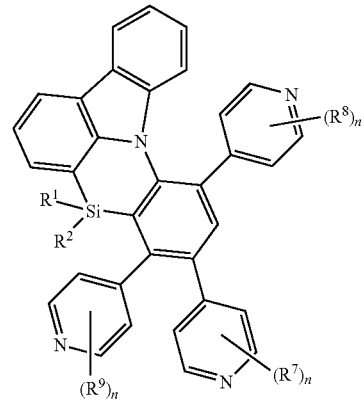
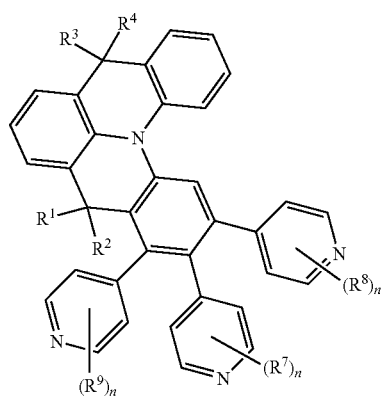
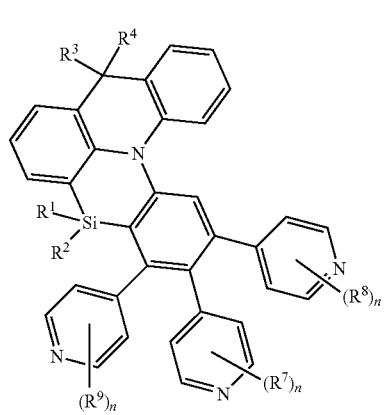
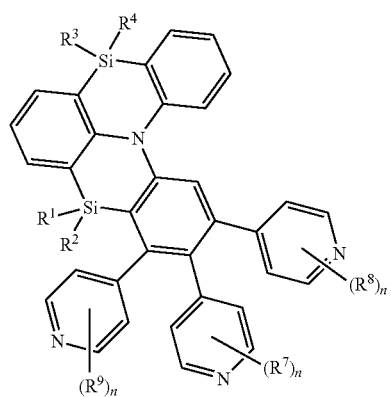
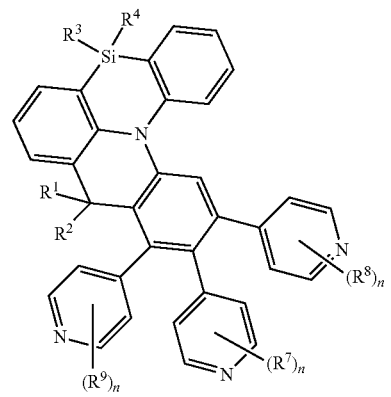
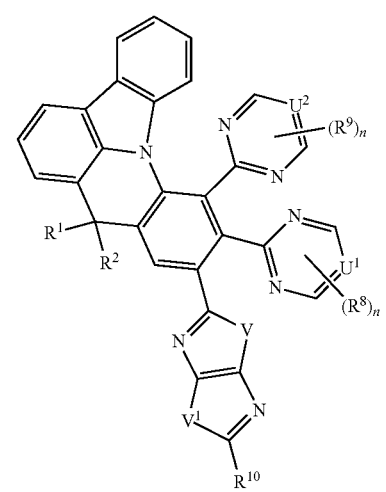

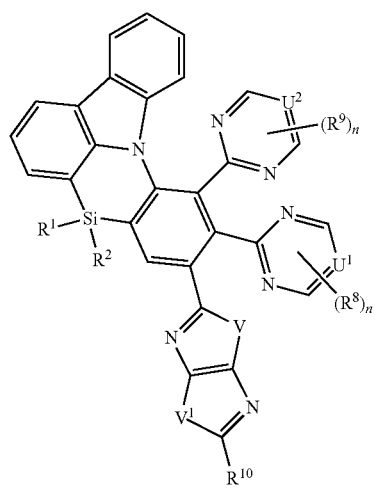
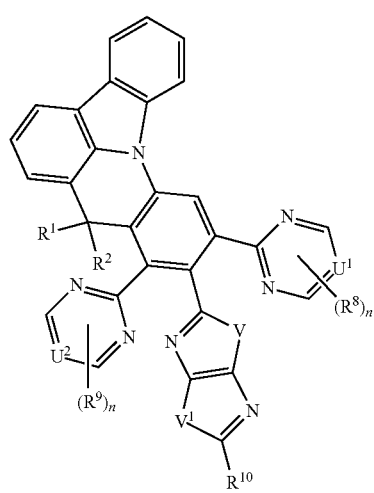
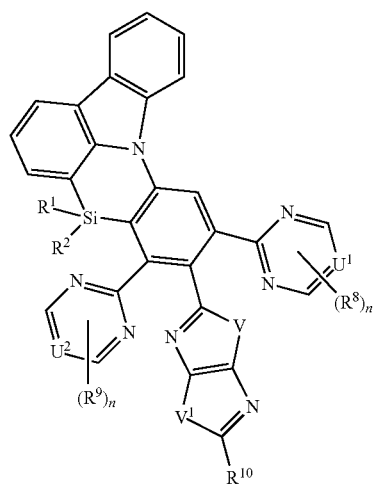
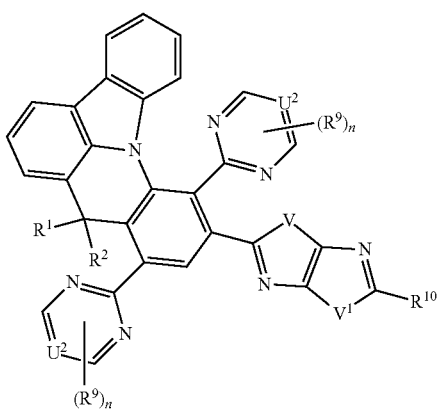
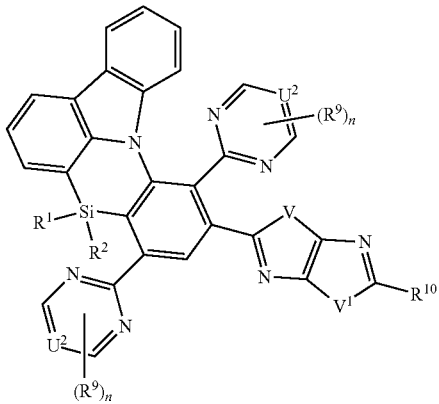
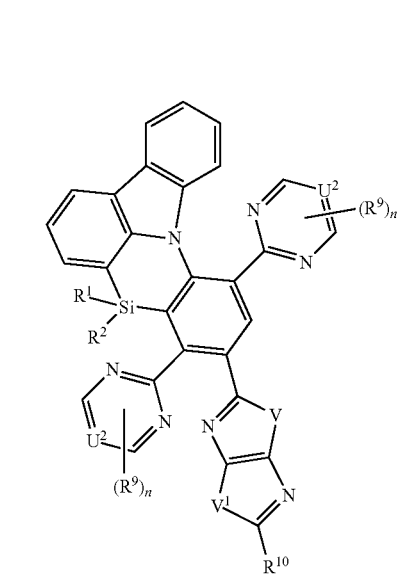

167
-continued
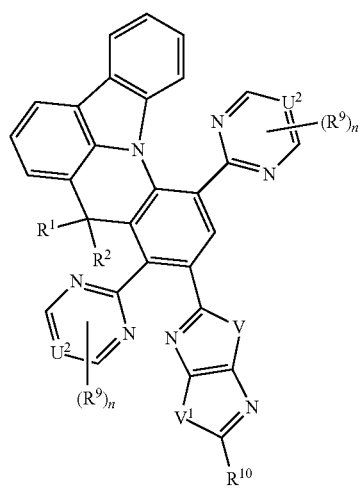
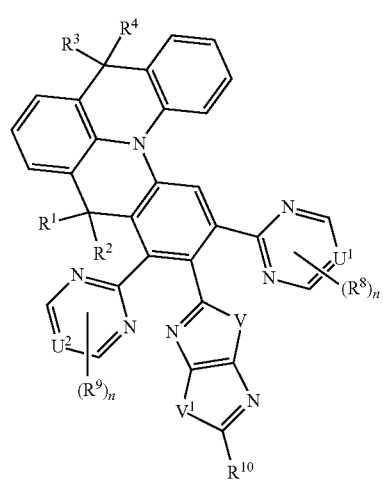
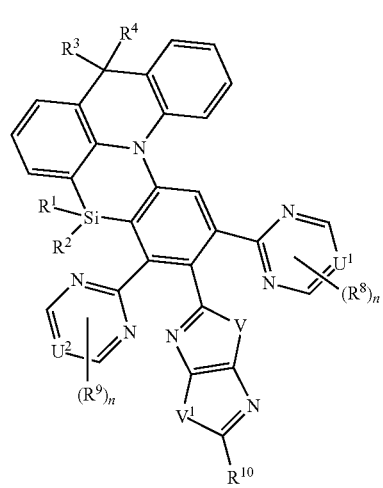
168
-continued
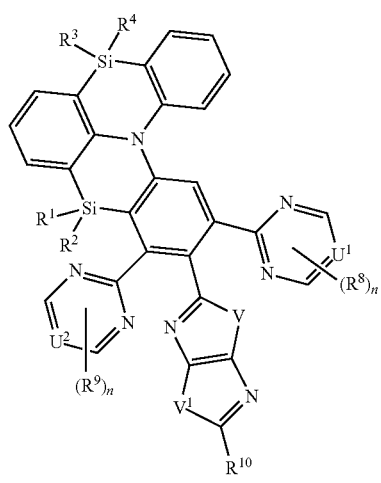
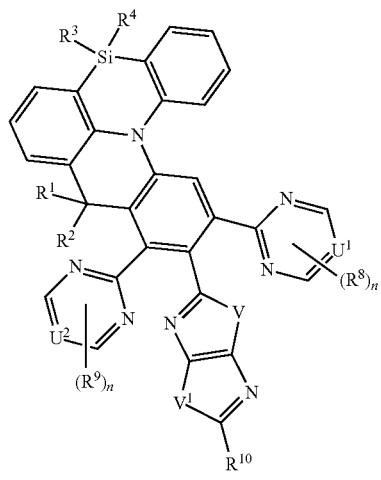
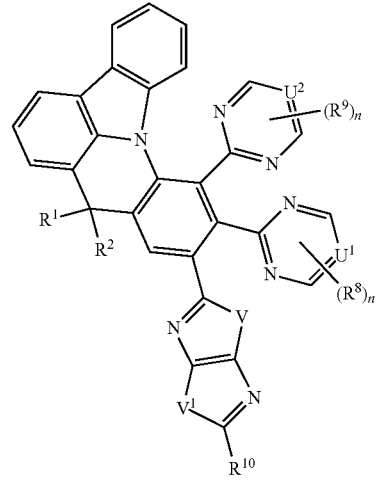

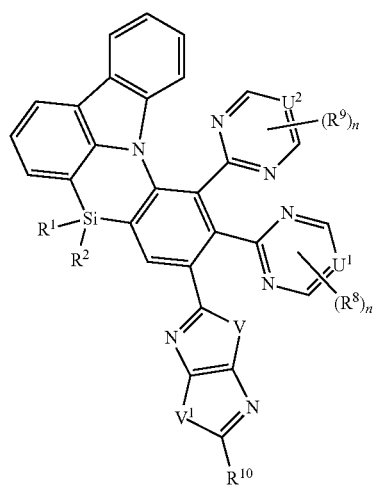
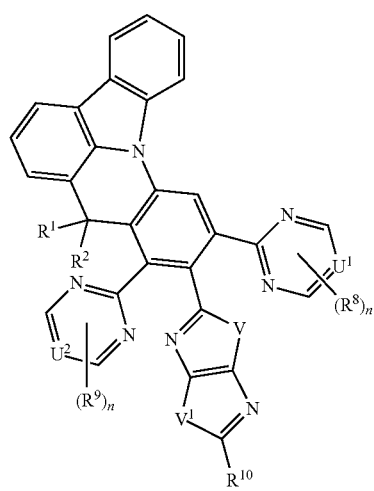
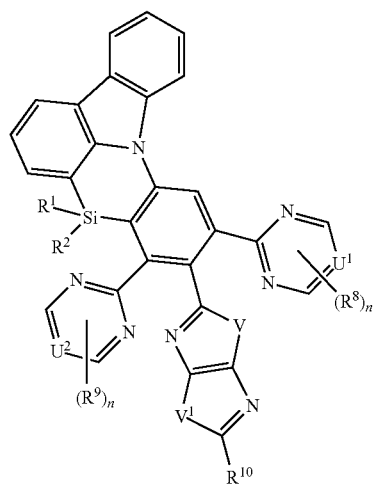
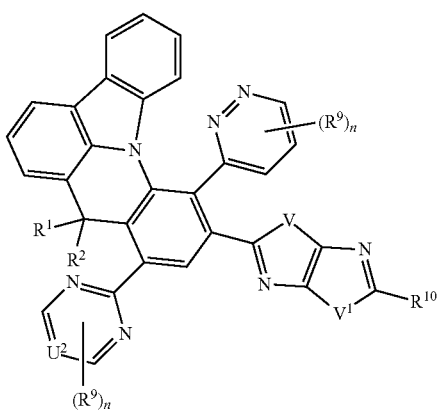
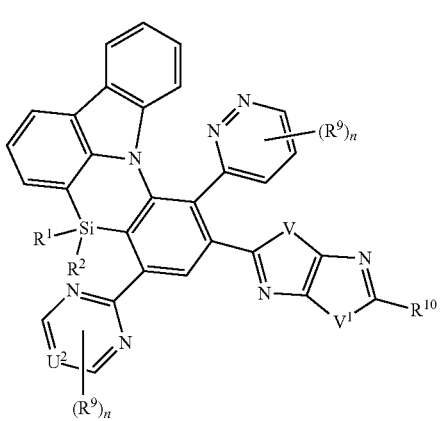
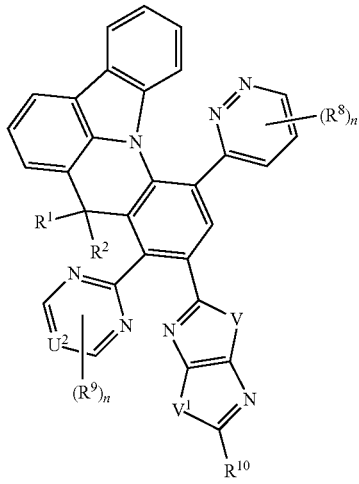

-continued

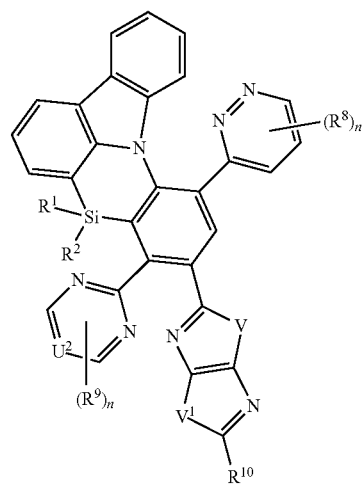

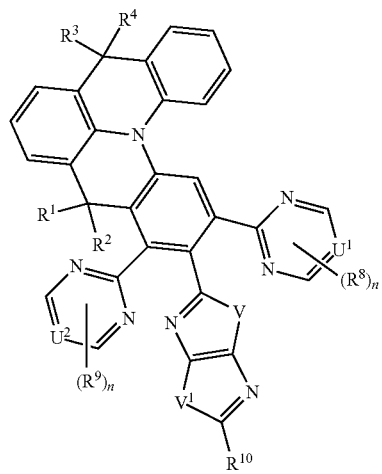

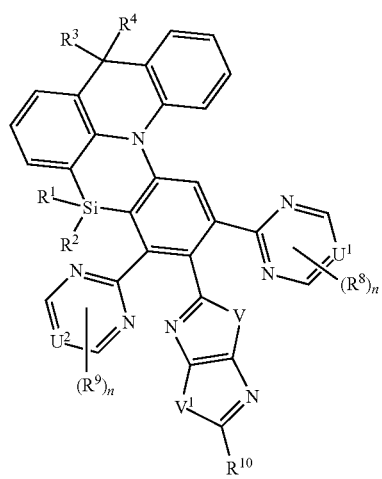

-continued

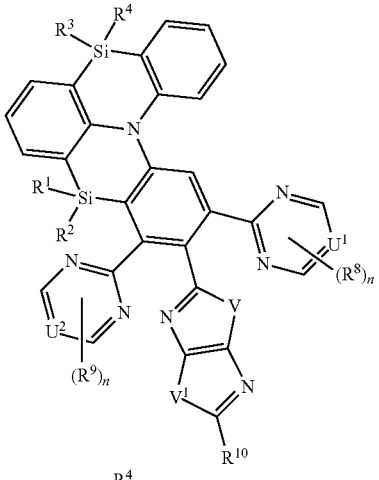

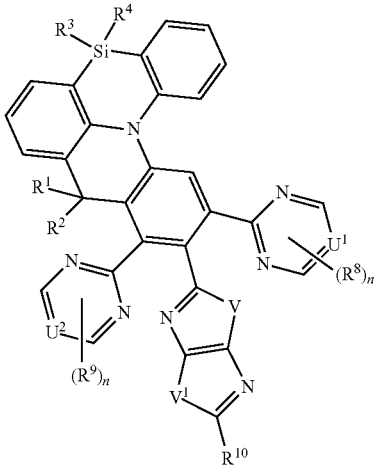

where $R^1$, $R^2$, $R^3$, $R^4$, $R^5$, $R^6$, $R^7$, $(R^7)_n$, $(R^8)_n$, $R^9$, and $R^{10}$ are as defined above. In some instances, $R^1$, $R^2$, $R^3$, $R^4$, $R^5$, $R^6$, $R^7$, $(R^7)_n$, $(R^8)_n$, $R^9$, and $R^{10}$ are each independently a hydrogen atom, a deuterium atom, a halogen atom, a hydroxyl group, a thiol group, a nitro group, a cyano group, a substituted or unsubstituted alkyl group, a substituted or unsubstituted haloalkyl group, a substituted or unsubstituted aralkyl group, a substituted or unsubstituted alkenyl group, a substituted or unsubstituted alkynyl group, a substituted or unsubstituted aryl group, an amino group, a mono- or dialkylamino group, a mono- or diarylamino group, a substituted or unsubstituted alkoxy group, a substituted or unsubstituted aryloxy group, a substituted or unsubstituted heteroaryl group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a mercapto group, a sulfo group, a carboxyl group, a hydrazino group, a substituted silyl group, a polymeric group, or a combination thereof. U, $U^1$, and $U^2$ each independently represents N or C of an aromatic ring, with the proviso that when U, $U^1$ and $U^2$ present in the same structure, at least one of them is N. V, and $V^1$ each independently represents NR, O, S, where R can be an alkyl, cycloalkyl, aryl, heteroaryl. In some instances, $R^1$, $R^2$, $R^3$, $R^4$, $R^5$, $R^6$, $R^7$, $(R^7)_n$, $(R^8)_n$, $R^9$, and $R^{10}$ are each independently a hydrogen atom, an alkyl group (e.g., methyl, ethyl or propyl group), or an aromatic (e.g., phenyl) group. In some embodiments, $(R^7)_n$ and $(R^8)_n$ include two aromatic groups with the balance of the substituents being hydrogen atoms.

In some embodiments, the compounds of the present invention can be represented by the following general structures:

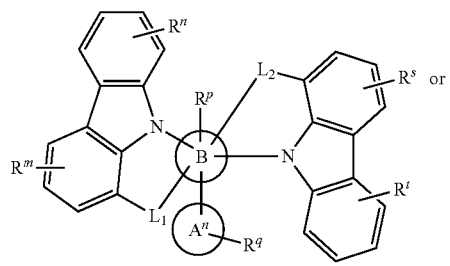

XI

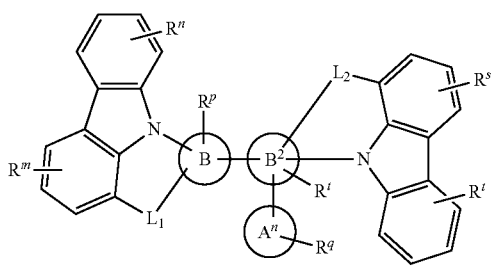

XII where $L_1$, $L_2$, $R^m$, $R^n$, $R^p$, $R^q$, and $A^n$, have been previously defined. B and $B^2$ can each be a substituted or unsubstituted electron-deficient aromatic group and can in combination with $A^n$ contribute to the LUMO of the level of the compound. $R^s$ and $R^t$ can each independently represents mono-, di-, tri, or tetra-substitution, and each independently represents one or more of a hydrogen atom, a deuterium atom, a halogen atom, a hydroxyl group, a thiol group, a nitro group, a cyano group, a substituted or unsubstituted alkyl group, a substituted or unsubstituted haloalkyl group, a substituted or unsubstituted aralkyl group, a substituted or unsubstituted alkenyl group, a substituted or unsubstituted alkynyl group, a substituted or unsubstituted aryl group, a substituted or unsubstituted amino group, a substituted or unsubstituted mono- or dialkylamino group, a substituted or unsubstituted mono- or diarylamino group, a substituted or unsubstituted alkoxy group, a substituted or unsubstituted aryloxy group, a substituted or unsubstituted heteroaryl group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a mercapto group, a sulfo group, a carboxyl group, a hydrazino group, a substituted silyl group, a polymeric group, or a combination thereof.

Non-limiting examples of structures XI and XII are:

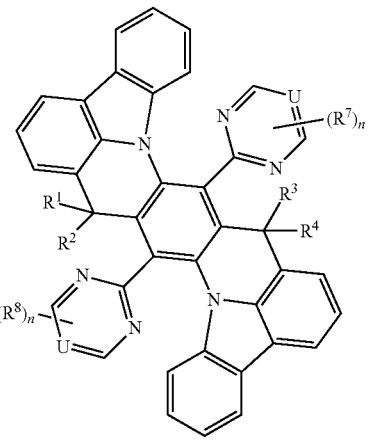

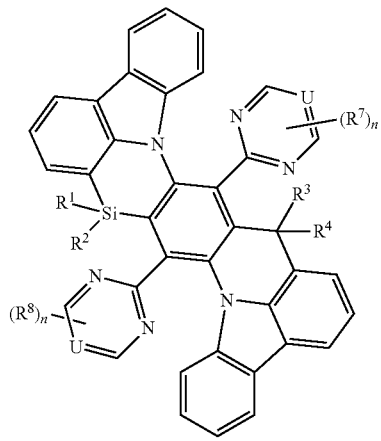

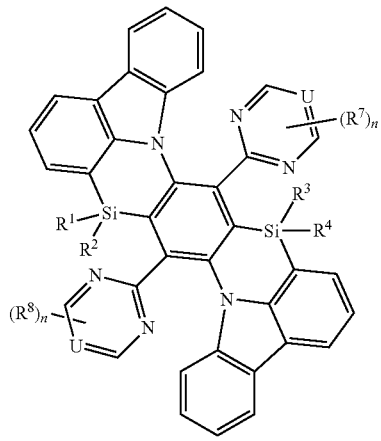

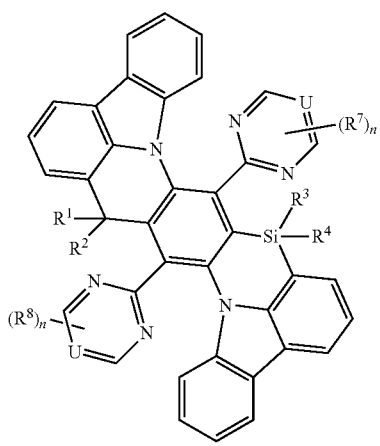
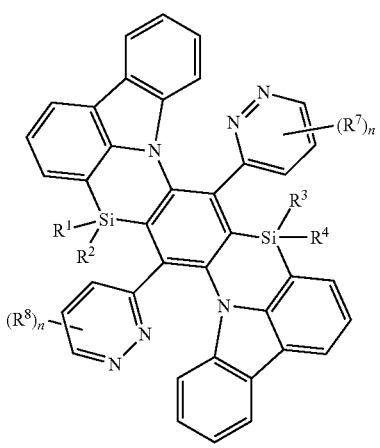
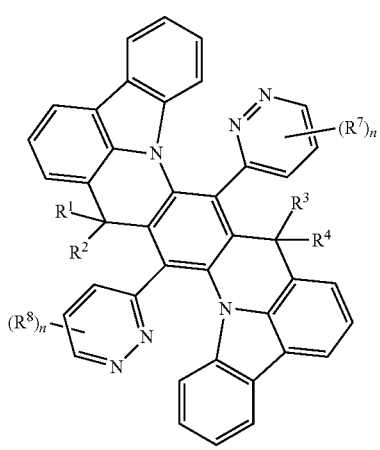
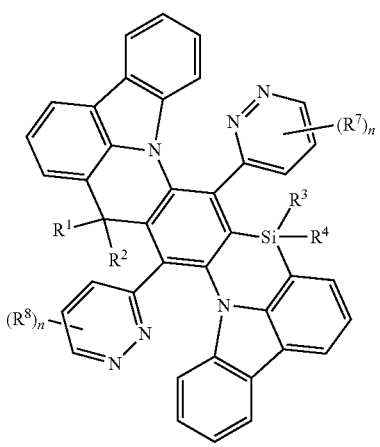
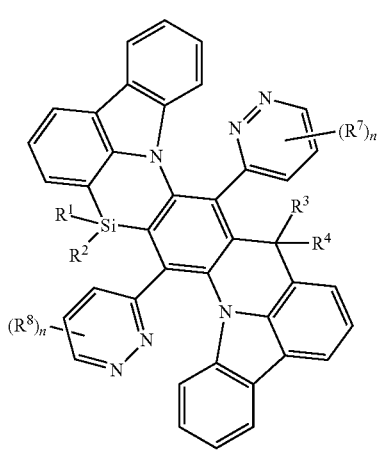
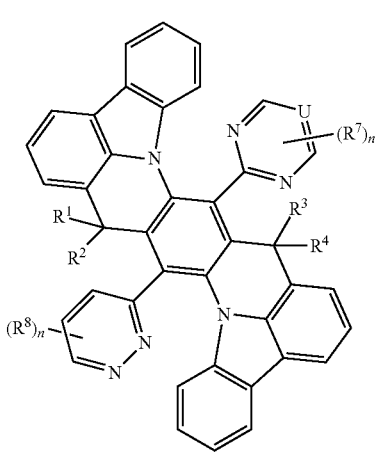

177
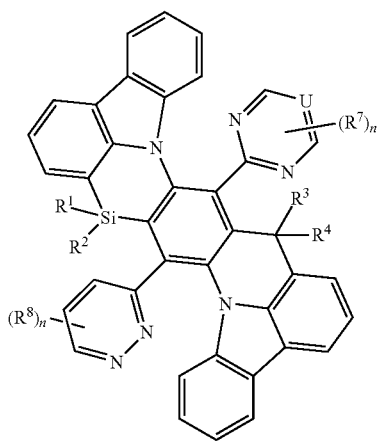
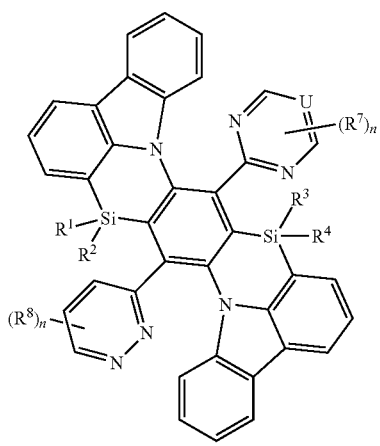
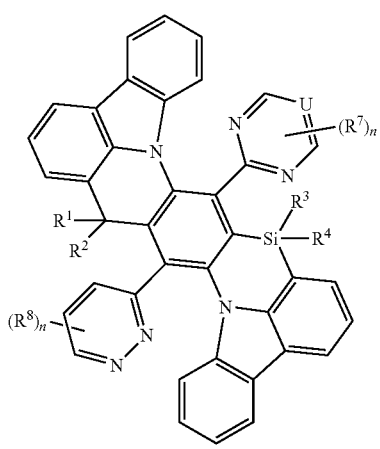
178
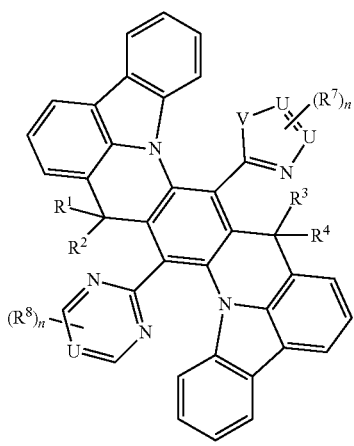
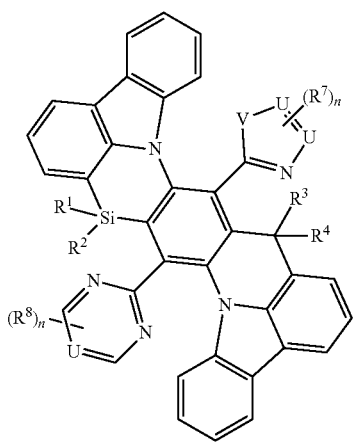
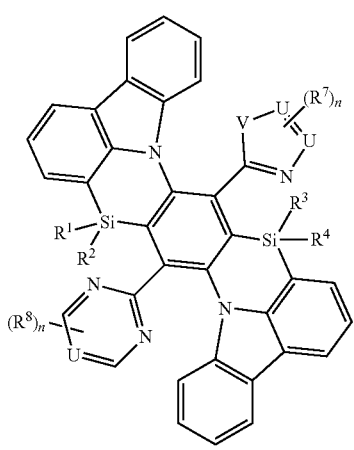

179
-continued
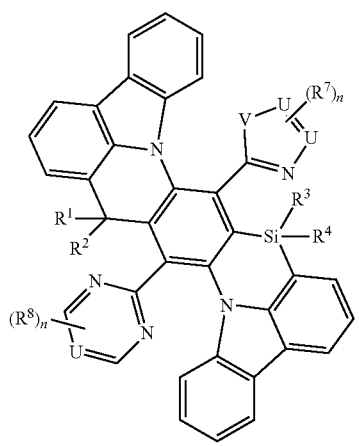
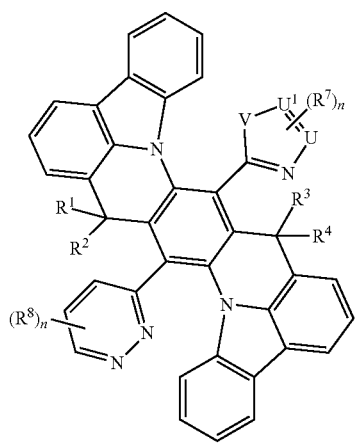
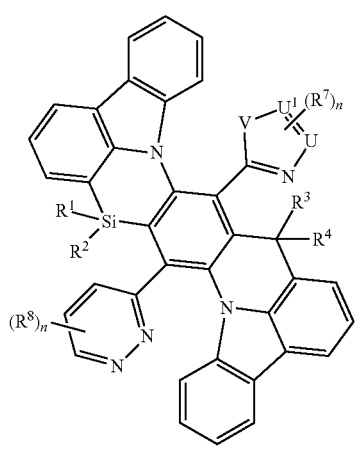
180
-continued
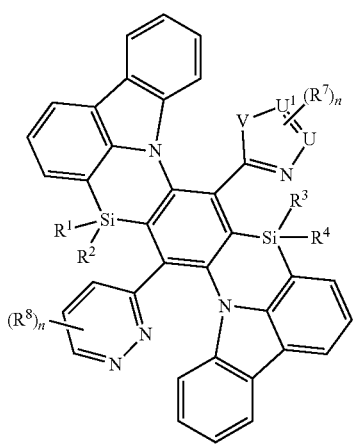
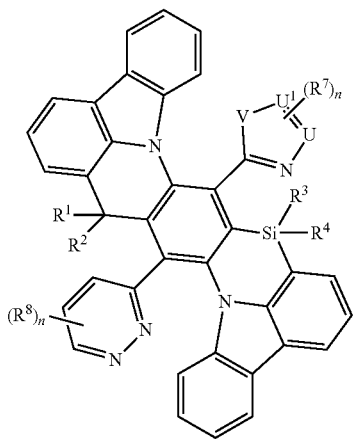
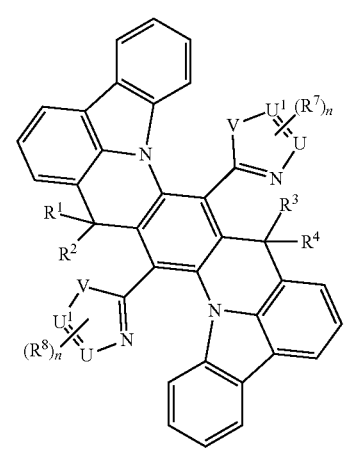

-continued
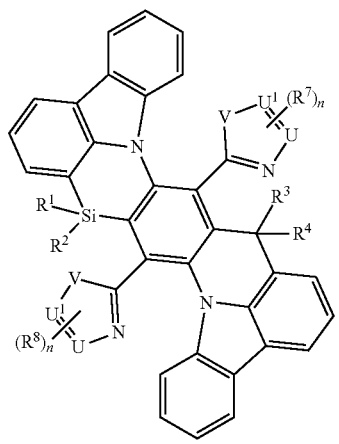
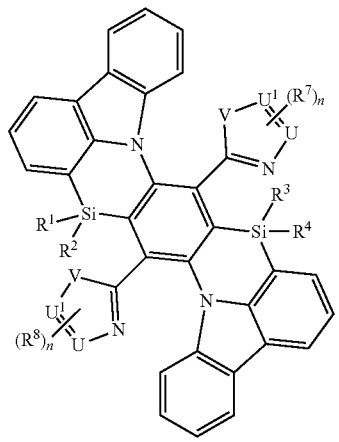
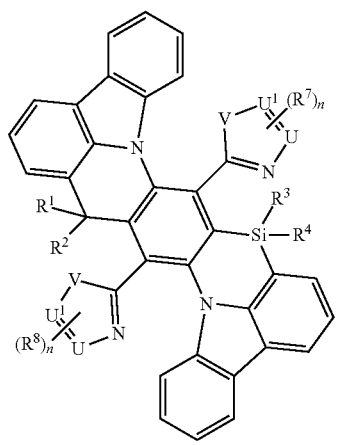
-continued
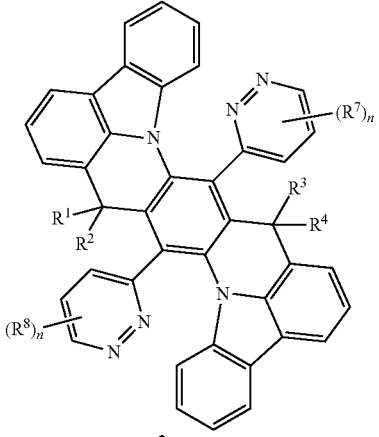
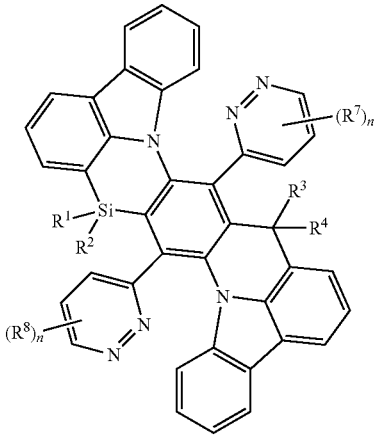
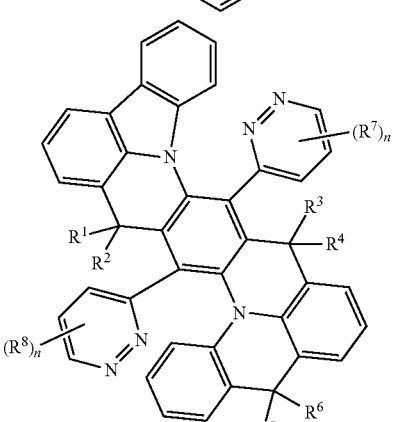
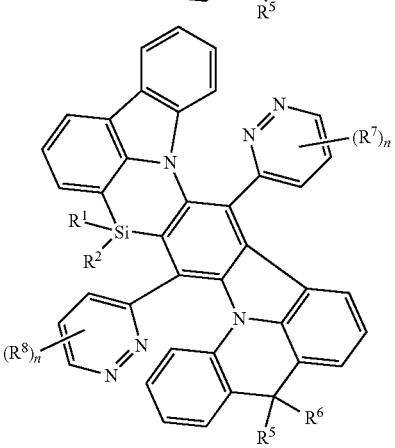

-continued
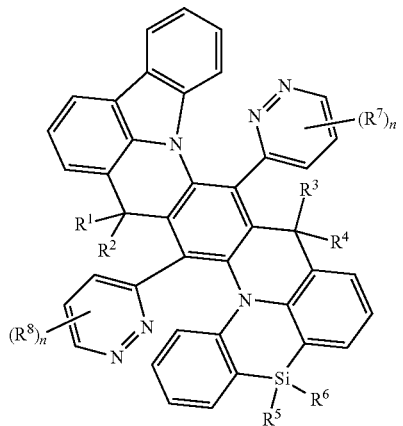
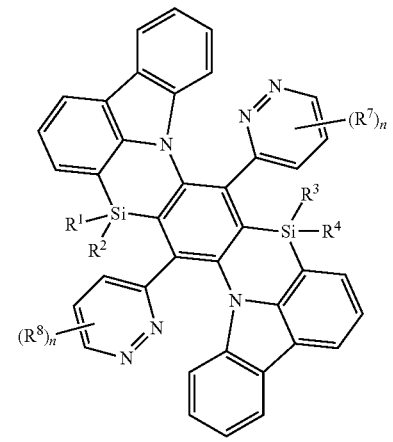
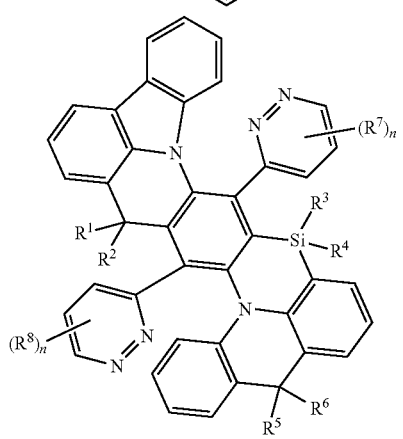
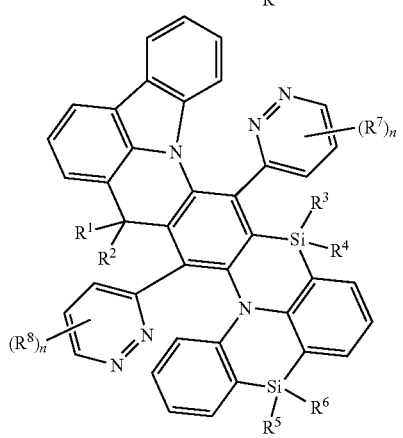
-continued
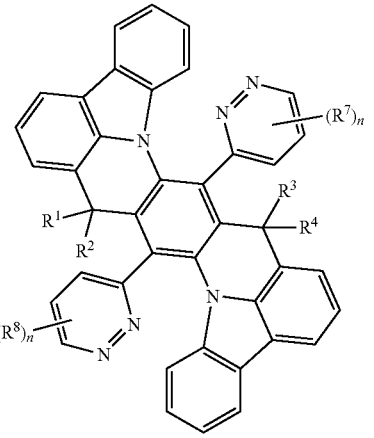
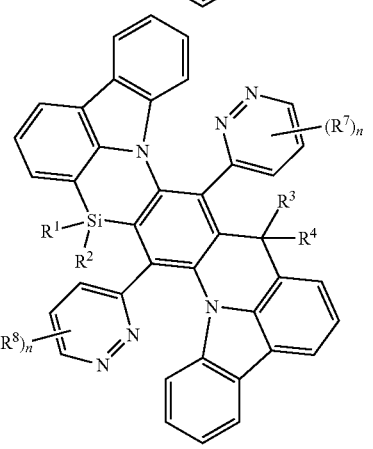
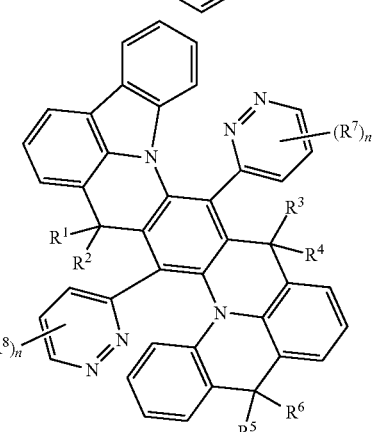
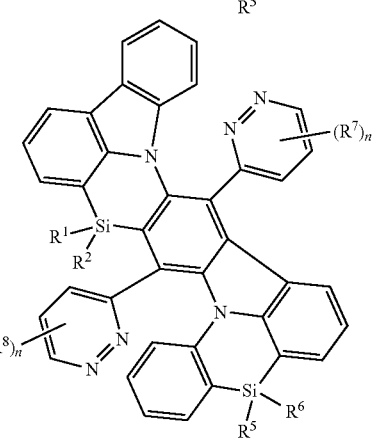

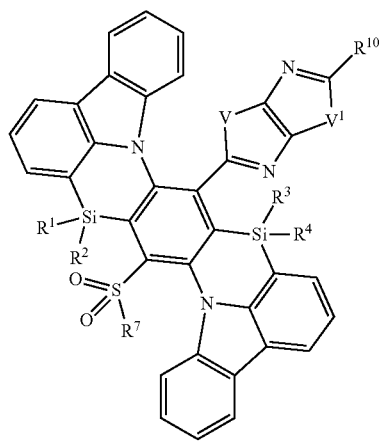
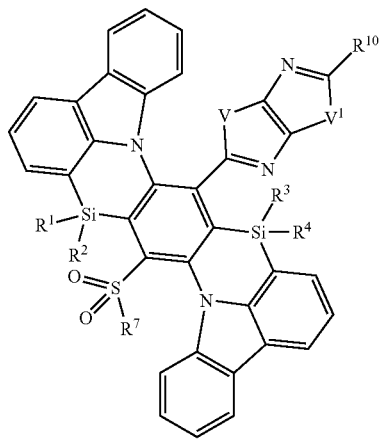
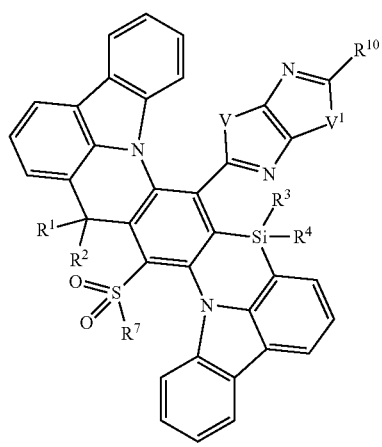
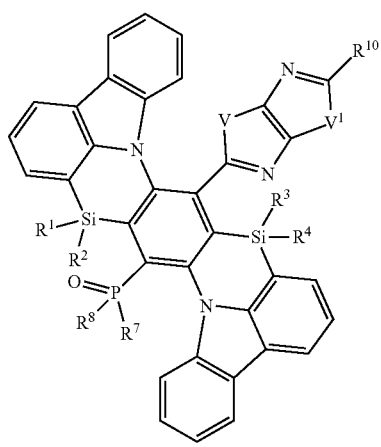
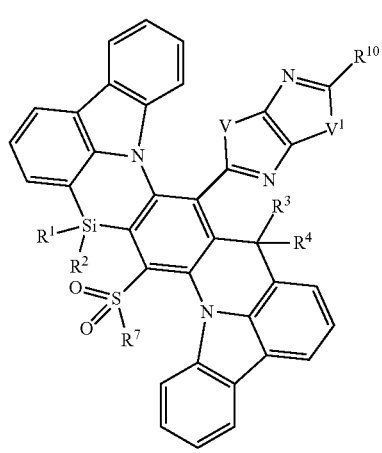
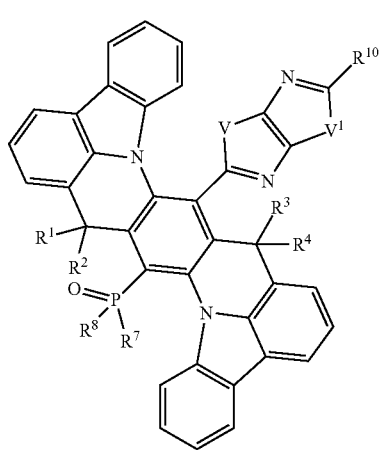

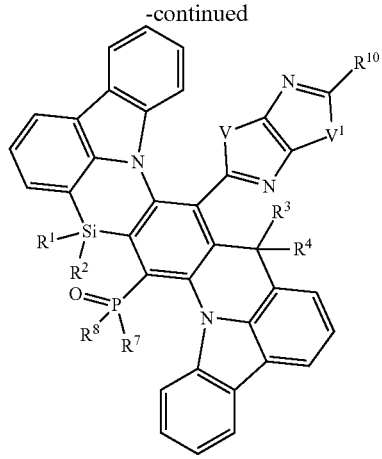

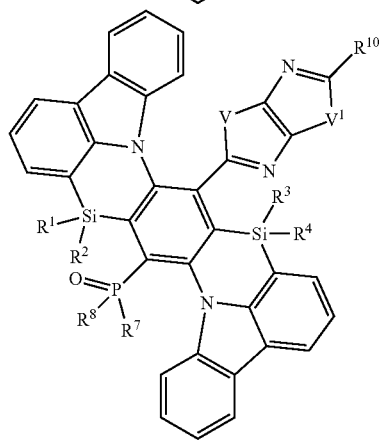

where $R^1$, $R^2$, $R^3$, $R^4$, $R^5$, $R^6$, $R^7$, $(R^7)_n$, $(R^8)_n$, $R^9$, and $R^{10}$ are as defined above. In some instances, $R^1$, $R^2$, $R^3$, $R^4$, $R^5$, $R^6$, $R^7$ $(R^7)_n$, $(R^8)_n$, $R^9$, and $R^{10}$ are each independently a hydrogen atom, a deuterium atom, a halogen atom, a hydroxyl group, a thiol group, a nitro group, a cyano group, a substituted or unsubstituted alkyl group, a substituted or unsubstituted haloalkyl group, a substituted or unsubstituted aralkyl group, a substituted or unsubstituted alkenyl group, a substituted or unsubstituted alkynyl group, a substituted or unsubstituted aryl group, an amino group, a mono- or dialkylamino group, a mono- or diarylamino group, a substituted or unsubstituted alkoxy group, a substituted or unsubstituted aryloxy group, a substituted or unsubstituted heteroaryl group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a mercapto group, a sulfo group, a carboxyl group, a hydrazino group, a substituted silyl group, a polymeric group, or a combination thereof. U, $U^1$, and $U^2$ each independently represents N or C of an aromatic ring, with the proviso that when U, $U^1$ and $U^2$ present in the same structure, at least one of them is N. V, and $V^1$ each independently represents NR, O, S, where R can be an alkyl, cycloalkyl, aryl, heteroaryl. In some instances, $R^1$, $R^2$, $R^3$, $R^4$, $R^5$, $R^6$, $R^7$, $(R^7)_n$, $(R^8)_n$, $R^9$, and $R^{10}$ are each independently a hydrogen atom, an alkyl group (e.g., methyl, ethyl, or propyl group), or an aromatic (e.g., phenyl) group.

In some embodiment, each B can include one or more acceptors $A^n$, and be represented by the following general structures.

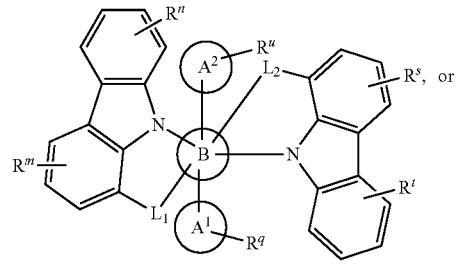

XIII

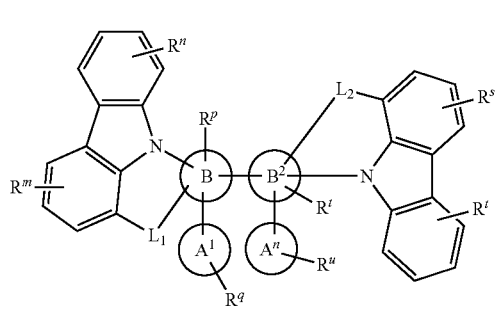

XIV where $L_1$, $L_2$, $R^m$, $R^n$, $R^p$, $R^q$, $R^s$, $R^t$, $R^u$, $A^1$, $A^2$, and B are as previously defined. Non-limiting examples of the above structures XIII and XIV include:

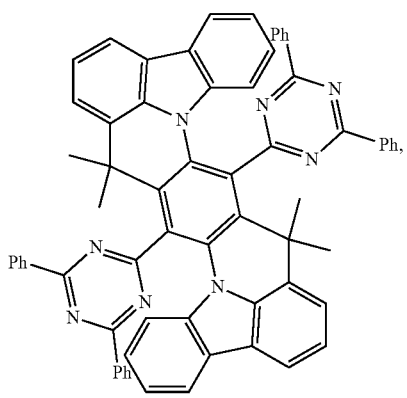

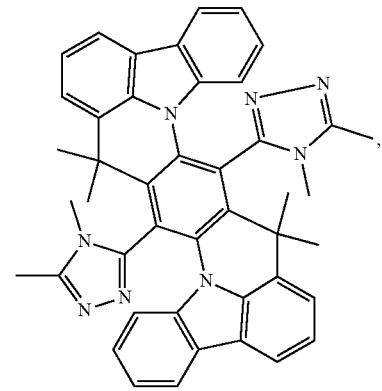

189
-continued
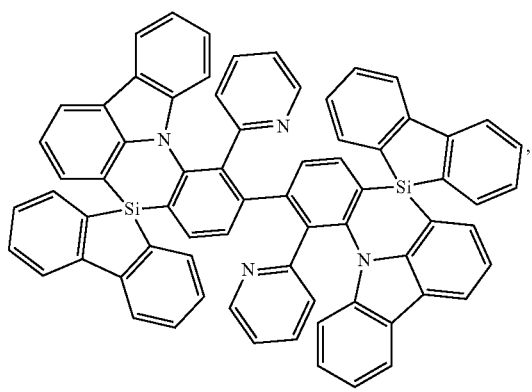
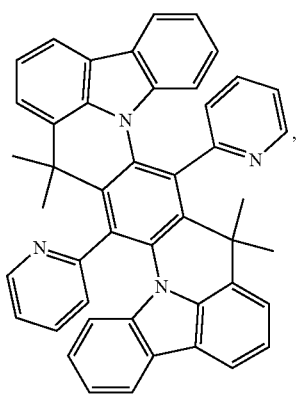
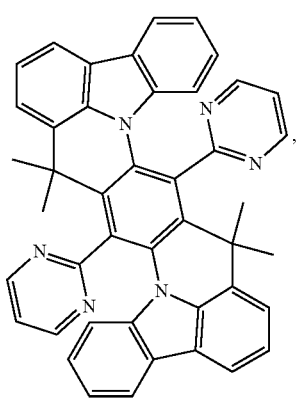
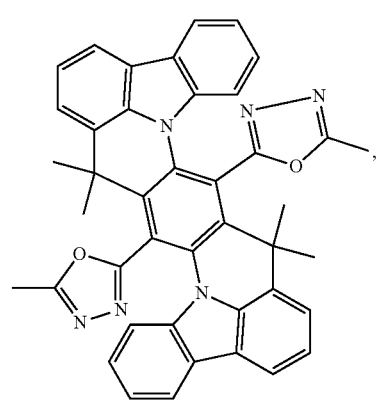
190
-continued
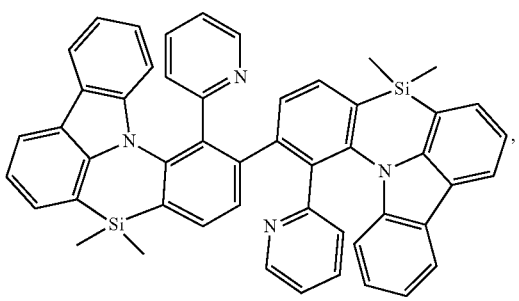
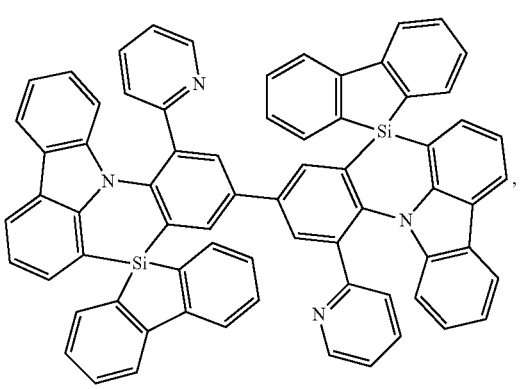
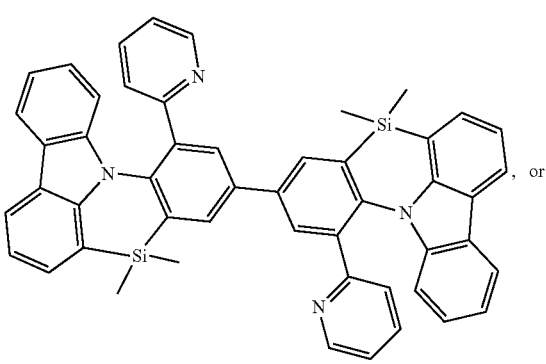
, or
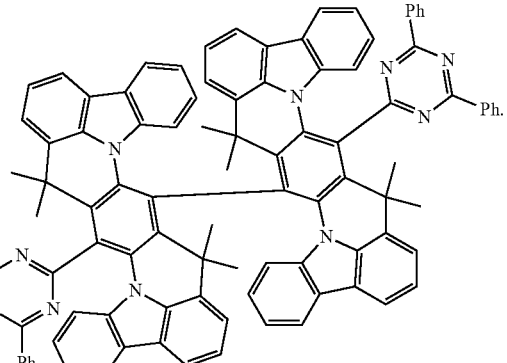

In some embodiments, the compounds can be represented by the following general structures:

XV

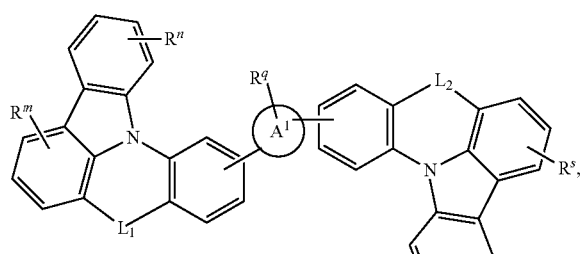

XVI

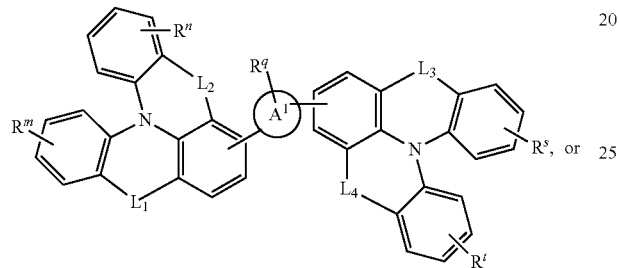

XVII

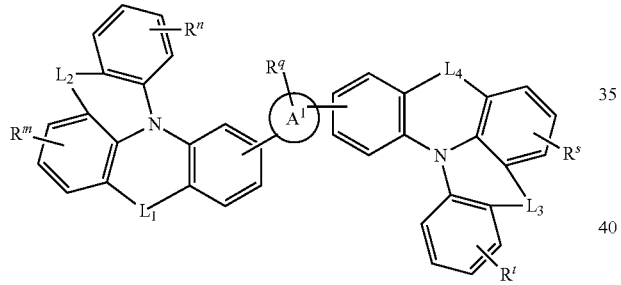

where $R^m$, $R^n$, $R^p$, $R^q$, $R^s$, $R^t$, and $A^1$ are as previously defined, and where $L_1$, $L_2$, $L_3$ and $L_4$ are linked directly or through a linking atom or group to $A^1$ and can be:

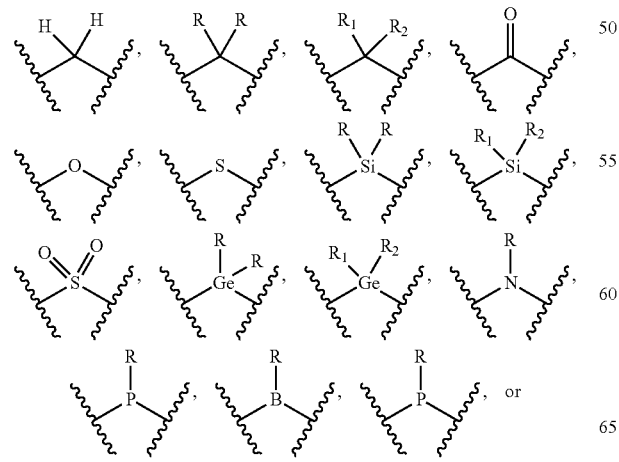

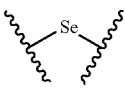

where R, $R_1$, and $R_2$ are as previously defined. Non-limiting examples of structures XV, XVI, and XVII include:

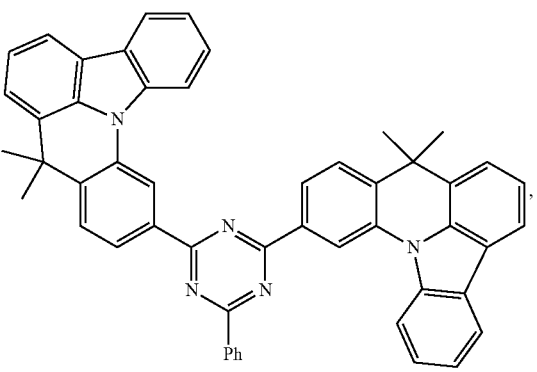

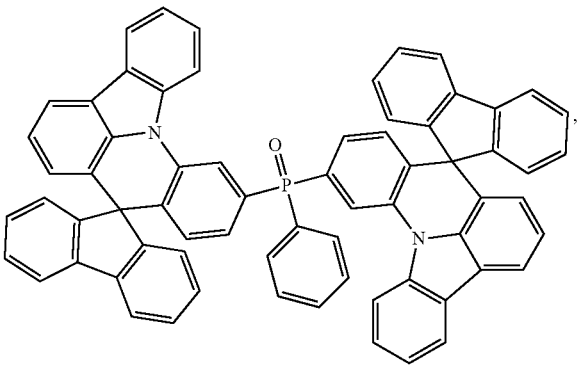

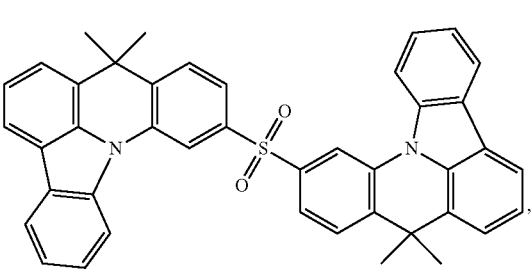

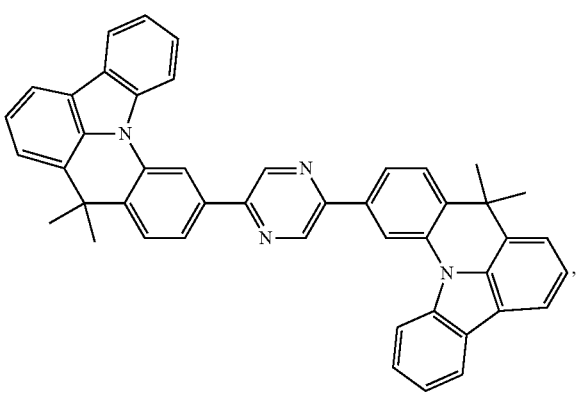

193
-continued
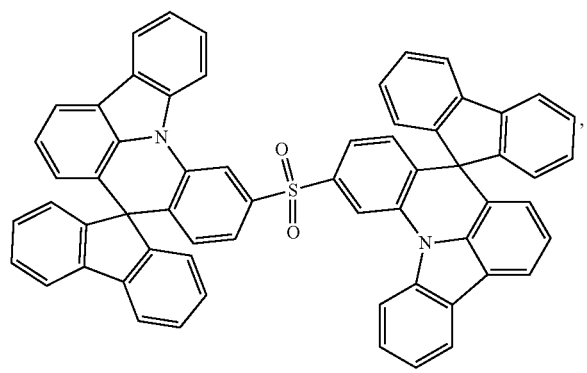
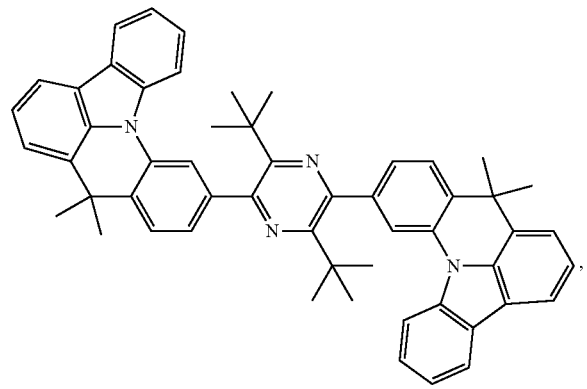
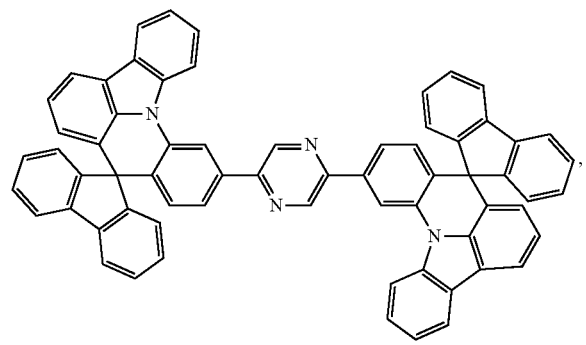
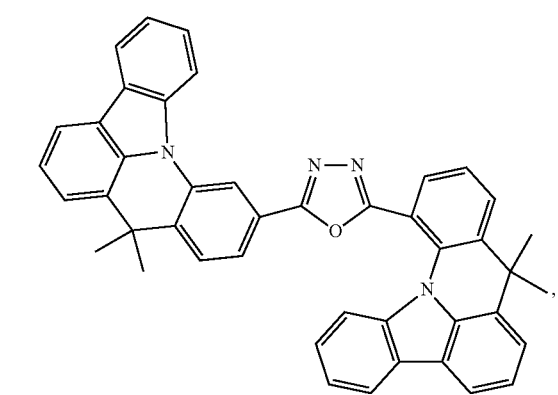
194
-continued
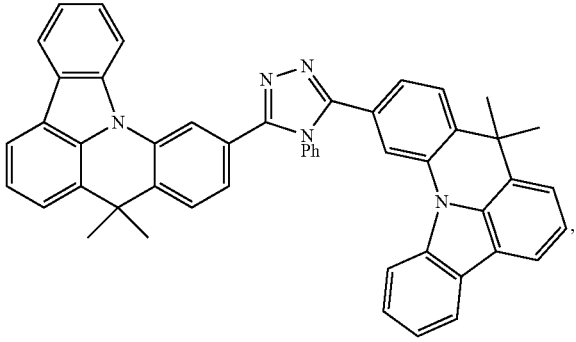
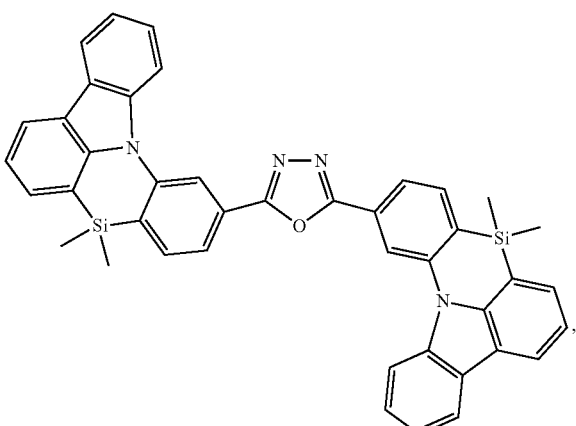
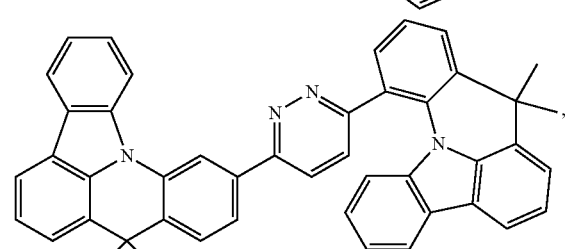
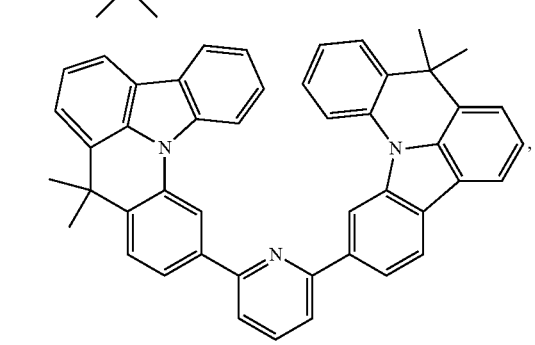
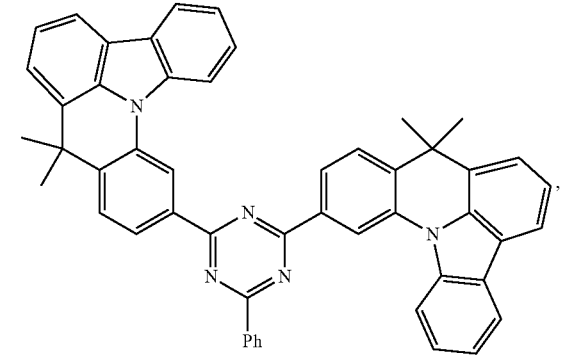

195
-continued
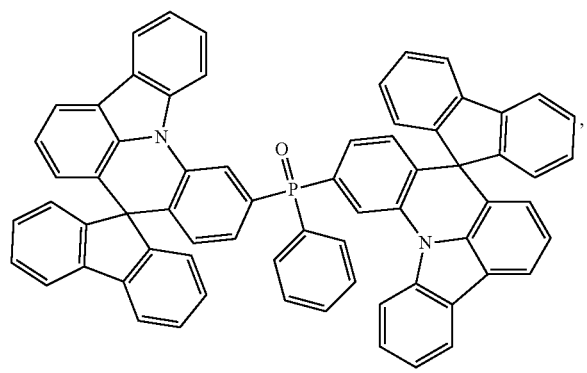
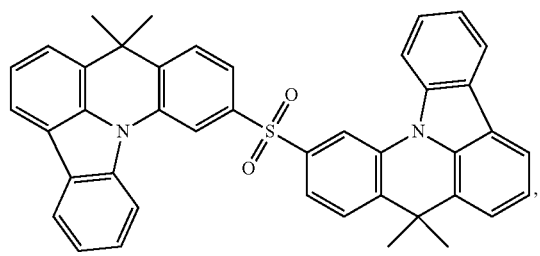
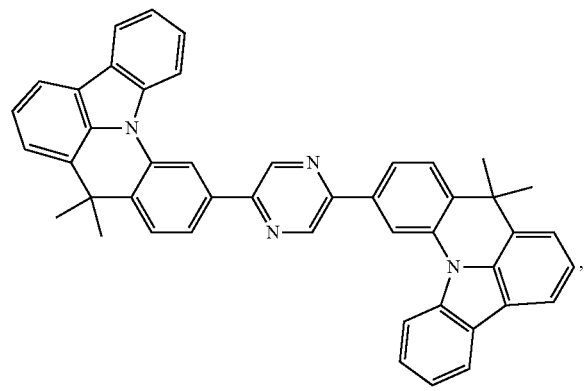
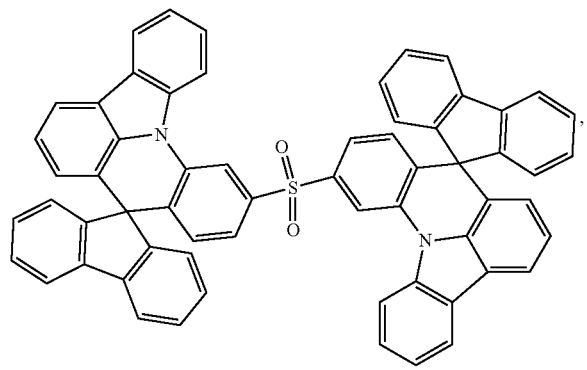
196
-continued
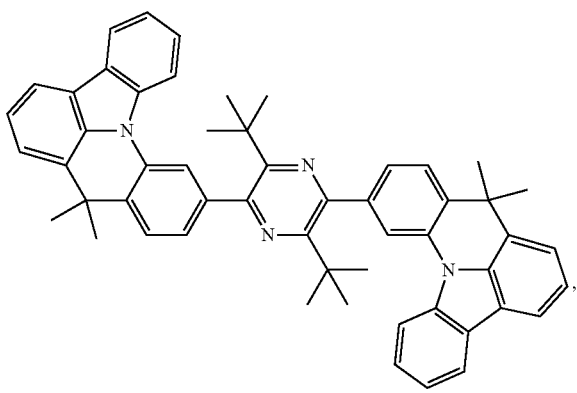
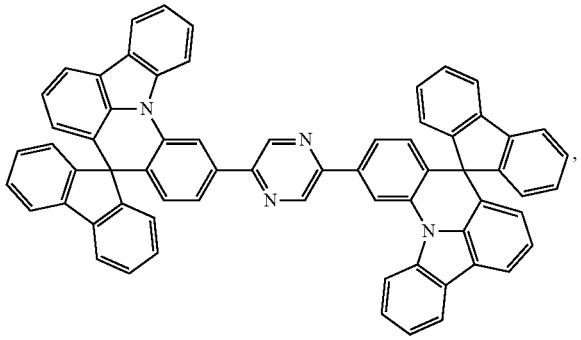
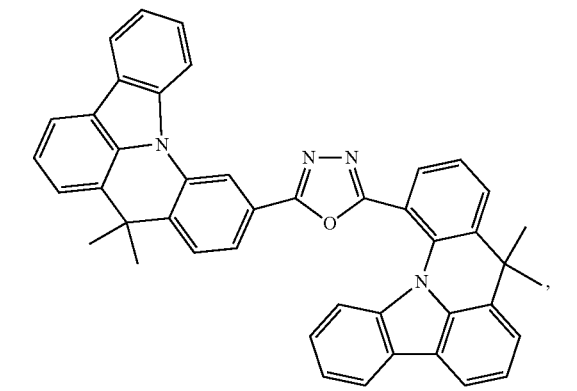
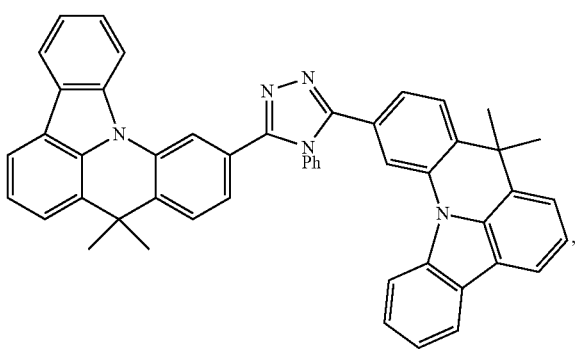

197
-continued
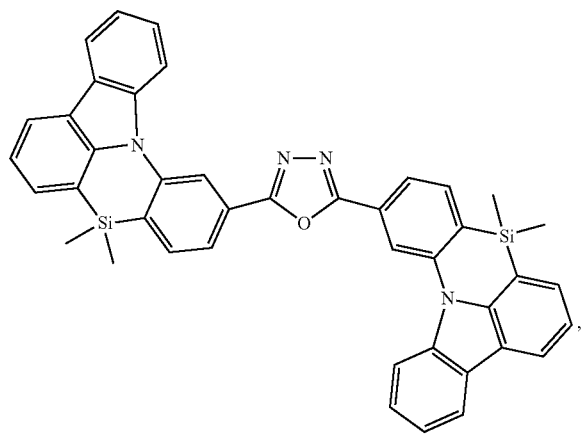
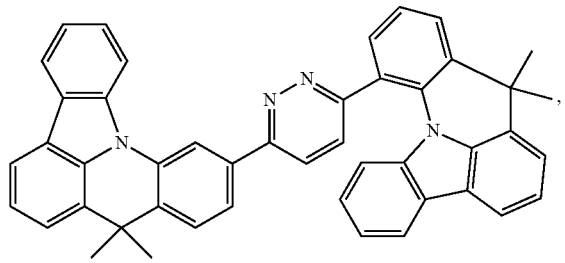
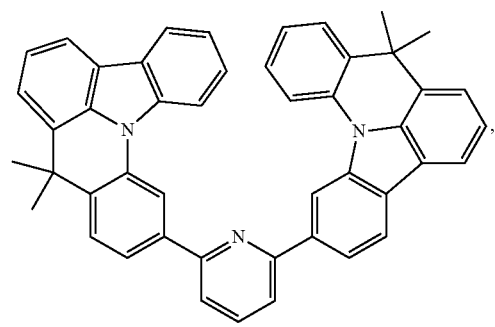
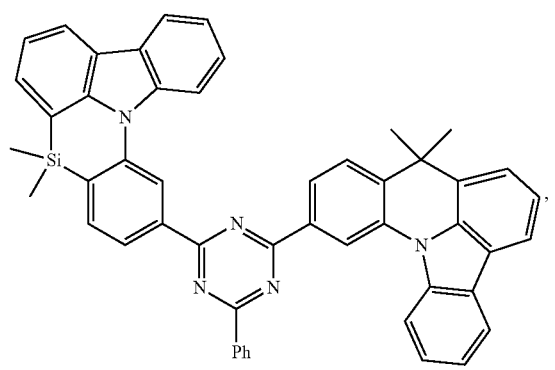
198
-continued
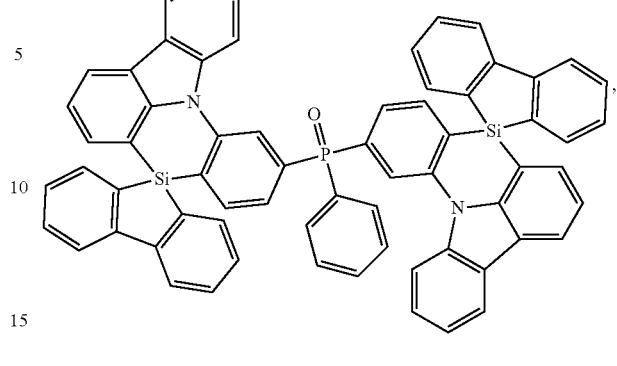
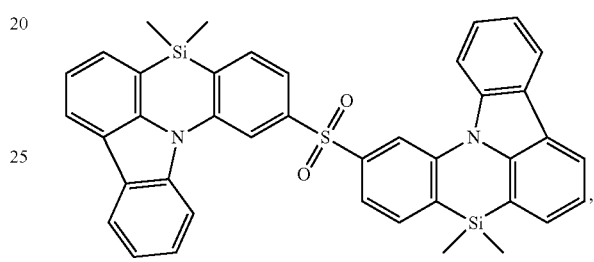
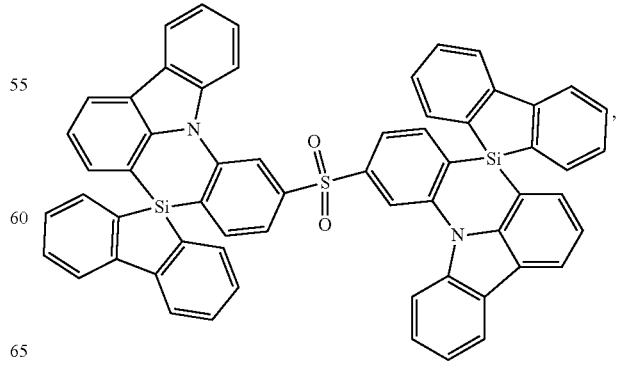

199
-continued
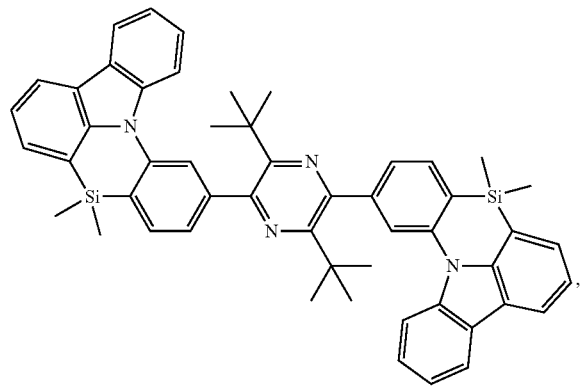
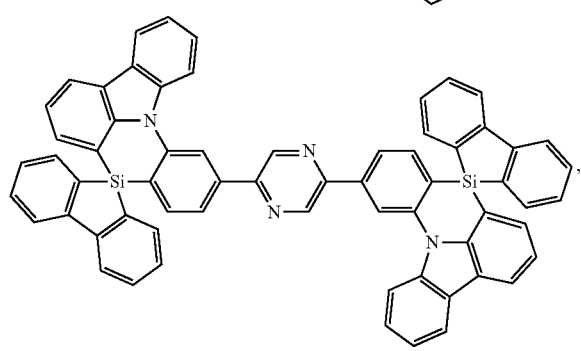
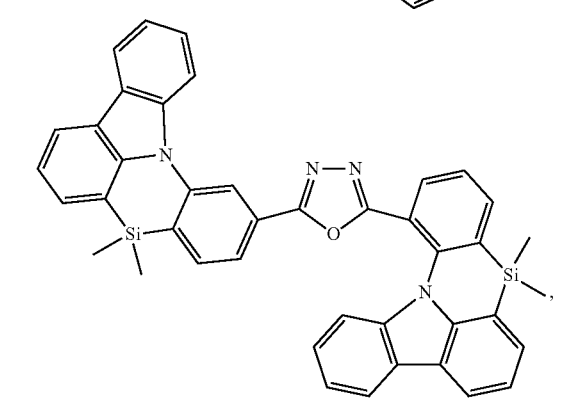
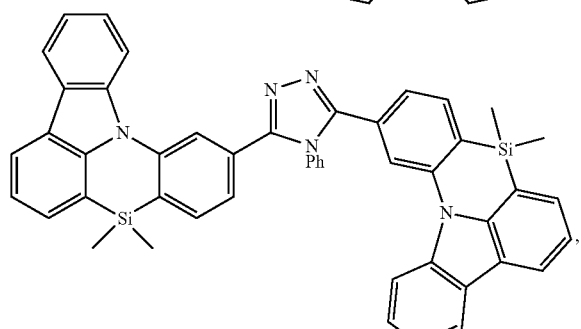
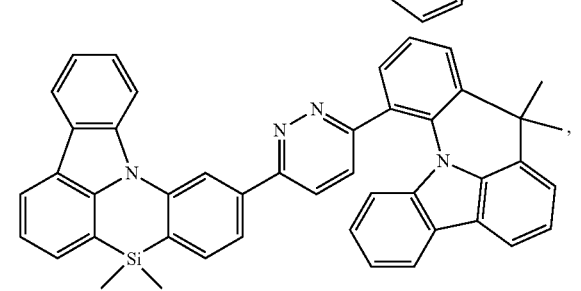
200
-continued
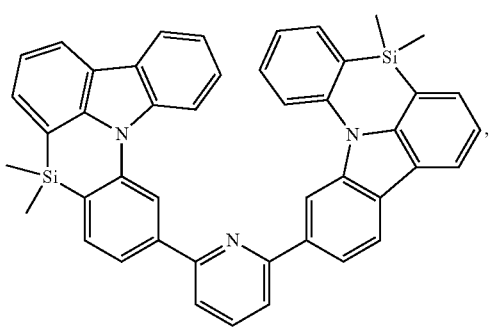
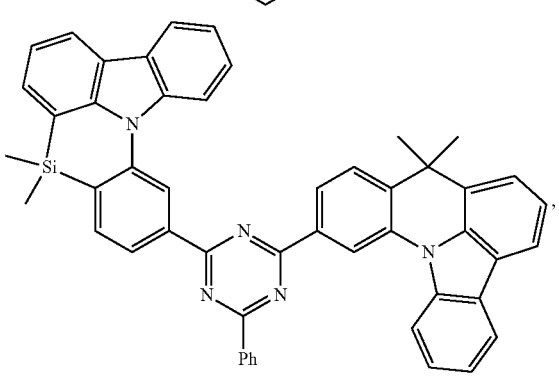
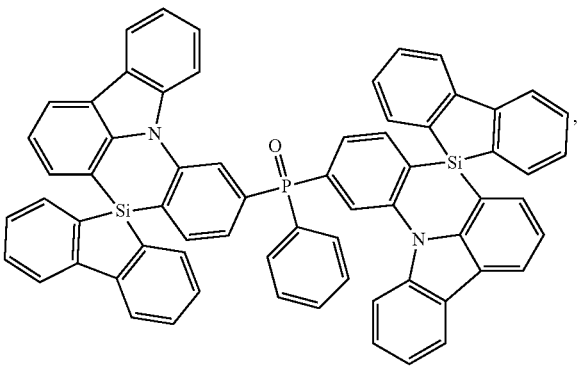
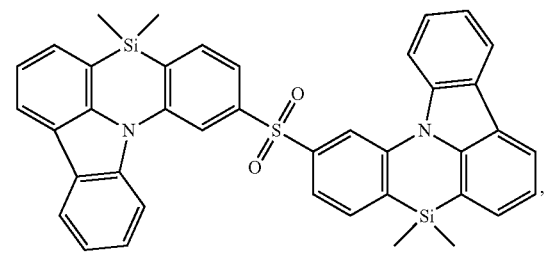
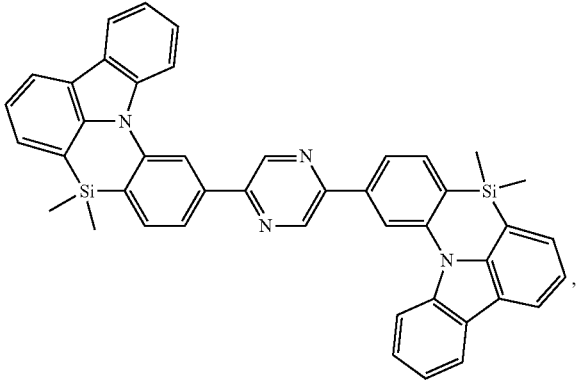

201
-continued
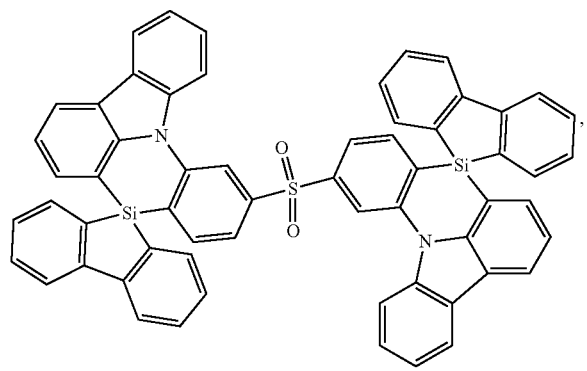
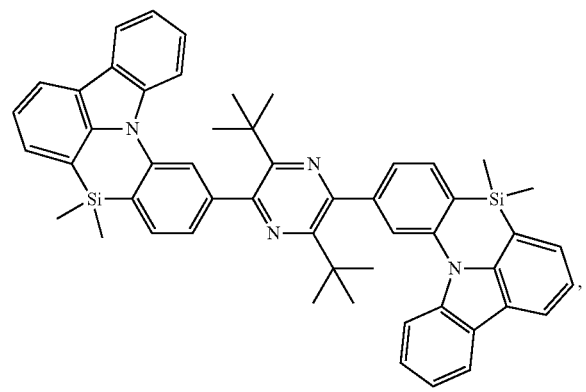
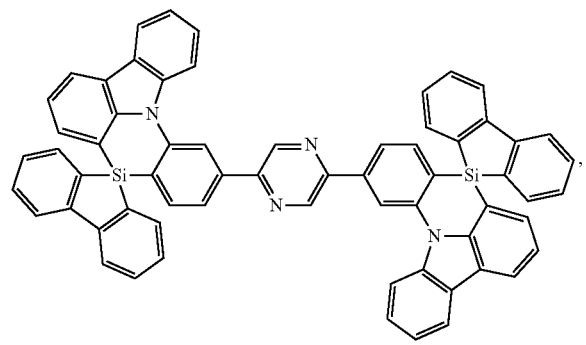
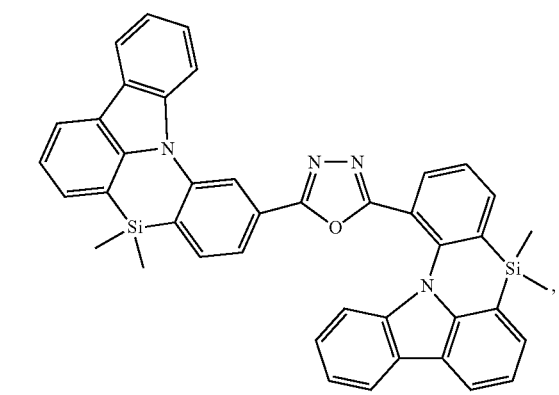
202
-continued
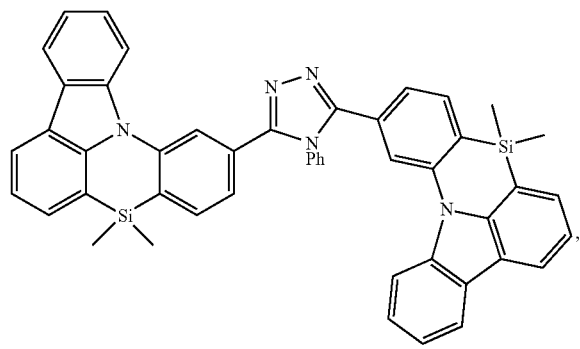
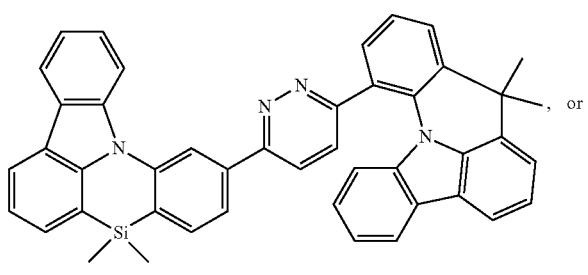
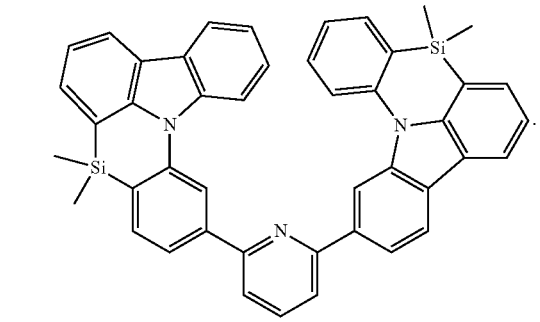
In some embodiments, the compositions disclosed herein include one or more of the following:
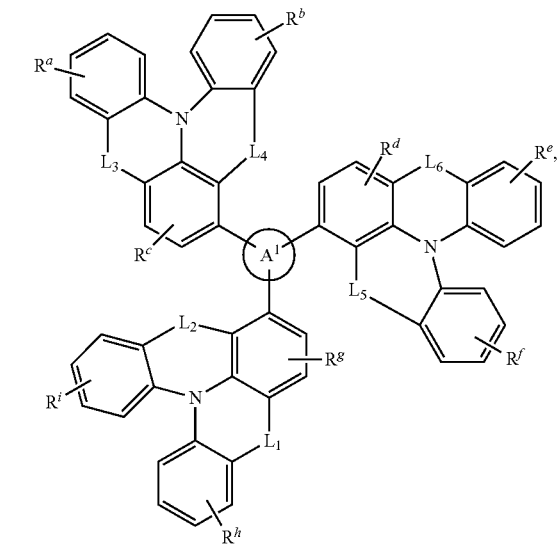
XVIII

XIX

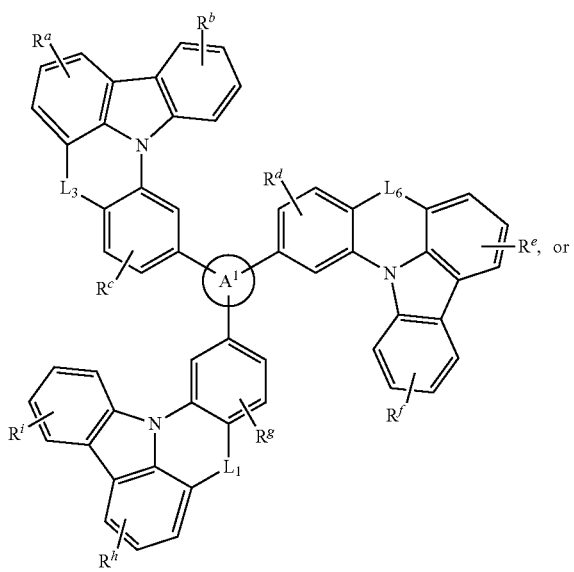

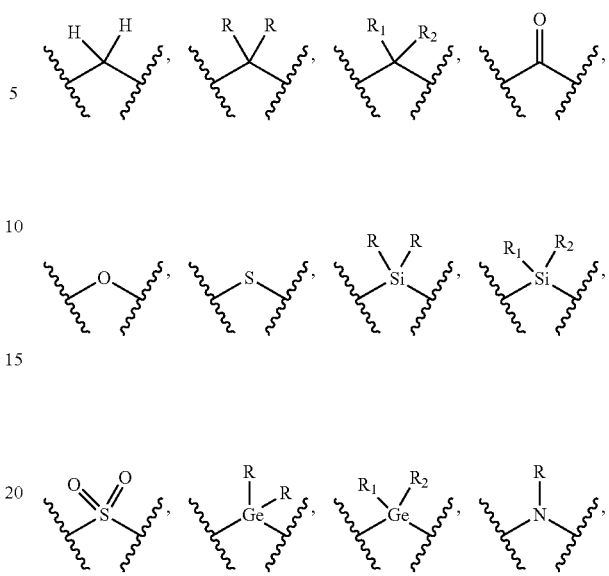

XX

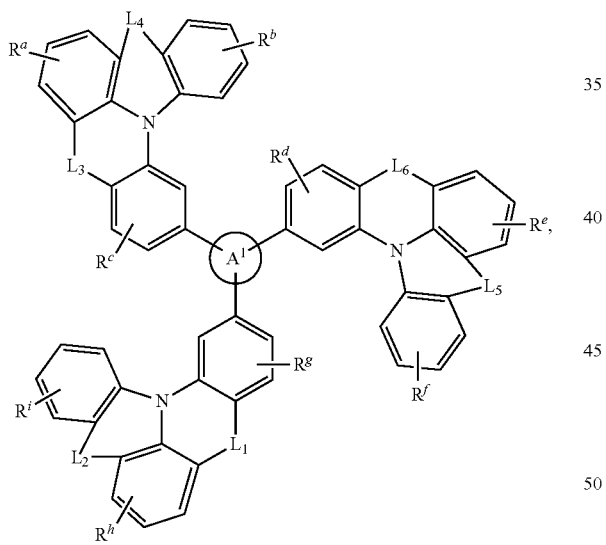

where A¹ is as defined above. $L_1$, $L_2$, $L_3$, $L_4$, $L_5$, and $L_6$ can be linkage groups, and can include an oxygen (O) containing group, a sulfur (S) containing group, a nitrogen (N) containing group, a carbon (C) containing group, a phosphorous (P) containing group, a silicon (Si) containing group, or a boron (B) containing group. In some embodiments, $L_1$, $L_2$, $L_3$, $L_4$, $L_5$, and $L_6$ can each independently be:

where R, $R_1$ and $R_2$ are as previously defined.

$R^a$, $R^b$, $R^c$, $R^d$, $R^e$, $R^f$, $R^g$, $R^h$, and $R^i$ can each independently represents mono-, di-, tri, or tetra-substitution, and each independently represents one or more of a hydrogen atom, a deuterium atom, a halogen atom, a hydroxyl group, a thiol group, a nitro group, a cyano group, a substituted or unsubstituted alkyl group, a substituted or unsubstituted haloalkyl group, a substituted or unsubstituted aralkyl group, a substituted or unsubstituted alkenyl group, a substituted or unsubstituted alkynyl group, a substituted or unsubstituted aryl group, a substituted or unsubstituted amino group, a substituted or unsubstituted mono- or dialkylamino group, a substituted or unsubstituted mono- or diarylamino group, a substituted or unsubstituted alkoxy group, a substituted or unsubstituted aryloxy group, a substituted or unsubstituted heteroaryl group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a mercapto group, a sulfo group, a carboxyl group, a hydrazino group, a substituted silyl group, a polymeric group, or a combination thereof.

Non-limiting examples of compounds XVIII, XIX, and XX include:
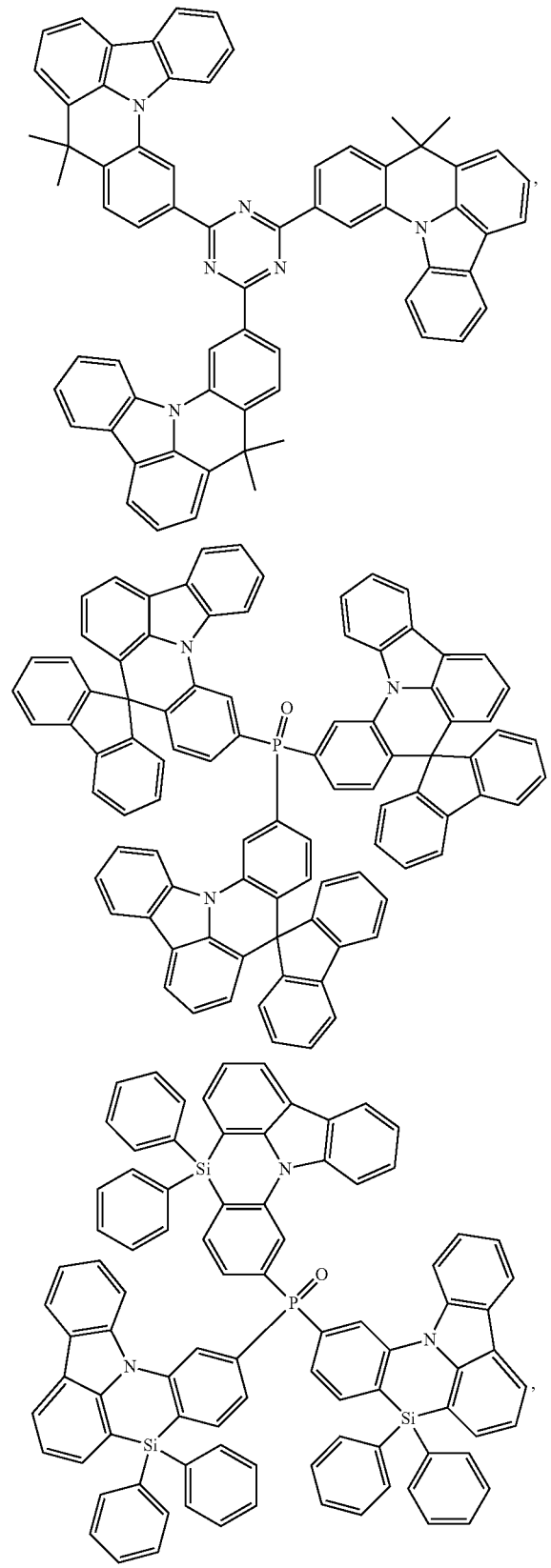
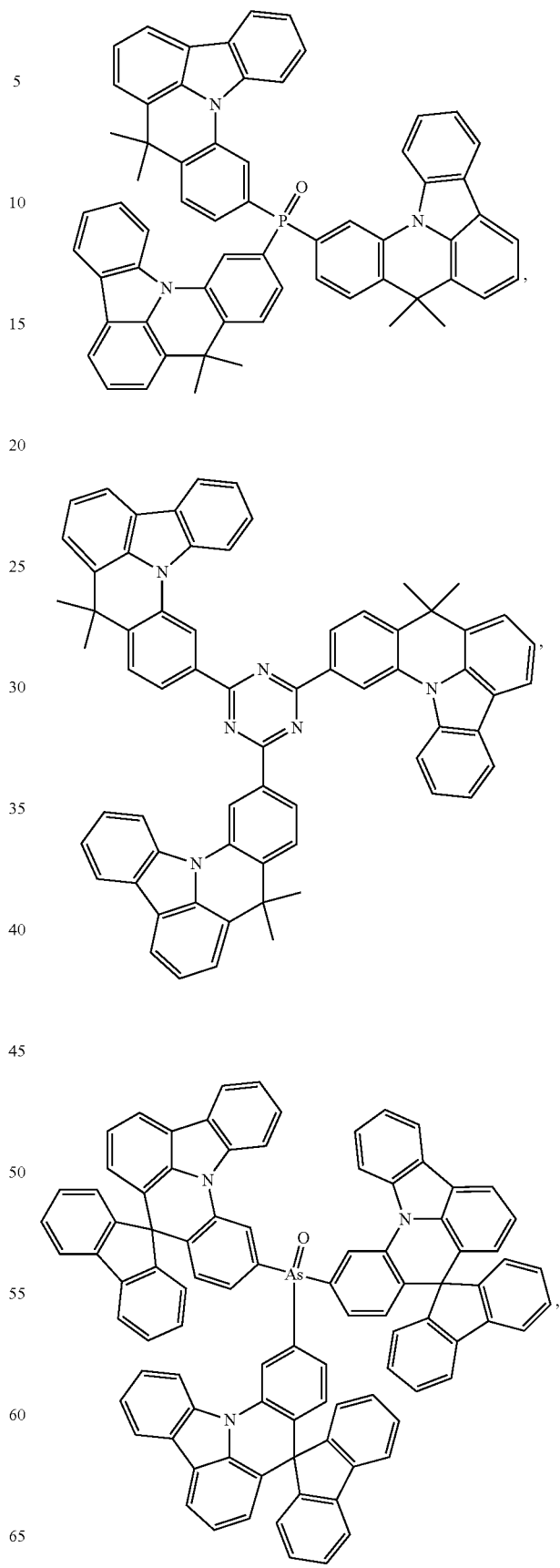

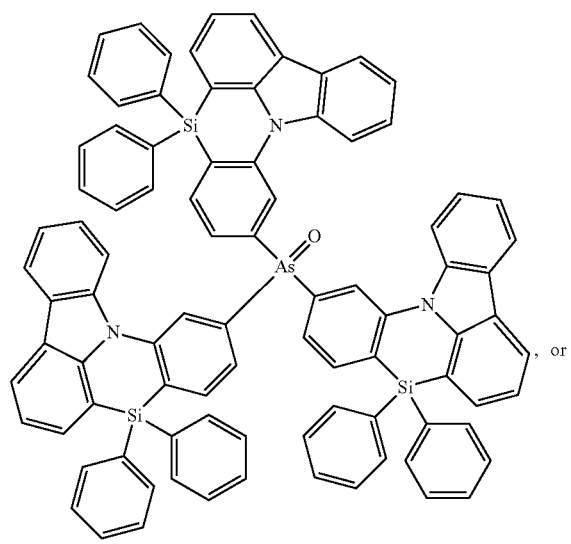

, or

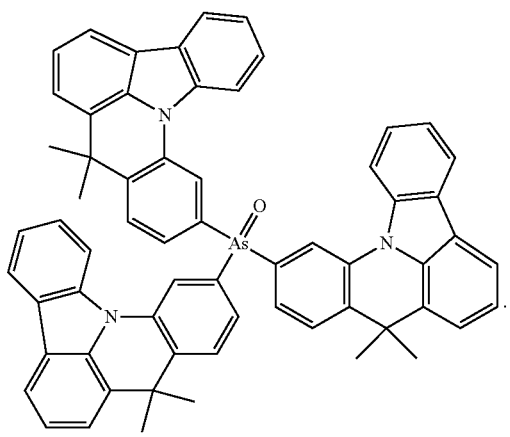

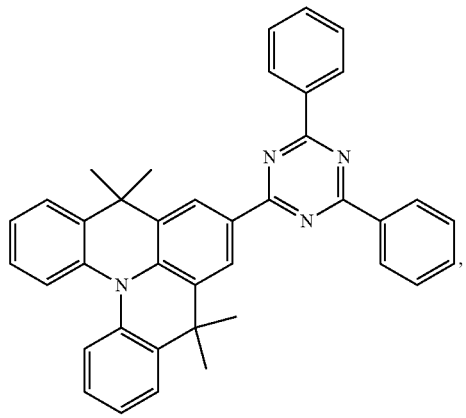

1

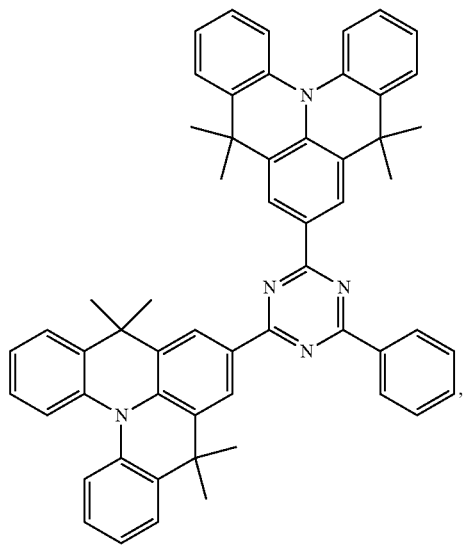

, 2

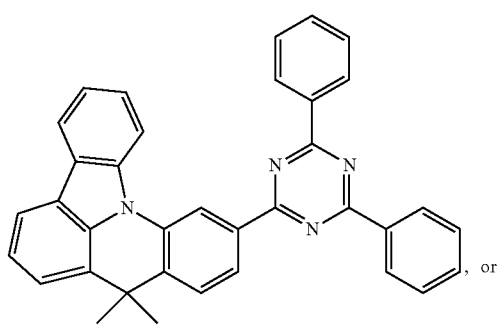

, or 3

Implementations of the present invention may include one or more of the following features. In some cases, for example, the polymeric group includes a polyalkylene, a polyether, or a polyester. In certain cases, for at least one of the compounds, at least one of the following is true: $R_a$ is fused to $L_1$, $R_b$ is fused to $L_2$, R is fused to $L_3$, and $R_d$ is fused to $L_4$. The composition, or a compound of the composition, may have a neutral charge.

In some embodiments, the thermally activated delayed fluorescent composition (TADF) can be compound shown herein or any mixture thereof. In certain embodiments, the thermally activated delayed fluorescent composition is compound 1, 2, 3, or 4 below, or any mixture thereof.

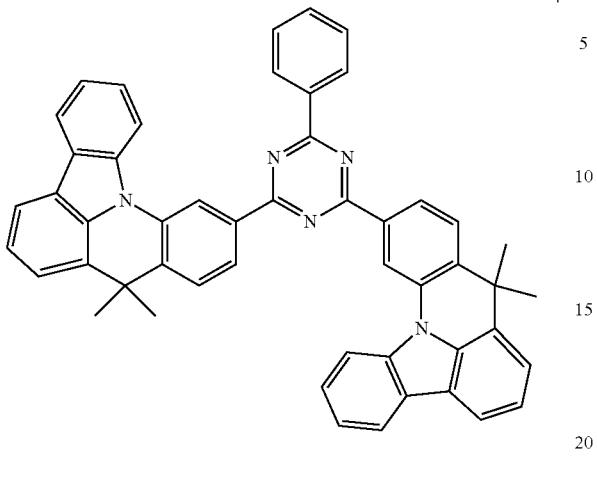

4

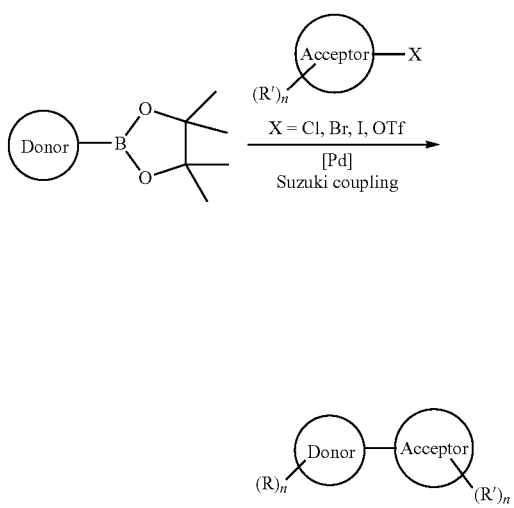

B. Method of Making Thermally Activated Delayed Fluorescent Compositions

The thermally activated delayed fluorescent compositions can be made using known organic synthetic methodology and exemplified in the Example section. In one non-limiting aspect, the thermally activated delayed fluorescent materials can be prepared using Suzuki-Miyaura reaction methodology. A general synthetic route for the synthesis of the thermally activated delayed fluorescent compositions is shown in reaction scheme (1).

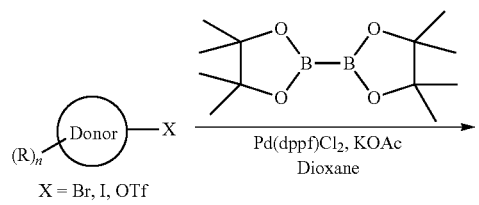

The donor portion of the TADF composition can include a leaving group (e.g., halogen (Br, I), or tosylate (OTf). The donor portion can be reacted with a diboride to form donor substituted borylated compound. The donor substituted borylated compound can then be coupled with a mono- or di-halogenated acceptor portion of the TADF composition to form the TADF compound having a donor portion and an acceptor portion. A non-limiting example of making compounds 1-4 are shown in reaction scheme (2), shown below. Aromatic halide 5 can be reacted with a diboride to form borylated compound 6. Borylated compound 6 can then be coupled with a mono- or di-halogenated aromatic compound to form thermally activated delayed fluorescent compounds 1 and 2. In a similar manner, aromatic halide 7 can be reacted with a diboride compound to form borylated compound 8. Borylated compound 6 can then be coupled with a mono- or di-halogenated aromatic compound to form thermally activated delayed fluorescent compounds 3 and 4.

(2)

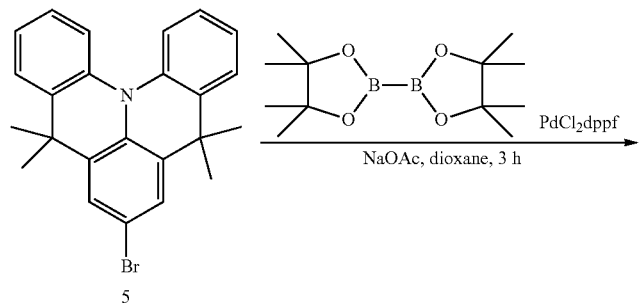

-continued
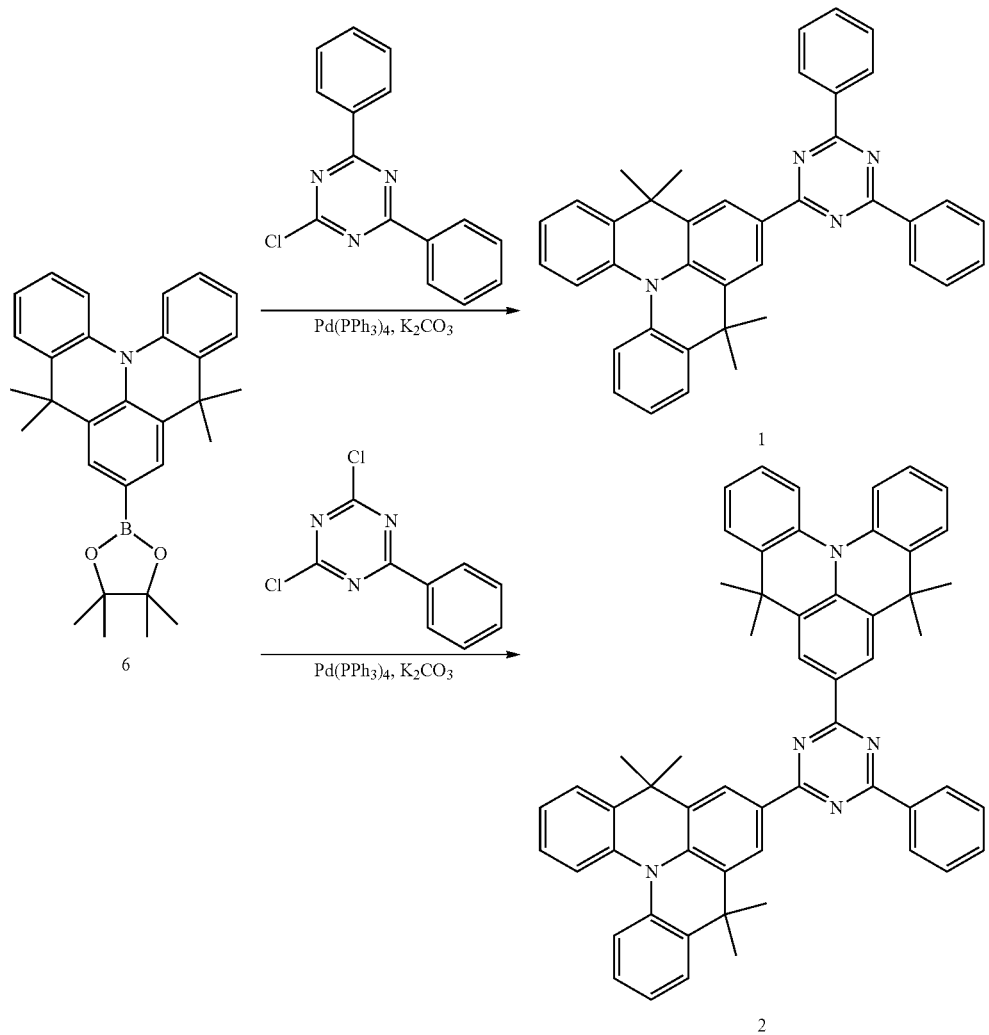
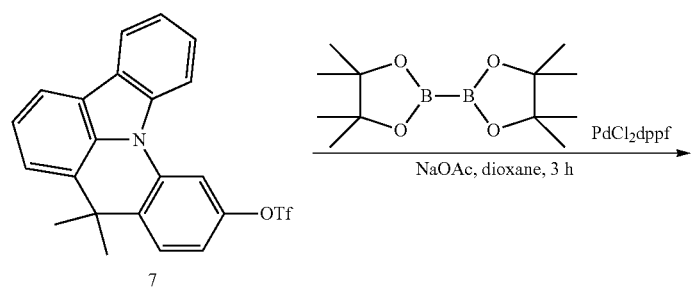

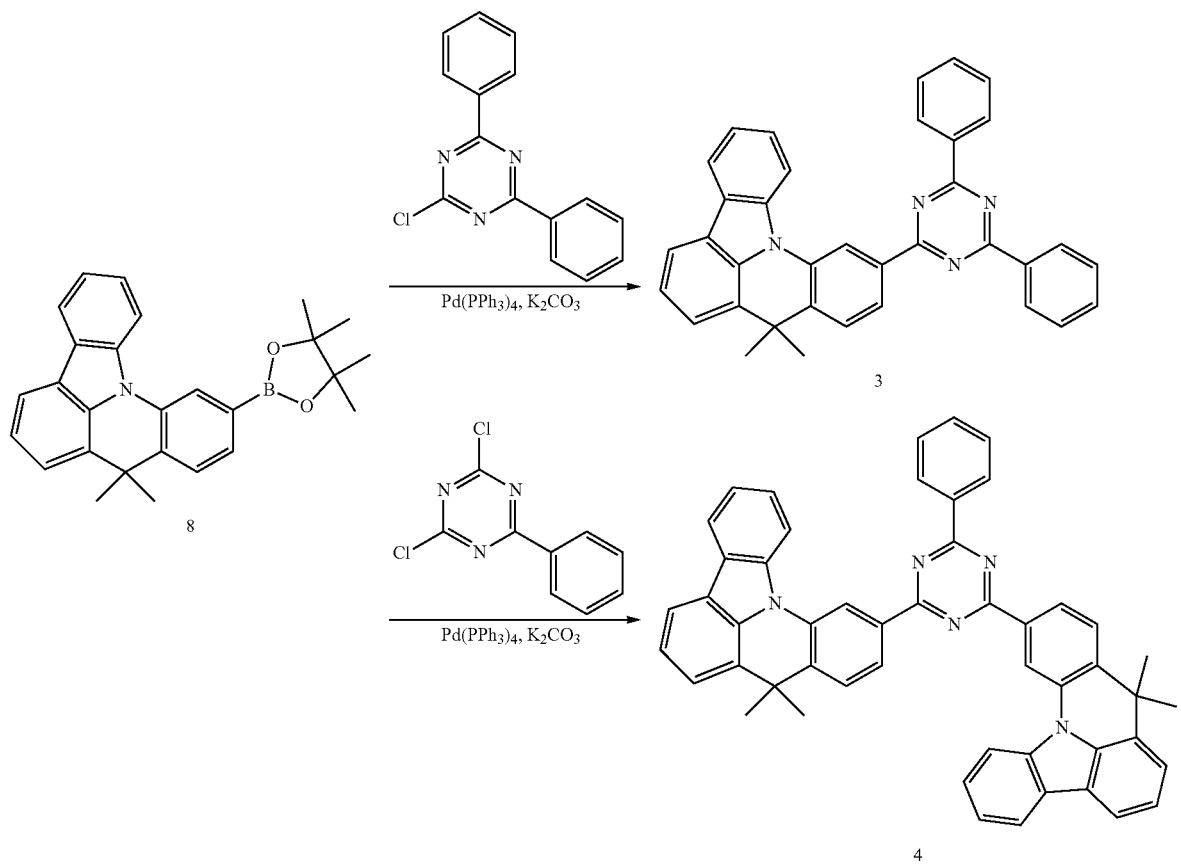

C. Uses of Thermally Activated Delayed Fluorescent Compounds

In some implementations, the compositions disclosed herein or blends thereof are used as host materials for OLED applications, such as full color displays. In one aspect, the compositions disclosed herein can be useful in a wide variety of applications, such as, for example, lighting devices. In a further aspect, one or more of the complexes can be useful as host materials for an organic light emitting display device. In another aspect, the compositions disclosed herein are useful in a variety of applications, for example, as light emitting materials. In a further aspect, the compounds can be useful in organic light emitting diodes (OLEDs), luminescent devices and displays, and other light emitting devices. In another aspect, the compositions disclosed herein can be useful as, for example, host materials for OLEDs, lighting applications, and combinations thereof. In another aspect, the compositions disclosed herein can provide improved efficiency and/or operational lifetimes in lighting devices. In some aspects, the compositions disclosed herein can provide improved efficiency and/or operational lifetimes for organic light emitting devices as compared to conventional materials.

Examples

The present invention will be described in greater detail by way of specific examples. The following examples are offered for illustrative purposes only, and are not intended to limit the invention in any manner. Those of skill in the art will readily recognize a variety of noncritical parameters, which can be changed or modified to yield essentially the same results.

Materials.

The materials used to make compounds 1-4 shown in reaction scheme (2) were obtained from commercial sources or made using known organic methods. Potassium acetate, dioxane, 1,1'-Bis(di-tert-butylphosphino)ferrocene]dichloropalladium(II) ((PdCl$_2$-(dppf)), dppf, bis(pinacolato)diboron, 2-chloro-4,6-diphenyl-1,3,5-triazine, 2,4-dichloro-6-phenyl-1,3,5-triazine, tetrakis(triphenylphosphine)palladium(0), tetrahydrofuran (THF), potassium carbonate, ethyl acetate, hexane, magnesium sulfate (MgSO$_4$), and chloroform were obtained from Sigma-Aldrich® (USA).

Synthesis of Compounds 6 and 8

Compounds 5 and 7 were made using general organic transformation methodology. The overall synthetic routes for compounds 5 and 7 are shown in reaction schemes (3) and (4) respectively. The reactant amounts, solvents, temperatures and time can be varied depending on the amount of compounds 5 and 7 produced and are within the general knowledge of one skilled in the art of organic synthesis.

215

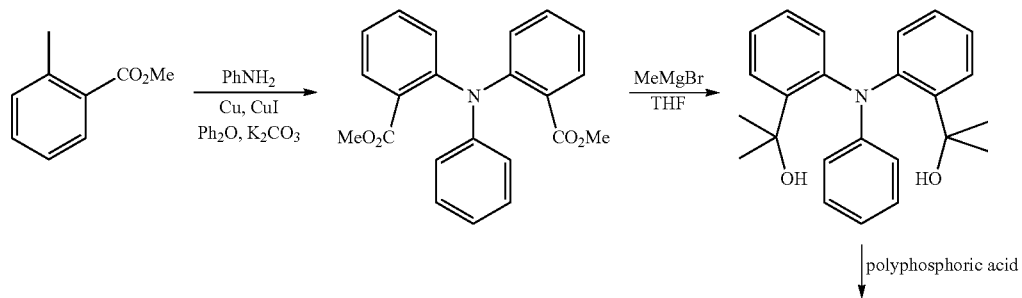

216

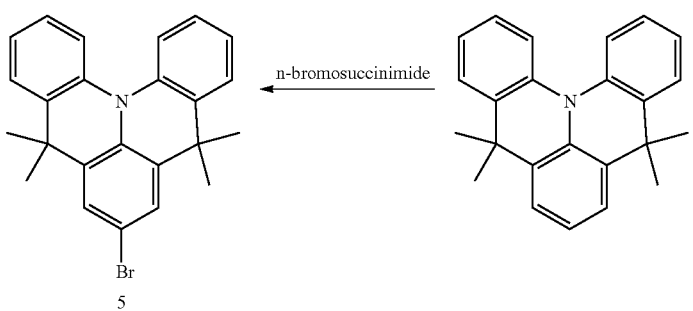

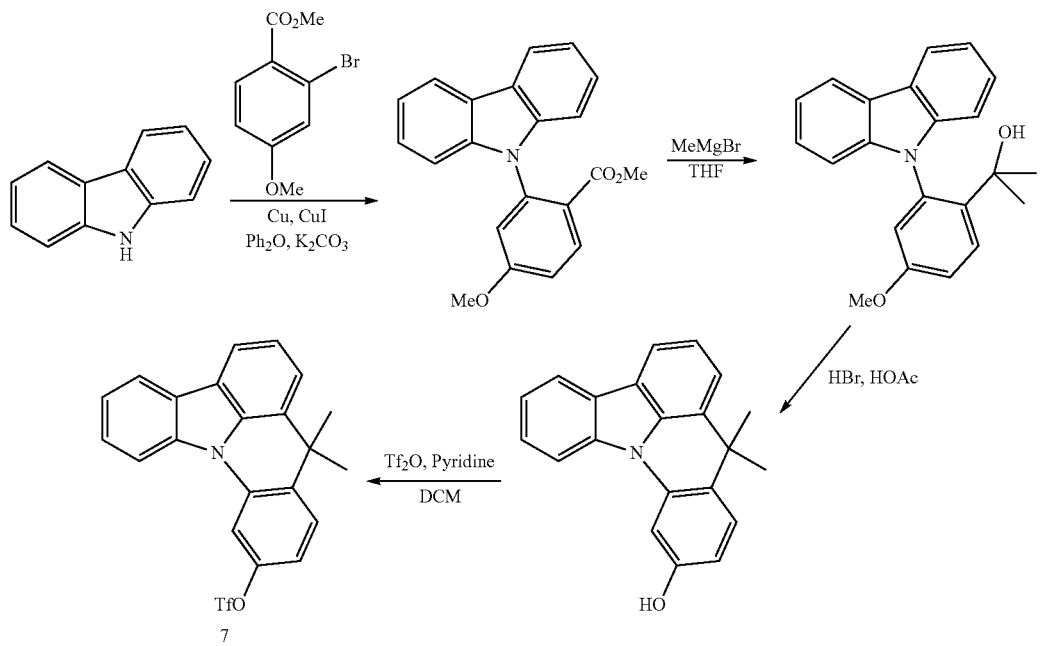

Referring to the reaction scheme (1), a mixture of potassium acetate (1.6 mmol), dry dioxane (3.3 mL), PdCl₂-(dppf), 13 mg, 0.016 mmol), dppf (9 mg, 0.016 mmol), bis(pinacolato)diboron (150 mg, 0.6 mmol) and compound 5 or 7 (150 mg, 0.54 mmol) was heated and stirred under argon, at reflux for 2 h. The reaction mixture was diluted with ethyl acetate (100 mL), washed with water (50 mL), dried over magnesium sulfate and concentrated in vacuo to a dark brown oil which was purified by flash column chromatography on florisil using gradient elution (from hexane to 5:95 ethyl acetate-hexane) to yield boronate 6 or 8, respectively (75 mg, 54%) as colorless needles.

Synthesis of Compounds 1, 2, 3, and 4

To a solution of 2-chloro-4,6-diphenyl-1,3,5-triazine or 2,4-dichloro-6-phenyl-1,3,5-triazine (2 mmol), 0.482 g of boronate compound 6 or 8 (2.2 mmol) and 1.16 g of tetrakis(triphenylphosphine) palladium(0) (0.1 mmol) in 10 ml of THF were added dropwise, with stirring, a solution of 0.55 g of potassium carbonate (4 mmol) in 10 mL of water. Subsequently, the mixture was stirred and refluxed for 2 days. The cooled mixture was partitioned between water and ethyl acetate. The organic layer was separated, and the aqueous layer was extracted with ethyl acetate. The combined organic layers were washed with brine, dried over Mg$_2$SO$_4$, and concentrated in vacuo. Then 100 mL of chloroform was added to it, the brown precipitate formed was collected by filtration, washed with 100 mL of chloroform, dried under vacuum, and the products were obtained. The yield was around 70%.

The invention claimed is:

1. A thermally activated delayed fluorescent compound represented by Formula I, Formula II, Formula III, or Formula IV:

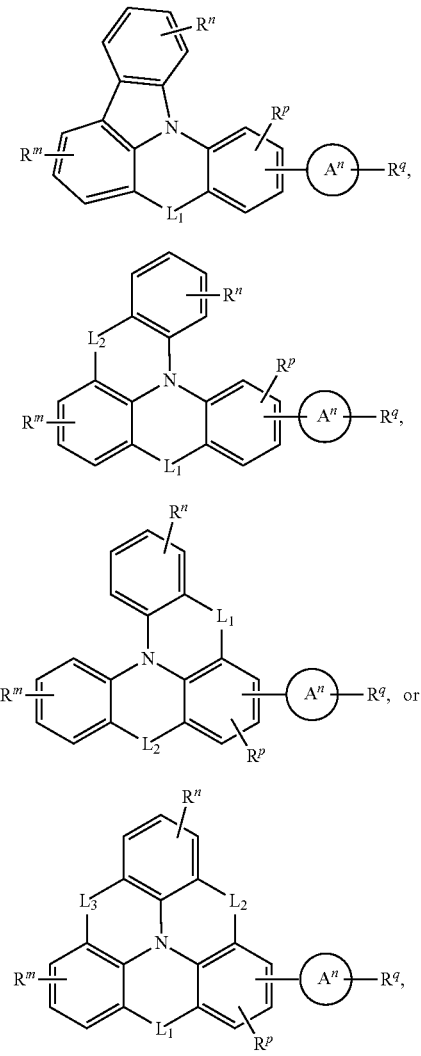

wherein:

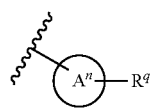

represents n acceptor moieties A, where A is a nitrogen-containing heteroaryl group, a R$^q$MO group, where M is C, S, P, or As, or a R$^q$SO$_2$ group, or any combination thereof; and n=1, 2, or 3, such that the compound includes a single acceptor moiety (A$^1$), two acceptor moieties (A$^1$ and A$^2$), or three acceptor moieties (A$^1$, A$^2$, and A$^3$), and wherein each acceptor moiety is substituted with R$^q$;

L$_1$, and L$_2$, and L$_3$ are each independently —CR$_2$-, —CO—, or —SiR$_2$-; and R$^m$, R$^n$, R$^p$, and R$^q$ each independently represent mono-, di-, tri, or tetra-substitution, valency permitting; and each R, R$^m$, R$^n$, R$^p$, and R$^q$ independently represents mono-, di-, tri, or tetra-substitution, valency permitting, and each independently represents a hydrogen atom, a deuterium atom, a halogen atom, a hydroxyl group, an —SH group, a nitro group, a cyano group, an alkyl group, a haloalkyl group, an aralkyl group, an alkenyl group, an alkynyl group, an aryl group, an amino group, a mono- or dialkylamino group, a mono- or diarylamino group, an alkoxy group, an aryloxy group, a heteroaryl group, an alkoxycarbonyl group, an alkylcarbonyloxy group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a sulfo group, a carboxyl group, a hydrazino group, a substituted silyl group, a polymeric group, or a combination thereof;

wherein the alkyl group, haloalkyl group, aralkyl group, alkenyl group, alkynyl group, aryl group, amino group, mono- or dialkylamino group, alkoxy group, aryloxy group, and heteroaryl group is optionally substituted with one or more substituents selected from the group consisting of a deuterium atom, a halogen atom, a hydroxyl group, an SH group, a nitro group, a cyano group, an alkyl group, a haloalkyl group, an aralkyl group, an alkenyl group, an alkynyl group, an aryl group, an amino group, a mono- or dialkylamino group, a mono- or diarylamino group, an alkoxy group, an aryloxy group, a heteroaryl group, an alkoxycarbonyl group, an alkylcarbonyloxy group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a sulfo group, a carboxyl group, a hydrazino group, a substituted silyl group, and a polymeric group;

with the proviso that when the compound is represented by Formula III, R$^m$ and R$^n$ are not pyridyl.

2. The compound of claim 1, wherein A is:

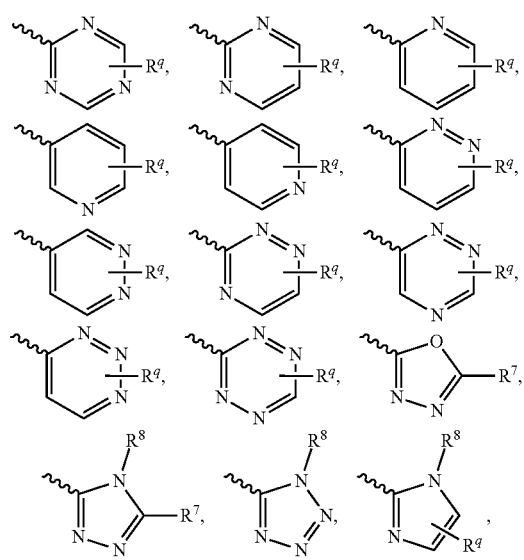

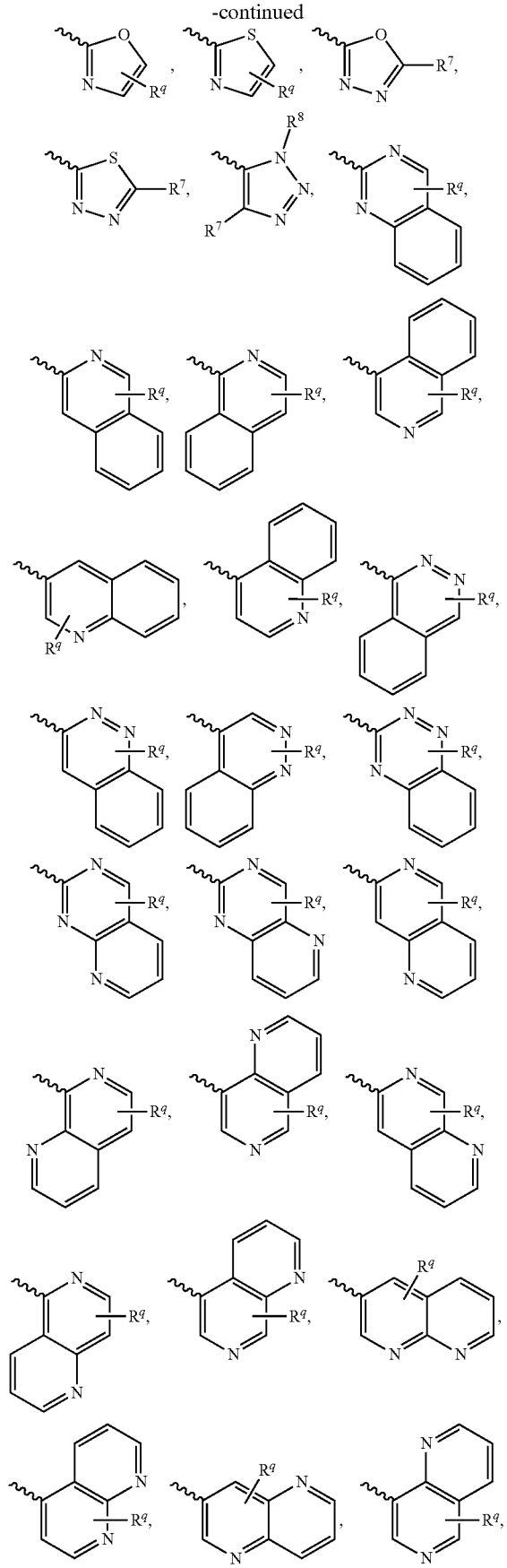
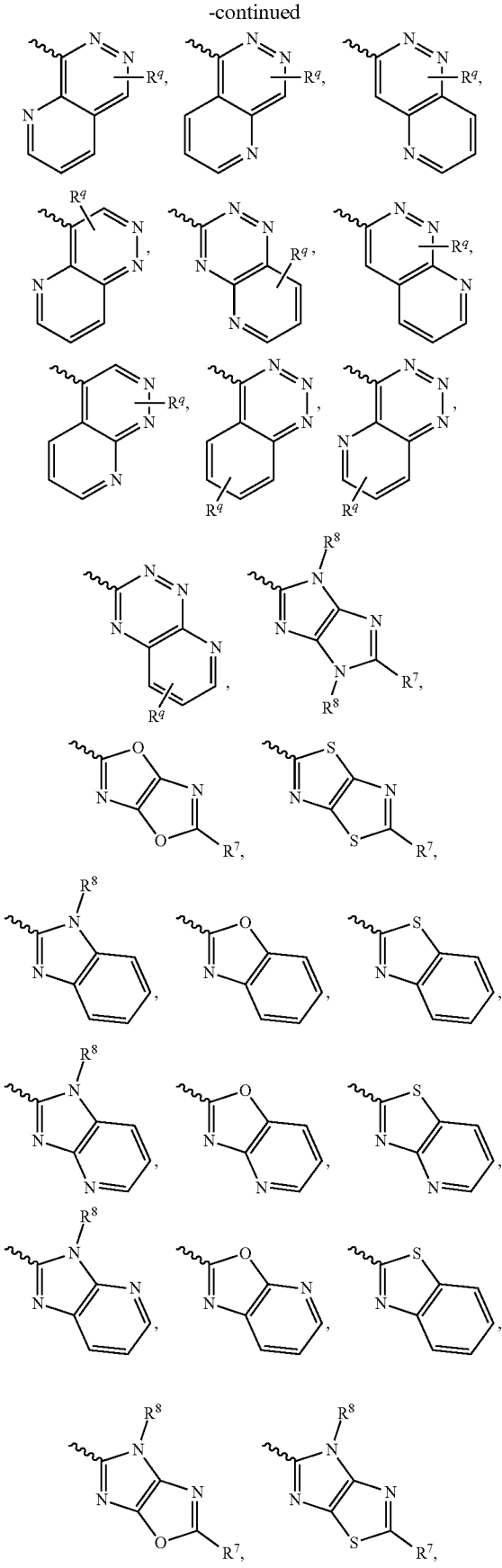

-continued
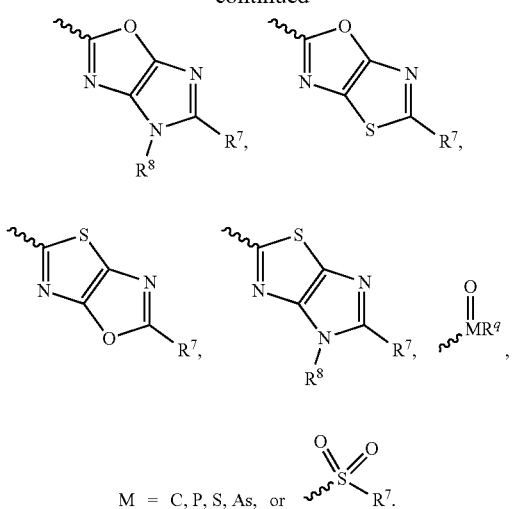
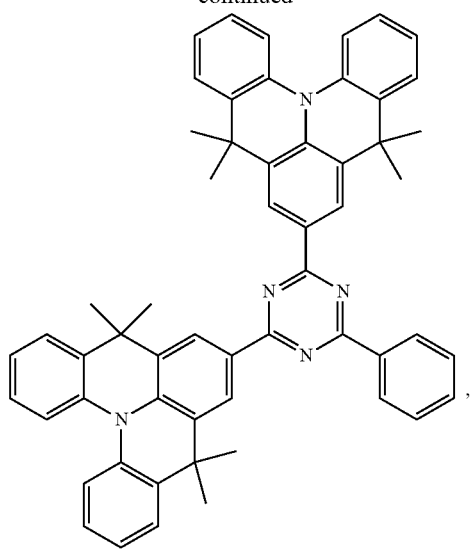
3. The compound of claim 2, wherein A is a nitrogen-containing heteroaryl group comprising 1 to 3 nitrogen atoms.
4. The compound of claim 1, wherein A is
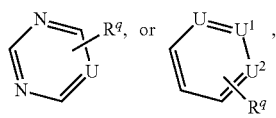
where U, U¹, and U² each independently represents N or C with the proviso that when U, U¹ and U² are present at least one of them is N.
5. The compound of claim 4, wherein A is
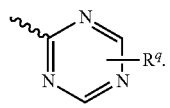
6. The compound of claim 5, wherein the compound is:
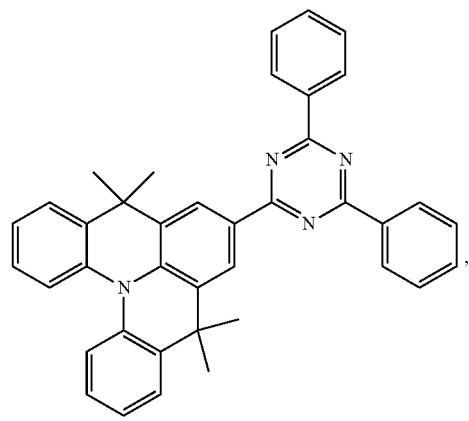
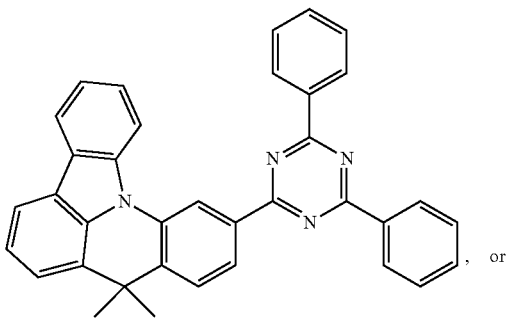
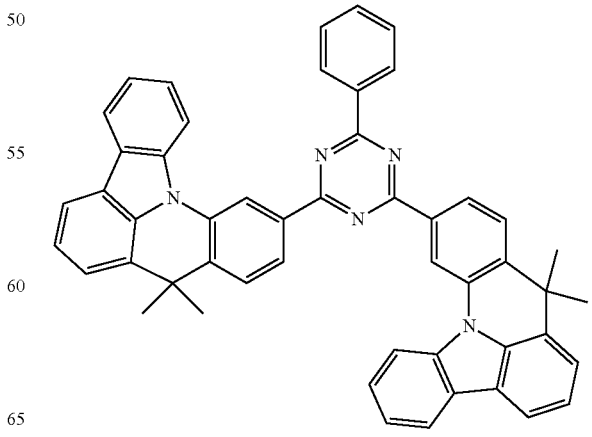

7. The compound of claim 6, wherein the compound is:

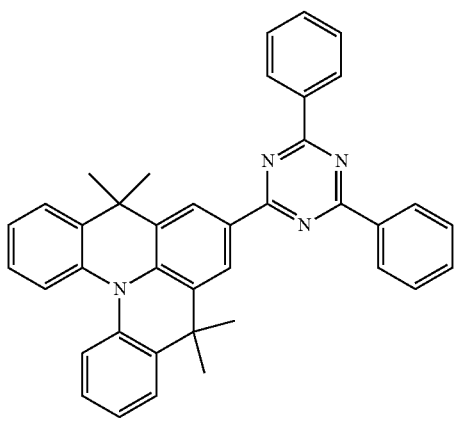 [SMILES: CC1(C)c2ccccc2N2c3ccccc3C(C)(C)c3cc(-c4nc(-c5ccccc5)nc(-c5ccccc5)n4)cc1c32]

or

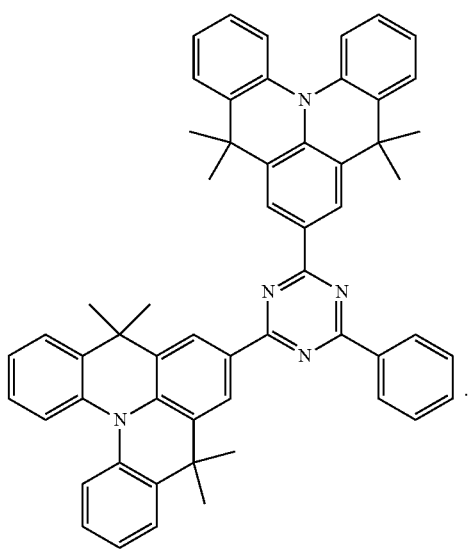 [SMILES: CC1(C)c2ccccc2N2c3ccccc3C(C)(C)c3cc(-c4nc(-c5ccccc5)nc(-c5cc6c7c(c5)C(C)(C)c5ccccc5N7c5ccccc5C6(C)C)n4)cc1c32]

8. The compound of claim 6, wherein the compound is:

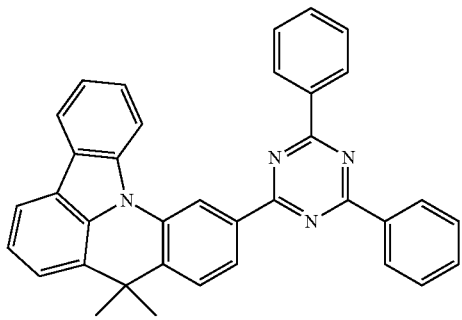 [SMILES: CC1(C)c2ccc(-c3nc(-c4ccccc4)nc(-c4ccccc4)n3)cc2-n2c3ccccc3c3cccc1c32]

or

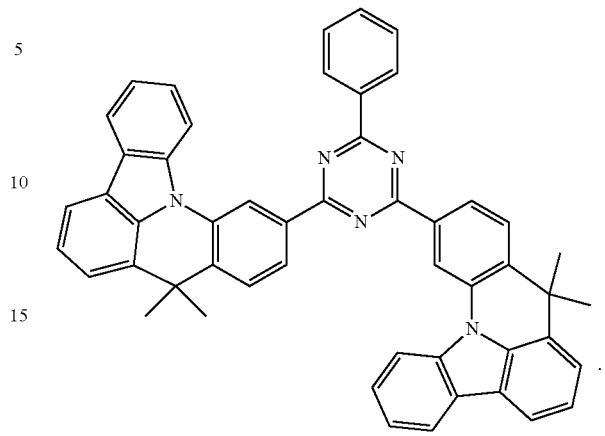

9. The compound of claim 1, wherein n is 2 and the compound has the structure selected from the group consisting of:

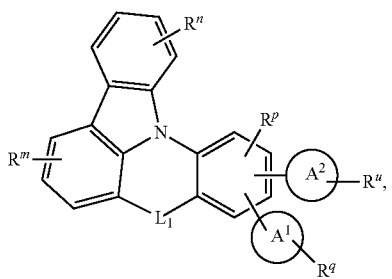

V

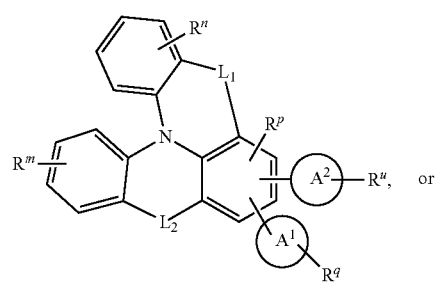

VI

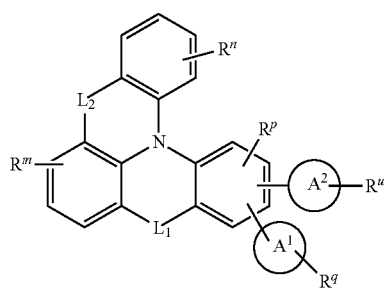

VII where:
$R^u$ represents mono-, di-, tri, or tetra-substitution, valency permitting;
and each independently represents a hydrogen atom, a deuterium atom, a halogen atom, a hydroxyl group, an —SH group, a nitro group, a cyano group, an alkyl group, a haloalkyl group, an aralkyl group, an alkenyl group, an alkynyl group, an aryl group, an amino group, a mono- or dialkylamino group, a mono- or diarylamino group, an alkoxy group, an aryloxy group, a heteroaryl group, an alkoxycarbonyl group, an alkylcarbonyloxy group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a sulfo group, a carboxyl group, a hydrazino group, a substituted silyl group, a polymeric group, or a combination thereof;

wherein the alkyl group, haloalkyl group, aralkyl group, alkenyl group, alkynyl group, aryl group, amino group, mono- or dialkylamino group, alkoxy group, aryloxy group, and heteroaryl group is optionally substituted with one or more substituents selected from the group consisting of a deuterium atom, a halogen atom, a hydroxyl group, an SH group, a nitro group, a cyano group, an alkyl group, a haloalkyl group, an aralkyl group, an alkenyl group, an alkynyl group, an aryl group, an amino group, a mono- or dialkylamino group, a mono- or diarylamino group, an alkoxy group, an aryloxy group, a heteroaryl group, an alkoxycarbonyl group, an alkylcarbonyloxy group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a sulfo group, a carboxyl group, a hydrazino group, a substituted silyl group, and a polymeric group.

10. The compound of claim 9, wherein n=3, and the compound has the structure selected from the group consisting of:

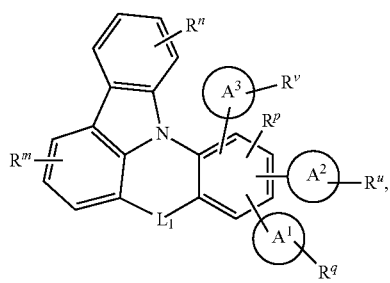

VIII

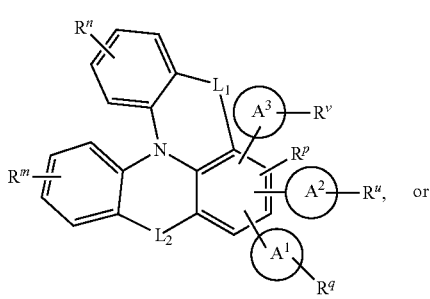

IX

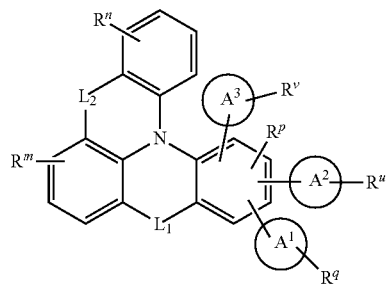

X where
R$^v$ represents mono-, di-, tri, or tetra-substitution, valency permitting;
and each independently represents a hydrogen atom, a deuterium atom, a halogen atom, a hydroxyl group, an —SH group, a nitro group, a cyano group, an alkyl group, a haloalkyl group, an aralkyl group, an alkenyl group, an alkynyl group, an aryl group, an amino group, a mono- or dialkylamino group, a mono- or diarylamino group, an alkoxy group, an aryloxy group, a heteroaryl group, an alkoxycarbonyl group, an alkylcarbonyloxy group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a sulfo group, a carboxyl group, a hydrazino group, a substituted silyl group, a polymeric group, or a combination thereof;
wherein the alkyl group, haloalkyl group, aralkyl group, alkenyl group, alkynyl group, aryl group, amino group, mono- or dialkylamino group, alkoxy group, aryloxy group, and heteroaryl group is optionally substituted with one or more substituents selected from the group consisting of a deuterium atom, a halogen atom, a hydroxyl group, an SH group, a nitro group, a cyano group, an alkyl group, a haloalkyl group, an aralkyl group, an alkenyl group, an alkynyl group, an aryl group, an amino group, a mono- or dialkylamino group, a mono- or diarylamino group, an alkoxy group, an aryloxy group, a heteroaryl group, an alkoxycarbonyl group, an alkylcarbonyloxy group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a sulfo group, a carboxyl group, a hydrazino group, a substituted silyl group, and a polymeric group.

11. The compound of claim 1, having the structure selected from the group consisting of:

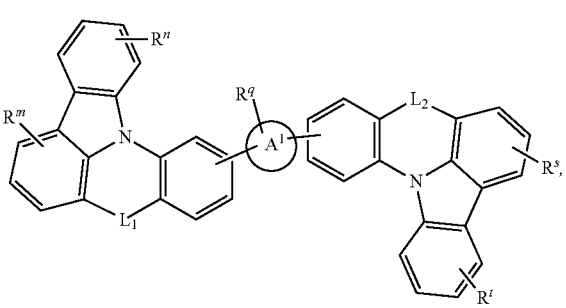

XV

-continued

XVI

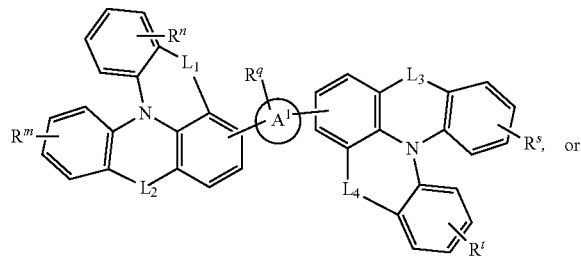

XVII

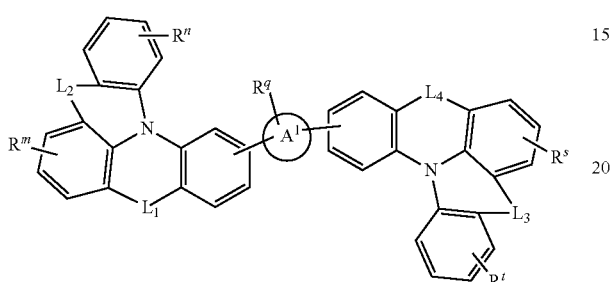

where:
- L$_3$ and L$_4$ are each independently —CR$_2$-, —CO—, or —SiR$_2$-; and
- R$^m$, R$^n$, R$^s$, R$^t$, each independently represents mono-, di-, tri, or tetra-substitution, valency permitting, and each independently represents a hydrogen atom, a deuterium atom, a halogen atom, a hydroxyl group, an —SH group, a nitro group, a cyano group, an alkyl group, a haloalkyl group, an aralkyl group, an alkenyl group, an alkynyl group, an aryl group, an amino group, a mono- or dialkylamino group, a mono- or diarylamino group, an alkoxy group, an aryloxy group, a heteroaryl group, an alkoxycarbonyl group, an alkylcarbonyloxy group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a sulfo group, a carboxyl group, a hydrazino group, a substituted silyl group, a polymeric group, or a combination thereof,
- where the alkyl group, haloalkyl group, aralkyl group, alkenyl group, alkynyl group, aryl group, amino group, mono- or dialkylamino group, alkoxy group, aryloxy group, and heteroaryl group is optionally substituted with one or more substituents selected from the group consisting of a deuterium atom, a halogen atom, a hydroxyl group, an SH group, a nitro group, a cyano group, an alkyl group, a haloalkyl group, an aralkyl group, an alkenyl group, a alkynyl group, an aryl group, an amino group, a mono- or dialkylamino group, a mono- or diarylamino group, an alkoxy group, an aryloxy group, a heteroaryl group, an alkoxycarbonyl group, an alkylcarbonyloxy group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a sulfo group, a carboxyl group, a hydrazino group, a substituted silyl group, and a polymeric group.

12. The compound of claim 11, wherein the structure is:

XVIII

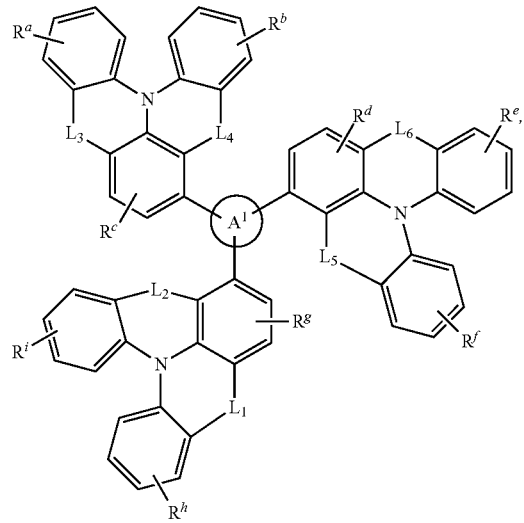

XIX

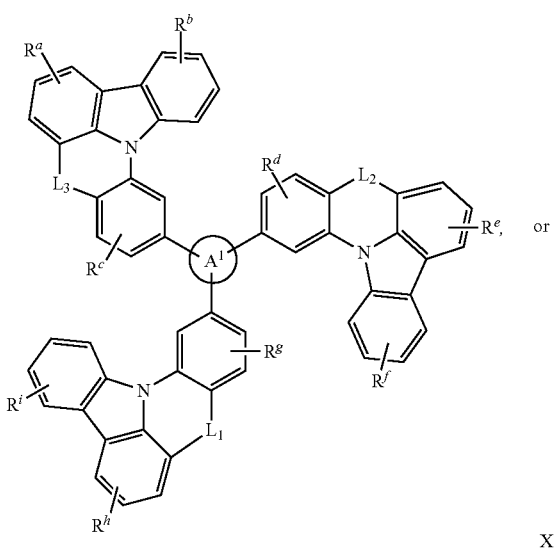 or

XX

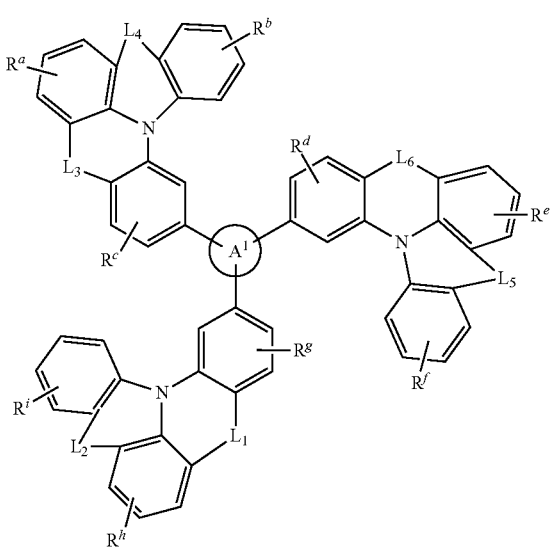

where n=1 and $L_1$, $L_2$, $L_3$, $L_4$, $L_5$, and $L_6$ are each independently —CR$_2$-, —CO—, or —SiR$_2$-; and R, $R_1$, $R_2$, $R^a$, $R^b$, $R^c$, $R^d$, $R^e$, $R^f$, $R^g$, $R^h$, and $R^i$ each independently represents mono-, di-, tri, or tetra-substitution, valency permitting, and each independently represents a hydrogen atom, a deuterium atom, a halogen atom, a hydroxyl group, an —SH group, a nitro group, a cyano group, an alkyl group, a haloalkyl group, an aralkyl group, an alkenyl group, an alkynyl group, an aryl group, an amino group, a mono- or dialkylamino group, a mono- or diarylamino group, an alkoxy group, an aryloxy group, a heteroaryl group, an alkoxycarbonyl group, an alkylcarbonyloxy group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a sulfo group, a carboxyl group, a hydrazino group, a substituted silyl group, a polymeric group, or a combination thereof;

wherein the alkyl group, haloalkyl group, aralkyl group, alkenyl group, alkynyl group, aryl group, amino group, mono- or dialkylamino group, alkoxy group, aryloxy group, and heteroaryl group is optionally substituted with one or more substituents selected from the group consisting of a deuterium atom, a halogen atom, a hydroxyl group, an SH group, a nitro group, a cyano group, an alkyl group, a haloalkyl group, an aralkyl group, an alkenyl group, an alkynyl group, an aryl group, an amino group, a mono- or dialkylamino group, a mono- or diarylamino group, an alkoxy group, an aryloxy group, a heteroaryl group, an alkoxycarbonyl group, an alkylcarbonyloxy group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a sulfo group, a carboxyl group, a hydrazino group, a substituted silyl group, and a polymeric group.

13. A thermally activated delayed fluorescent compound having a structure selected from the group consisting of:

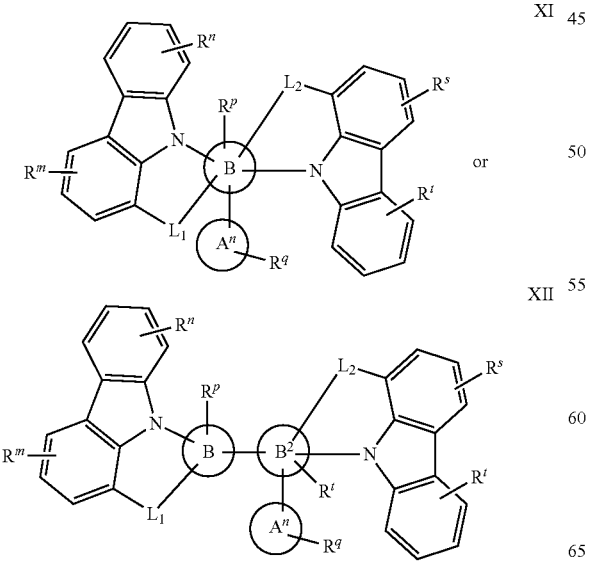

where:

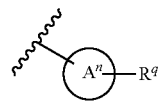

represents n acceptor moieties A, where A is a nitrogen-containing heteroaryl group, a $R^qMO$ group, where M is C, S, P, or As, or a $R^qSO_2$ group, or any combination thereof, and n=1, 2, or 3, such that the compound includes a single acceptor moiety ($A^1$), two acceptor moieties ($A^1$ and $A^2$), or three acceptor moieties ($A^1$, $A^2$, and $A^3$), and wherein each acceptor moiety is substituted with $R^q$;

B and $B^2$ are each independently a substituted electron-deficient aromatic group, $L_1$ and $L_2$ are each independently —CR$_2$-, —CO—, or —SiR$_2$-;

$R^m$, $R^n$, $R^s$, and $R^t$ each independently represents mono-, di-, tri, or tetra-substitution, valency permitting, and each independently represents a hydrogen atom, a deuterium atom, a halogen atom, a hydroxyl group, an —SH group, a nitro group, a cyano group, an alkyl group, a haloalkyl group, an aralkyl group, an alkenyl group, an alkynyl group, an aryl group, an amino group, a mono- or dialkylamino group, a mono- or diarylamino group, an alkoxy group, an aryloxy group, a heteroaryl group, an alkoxycarbonyl group, an alkylcarbonyloxy group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a sulfo group, a carboxyl group, a hydrazino group, a substituted silyl group, a polymeric group, or a combination thereof, wherein the alkyl group, haloalkyl group, aralkyl group, alkenyl group, alkynyl group, aryl group, amino group, mono- or dialkylamino group, alkoxy group, aryloxy group, and heteroaryl group is optionally substituted with one or more substituents selected from the group consisting of a deuterium atom, a halogen atom, a hydroxyl group, an SH group, a nitro group, a cyano group, an alkyl group, a haloalkyl group, an aralkyl group, an alkenyl group, an alkynyl group, an aryl group, an amino group, a mono- or dialkylamino group, a mono- or diarylamino group, an alkoxy group, an aryloxy group, a heteroaryl group, an alkoxycarbonyl group, an alkylcarbonyloxy group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a sulfo group, a carboxyl group, a hydrazino group, a substituted silyl group, and a polymeric group.

14. The compound of claim 13, wherein n=2, and the compound is:

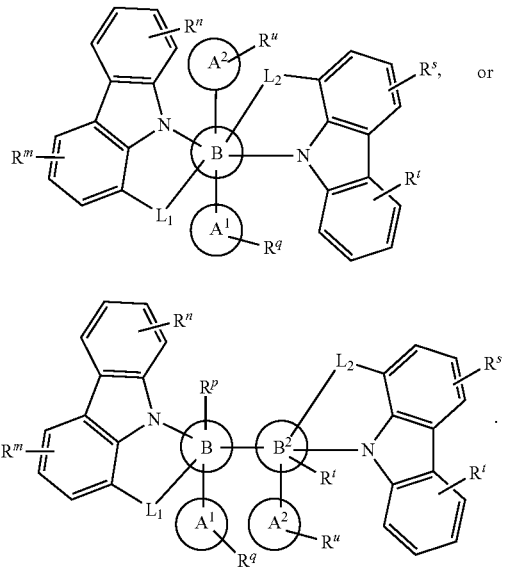

15. The compound of claim 13, wherein B is an aryl group.

16. A light emitting device comprising the thermally activated delayed fluorescent compound of claim 1.

17. The light emitting device of claim 16, wherein the light emitting device is an organic light emitting diode.

18. The light emitting device of claim 16, wherein the device comprises a full color display, a photovoltaic device, a luminescent display device or a phosphorescent display device.

19. A thermally activated delayed fluorescent compound represented by Formula II, Formula III, or Formula IV:

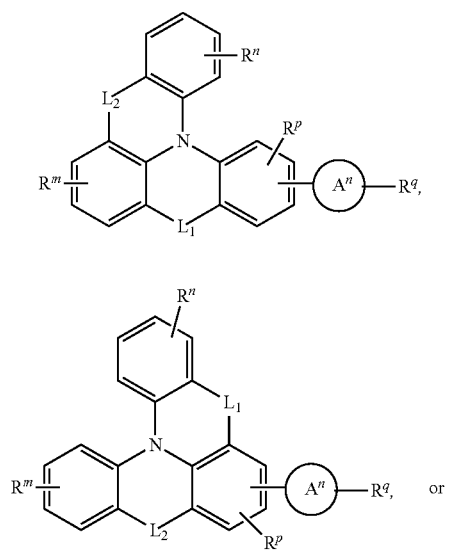

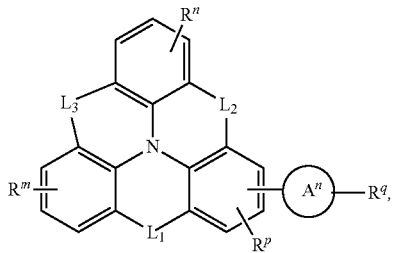

wherein:

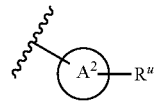

represents n acceptor moieties A, where A is a nitrogen-containing heteroaryl group, a $R^qMO$ group, where M is C, S, P, or As, or a $R^qSO_2$ group, or any combination thereof; and n=1, 2, or 3, such that the compound includes a single acceptor moiety ($A^1$), two acceptor moieties ($A^1$ and $A^2$), or three acceptor moieties ($A^1$, $A^2$, and $A^3$), and wherein each acceptor moiety is substituted with $R^q$;

$L_1$, $L_2$, and $L_3$ are each independently —$CR_2$-, —CO—, or —$SiR_2$-; and $R^m$, $R^n$, $R^p$, and $R^q$ each independently represent mono-, di-, tri, or tetra-substitution, valency permitting; and each R, $R^m$, $R^n$, $R^p$, and $R^q$ independently represents mono-, di-, tri, or tetra-substitution, valency permitting, and each independently represents a hydrogen atom, a deuterium atom, a halogen atom, a hydroxyl group, an —SH group, a nitro group, a cyano group, an alkyl group, a haloalkyl group, an aralkyl group, an alkenyl group, an alkynyl group, an aryl group, an amino group, a mono- or dialkylamino group, a mono- or diarylamino group, an alkoxy group, an aryloxy group, a heteroaryl group, an alkoxycarbonyl group, an alkylcarbonyloxy group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a sulfo group, a carboxyl group, a hydrazino group, a substituted silyl group, a polymeric group, or a combination thereof;

wherein the alkyl group, haloalkyl group, aralkyl group, alkenyl group, alkynyl group, aryl group, amino group, mono- or dialkylamino group, alkoxy group, aryloxy group, and heteroaryl group is optionally substituted with one or more substituents selected from the group consisting of a deuterium atom, a halogen atom, a hydroxyl group, an SH group, a nitro group, a cyano group, an alkyl group, a haloalkyl group, an aralkyl group, an alkenyl group, an alkynyl group, an aryl group, an amino group, a mono- or dialkylamino group, a mono- or diarylamino group, an alkoxy group, an aryloxy group, a heteroaryl group, an alkoxycarbonyl group, an alkylcarbonyloxy group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a sulfo group, a carboxyl group, a hydrazino group, a substituted silyl group, and a polymeric group;

with the proviso that when the compound is represented by Formula III, $R'''$ and $R''$ are not pyridyl.

20. The thermally activated delayed fluorescent compound of claim 19, wherein the compound is represented by Formula III.

* * * * *